United States Patent
Rehwinkel et al.

(10) Patent No.: US 7,638,515 B2
(45) Date of Patent: *Dec. 29, 2009

(54) TETRAHYDRONAPHTHALENE DERIVATIVES, PROCESS FOR THEIR PRODUCTION AND THEIR USE AS ANTI-INFLAMMATORY AGENTS

(75) Inventors: Hartmut Rehwinkel, Berlin (DE); Stefan Baeurle, Berlin (DE); Markus Berger, Berlin (DE); Norbert Schmees, Berlin (DE); Heike Schaecke, Berlin (DE); Konrad Krolikiewicz, Berlin (DE); Anne Mengel, Berlin (DE); Duy Nguyen, Berlin (DE); Stefan Jaroch, Berlin (DE); Werner Skuballa, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 415 days.

This patent is subject to a terminal disclaimer.

(21) Appl. No.: 10/961,406

(22) Filed: Oct. 12, 2004

(65) Prior Publication Data
US 2005/0209324 A1 Sep. 22, 2005

Related U.S. Application Data

(60) Provisional application No. 60/511,575, filed on Oct. 16, 2003.

(30) Foreign Application Priority Data
Oct. 8, 2003 (DE) ................. 103 47 383

(51) Int. Cl.
| | |
|---|---|
| A61K 31/50 | (2006.01) |
| A61K 31/47 | (2006.01) |
| C07D 237/02 | (2006.01) |
| C07D 239/70 | (2006.01) |
| C07D 411/12 | (2006.01) |
| C07D 453/04 | (2006.01) |
| C07D 272/22 | (2006.01) |
| C07C 211/03 | (2006.01) |
| C07C 62/38 | (2006.01) |
| C07C 255/02 | (2006.01) |

(52) U.S. Cl. ............... 514/247; 514/253; 514/521; 514/312; 514/415; 514/567; 544/239; 544/253; 546/134; 546/141; 548/454; 558/410; 562/462; 564/428

(58) Field of Classification Search .............. 514/521, 514/567, 657, 247, 312, 415; 558/410; 562/457, 562/462; 564/428; 544/239, 253; 546/134, 546/141; 548/454
See application file for complete search history.

(56) References Cited

U.S. PATENT DOCUMENTS

| 3,907,879 A * | 9/1975 | Murakami et al. .......... 562/457 |
|---|---|---|
| 5,059,609 A | 10/1991 | Eggler et al. |
| 5,112,834 A | 5/1992 | Senn-Bilfinger |
| 5,446,069 A | 8/1995 | Shih et al. |
| 5,489,584 A | 2/1996 | Vuligonda et al. |
| 6,197,783 B1 | 3/2001 | Senn-Bilfinger et al. |
| 6,897,224 B2 | 5/2005 | Jaroch et al. |
| 7,348,322 B2 | 3/2008 | Gong et al. |
| 2003/0199690 A1 | 10/2003 | Dahanukar et al. |
| 2005/0090559 A1 | 4/2005 | Berger |
| 2005/0171109 A1 | 8/2005 | Rehwinkel et al. |
| 2005/0222154 A1 | 10/2005 | Rehwinkel et al. |
| 2005/0272823 A1 | 12/2005 | Rehwinkel et al. |
| 2006/0040933 A1 | 2/2006 | Jaroch et al. |
| 2006/0084652 A1 | 4/2006 | Baeurle et al. |
| 2006/0165915 A1 | 7/2006 | Lietzau et al. |
| 2006/0167025 A1 | 7/2006 | Berger |
| 2006/0202163 A1 | 9/2006 | Lietzau et al. |
| 2006/0229305 A1 | 10/2006 | Berger et al. |
| 2006/0247213 A1 | 11/2006 | Buckman et al. |
| 2007/0015750 A1 | 1/2007 | Baeurle et al. |
| 2007/0015761 A1 | 1/2007 | Mengel et al. |
| 2007/0129359 A1 | 6/2007 | Huwe et al. |
| 2007/0225290 A1 | 9/2007 | Berger et al. |
| 2008/0153859 A1 | 6/2008 | Rehwinkel et al. |

FOREIGN PATENT DOCUMENTS

| CN | 1524835 A | 9/2004 |
|---|---|---|
| EP | 0291327 A2 | 11/1988 |
| EP | 0299470 A1 | 1/1989 |
| EP | 0439265 | 7/1991 |
| EP | 05/79223 A1 | 1/1994 |
| JP | 63220242 A | 9/1988 |
| JP | 2000/256255 A2 | 9/2000 |
| WO | WO 88/08836 A2 | 11/1988 |
| WO | WO 96/20930 A | 7/1996 |
| WO | WO 99/04778 A1 | 2/1999 |
| WO | WO 99/06388 A2 | 2/1999 |
| WO | WO 99/37607 A1 | 7/1999 |
| WO | WO 99/50205 A2 | 10/1999 |

(Continued)

OTHER PUBLICATIONS

Int'l Search Report dated issued Jan. 18, 2006 in PCT/EP2005/009623.

(Continued)

*Primary Examiner*—James O Wilson
*Assistant Examiner*—Ebenezer Sackey
(74) *Attorney, Agent, or Firm*—Millen, White, Zelano & Branigan, P.C.

(57) ABSTRACT

The invention relates to tetrahydronaphthalene derivatives, process for their production and their use as anti-inflammatory agents.

26 Claims, No Drawings

FOREIGN PATENT DOCUMENTS

| | | |
|---|---|---|
| WO | WO 00/10977 A1 | 3/2000 |
| WO | WO 01/30734 A1 | 5/2001 |
| WO | WO 02/10143 A | 2/2002 |
| WO | WO 02/16318 | 2/2002 |
| WO | WO 03/000694 A1 | 1/2003 |
| WO | WO 03/027061 A2 | 4/2003 |
| WO | WO 03/040107 A1 | 5/2003 |
| WO | WO 03/045924 A1 | 6/2003 |
| WO | WO 03/082280 A | 10/2003 |
| WO | WO 03/082827 A | 10/2003 |
| WO | WO 2004/020375 A1 | 3/2004 |
| WO | WO 2004/063163 A | 7/2004 |
| WO | WO 2004/075864 A | 9/2004 |
| WO | WO 2005/003098 A1 | 1/2005 |
| WO | WO 2005/021682 A1 | 3/2005 |
| WO | WO 2006/027236 A | 3/2005 |
| WO | WO 2005/034939 A | 4/2005 |
| WO | WO 2005/090343 A | 9/2005 |
| WO | WO 2006/015870 A | 2/2006 |
| WO | WO 2006/066950 A | 6/2006 |
| WO | WO 2006/100100 A | 9/2006 |
| WO | WO 2006/108699 A | 10/2006 |
| WO | WO 2006/108714 A | 10/2006 |

OTHER PUBLICATIONS

Evans, D.A. et al., "C2-symmetric copper (II) complexes as chiral lewis acids. Catalytic enantioselective carbonyl-ene reactions with glyoxylate and pyruvate esters," Journal of the American Chemical Society, 2000, pp. 7936-7943, vol. 122, Washington, D.C..

Cleghorn, L.A.T. et al., "Three-component bimetallic (pd/In) mediated cascade allylation of C=X functionality—Part 1. Scope and class 1 examples with aldehydes and ketones," Journal of Organometallic Chemistry, Dec. 7, 2003, pp. 483-493, vol. 687 No. 2. Elsevier-sequoia S.A. Lausanne, CH.

Ene reaction, Wikipedia, 1945.

Noseworthy et al., The New England Journal of Medicine, p. 949, vol. 343, No. 13, (2005).

Jordan, V.C. Nature Reviews: Drug Discovery, 2, 2003, p. 205.

Dorwald, F. Zaragoza. Side Reactions in Organic Synthesis: A Guide to Sucessful Synthesis Design, Weinheim: Wiley-VCH Verlag Gmbh & Co. KgaA, 2005, Preface.

Database CA (Online), Chemical Abstracts Service, Columbus, OH, 2004. Patonay, Tamas et al., "Synthesis of racemic and enantiomerically enriched .alpha.-Osyfunctionalized benzocyclanones and chromanones by dimethyldioxirane and dimethyldioxirane/Mn(III) salen system," XP002397132.

Database CA (Online), Chemical Abstracts Service, Columbus, OH, 2001. Ferraz, Helena et al., "The reaction of 1-tetralones with thallium trinitrate supported on clay : ring contraction vs. .alpha.-oxidation," XP002397132.

Database CA (Online), Chemical Abstracts Services, Columbus, OH, 1994. Srivastava, J.N. et al., "Syntheisis of 7-methoxy- and 6-mthoxytatralino[3,4-c]isocumarins and 7-methoxy- and 6-methoxytetralino[3,4-c]isoquinolones," XP002397133.

Database CA (Online), Chemical Abstracts Service, Columbus, OH, 1983. Thiem, Joachim et al., "2, 6-dideoxy sacchride glycosides of . alpha.-hydroxy ketones: synthesis and configurational assignment of glycosides with the tetralone substructure of olivomycin," XP 002397135.

Chemical Abstracts 138:385424, 138:287411, 143:193936, 141:218306, 140:357328, 134:326287, 134:71375, 126:34370, 89:42860.

Cecil Textbook of Medicine, edited by Bennet, J.C., and Plum F., 20$^{th}$ edition, vol. 1m 1004-1010, 1996.

Smoak et al., Mechanism of Ageing and Development, 125 697-706, 2004.

Saklavala et al., Arthritis Research 4(3), 146-150, 2002.

Barnes, P.J., Eur. Respir. J., 27(2), 413-426, 2006.

Bellucci et al., Tatrahedron Asymmetry, 8, 895-902, 1997.

Hachisu et al. Thiazolium ylide- catalyzed intramolecular aldehyde-ketone benzoin-forming reactionsl Advanced Synthesis & Catalysis, 2004, col. 346 (9+ 10), pp. 1097-1100: HCAPLUS abstract, Doc. No. 142:260997.

Dehmlow et al. Monodeazacinchona Alkaloid Derivatives: Synthesis and Preliminary Applications as Phase-Transfer Catalyst European Journal of Organic Chemistry, 2002 (13), pp. 2087-2093.

Nagao et al. New Ring-Expansion Reactions of Hydroxy Propenoyl Cyclic Compounds under Palladium (O)/Phosine-Catalyzed Conditions. Organic Letters, 2004, vol. 6 (13), pp. 2133-2136.

Greene. Protective Groups in Organic Synthesis, 1999, pp. 17-23.

Warner-Lambert. Expert Opinion on Therapeutic Patents, 2000, 10 (1), 121-23.

Int'l Search Report dated issued Mar. 15, 2007 in PCT/EP2007/002432.

Tchilibon et al., Biochemical Pharmacology, 70 (2005), 381-393.

Non-Final Rejection dated Mar. 10, 2008 in related U.S. Appl. No. 10/960,754, filed Oct. 8, 2004.

Final Rejection dated Sep. 15, 2008 in related U.S. Appl. No. 10/960,754, filed Oct. 8, 2004.

Non-Final Rejection dated Oct. 3, 2007 in related U.S. Appl. No. 10/962,169, filed Oct. 12, 2004.

Final Rejection dated Jul. 14, 2008 in related U.S. Appl. No. 10/962,169, filed Oct. 12, 2004.

Non-Final Rejection dated Apr. 24, 2007 in related U.S. Appl. No. 11/222,250, filed Sep. 9, 2005.

Final Rejection dated Sep. 28, 2007 in related U.S. Appl. No. 11/222,250, filed Sep. 9, 2005.

Non-Final Rejection dated May 28, 2008 in related U.S. Appl. No. 11/717,782, filed Mar. 14, 2007.

Final Rejection dated Jan. 9, 2009 in related U.S. Appl. No. 11/717,782, filed Mar. 14, 2007.

Non-Final Rejection dated Aug. 18, 2008 in related U.S. Appl. No. 11/717,782, filed Mar. 14, 2007.

* cited by examiner

TETRAHYDRONAPHTHALENE DERIVATIVES, PROCESS FOR THEIR PRODUCTION AND THEIR USE AS ANTI-INFLAMMATORY AGENTS

This application is a CIP of U.S. application Ser. No. 10/960,754, which claims the benefit of U.S. Ser. No. 60/511,575 filed Oct. 16, 2003, all of which are incorporated by reference herein.

The invention relates to tetrahydronaphthalene derivatives, process for their production and their use as anti-inflammatory agents.

Open-chain, non-steroidal anti-inflammatory agents are known from the prior art (DE 100 38 639 and WO 02/10143). In the experiment, these compounds show dissociations of action between anti-inflammatory and undesirable metabolic actions and are superior to the previously described nonsteroidal glucocorticoids or exhibit at least just as good an action.

The selectivity compared to the other steroid receptors as well as the pharmacokinetic parameters of the compounds of the prior art still requires improvement, however.

It was therefore the object of this invention to make available compounds whose selectivity compared to the other steroid receptors as well as their pharmacokinetic properties are at least just as good or better than the compounds of the prior art.

This object is achieved by the compounds of this invention, explained in the claims.

This invention therefore relates to compounds of general formula (I)

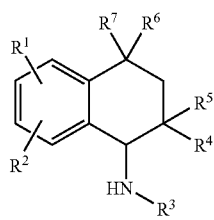

in which
R$^1$ and R$^2$, independently of one another, mean a hydrogen atom, a hydroxy group, a halogen atom, an optionally substituted (C$_1$-C$_{10}$)-alkyl group, an optionally substituted (C$_1$-C$_{10}$)-alkoxy group, a (C$_1$-C$_{10}$)-alkylthio group, a (C$_1$-C$_5$)-perfluoroalkyl group, a cyano group, or a nitro group, or R$^1$ and R$^2$ together mean a group that is selected from the groups —O—(CH$_2$)$_n$—O—, —O—(CH$_2$)$_n$—CH$_2$—, —O—CH=CH—, —(CH$_2$)$_{n+2}$—, —NH—(CH$_2$)$_{n+1}$, N(C$_1$-C$_3$-alkyl)-(CH$_2$)$_{n+1}$, or —NH—N=CH—,
whereby n=1 or 2, and the terminal oxygen atoms and/or carbon atoms and/or nitrogen atoms are linked to directly adjacent ring-carbon atoms, or NR$^8$R$^9$,
whereby R$^8$ and R$^9$, independently of one another, can be hydrogen, C$_1$-C$_5$-alkyl or (CO)—C$_1$-C$_5$-alkyl,
R$^3$ means a C$_1$-C$_{10}$-alkyl group that optionally is substituted by 1-3 hydroxy groups, halogen atoms, 1-3 (C$_1$-C$_5$)-alkoxy groups, an optionally substituted (C$_3$-C$_7$)-cycloalkyl group, an optionally substituted heterocyclyl group, an optionally substituted aryl group, a monocyclic or bicyclic heteroaryl group that optionally contains 1-4 nitrogen atoms and/or 1-2 oxygen atoms and/or 1-2 sulfur atoms and/or 1-2 keto groups and that optionally is substituted by one or more groups selected from (C$_1$-C$_5$)-alkyl groups (which optionally can be substituted by 1-3 hydroxy groups or 1-3 COOR$^{13}$ groups, whereby R$^{13}$ means hydrogen or a C$_1$-C$_5$-alkyl group); (C$_1$-C$_5$)-alkoxy groups, halogen atoms, hydroxy groups, NR$^8$R$^9$ groups, exomethylene groups, or oxygen, whereby this group can be linked via any position to the amine of the tetrahydronaphthalene system and optionally can be hydrogenated at one or more locations, R$^4$ means a hydroxy group, a group OR$^{10}$, or an O(CO)R$^{10}$ group, whereby R$^{10}$ means any hydroxy protective group or a C$_1$-C$_{10}$-alkyl group, R$^{5-}$ means a (C$_1$-C$_{10}$)-alkyl group or an optionally partially or completely fluorinated (C$_1$-C$_{10}$)-alkyl group, R$^6$ and R$^7$, independently of one another, mean a hydrogen atom, a methyl or ethyl group or together with the carbon atom of the tetrahydronaphthalene system mean a (C$_3$-C$_6$)-cycloalkyl ring.

Compounds of general formula (I),

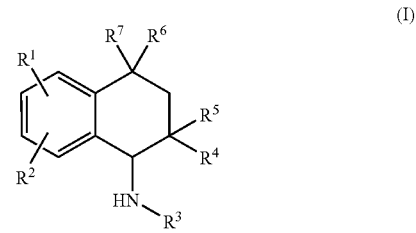

in which
R$^1$ and R$^2$, independently of one another, mean a hydrogen atom, a hydroxy group, a halogen atom, a (C$_1$-C$_{10}$)-alkyl group, a (C$_1$-C$_{10}$)-alkoxy group, a (C$_1$-C$_{10}$)-alkylthio group, a (C$_1$-C$_5$)-perfluoroalkyl group, a cyano group, or a nitro group, or R$^1$ and R$^2$ together mean a group that is selected from the groups —O—(CH$_2$)$_n$—O—, —O—(CH$_2$)$_n$—CH$_2$—, —O—CH=CH—, —(CH$_2$)$_{n+2}$—, —NH—(CH$_2$)$_{n+1}$, —N(C$_1$-C$_3$-alkyl)-(CH$_2$)$_{n+1}$, and —NH—N=CH—,
whereby n=1 or 2, and the terminal oxygen atoms and/or carbon atoms and/or nitrogen atoms are linked to directly adjacent ring-carbon atoms, or NR$^8$R$^9$,
whereby R$^8$ and R$^9$, independently of one another, can be hydrogen, C$_1$-C$_5$-alkyl or (CO)—C$_1$-C$_5$-alkyl,
R$^3$ means a C$_1$-C$_{10}$-alkyl group that optionally can be substituted by 1-3 hydroxy groups, halogen atoms, or 1-3 (C$_1$-C$_5$)-alkoxy groups, an optionally substituted (C$_3$-C$_7$)-cycloalkyl group, an optionally substituted heterocyclyl group, an optionally substituted aryl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted by one or more groups that are selected from (C$_1$-C$_5$)-alkyl groups (which optionally can be substituted by 1-3 hydroxy groups or 1-3 COOR$^6$ groups); (C$_1$-C$_5$)-alkoxy groups, halogen atoms, or exomethylene groups,
whereby this group can be linked via any position to the amine of the tetrahydronaphthalene system and optionally can be hydrogenated at one or more locations, $R^4$ means a hydroxy group, or a group $OR^{10}$, $R^5$ means a $(C_1$-$C_5)$-alkyl group or an optionally partially or completely fluorinated $(C_1$-$C_5)$-alkyl group, $R^6$ and $R^7$, independently of one another, mean a hydrogen atom, a methyl or ethyl group or together with the carbon atom of the tetrahydronaphthalene system mean a $(C_3$-$C_6)$-cycloalkyl ring, are a subject of this invention.

Compounds of general formula (I),

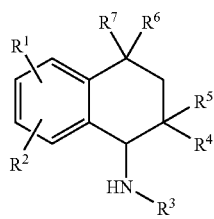

(I)

in which
- $R^1$ and $R^2$, independently of one another, mean a hydrogen atom, a hydroxy group, a halogen atom, an optionally substituted $(C_1$-$C_{10})$-alkyl group, an optionally substituted $(C_1$-$C_{10})$-alkoxy group, a $(C_1$-$C_{10})$-alkylthio group, a $(C_1$-$C_5)$-perfluoroalkyl group, a cyano group, or a nitro group, or $R^1$ and $R^2$ together mean a group that is selected from the groups —O—$(CH_2)_n$—O—, —O—$(CH_2)_n$—$CH_2$—, —O—CH=CH—, —$(CH_2)_{n+2}$—, —NH—$(CH_2)_{n+1}$, N($C_1$-$C_3$-alkyl)-$(CH_2)_{n+1}$, and —NH—N=CH—, whereby n=1 or 2, and the terminal oxygen atoms and/or carbon atoms and/or nitrogen atoms are linked to directly adjacent ring-carbon atoms, or $NR^8R^9$, whereby $R^8$ and $R^9$, independently of one another, can be hydrogen, $C_1$-$C_5$-alkyl or (CO)—$C_1$-$C_5$-alkyl,

- $R^3$ means a monocyclic or bicyclic heteroaryl group that optionally contains 1-4 nitrogen atoms and/or 1-2 oxygen atoms and/or 1-2 sulfur atoms and/or 1-2 keto groups and that optionally is substituted by one or more groups that are selected from $(C_1$-$C_5)$-alkyl groups (which optionally can be substituted by 1-3 hydroxy or 1-3 $COOR^{13}$ groups, whereby $R^{13}$ means hydrogen or a $C_1$-$C_5$-alkyl group); $(C_1$-$C_5)$-alkoxy groups, halogen atoms, hydroxy groups, $NR^8R^9$ groups, exomethylene groups, or oxygen, whereby this group can be linked via any position to the amine of the tetrahydronaphthalene system and optionally can be hydrogenated at one or more locations,

- $R^4$ means a hydroxy group, a group $OR^{10}$ or an $O(CO)R^{10}$ group, whereby $R^{10}$ means any hydroxy protective group or a $C_1$-$C_{10}$-alkyl group,

- $R^5$ means a $(C_1$-$C_{10})$-alkyl group or an optionally partially or completely fluorinated $(C_1$-$C_{10})$-alkyl group,

- $R^6$ and $R^7$, independently of one another, mean a hydrogen atom, a methyl or ethyl group, or together with the carbon atom of the tetrahydronaphthalene system mean a $(C_3$-$C_6)$-cycloalkyl ring, are another subject of this invention.

Compounds of general formula (I),

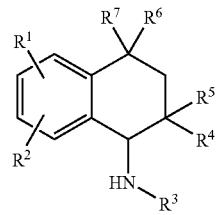

in which
- $R^1$ and $R^2$, independently of one another, mean a hydrogen atom, a hydroxy group, a halogen atom, an optionally substituted $(C_1$-$C_{10})$-alkyl group, an optionally substituted $(C_1$-$C_{10})$-alkoxy group, a $(C_1$-$C_{10})$-alkylthio group, a $(C_1$-$C_5)$-perfluoroalkyl group, a cyano group, or a nitro group, or $R^1$ and $R^2$ together mean a group that is selected from the groups —O—$(CH_2)_n$—O—, —O—$(CH_2)_n$—$CH_2$—, —O—CH=CH—, —$(CH_2)_{n+2}$—, —NH—$(CH_2)_{n+1}$, N($C_1$-$C_3$-alkyl)-$(CH_2)_{n+1}$, or —NH—N=CH—, whereby n=1 or 2, and the terminal oxygen atoms and/or carbon atoms and/or nitrogen atoms are linked to directly adjacent ring-carbon atoms, or $NR^8R^9$, whereby $R^8$ and $R^9$, independently of one another, can be hydrogen, $C_1$-$C_5$-alkyl or (CO)—$C_1$-$C_5$-alkyl,

- $R^3$ means a monocyclic or bicyclic heteroaryl group that optionally contains 1-4 nitrogen atoms and/or 1-2 oxygen atoms and/or 1-2 sulfur atoms and/or 1-2 keto groups and that optionally is substituted by one or more groups that are selected from $(C_1$-$C_5)$-alkyl groups (which optionally can be substituted by 1-3 hydroxy groups or 1-3 $COOR^{13}$ groups, whereby $R^{13}$ means hydrogen or a $C_1$-$C_5$-alkyl group), $(C_1$-$C_5)$-alkoxy groups, halogen atoms, hydroxy groups, $NR^8R^9$ groups, exomethylene groups, or oxygen, whereby this group can be linked via any position to the amine of the tetrahydronaphthalene system and optionally can be hydrogenated at one or more locations,

- $R^4$ means a hydroxy group, a group $OR^{10}$, or an $O(CO)R^{10}$ group, whereby $R^{10}$ means any hydroxy protective group or a $C_1$-$C_{10}$-alkyl group,

- $R^5$ means an optionally partially or completely fluorinated $(C_1$-$C_{10})$-alkyl group,

- $R^6$ and $R^7$, independently of one another, mean a hydrogen atom, a methyl or ethyl group or together with the carbon atom of the tetrahydronaphthalene system mean a $(C_3$-$C_6)$-cycloalkyl ring.

Compounds that on the aromatic ring of the tetrahydronaphthalene system carry one or two substituents, selected from the group optionally substituted $C_1$-$C_5$-alkyl, optionally substituted $C_1$-$C_5$-alkoxy, $C_1$-$C_5$-perfluoroalkyl, halogen, hydroxy, cyano, nitro, —O—$(CH_2)_n$—O—, —O—$(CH_2)_n$—$CH_2$—, —O—CH=CH—, —$(CH_2)_{n+2}$—, —NH—$(CH_2)_{n+1}$, $N(C_1$-$C_3$-alkyl)-$(CH_2)_{n+1}$, or —NH—N=CH—, whereby n=1 or 2, are a special subject of the invention, and the terminal oxygen atoms and/or carbon atoms and/or nitrogen atoms are linked to directly adjacent ring-carbon atoms.

Compounds that on the aromatic ring of the tetrahydronaphthalene system carry one or two substituents, selected from the group $C_1$-$C_5$-alkyl, $C_1$-$C_5$-alkoxy, $C_1$-$C_5$-perfluoroalkyl, halogen, hydroxy, nitro, —O—$(CH_2)_n$—O—, —O—$(CH_2)_n$—$CH_2$—, —O—CH=CH—, —$(CH_2)_{n+2}$—, —NH—$(CH_2)_{n+1}$, N($C_1$-$C_3$-alkyl)-$(CH_2)_{n+1}$, or —NH—N=CH—, whereby n=1 or 2, are another subject of the invention, and the terminal oxygen atoms and/or carbon atoms and/or nitrogen atoms are linked to directly adjacent ring-carbon atoms.

The compounds in which $R^1$ and $R^2$ together mean the radicals —O—$(CH_2)_n$—O—, —O—$(CH_2)_n$—$CH_2$—, —O—CH=CH—, —$(CH_2)_{n+2}$—, —NH—$(CH_2)_{n+1}$, N($C_1$-$C_3$-alkyl)-$(CH_2)_{n+1}$, and —NH—N=CH— are a subgroup of these compounds. —O—$(CH_2)_n$—O—, —O—$(CH_2)_n$—$CH_2$—, and —O—CH=CH— are preferred.

The compounds in which alkyl radicals $R^1$ and $R^2$ have the meaning —$(CH_2)_{n+2}$— and thus form a 5- to 6-membered ring together with the carbon atom of the chain represent another subgroup.

Compounds of general formula I according to claim 1, in which $R^3$ a $C_1$-$C_{10}$-alkyl group, which optionally can be substituted by 1-3 hydroxy groups, halogen atoms, 1-3 ($C_1$-$C_5$)-alkoxy groups, an optionally substituted ($C_3$-$C_7$)-cycloalkyl group, an optionally substituted heterocyclyl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted by one or more groups that are selected from ($C_1$-$C_5$)-alkyl groups, ($C_1$-$C_5$)-alkoxy groups, halogen atoms, and exomethylene groups, whereby these groups can be linked via any position to the amine of the tetrahydronaphthalene system and optionally can be hydrogenated at one or more locations, are another subject of the invention.

Compounds of formula I, in which $R^3$ means a $C_1$-$C_{10}$-alkyl group, which optionally can be substituted by 1-3 hydroxy groups, halogen atoms, an optionally substituted phenyl group, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms, or 1-2 exomethylene groups, whereby these groups can be linked via any position to the nitrogen atom of the tetrahydronaphthalene system and optionally can be hydrogenated at one or more locations, are another subject of the invention.

Compounds of formula I according to claims 1 to 5, in which $R^3$ means a monocyclic or bicyclic heteroaryl group that optionally contains 1-4 nitrogen atoms and/or 1-2 oxygen atoms and/or 1-2 sulfur atoms and/or 1-2 keto groups and that optionally is substituted by one or more groups, independently of one another, selected from ($C_1$-$C_5$)-alkyl groups, which themselves optionally can be substituted by 1-3 hydroxy groups or 1-3 $COOR^{13}$ groups, whereby $R^{13}$ means hydrogen or ($C_1$-$C_5$)-alkyl; ($C_1$-$C_5$)-alkoxy groups, halogen atoms, hydroxy groups, $NR^8R^9$ groups, exomethylene groups, or oxygen, whereby this group can be linked via any position to the amine of the tetrahydronaphthalene system and optionally can be hydrogenated at one or more locations, are a preferred subject of the invention.

Compounds of general formula I, in which $R^3$ means a monocyclic or bicyclic heteroaryl group that optionally contains 1-4 nitrogen atoms and/or 1-2 oxygen atoms and/or 1-2 sulfur atoms and/or 1-2 keto groups and that optionally is substituted by one or more groups, independently of one another, selected from ($C_1$-$C_5$)-alkyl groups, which themselves optionally can be substituted by 1-3 hydroxy groups or 1-3 $COOR^{13}$ groups, whereby $R^{13}$ means hydrogen or ($C_1$-$C_5$)-alkyl; ($C_1$-$C_5$)-alkoxy groups, halogen atoms, hydroxy groups, $NR^8R^9$ groups, exomethylene groups, or oxygen, whereby this group can be linked via any position to the amine of the tetrahydronaphthalene system and optionally can be hydrogenated at one or more locations, and $R^5$ means an optionally partially or completely fluorinated ($C_1$-$C_5$)-alkyl group, are another preferred subject of this invention.

Compounds of general formula I, in which $R^3$ means a $C_1$-$C_{10}$-alkyl group, which optionally can be substituted by 1-3 hydroxy groups, halogen atoms, a phenyl, phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazole or indolyl group that optionally is substituted with $C_1$-$C_5$-alkyl, halogen, hydroxy, or $C_1$-$C_5$-alkoxy, are a preferred subject of the invention.

Compounds of general formula I, in which $R^3$ a phenyl or naphthyl, phthalidyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazole or indolyl group that optionally is substituted with $C_1$-$C_5$-alkyl, halogen, hydroxy, or $C_1$-$C_5$-alkoxy, are an also preferred subject.

Stereoisomers of general formula I or II, in which $R^3$ means an optionally substituted isoquinolonyl, quinolonyl, quinazolinyl, phthalazinyl, indazolyl, quinolinyl, isoquinolinyl, isoquinolonyl, dihydroindolonyl, dihydroindolyl, dihydroindolonyl, naphthyl, pyridyl, or phthalidyl group, are another subject of the invention. Stereoisomers of general formula I in which $R^3$ means isoquinolin-1(2H)on-5yl, quinolin-2(1H)-on-5yl-, 8- or 7-fluoro-2-methyl-quinazoline, 7,8-difluoro-4-methyl-quinazoline, 7,8-difluoro-2-methyl-quinazoline or 2-methyl-phthalazin-1-one, are another subject of the invention.

Radical $R^3$ is bonded via the amine to the tetrahydronaphthalene system. If radical $R^3$ exhibits several positions that are chemically possible to be bonded to the ring system, then this invention comprises all these possibilities.

Radical $R^3$ is also part of this invention when it is hydrogenated at one or more locations.

As substituents of the monocyclic or bicyclic heteroaryl groups (heterocyclic groups) $R^3$, just as it was first defined, for example, hydroxy, halogen atoms, in particular fluorine and chlorine, ($C_1$-$C_5$)-alkyl groups (which themselves optionally can be substituted by hydroxy groups, ($C_1$-$C_5$)-alkoxy groups or $COOR^{13}$ groups, whereby $R^{13}$ means hydrogen or ($C_1$-$C_5$)-alkyl), in particular methyl, ($C_2$-$C_5$)-alkenyl groups, completely or partially fluorinated ($C_1$-$C_5$)-alkyl groups, in particular $CF_3$, $CFH_2$ or $C_2F_5$, ($C_1$-$C_5$)-alkoxy groups, in particular methoxy and ethoxy, $NR^8R^9$ groups, in particular $NH_2$, $N(CH_3)_2$ or $NH(CH_3)$, cyano groups as well as keto groups, which are formed with a carbon atom of a ring of the heteroaryl group, and oxygen, which forms an N-oxide with an optionally present nitrogen atom of the ring, are suitable at chemically suitable positions. The group that consists of fluorine, chlorine, OH, $CH_3$, $CF_3$, $CFH_2$, or $C_2F_5$, $OCH_3$, $OC_2H_5$, $NH_2$, $N(CH_3)_2$ and $NH(CH_3)$, cyano, keto and oxygen follows from the above as a preferred group of substituents for radical $R^3$ as it is defined in claim 1 and for all additional claims.

The hydroxy group in $R^4$ can be protected by one of the common hydroxy protective groups, such as, for example, silyl ether or ester of organic $C_1$-$C_{10}$-acids or can be present as $C_1$-$C_5$-ethers or benzyl ether, preferably as one of the common hydroxy protective groups or as $C_1$-$C_5$-ether or preferably present as $C_1$-$C_5$-ether.

The hydroxy group is preferred as radical $R^4$.

The common hydroxy protective groups are described in detail in T. W. Greene, P. G. M. Wuts "Protective Groups in Organic Synthesis," 2$^{nd}$ Edition, John Wiley & Sons, 1991).

The protective groups are preferably alkyl-, aryl- or mixed alkylaryl-substituted silyl groups, e.g., the trimethylsilyl (TMS), triethylsilyl (TES), tert-butyldimethylsilyl (TBDMS), tert-butyldiphenylsilyl (TBDPS) or triisopropylsilyl groups (TIPS) or another conventional hydroxy protective group (methoxymethyl, methoxyethoxymethyl, ethoxyethyl, tetrahydrofuranyl, and tetrahydropyranyl groups).

Compounds of general formula I in which $R^5$ means an optionally partially or completely fluorinated ($C_1$-$C_5$)-alkyl group, preferably a completely fluorinated ($C_1$-$C_5$)-alkyl group, are a subject of the invention. $R^5$ especially preferably stands for the trifluoromethyl group or the pentafluoroethyl group.

The radicals and all their subcombinations, which are confirmed by the examples, represent an especially preferred subgroup, as it was disclosed for this invention.

The designation halogen atom or halogen means a fluorine, chlorine, bromine or iodine atom. A fluorine, chlorine or bromine atom is preferred.

The $C_1$-$C_5$-alkyl groups $R^1$, $R^2$, $R^4$, $R^6$, and $R^7$ can be straight-chain or branched and stand for a methyl, ethyl, n-propyl, iso-propyl, n-butyl, iso-butyl, tert.-butyl or n-pentyl, 2,2-dimethylpropyl, 2-methylbutyl or 3-methylbutyl group. A methyl or ethyl group is preferred. The abovementioned alkyl groups optionally can be substituted by 1-5 groups, independently of one another, selected from hydroxy, cyano, nitro, $COOR^{13}$, $C_1$-$C_5$-alkoxy groups, halogen, $NR^8R^9$, a partially or completely fluorinated $C_1$-$C_3$-alkyl group; fluorine, cyano, methoxy and hydroxy groups are preferred.

They can optionally be substituted by 1-3 hydroxy groups and/or 1-3 $COOR^{13}$ groups. Hydroxy groups are preferred.

For a partially or completely fluorinated $C_1$-$C_3$-alkyl group, the following partially or completely fluorinated groups are considered: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl. Of the latter, the trifluoromethyl group or the pentafluoroethyl group is preferred. The reagents, which optionally are used during the synthesis, are commercially available, or the published syntheses of the corresponding reagents are part of the prior art, or published syntheses can be applied analogously.

The $C_1$-$C_5$-alkoxy groups can be straight-chain or branched and stand for a methoxy, ethoxy, n-propoxy, iso-propoxy-, n-butoxy, iso-butoxy, tert.-butoxy or n-pentoxy, 2,2-dimethylpropoxy, 2-methylbutoxy or 3-methylbutoxy group. A methoxy or ethoxy group is preferred. The abovementioned alkoxy groups optionally can be substituted with 1-3 groups that are selected from halogen, in particular fluorine, chlorine, hydroxy and cyano.

The $C_1$-$C_5$-alkylthio groups can be straight-chain or branched and stand for a methylthio, ethylthio, n-propylthio, iso-propylthio, n-butylthio, iso-butylthio, tert.-butylthio or n-pentylthio, 2,2-dimethylpropylthio, 2-methylbutylthio or 3-methylbutylthio group. A methylthio or ethylthio group is preferred.

Substituent $NR^8R^9$ means, for example, $NH_2$, $NH(CH_3)$, $N(CH_3)_2$, $NH(C_2H_5)$, $N(C_2H_5)_2$, $NH(C_3H_7)$, $N(C_3H_7)_2$, $NH(C_4H_9)$, $N(C_4H_9)_2$, $NH(C_5H_{11})$, $N(C_5H_{11})_2$, $NH(CO)CH_3$, $NH(CO)C_2H_5$, $NH(CO)C_3H_7$, $NH(CO)C_4H_9$, or $NH(CO)C_5H_{11}$.

The cycloalkyl group means a saturated cyclic group that optionally is substituted by one or more groups selected from hydroxy groups, halogen atoms, ($C_1$-$C_5$)-alkyl groups, ($C_1$-$C_5$)-alkoxy groups, $NR^8R^9$ groups, $COOR^{13}$ groups, CHO, and cyano, and said group has 3 to 7 ring-carbon atoms, such as, for example, cyclopropyl, methylcyclopropyl, cyclobutyl, methylcyclobutyl, cyclopentyl, methylcyclopentyl, cyclohexyl, methylcyclohexyl, cycloheptyl, and methylcycloheptyl.

The heterocyclyl group is not aromatic and can be, for example, pyrrolidine, imidazolidine, pyrazolidine, or piperidine.

As substituents for heterocyclyl and heteroaryl groups, for example, substituents from the group optionally substituted $C_1$-$C_5$-alkyl group, hydroxy-, $C_1$-$C_5$-alkoxy-, $NR^8R^9$—, halogen, cyano-, $COOR^{13}$—, and CHO— are suitable. The substituents can optionally also be bonded to the nitrogen atom; then N-oxides are also included in the definition.

Aryl groups in terms of the invention are aromatic or partially aromatic carbocyclic groups with 6 to 14 carbon atoms, which exhibit a ring, such as, e.g., phenyl or phenylene, or several condensed rings, such as, e.g., naphthyl or anthranyl. By way of example, phenyl, naphthyl, tetralinyl, anthranyl, indanyl, and indenyl can be mentioned.

The aryl groups can be substituted at any suitable position that results in a stable stereoisomer by one or more radicals from the group hydroxy, halogen; $C_1$-$C_5$-alkyl that optionally is substituted by 1-3 hydroxy groups or $COOR^{13}$ groups; $C_1$-$C_5$-alkoxy, cyano, $CF_3$, and nitro. The optionally substituted phenyl group and the naphthyl group are preferred.

The monocyclic or bicyclic heteroaryl group can optionally be substituted by one or more substituents that are selected from the $C_1$-$C_5$-alkyl group, $C_1$-$C_5$-alkoxy group, halogen or exomethylene that optionally is substituted by 1-3 hydroxy groups or 1-3 $COOR^{13}$ groups. The substituents optionally also can be directly bonded to the heteroatom. N-oxides are also included in this invention.

The monocyclic or bicyclic heteroaryl group optionally can contain 0-9 groups from the group nitrogen atoms, oxygen atoms, sulfur atoms or keto groups, of which at most 3 (4?) nitrogen atoms, at most 2 oxygen atoms, at most 2 sulfur atoms and at most 2 keto groups can be contained. Any subcombination of these groups is possible. The heteroaryl group can be hydrogenated at one or more locations.

Monocyclic heteroaryl groups can be, for example, pyridine, pyrazine, pyrimidine, pyridazine, triazine, azaindolizine, 2H- and 4H-pyran, 2H- and 4H-thiopyran, furan, thiophene, 1H- and 4H-pyrazole, 1H- and 2H-pyrrole, oxazole, thiazole, furazan, 1H- and 4H-imidazole, isoxazole, isothiazole, oxadiazole, triazole, tetrazole, or thiadiazole.

Bicyclic heteroaryl groups can be, for example, a phthalidyl, thiophthalidyl, indolyl, isoindolyl, dihydroindolyl, dihydroisoindolyl, indazolyl, benzothiazolyl, indolonyl, dihydroindolonyl, isoindolonyl, dihydroisoindolonyl, benzofuranyl, benzimidazolyl, dihydroisoquinolinyl, dihydroquinolinyl, benzoxazinonyl, phthalazinonyl, quinolinyl, isoquinolinyl, quinolonyl, isoquinolonyl, quinazolinyl, quinoxalinyl, cinnolinyl, phthalazinyl, 1,7- or 1,8-naphthyridinyl, cumarinyl, isocumarinyl, indolizinyl, isobenzofuranyl, azaindolyl, azaisoindolyl, furanopyridyl, furanopyrimidinyl, furanopyrazinyl, furanopyridazinyl, dihydrobenzofuranyl, dihydrofuranopyridyl, dihydrofuranopyrimidinyl, dihydrofuranopyrazinyl, dihydrofuranopyridazinyl, or dihydrobenzofuranyl group.

If the heteroaryl groups are partially or completely hydrogenated, stereoisomers of formula I or II, in which $R^3$ means tetrahydropyranyl, 2H-pyranyl, 4H-pyranyl, piperidyl, tetrahydropyridyl, dihydropyridyl, 1H-pyridin-2-onyl, 1H-pyridin-4-onyl, 4-aminopyridyl, 1H-pyridin-4-ylidenaminyl, chromanyl, isochromanyl, thiochromanyl, decahydroquinolinyl, tetrahydroquinolinyl, dihydroquinolinyl, 5,6,7,8-tetrahydro-1H-quinolin-4-onyl, decahydroisoquinolinyl, tetrahydroisoquinolinyl, dihydroisoquinolinyl, 3,4-dihydro-2H-benz[1,4]oxazinyl, 1,2-dihydro[1,3]benzoxazin-4-onyl, 3,4-dihydrobenz[1,4]oxazin-4-onyl, 3,4-dihydro-2H-benzo[1,4]thiazinyl, 4H-benzo[1,4]thiazinyl, 1,2,3,4-tetrahydroquinoxalinyl, 1H-cinnolin-4-onyl, 3H-quinazolin-4-onyl, 1H-quinazolin-4-onyl, 3,4-dihydro-1H-quinoxalin-2-onyl, 2,3-1,2,3,4-tetrahydro[1,5]naphthyridinyl, dihydro-1H-[1,5]naphthyridyl, 1H-[1,5]naphthyrid-4-onyl, 5,6,7,8-tetrahydro-1H-naphthyridin-4-onyl, 1,2-dihydropyrido[3,2-d][1,3]oxazin-4-onyl, octahydro-1H-indolyl, 2,3-dihydro-1H-indolyl, octahydro-2H-isoindolyl, 1,3-dihydro-2H-isoindolyl, 1,2-dihydroindazolyl, 1H-pyrrolo[2,3-b]pyridyl, 2,3-dihydro-1H-pyrrolo[2,3-b]pyridyl, or 2,2-dihydro-1H-pyrrolo[2,3-b]pyridin-3-onyl, are part of this invention.

The compounds of general formula I according to the invention can be present as stereoisomers because of the presence of asymmetry centers. All possible diastereomers (e.g.: RR, RS, SR, SS) both as racemates and in enantiomer-pure form are subjects of this invention. The term stereoisomers also comprises all possible diastereomers and regioisomers and tautomers (e.g., keto-enol tautomers), in which the stereoisomers according to the invention can be present, which thus are also a subject of the invention.

The compounds according to the invention can also be present in the form of salts with physiologically compatible anions, for example in the form of hydrochloride, sulfate, nitrate, phosphate, pivalate, maleate, fumarate, tartrate, benzoate, mesylate, citrate or succinate.

The compounds according to the invention are produced by the open-chain precursors of general formula II being generated according to methods that are known in the prior art

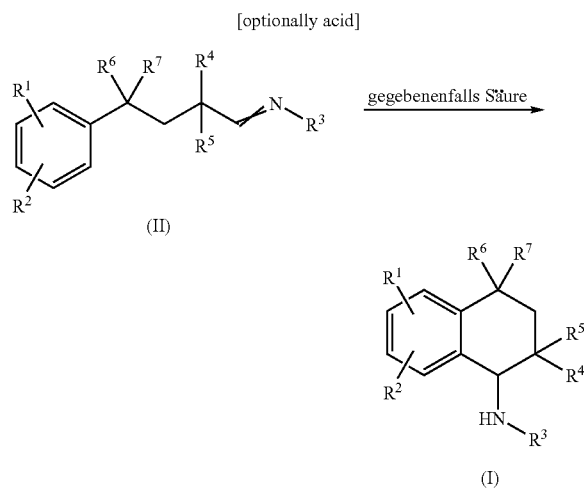

and then being cyclized to the compounds of general formula I either without additional reagent in a solvent, preferably chlorinated hydrocarbons, such as, e.g., methylene chloride or dichloroethane or concentrated organic acids, preferably glacial acetic acid, or by adding inorganic or organic acids or Lewis acids under temperatures in the range of −70° C. to +80° C. (preferably in the range of −30° C. to +80° C.).

A method for the production of stereoisomers of general formula I, which is characterized in that imines of general formula II are cyclized to the stereoisomers of general formula I either without additional reagent in a solvent or concentrated organic acids, or by adding inorganic or organic acids or Lewis acids under temperatures in the range of −70° C. to +80° C. (preferably in the range of −30° C. to +80° C.), as well as their direct precursors of formula II, is thus also a subject of this invention.

The new imines for the cyclization are also subjects of this invention, in particular those that were disclosed by the examples.

The binding of the substances to the glucocorticoid receptor (GR) and other steroid-hormone receptors (mineral corticoid receptor (MR), progesterone receptor (PR) and androgen receptor (AR)) is examined with the aid of recombinantly produced receptors. Cytosol preparations of Sf9 cells, which had been infected with recombinant baculoviruses that code for the GR, are used for the binding studies. In comparison to the reference substance [$^3$H]-dexamethasone, the substances show a high affinity to the GR. $IC_{50}$(GR)=95 nM and $IC_{50}$(PR)=460 were measured for the compound from Example 49.

The GR-mediated inhibition of the transcription of cytokines, adhesion molecules, enzymes and other pro-inflammatory factors is considered to be an essential, molecular mechanism for the anti-inflammatory action of glucocorticoids. This inhibition is produced by an interaction of the GR with other transcription factors, e.g., AP-1 and NF-kappa-B (for a survey, see Cato, A. C. B. and Wade, E., BioEssays 18, 371-378, 1996).

The compounds of general formula I according to the invention inhibit the secretion of cytokine IL-8 into the human monocyte cell line THP-1 that is triggered by lipopolysaccharide (LPS). The concentration of the cytokines was determined in the supernatant by means of commercially available ELISA kits. The compound of Example 49 showed an inhibition $IC_{50}$(IL8)=19 nM.

The anti-inflammatory action of the compounds of general formula I was tested in the animal experiment by tests in the croton oil-induced inflammation in rats and mice (J. Exp. Med. (1995), 182, 99-108). To this end, croton oil in ethanolic solution was applied topically to the animals' ears. The test substances were also administered topically or systemically at the same time or two hours before the croton oil. After 16-24 hours, the ear weight was measured as a yardstick for inflammatory edema, the peroxidase activity as a yardstick for the invasions of granulocytes, and the elastase activity as a yardstick for the invasion of neutrophilic granulocytes. In this test, the compounds of general formula I inhibit the three above-mentioned inflammation parameters both after topical administration and after systemic administration.

One of the most frequent undesirable actions of a glucocorticoid therapy is the so-called "steroid diabetes" [cf., Hatz, H. J., Glucocorticoide: Immunologische Grundlagen, Pharmakologie und Therapierichtlinien, [Glucocorticoids: Immunological Bases, Pharmacology and Therapy Guidelines], Wissenschaftliche Verlagsgesellschaft mbH, Stuttgart, 1998]. The reason for this is the stimulation of gluconeogenesis in the liver by induction of the enzymes responsible in this respect and by free amino acids, which are produced from the degradation of proteins (catabolic action of glucocorticoids). A key enzyme of the catabolic metabolism in the liver is tyrosinamino transferase (TAT). The activity of this enzyme can be determined from liver homogenates by photometry and represents a good measurement of the undesirable metabolic actions of glucocorticoids. To measure the TAT induction, the animals are sacrificed 8 hours after the test substances are administered, the livers are removed, and the TAT activity is measured in the homogenate. In this test, at doses in which they have an anti-inflammatory action, the compounds of general formula I induce little or no tyrosinamino transferase.

Because of their anti-inflammatory action, and, in addition, anti-allergic, immunosuppressive and antiproliferative action, the compounds of general formula I according to the invention can be used as medications for treatment or prophylaxis of the following pathologic conditions in mammals and humans: In this case, the term "DISEASE" stands for the following indications:

(i) Lung diseases that are accompanied by inflammatory, allergic and/or proliferative processes:
  Chronic, obstructive lung diseases of any origin, primarily bronchial asthma
  Bronchitis of different origins
  All forms of restrictive lung diseases, primarily allergic alveolitis,
  All forms of pulmonary edema, primarily toxic pulmonary edema
  Sarcoidoses and granulomatoses, especially Boeck's disease (ii) Rheumatic diseases/autoimmune diseases/joint diseases that are accompanied by inflammatory, allergic and/or proliferative processes:
  All forms of rheumatic diseases, especially rheumatoid arthritis, acute rheumatic fever, polymyalgia rheumatica
  Reactive arthritis
  Inflammatory soft-tissue diseases of other origins
  Arthritic symptoms in the case of degenerative joint diseases (arthroses)
  Traumatic arthritides
  Collagenoses of any origin, e.g., systemic lupus erythematodes, sclerodermia, polymyositis, dermatomyositis, Sjögren's syndrome, Still's syndrome, Felty's syndrome (iii) Allergies that are accompanied by inflammatory and/or proliferative processes:
  All forms of allergic reactions, e.g., Quincke's edema, hay fever, insect bites, allergic reactions to pharmaceutical agents, blood derivatives, contrast media, etc., anaphylactic shock, urticaria, contact dermatitis (iv) Vascular inflammations (vasculitides)
  Panarteritis nodosa, temporal arteritis, erythema nodosum (v) Dermatological diseases that are accompanied by inflammatory, allergic and/or proliferative processes:
  Atopic dermatitis (primarily in children)
  Psoriasis
  Pityriasis rubra pilaris
  Erythematous diseases, triggered by different noxae, e.g., radiation, chemicals, burns, etc.
  Bullous dermatoses
  Diseases of the lichenoid group,
  Pruritis (e.g., of allergic origin)
  Seborrheal eczema
  Rosacea
  Pemphigus vulgaris
  Erythema exudativum multiforme
  Balanitis
  Vulvitis
  Hair loss such as alopecia areata
  Cutaneous T-cell lymphoma (vi) Kidney diseases that are accompanied by inflammatory, allergic and/or proliferative processes:
  Nephrotic syndrome
  All nephritides (vii) Liver diseases that are accompanied by inflammatory, allergic and/or proliferative processes:
  Acute liver cell decomposition
  Acute hepatitis of different origins, e.g., viral, toxic, pharmaceutical agent-induced
  Chronic aggressive hepatitis and/or chronic intermittent hepatitis (viii) Gastrointestinal diseases that are accompanied by inflammatory, allergic and/or proliferative processes:
  Regional enteritis (Crohn's disease)
  Colitis ulcerosa
  Gastritis
  Reflux esophagitis
  Ulcerative colitis of other origins, e.g., native sprue (ix) Proctologic diseases that are accompanied by inflammatory, allergic and/or proliferative processes:
  Anal eczema
  Fissures
  Hemorrhoids
  Idiopathic proctitis (x) Eye diseases that are accompanied by inflammatory, allergic and/or proliferative processes:
  Allergic keratitis, uveitis, iritis
  Conjunctivitis
  Blepharitis
  Optic neuritis
  Chorioiditis
  Sympathetic ophthalmia (xi) Diseases of the ear-nose-throat area that are accompanied by inflammatory, allergic and/or proliferative processes:
  Allergic rhinitis, hay fever
  Otitis externa, e.g., caused by contact dermatitis, infection, etc.
  Otitis media (xii) Neurological diseases that are accompanied by inflammatory, allergic and/or proliferative processes:
  Cerebral edema, primarily tumor-induced cerebral edema
  Multiple sclerosis
  Acute encephalomyelitis
  Meningitis
  Various forms of convulsions, e.g., infantile nodding spasms (xiii) Blood diseases that are accompanied by inflammatory, allergic and/or proliferative processes:
  Acquired hemolytic anemia
  Idiopathic thrombocytopenia (xiv) Tumor diseases that are accompanied by inflammatory, allergic and/or proliferative processes:
  Acute lymphatic leukemia
  Malignant lymphoma
  Lymphogranulomatoses
  Lymphosarcoma
  Extensive metastases, mainly in breast, bronchial and prostate cancers (xv) Endocrine diseases that are accompanied by inflammatory, allergic and/or proliferative processes:
  Endocrine orbitopathy
  Thyreotoxic crisis
  De Quervain's thyroiditis
  Hashimoto's thyroiditis
  Basedow's disease (xvi) Organ and tissue transplants, graft-versus-host disease (xvii) Severe shock conditions, e.g., anaphylactic shock, systemic inflammatory response syndrome (SIRS)

(xviii) Substitution therapy in:
  Innate primary suprarenal insufficiency, e.g., congenital adrenogenital syndrome Acquired primary suprarenal insufficiency, e.g., Addison's disease, autoimmune adrenalitis, meta-infective tumors, metastases, etc.

Innate secondary suprarenal insufficiency, e.g., congenital hypopituitarism

Acquired secondary suprarenal insufficiency, e.g., meta-infective tumors, etc.

(xix) Vomiting that is accompanied by inflammatory, allergic and/or proliferative processes:
e.g., in combination with a 5-HT3 antagonist in cytostatic-agent-induced vomiting (xx) Pains of inflammatory origins, e.g., lumbago.

Moreover, the compounds of general formula I according to the invention can be used for treatment and prophylaxis of additional pathologic conditions that are not mentioned above, for which synthetic glucocorticoids are now used (see in this respect Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xx) are described in more detail in Hatz, H. J., Glucocorticoide: Immunologische Grundlagen, Pharmakologie und Therapierichtlinien, Wissenschaftliche Verlagsgesellschaft mbH, Stuttgart, 1998.

For the therapeutic actions in the above-mentioned pathologic conditions, the suitable dose varies and depends on, for example, the active strength of the compound of general formula I, the host, the type of administration, and the type and severity of the conditions that are to be treated, as well as the use as a prophylactic agent or therapeutic agent.

In addition, the invention provides:
(i) The use of one of the compounds of formula I according to the invention or mixture thereof for the production of a medication for treating a DISEASE;
(ii) A process for treating a DISEASE, said process comprises an administration of an amount of the compound according to the invention, whereby the amount suppresses the disease and whereby the amount of compound is given to a patient who requires such a medication;
(iii) A pharmaceutical composition for treating a DISEASE, said treatment comprises one of the compounds according to the invention or mixture thereof and at least one pharmaceutical adjuvant and/or vehicle.

In general, satisfactory results can be expected in animals when the daily doses comprise a range of 1 μg to 100,000 μg of the compound according to the invention per kg of body weight. In the case of larger mammals, for example the human, a recommended daily dose lies in the range of 1 μg to 100,000 μg per kg of body weight. Preferred is a dose of 10 to 30,000 μg per kg of body weight, and more preferred is a dose of 10 to 10,000 μg per kg of body weight. For example, this dose is suitably administered several times daily. For treating acute shock (e.g., anaphylactic shock), individual doses can be given that are significantly above the above-mentioned doses.

The formulation of the pharmaceutical preparations based on the new compounds is carried out in a way that is known in the art by the active ingredient being processed with the vehicles, fillers, substances that influence decomposition, binding agents, moisturizers, lubricants, absorbents, diluents, flavoring correctives, coloring agents, etc., that are commonly used in galenicals and converted into the desired form of administration. In this case, reference is made to Remington's Pharmaceutical Science, 15$^{th}$ Edition, Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local treatment.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%-20% in these preparations to achieve a sufficient pharmacological action.

The invention also comprises the compounds of general formula I according to the invention as therapeutic active ingredients. In addition, the compounds of general formula I according to the invention are part of the invention as therapeutic active ingredients together with pharmaceutically compatible and acceptable adjuvants and vehicles.

The invention also comprises a pharmaceutical composition that contains one of the pharmaceutically active compounds according to the invention or mixtures thereof or a pharmaceutically compatible salt thereof and a pharmaceutically compatible salt or pharmaceutically compatible adjuvants and vehicles.

EXPERIMENTS

Example 1

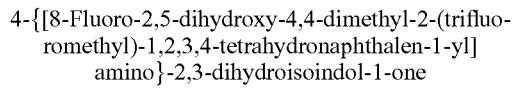

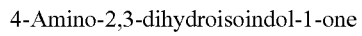

30 g (165.6 mmol) of 2-methyl-3-nitrobenzoic acid is added to 150 ml of methanol, and it is refluxed for two days after 2.9 ml of concentrated sulfuric acid is added. After cooling, the crystallizate (25.55 g=79%) is suctioned off and thus incorporated into the next stage.

$^1$H-NMR (300 MHz, DMSO-d$_6$): δ=2.50 (3H), 3.85 (3H), 7.56 (1H), 8.00 (1H), 8.05 (1H).

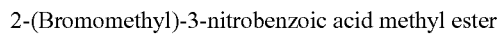

25.55 g (130.9 mmol) of 2-methyl-3-nitrobenzoic acid methyl ester is added to 300 ml of carbon tetrachloride, and mixed with 25.6 g (141.7 mmol) of N-bromosuccinimide and 62.8 mg of benzoyl peroxide. After seven days of refluxing, the succinimide is suctioned off after cooling, and then the filtrate is spun in until a dry state is reached. The desired compound that is incorporated in crude form into the next stage remains.

¹H-NMR (300 MHz, CDCl₃): δ=4.00 (3H), 5.66 (2H), 7.55 (1H), 7.95 (1H), 8.10 (1H).

2-(Azidomethyl)-3-nitrobenzoic acid methyl ester 10 g (36.5 mmol) of 2-(bromomethyl)-3-nitrobenzoic acid methyl ester is mixed with 36 ml of N,N-dimethylformamide and 24 ml of water. After 3.54 g of sodium azide is added, the batch is stirred overnight. The reaction mixture is diluted with methyl-tert butyl ether, and washed twice with water and once with brine. After drying on sodium sulfate, it is filtered, and the solvent is spun off. The desired azide is obtained in a yield of 89.6% (7.72 g) and further incorporated in crude form.

¹H-NMR (300 MHz, CDCl₃): δ=4.00 (3H), 4.93 (2H), 7.58 (1H), 7.96 (1H), 8.12 (1H).

4-Amino-2,3-dihydroisoindol-1-one 1 g (4.2 mmol) of 2-(azidomethyl)-3-nitrobenzoic acid methyl ester is added to 10 ml of ethanol and 2 ml of glacial acetic acid and mixed with 148.5 mg of Pd/C. After stirring overnight at room temperature under hydrogen atmosphere, the catalyst is suctioned off via a glass-fiber filter, and the filtrate is evaporated to the dry state. The residue is chromatographed on a Flashmaster (mobile solvent). 391.5 mg (62.4%) of the desired compound is isolated.

¹H-NMR (300 MHz, DMSO-d₆): δ=4.10 (2H), 5.36 (2H), 6.75 (1H), 6.85 (1H), 7.15 (1H), 8.35 (1H).

4-(5-Fluoro-2-methoxyphenyl)-2-hydroxy-4-methyl-2-trifluoromethyl)-pentanal 6.55 g (21.11 mmol) of rac-4-(5-fluoro-2-methoxyphenyl)-4-methyl-2-trifluoromethyl)-pentane-1,2-diol (WO 00/32584) is dissolved in 224 ml of dichloromethane and mixed at room temperature with 74 ml of dry dimethyl sulfoxide and 10.68 g (105.55 mmol) of triethylamine. At 15 to 18° C., 10.08 g (63.33 mmol) of the SO₃/pyridine complex is added in portions within 40 minutes. After being stirred overnight at room temperature, 84 ml of saturated ammonium chloride solution is added. A slight heating occurs. After 15 minutes of stirring at room temperature, it is extracted twice with 300 ml each of diethyl ether. The organic phases are washed with water and brine and dried (sodium sulfate). After the solvent is filtered off and after the solvent is spun off, the remaining residue is chromatographed on silica gel (mobile solvent ethyl acetate/hexane). 5.85 g (90%) of the desired compound is isolated.

¹H-NMR (300 MHz, CDCl₃): δ=1.40 (3H), 1.46 (3H), 2.22 (1H), 3.38 (1H), 3.59 (1H), 3.86 (1H), 6.70-6.80 (1H), 6.82-6.97 (2H), 9.05 (1H).

4-{[(4-(5-Fluoro-2-methoxyphenyl)-2-hydroxy-4-methyl-2-(trifluoromethyl)-pentylidene]amino}2,3-dihydroisoindol-1-one 400 mg (1.297 mmol) of rac-4-(5-fluoro-2-methoxyphenyl)-2-hydroxy-4-methyl-2-trifluoromethyl)-pentanal is stirred with 192.1 mg (1.297 mmol) of 4-amino-2,3-dihydroisoindol-1-one in 1.89 ml of glacial acetic acid for four days at room temperature. The mixture is mixed three times with toluene and evaporated to the dry state in a rotary evaporator. The residue is chromatographed on silica gel (mobile solvent ethyl acetate/hexane). 429.7 mg (75.5%) of the desired compound is isolated.

¹H-NMR (300 MHz, CDCl₃): δ=1.37 (3H), 1.52 (3H), 2.22 (1H), 3.42 (1H), 3.84 (3H), 4.37 (2H), 4.68 (1H), 6.53-6.68 (3H), 6.72-6.95 (2H), 7.37 (1H), 7.49 (1H), 7.75 (1H).

4-{[8-Fluoro-2-hydroxy-5-methoxy-4,4-dimethyl-2-(trifluoromethyl)-1,2,3,4-tetrahydronaphthalen-1-yl]amino}-2,3-dihydroisoindol-1-one (Diastereomer A);

4-{[8-Fluoro-2,5 dihydroxy-4,4-dimethyl-2-(trifluoromethyl)-1,2,3,4-tetrahydronaphthalen-1-yl]amino}-2,3-dihydroisoindol-1-one (Diastereomer A);

4-{[8-Fluoro-2,5-dihydroxy-4,4-dimethyl-2-(trifluoromethyl)-1,2,3,4-tetrahydronaphthalen-1-yl]amino}-2,3-dihydroisoindol-1-one (Diastereomer B)

420 mg (0.958 mmol) of the compound 4-{[4-(5-fluoro-2-methoxyphenyl)-2-hydroxy-4-methyl-2-(trifluoromethyl) pentylidene]amino}-2,3-dihydroisoindol-1-one that is described in the paragraph above is mixed with 9.6 ml of a 1 M solution of boron tribromide in dichloromethane, and it is stirred for 1¾ hours at room temperature. The reaction mixture is mixed drop by drop with saturated sodium bicarbonate at −30° C., specifically up to pH 8. After dilution with ethyl acetate, the cold bath is removed and stirred vigorously for 15 minutes. After 2× extraction with ethyl acetate, the organic phases are washed with water and saturated sodium chloride solution. After the solvent is dried (sodium sulfate) and spun off, the residue is chromatographed on a Flashmaster (silica gel, NH₂ phase) (mobile solvent dichloromethane/methanol). 67.7 mg (16.6%) of 4-{[8-fluoro-2-hydroxy-5-methoxy-4,4-dimethyl-2-(trifluoromethyl)-1,2,3,4-tetrahydronaphthalen-1-yl]amino}-2,3-dihydroisoindol-1-one (diastereomer A, F1); 12.9 mg (3.2%) of 4-{[8-fluoro-2,5 dihydroxy-4,4-dimethyl-2-(trifluoromethyl)-1,2,3,4-tetrahydronaphthalen-1-yl]amino}-2,3-dihydroisoindol-1-one (diastereomer A, F2), and 32.2 mg (7.9%) of 4-{[8-fluoro-2,5-dihydroxy-4,4-dimethyl-2-(trifluoromethyl)-1,2,3,4-tetrahydronaphthalen-1-yl]amino}-2,3-dihydroisoindol-1-one (diastereomer B, F3) are isolated.

F1: ¹H-NMR (300 MHz, MeOD): δ=1.47 (3H), 1.60 (3H), 2.07 (1H), 2.25 (1H), 3.49 (3H), 4.19-4.40 (2H), 5.20 (1H), 6.31 (1H), 7.00 (1H), 7.15-7.30 (2H), 7.38 (1H).

F2: ¹H-NMR (300 MHz, MeOD): δ=1.50 (3H), 1.59 (3H), 2.05 (1H), 2.28 (1H), 4.20-4.42 (2H), 5.18 (1H), 6.61 (1H), 6.80-6.90 (1H), 7.15 (1H), 7.20-7.40 (2H).

F3: ¹H-NMR (300 MHz, MeOD): δ=1.52 (3H), 1.69 (3H), 2.03 (1H), 2.23 (1H), 4.20-4.39 (2H), 5.18 (1H), 6.65-6.80 (2H), 7.10-7.23 (2H), 7.35 (1H).

Example 2

5-{[7-Chloro-2,5-dihydroxy-4,4-dimethyl-2-(trifluoromethyl)-1,2,3,4-tetrahydronaphthalen-1-yl]amino}-isoquinolin-1(2H)-one 5-Amino-isoquinolin-1(2H)-one 5-Nitroisocoumarin 16.4 g (84.03 mmol) of the 2-methyl-3-nitrobenzoic acid methyl ester that is described under Example 1 is stirred with 26.8 g (225.1 mmol) of N,N-dimethylformamide dimethyl acetal in 85 ml of dimethylformamide for 12 hours at 130° C.

The solvent is drawn off in a rotary evaporator, the residue is taken up in methyl tert-butyl ether and washed three times with water. After washing with saturated NaCl solution, the organic phase is dried. After the desiccant is filtered off and the solvent is spun off, the remaining residue is chromatographed on silica gel (mobile solvent ethyl acetate/hexane). 8.73 g (54.4%) of the desired compound is isolated.

$^1$H-NMR (300 MHz, CDCl$_3$): δ=7.39 (1H), 7.45 (1H), 7.68 (1H), 8.49 (1H), 8.65 (1H).

5-Nitroisoquinolin-1(2H)-one 2.51 g (13.13 mmol) of 5-nitroisocoumarin is added in 100 ml of ethanol. Ammonia is pressure-forced in an autoclave. The product precipitates and is suctioned off. 1.98 g (79.7%) of the desired compound is isolated.

$^1$H-NMR (300 MHz, DMSO-d$_6$): δ=6.97 (1H), 7.45 (1H), 7.65 (1H), 8.43 (1H), 8.57 (1H), 11.5 (1H).

5-Aminoisoquinolin-1(2H)-one 268.3 mg (1.51 mmol) of 5-nitroisoquinolin-1(2H)-one is added with 376.5 mg of ammonium chloride and 2.6 ml of water in 14 ml of ethanol and 5.4 ml of tetrahydrofuran. After addition in portions of 1.23 g of zinc powder (heating to 30 to 35° C.), it is stirred for two hours. The reaction mixture is suctioned off through a glass-fiber filter and rewashed with ethyl acetate. After the filtrate is washed with water and saturated sodium chloride solution, the organic phase is dried as usual. Filtering off the desiccant and spinning off the solvent produce 196.5 mg (88.1%) of the desired amine.

$^1$H-NMR (300 MHz, DMSO-d$_6$): δ=5.6 (2H), 6.68 (1H), 6.87.45 (1H), 7.00 (1H), 7.17 (1H), 7.39 (1H), 11.7 (1H).

4-(4-Chloro-2-methoxyphenyl)-2-hydroxy-4-methyl-2-(trifluoromethyl)pentan-1-ol

A solution of 3 g of 2-hydroxy-4-methylene-2-(trifluoromethyl)valeric acid ethyl ester in 22 ml of 3-chloroanisole is mixed at room temperature in portions with aluminum trichloride. After 48 hours of stirring at room temperature, the batch is mixed with 2N hydrochloric acid and hexane, and it is stirred for another hour. After washing with 2N hydrochloric acid and water, excess 3-chloroanisole is distilled off in a vacuum. The remaining residue is purified by chromatography on silica gel (mobile solvent hexane/ethyl acetate). 2.85 g of a mixture of 4-(4-chloro-2-methoxyphenyl)-2-hydroxy-4-methyl-2-(trifluoromethyl)valeric acid ethyl ester and the regioisomeric compound 4-(2-chloro-4-methoxyphenyl)-2-hydroxy-4-methyl-2-(trifluoromethyl)valeric acid ethyl ester is obtained as a yellow oil. This substance mixture is mixed in 90 ml of ether at 0° C. with 445 mg of lithium aluminum hydride and stirred for 12 hours. The batch is added to saturated sodium bicarbonate solution and filtered through diatomaceous earth. The phases are separated, and the aqueous phase is extracted with ethyl acetate. It is washed with water and brine, dried with sodium sulfate and concentrated by evaporation in a vacuum. After chromatography on silica gel (mobile solvent hexane/ethyl acetate), 1.87 g of the desired compound 4-(4-chloro-2-methoxyphenyl)-2-hydroxy-4-methyl-2-(trifluoromethyl)pentan-1-ol as a first fraction and 160 mg of the regioisomeric compound 4-(2-chloro-4-methoxyphenyl)-2-hydroxy-4-methyl-2-(trifluoromethyl)pentan-1-ol as a second fraction are obtained as colorless oils.

1st Fraction: $^1$H-NMR (CDCl$_3$), δ=1.41 (3H), 1.51 (3H), 2.24 (1H), 2.51 (1H), 2.84 (1H), 3.36 (1H), 3.48 (1H), 3.85 (3H), 6.88 (1H), 6.92 (1H), 7.24 (1H).

2nd Fraction: $^1$H-NMR (CDCl$_3$), δ=1.52 (3H), 1.62 (3H), 2.18 (1H), 2.76 (1H), 2.93 (1H), 3.33 (1H), 3.55 (1H), 3.80 (3H), 6.78 (1H), 6.90 (1H), 7.38 (1H).

4-(4-Chloro-2-methoxyphenyl)-2-hydroxy-4-methyl-2-(trifluoromethyl)pentanal 854.6 mg (6.733 mmol) of oxalyl chloride in 14.5 ml of dichloromethane is introduced into a heated flask. At −70° C., 1.05 ml of DMSO, dissolved in 3 ml of dichloromethane, is added in drops, and the batch is stirred for five more minutes. Then, 2 g (6.12 mmol) of 4-(4-chloro-2-methoxyphenyl)-2-hydroxy-4-methyl-2-trifluoromethyl-pentan-1-ol, dissolved in six milliliters of dichloromethane, is added in drops. After 20 minutes of stirring, the batch is carefully mixed with 4.24 ml (30.61 mmol) of triethylamine, specifically in a temperature range of between −70 and −60° C. After five minutes of stirring at −70° C., the reaction mixture is allowed to slowly come to room temperature. 25 ml of water is added, and the batch is stirred for another hour at room temperature. After phase separation, the aqueous phase is shaken once with 100 ml of dichloromethane. The combined organic extracts are washed with 1% sulfuric acid, 5% sodium bicarbonate solution and brine. According to the conventional procedure, 1.92 g (96.9%) of the desired aldehyde is obtained, which is incorporated in crude form into the next stage.

$^1$H-NMR (300 MHz, CDCl$_3$): δ=1.37 (3H), 1.45 (3H), 2.22 (1H), 3.35 (1H), 3.59 (1H), 3.90 (3H), 6.80-6.92 (2H), 7.04 (1H), 9.02 (1H).

5-{[4-(4-Chloro-2-methoxyphenyl)-2-hydroxy-4-methyl-2-trifluoromethyl)-pentylidene]amino}isoquinolin-1(2H)-one 300 mg (0.924 mmol) of 4-(4-chloro-2-methoxyphenyl)-2-hydroxy-4-methyl-2-(trifluoromethyl)-pentanal is stirred with 148 mg (0.924 mmol) of 5-amino-isoquinolin-1-one in 1.33 ml of glacial acetic acid for four days at room temperature. The mixture is mixed three times with toluene and evaporated to the dry state in a rotary evaporator. The residue is chromatographed on silica gel (mobile solvent ethyl acetate/hexane). 382.4 mg (88.6%) of the desired compound is isolated.

$^1$H-NMR (300 MHz, CDCl$_3$): δ=1.37 (3H), 1.58 (3H), 2.26 (1H), 3.43 (1H), 3.85 (3H), 4.80 (1H), 6.43 (1H), 6.59 (1H), 6.70-6.77 (2H), 7.00 (1H), 7.15-7.25 (1H), 7.30-7.45 (2H), 8.32 (1H), 11.00 (1H).

5-{[7-Chloro-2,5-dihydroxy-4,4-dimethyl-2-(trifluoromethyl)-1,2,3,4-tetrahydronaphthalen-1-yl]amino}-isoquinolin-1(2H)-one 50 mg (0.107 mmol) of the compound 5-{[4-(4-chloro-2-methoxyphenyl)-2-hydroxy-4-methyl-2-(trifluoromethyl)pentylidene]amino}-2,3-isoquinolin-1-one that is described in the paragraph above is mixed at −20° C. with 2.1 ml of a 1 M solution of boron tribromide in dichloromethane, and it is stirred for two and one-half hours in a temperature range of between −20° C. and 0° C. The reaction mixture is mixed drop by drop at −20° C. with saturated sodium bicarbonate solution. After dilution with ethyl acetate, the batch is allowed to come to room temperature, stirred for 15 minutes and extracted twice with ethyl acetate. The combined organic extracts are washed with water and saturated NaCl solution. After drying on sodium sulfate, the solvent is spun off, and the remaining residue is chromatographed on silica gel (mobile solvent ethyl acetate/hexane). 12.5 mg (25%) of the desired compound is isolated.

$^1$H-NMR (300 MHz, MeOD): δ=1.55 (3H), 1.65 (3H), 2.03-2.20 (2H), 5.13 (1H), 6.73 (1H), 6.80 (1H), 6.87 (1H), 7.09 (1H), 7.19 (1H), 7.40 (1H), 7.70 (1H).

Example 3

(+)-6-Fluoro-1-[(1H-indazol-4-yl)amino]-4,4-dimethyl-2-(trifluoromethyl)-1,2,3,4-tetrahydronaphthalene-2,5-diol and (−)-6-Fluoro-1-[(1H-indazol-4-yl)amino]-4,4-dimethyl-2-(trifluoromethyl)-1,2,3,4-tetrahydronaphthalene-2,5-diol 2,6-Difluoroanisole 20 g (153.74 mmol) of 2,6-difluorophenol is dissolved in 200 ml of acetone and mixed under nitrogen with 42.5 g (307.48 mmol) of potassium carbonate. After 19.1 ml of methyl iodide (2 equivalents) is added, it is refluxed for three and one-half hours. After cooling, the reaction mixture is filtered, the filter residue is washed with acetone, and the filtrate is spun in until a dry state is reached. The residue is chromatographed on silica gel (mobile solvent ethyl acetate/hexane). 17.27 g (77.9%) of the desired product is obtained. It should be noted that the product is slightly volatile. The bath temperature should not exceed 30° C., and the vacuum of the rotary evaporator is to be adapted.

$^1$H-NMR (300 MHz, CDCl$_3$): δ=4.00 (3H), 6.80-7.00 (3H).

2-(3-Fluoro-2-methoxyphenyl)-2-methylpropanenitrile 10 g (69.39 mol) of 2,6-difluoroanisole is dissolved in 200 ml of toluene and mixed at room temperature with 5.75 g (83.27 mmol) of isobutyric acid nitrile. 166.5 ml of a 0.5 molar solution of potassium hexamethyldisilazide in toluene is added in drops within 35 minutes. In this case, a slight temperature rise to 27.5° C. takes place. After 16 hours of stirring at room temperature, the reaction mixture is mixed with 200 ml of water and 400 ml of ethyl acetate and acidified with 10% sulfuric acid to a pH of 4. The organic phase is separated, and the aqueous phase is shaken once with ethyl acetate (200 ml). The combined organic extracts are shaken with water and brine. After the solvent is dried, filtered and spun off, the residue is chromatographed on silica gel (mobile solvent ethyl acetate/hexane). 7.66 g (57.1%) of the desired compound is isolated.

$^1$H-NMR (300 MHz, CDCl$_3$): δ=1.76 (6H), 4.08 (3H), 6.95-7.13 (3H).

2-(3-Fluoro-2-methoxyphenyl)-2-methylpropanal 7.66 g (39.64 mmol) of the above-described nitrile is dissolved in 158 ml of toluene. At −65 to −60° C., 49.5 ml of a 1.2 molar solution of DIBAH in toluene is added in drops within 40 minutes. After one hour of stirring at this temperature, the dropwise addition of 493 ml of a 10% L-(+)-tartaric acid solution is begun. After 100 milliliters, the temperature is increased to −10° C. The remainder of the tartaric acid solution is quickly added, and the batch is stirred vigorously for two hours at room temperature. The reaction mixture is shaken twice with 400 ml each of diethyl ether. The combined organic extracts are shaken with water and brine, dried, and the solvent is spun off. The residue that is obtained (7.8 g=102%) is incorporated in crude form into the next stage.

$^1$H-NMR (300 MHz, CDCl$_3$): δ=1.40 (6H), 3.88 (3H), 6.95-7.10 (3H), 9.60 (1H).

(E/Z)-4-(3-Fluoro-2-methoxyphenyl)-4-methylpent-2-enoic acid ethyl ester 21.3 ml of a 2 molar LDA solution in THF is added in drops at 0° C. to a solution of 9.87 g (39.75 mmol) of 2-ethoxyphosphonoacetic acid triethyl ester in 40 ml of absolute THF. After 30 minutes of stirring at 0° C., 7.8 g (39.75 mmol) of 2-(3-fluoro-2-methoxyphenyl)-2-methylpropanal, dissolved in 26 ml of THF, is quickly added in drops at 0° C. The cold bath is removed, and the batch is stirred for 16 hours at room temperature. The reaction mixture is poured into water and extracted twice with ethyl acetate. The combined organic extracts are washed with water and brine, dried, and the solvent is spun off after the desiccant is filtered off. The residue is chromatographed on silica gel (mobile solvent ethyl acetate/hexane). 8.39 g (68.2%) of the desired compound is isolated.

MS (CI): 328 (29%), 265 (100%), 181 (56%), 167 (42%).

(E/Z)-4-(3-Fluoro-2-methoxyphenyl)-4-methylpent-2-enoic acid 8.39 g (27.03 mmol) of (E/Z)-4-(3-fluoro-2-methoxyphenyl)-4-methylpent-2-enoic acid ethyl ester is mixed with 270 ml of 1N NaOH in ethanol/water (2:1) and stirred for two days at room temperature. The ethanol is drawn off in a rotary evaporator, and the residue is extracted twice with 150 ml each of diethyl ether. The combined organic extracts are washed with water and discarded after TLC monitoring. The aqueous phases are acidified to a pH of 3 with concentrated hydrochloric acid and extracted twice with 300 ml each of diethyl ether. The ether extracts are washed with water and brine, dried, the solvent is spun off, and the residue (5.89 g=77.2%) is incorporated in crude form into the next stage.

MS (CI): 300 (100%), 282 (10%0, 237 (27%), 167 (26%).

4-(3-Fluoro-2-methoxyphenyl)-4-methyl-2-oxo-pentanoic acid 5.89 g (20.86 mmol) of (E/Z)-4-(3-fluoro-2-methoxyphenyl)-4-methylpent-2-enoic acid is mixed at room temperature with 126 ml of a 1 molar sulfuric acid, and after 21 ml of glacial acetic acid is added, it is stirred for 15 hours at a bath temperature of 90° C. While being cooled in an ice bath, the reaction mixture is carefully mixed (heavily foaming) with solid potassium carbonate until a pH of 9 is reached. It is extracted twice with diethyl ether. The combined organic extracts are washed with water and discarded after TLC. The combined aqueous phases are acidified with concentrated hydrochloric acid until a pH of 4 is reached, and extracted twice with 300 ml each of diethyl ether. The ether extracts are washed with water and brine, dried, and the solvent is spun off. Since the residue still contains acetic acid, it is spun off twice with 100 ml each of toluene. The remaining residue (4.14 g=78.1%) is incorporated in crude form into the next stage.

$^1$H-NMR (300 MHz, CDCl$_3$): δ=1.50 (6H), 3.53 (2H), 3.93 (3H), 6.90-7.10 (3H).

4-(3-Fluoro-2-methoxyphenyl)-4-methyl-2-oxo-pentanoic acid ethyl ester 4.14 g (16.28 mmol) of 4-(3-fluoro-2-methoxyphenyl)-4-methyl-2-oxo-pentanoic acid is dissolved in 97 ml of ethanol, mixed with 1.79 ml of sulfuric acid and refluxed for four hours. The ethanol is drawn off in a rotary evaporator, and the residue is carefully mixed with saturated sodium bicarbonate solution until a pH of 9 is reached. It is extracted twice with 100 ml each of ethyl acetate, and the combined organic extracts are washed with water and then with brine. After the desiccant is dried and filtered off, and after the solvent is spun in, the residue is chromatographed on silica gel (mobile solvent ethyl acetate/hexane). 4.16 g (90.6%) of the desired compound is isolated.

$^1$H-NMR (300 MHz, CDCl$_3$): δ=1.29 (3H), 1.48 (6H), 3.40 (2H), 3.98 (3H), 6.89-7.09 (3H).

4-(3-Fluoro-2-methoxyphenyl)-4-methyl-2-(trifluoromethyl)-2-trimethylsilyloxy-pentanoic acid ethyl ester 4.16 g (14.74 mmol) of 4-(3-fluoro-2-methoxyphenyl)-4-methyl-2-oxo-pentanoic acid ethyl ester is dissolved in 24 ml of THF and mixed at 0° C. with 2.51 g (17.68 mmol) of (trifluoromethyl)-trimethylsilane and 36.1 mg of tetrabutylammonium fluoride. After two and one-half hours of stirring between 0 and 5° C., the batch is poured into 50 ml of ice water. It is extracted twice with 150 ml each of diethyl ether, and the combined organic extracts are worked up as usual. After chromatography on silica gel (mobile solvent ethyl acetate/hexane), 5.24 g (83.8%) of the desired compound is obtained.

MS (CI): 442 (100%), 425 (41%).

4-(3-Fluoro-2-methoxyphenyl)-4-methyl-2-(trifluoromethyl)-2-trimethylsilyloxy-pentan-1-ol 5.24 g (12.34 mmol) of 4-(3-fluoro-2-methoxyphenyl)-4-methyl-2-trifluoromethyl-2-trimethylsilyloxy-pentanoic acid ethyl ester is dissolved in 45 ml of diethyl ether and mixed at 0 to 5° C. in portions with 936.9 mg (24.69 mmol) of LiAlH$_4$. After four and one-half hours of stirring at room temperature, the reaction mixture is carefully mixed with saturated NaHCO$_3$ while being stirred in an ice bath, stirred for one hour under cold conditions and overnight at room temperature. After the conventional working-up, 4.11 g (87.1%) of a mixture that consists of the desired compound and the compound is obtained, in which the silyl ether has migrated. The mixture is incorporated in crude form into the next stage.

4-(3-Fluoro-2-methoxyphenyl)-2-hydroxy-4-methyl-2-(trifluoromethyl)-pentan-1-ol 4.11 g (10.75 mmol) of 4-(3-fluoro-2-methoxyphenyl)-4-methyl-2-trifluoromethyl-2-trimethylsilyloxy-pentan-1-ol is dissolved in 61 ml of THF, mixed with 3.39 g (10.746 mmol) of Bu$_4$NF trihydrate, and stirred for one hour at room temperature. The reaction mixture is poured into water and extracted twice with diethyl ether. The organic phases are washed as usual with water and brine. After the desiccant is dried and filtered off, and after the solvent is spun in, the remaining residue is chromatographed on silica gel (mobile solvent ethyl acetate/hexane). 2.71 g (81.4%) of the desired compound is isolated.

$^1$H-NMR (300 MHz, CDCl$_3$): δ=1.45 (3H), 1.54 (3H), 2.20 (1H), 2.54 (1H), 2.90 (1H), 3.30-3.50 (2H), 3.98 (3H), 6.90-7.13 (3H).

4-(3-Fluoro-2-methoxyphenyl)-2-hydroxy-4-methyl-2-trifluoromethyl-pentanal 765 mg (6.03 mmol) of oxalyl chloride in 13 ml of dichloromethane is introduced into a heated flask. At −78° C., 0.855 ml of DMSO, dissolved in 2.5 ml of dichloromethane, is added in drops, and the batch is stirred for five more minutes. Then, 1.7 g (5.48 mmol) of 4-(3-fluoro-2-methoxyphenyl)-2-hydroxy-4-methyl-2-(trifluoromethyl)-pentanol, dissolved in five milliliters of dichloromethane, is added in drops. After 15 minutes of stirring, the batch is carefully mixed with 3.79 ml (27.40 mmol) of triethylamine, stirred for five minutes at −78° C. and then allowed to come slowly to room temperature. 20 ml of water is added, and the batch is stirred for another hour at room temperature. After phase separation, the aqueous phase is shaken once with 100 ml of dichloromethane. The combined organic extracts are washed with 1% sulfuric acid, 5% sodium bicarbonate solution and brine. After the conventional procedure, 1.617 g (96.2%) of aldehyde is obtained, which is incorporated in crude form into the next stage.

$^1$H-NMR (300 MHz, CDCl$_3$): δ=1.40 (3H), 1.49 (3H), 2.29 (1H), 3.29 (1H), 3.59 (1H), 4.00 (3H), 6.85-7.08 (3H), 9.13 (1H).

1,1,1-Trifluoro-4-(3-fluoro-2-methoxyphenyl)-2-[(1H-indazol-4-yl)iminomethyl]-4-methylpentan-2-ol 1.46 g (4.746 mmol) of 4-(3-fluoro-2-methoxyphenyl)-2-hydroxy-4-methyl-2-(trifluoromethyl)-pentanal is stirred with 632 mg (4.746 mmol) of 4-aminoindazole in 6.78 ml of glacial acetic acid for two days at room temperature. The reaction mixture is drawn off three times with toluene in a rotary evaporator, and the residue is chromatographed on silica gel (mobile solvent ethyl acetate/hexane). 1.47 g (73.5%) of the desired compound is isolated.

MS (ES+): 424 (100%).

(+)-6-Fluoro-5-methoxy-1-[(1H-indazol-4-yl)amino]-4,4-dimethyl-2-(trifluoromethyl)-1,2,3,4-tetrahydronaphthalen-2-ol and

(−)-6-Fluoro-5-methoxy-1-[(1H-indazol-4-yl)amino]-4,4-dimethyl-2-(trifluoromethyl)-1,2,3,4-tetrahydronaphthalen-2-ol 1.32 g (3.117 mmol) of the above-described imine, 1,1,1-trifluoro-4-(3-fluoro-2-methoxyphenyl)-2-[(1H-indazol-4-yl)iminomethyl]-4-methylpentan-2-ol, is dissolved in 22.8 ml of dichloromethane. 9.35 ml of a 1 M solution of TiCl$_4$ in dichloromethane (3 equivalents) is added to this solution at −30° C., specifically under nitrogen within 15 minutes. The reaction mixture is stirred for three and one-half hours at −30 to −15° C. The batch is mixed drop by drop with saturated sodium bicarbonate solution at −30° C. After dilution with ethyl acetate, it is stirred for 15 minutes at room temperature. After 2× extraction with 150 ml each of ethyl acetate, the organic phases are washed (water, brine), dried (Na$_2$SO$_4$), and the solvent is spun off. After chromatography on silica gel (mobile solvent dichloromethane/methanol), 1.07 g (81.1%) of the desired product is obtained as a racemate. The product is separated into its enantiomers (Chiralpak AD 5μ; mobile solvent hexane/ethanol). The (+)-enantiomer shows an angle of rotation of [α]$_D$=+1.6° (c=1, MeOH), and the (−)-enantiomer shows an angle of rotation of [α]$_D$=−1.3° (c=1, MeOH).

(+)-6-Fluoro-1-[(1H-indazol-4-yl)amino]-4,4-dimethyl-2-(trifluoromethyl)-1,2,3,4-tetrahydronaphthalene-2,5-diol 200 mg (0.472 mmol) of the above-described (+)-6-fluoro-5-methoxy-1-[(1H-indazol-4-yl)amino]-4,4-dimethyl-2-(trifluoromethyl)-1,2,3,4-tetrahydronaphthalen-2-ol is mixed at room temperature with 4.7 ml of a 1 M solution of $BBr_3$ in dichloromethane and stirred for three and one-half hours at room temperature. The reaction mixture is mixed drop by drop with saturated sodium bicarbonate solution at −30° C., specifically until a pH of 8 is reached. After dilution with ethyl acetate, the cold bath is removed, and the batch is stirred vigorously for 15 minutes. After 2× shaking with ethyl acetate, the combined organic extracts are washed with water and saturated brine. After drying on sodium sulfate, and after the solvent is filtered and spun off, the residue is chromatographed on silica gel (mobile solvent dichloromethane/methanol). 171.3 mg (88.6%) of the desired compound is obtained. The angle of rotation, measured at room temperature, is $[\alpha]_D=+7.3$ (c=1, MeOH).

(−)-6-Fluoro-1-[(1H-indazol-4-yl)amino]-4,4-dimethyl-2-(trifluoromethyl)-1,2,3,4-tetrahydronaphthalene-2,5-diol 200 mg (0.472 mmol) of the above-described (−)-6-fluoro-5-methoxy-1-[(1H-indazol-4-yl)amino]-4,4-dimethyl-2-(trifluoromethyl)-1,2,3,4-tetrahydronaphthalen-2-ol is mixed at room temperature with 4.7 ml of a 1 M solution of $BBr_3$ in dichloromethane and stirred for three and three-quarters hours at room temperature. The reaction mixture is mixed drop by drop at −30° C. with saturated sodium bicarbonate solution, specifically until a pH of 8 is reached. After dilution with ethyl acetate, the cold bath is removed, and the batch is stirred vigorously for 15 minutes. After 2× shaking with ethyl acetate, the combined organic extracts are washed with water and saturated brine. After drying on sodium sulfate, and after the solvent is filtered and spun off, the residue is chromatographed on silica gel (mobile solvent dichloromethane/methanol). 179.4 mg (92.8%) of the desired compound is obtained. The angle of rotation, measured at room temperature, is $[\alpha]_D=-7.8$ (c=1, MeOH).

Example 4

4-{[8-Fluoro-2,5-dihydroxy-4,4-dimethyl-2-(trifluoromethyl)-1,2,3,4-tetrahydronaphthalen-1-yl]amino}-6-fluoro-2,3-dihydroisoindol-1-one

4-Amino-6-fluoro-2,3-dihydroisoindol-1-one

2-Methyl-5-fluoro-3-nitrobenzoic acid 116 ml of sulfuric acid is introduced and mixed in portions at −15° C. with 14.70 g (95.37 mmol) of 5-fluoro-2-methylbenzoic acid. A mixture of nitrating acid (4.79 ml of fuming nitric acid and 21.8 ml of concentrated sulfuric acid) is added in drops to this mixture, specifically at −15 to −10° C. during a period of 90 minutes. After three more hours of stirring, the reaction mixture is poured into ice water and stirred vigorously for about one-half hour. The precipitated crystallizate is suctioned off, washed neutral with water and dried. The yield is 8.56 g (45.1%) of a mixture of various regioisomers and by-products. This mixture is incorporated into the next stage (esterification) and purified in this stage.

2-Methyl-5-fluoro-3-nitrobenzoic acid methyl ester 8.56 g (42.99 mmol) of 2-methyl-5-fluoro-3-nitrobenzoic acid is added in 76 ml of N,N-dimethylformamide and mixed with 9.15 g (64.48 mmol) of methyl iodide and 8.91 g (64.48 mmol) of potassium carbonate. After 65 hours of stirring at room temperature, the reaction mixture is added to ice water and extracted several times with ethyl acetate. The combined organic extracts are washed with water and brine. After drying (sodium sulfate), desiccant is suctioned out, and the solvent is spun off. Repeated chromatography on silica gel (mobile solvent ethyl acetate/hexane) yields the desired compound, specifically in a yield of 25.9% (2.37 g).

$^1$H-NMR (300 MHz, $CDCl_3$): δ=2.60 (3H), 3.96 (3H), 7.61 (1H), 7.77 (1H).

2-(Bromomethyl)-5-fluoro-3-nitrobenzoic acid methyl ester 2.37 g (11.12 mmol) of 5-fluoro-2-methyl-3-nitrobenzoic acid methyl ester is added in 35 ml of carbon tetrachloride and mixed with 2.24 g (12.24 mmol) of N-bromosuccinimide and 5.4 mg of benzoyl peroxide. After four days of refluxing, the succinimide is suctioned off (glass-fiber filter) after cooling, and then the filtrate is spun in until a dry state is reached. Chromatography on a Flashmaster yields 2.47 g (75.9%) of the desired compound.

$^1$H-NMR (300 MHz, $CDCl_3$): δ=4.01 (3H), 5.13 (2H), 7.72 (1H), 7.87 (1H).

2-(Azidomethyl)-5-fluoro-3-nitrobenzoic acid methyl ester 2.47 g (8.46 mmol) of 2-(bromomethyl)-5-fluoro-3-nitrobenzoic acid methyl ester is mixed with 8.3 ml of N,N-dimethylformamide and 5.5 ml of water. After 0.82 g (12.66 mmol) of sodium azide is added, the batch is stirred overnight. The reaction mixture is added to water and extracted three times with methyl tert-butyl ether. The combined organic extracts are washed with water and with brine. After drying on sodium sulfate, it is filtered, and the solvent is spun off. Chromatography on a Flashmaster yields 2.06 g (95.8%) of the desired azide.

$^1$H-NMR (300 MHz, $CDCl_3$): δ=4.00 (3H), 4.90 (2H), 7.73 (1H), 7.87 (1H).

4-Amino-6-fluoro-2,3-dihydroisoindol-1-one 1.86 g (7.32 mmol) of 2-(azidomethyl)-5-fluoro-3-nitrobenzoic acid methyl ester is added in 46 ml of ethanol and 3.4 ml of glacial acetic acid and mixed with 256.6 mg of Pd/C. After stirring overnight at room temperature under hydrogen atmosphere, the catalyst is suctioned off via a glass-fiber filter, and the filtrate is evaporated to the dry state. The residue, 1.18 mg (97.5%) of the desired compound, is further incorporated in crude form.

$^1$H-NMR (300 MHz, DMSO-$d_6$): δ=4.10 (2H), 5.75 (2H), 6.46-6.57 (2H), 8.50 (1H).

4-{[4-(5-Fluoro-2-methoxyphenyl)-2-hydroxy-4-methyl-2-(trifluoromethyl)-pentylidene]amino}6-fluoro-2,3-dihydroisoindol-1-one 400 mg (1.297 mmol) of rac-4-(5-fluoro-2-methoxyphenyl)-2-hydroxy-4-methyl-2-trifluoromethyl)-pentanal is stirred with 215.5 mg (1.297 mmol) of 4-amino-6-fluoro-2,3-dihydroisoindol-1-one in 1.89 ml of glacial acetic acid for four days at room temperature. Since starting material is still present according to TLC, the reaction mixture is mixed with toluene and boiled in a water separator for 20 hours. The mixture is mixed three times with toluene and evaporated to the dry state in a rotary evaporator. The residue is chromatographed on silica gel (mobile solvent ethyl acetate/hexane). 383.4 mg (64.7%) of the desired compound is isolated.

$^1$H-NMR (300 MHz, CDCl$_3$): δ=1.37 (3H), 1.53 (3H), 2.20 (1H), 3.47 (1H), 3.88 (3H), 4.32 (2H), 4.57 (1H), 6.22 (1H), 6.63-6.88 (4H), 7.42 (1H), 7.48 (1H).

4-{[8-Fluoro-2,5-dihydroxy-4,4-dimethyl-2-(trifluoromethyl)-1,2,3,4-tetrahydronaphthalen-1-yl]amino}-6-fluoro-2,3-dihydroisoindol-1-one 380 mg (0.832 mmol) of 4-{[4-(5-fluoro-2-methoxyphenyl)-2-hydroxy-4-methyl-2-(trifluoromethyl)pentylidene]amino}6-fluoro-2,3-dihydroisoindol-1-one is mixed at room temperature with 8.3 ml of a 1 M solution of BBr$_3$ in dichloromethane and stirred for one hour at ice bath temperature. The working-up of the batch is carried out as described in Example 4. After chromatography of the crude product on a Flashmaster (amine phase; mobile solvent methanol/dichloromethane), 9.2 mg (2.7%) of the desired compound is obtained.

$^1$H-NMR (300 MHz, CD$_3$OD): δ=1.53 (3H), 1.69 (3H), 2.02 (1H), 2.22 (1H), 4.28 (2H), 5.09 (1H), 6.60-7.00 (4H).

Example 5

4-{[5-Fluoro-2,6-dihydroxy-4,4-dimethyl-2-(trifluoromethyl)-1,2,3,4-tetrahydronaphthalen-1-yl]amino}-2,3-dihydroisoindol-1-one

2-Fluoro-3-methoxybenzaldehyde 27 ml (240.62 mmol) of 2-fluoroanisole is dissolved in 700 ml of tetrahydrofuran. At −70° C., 200 ml of sec-BuLi (1.3 M solution in cyclohexane) is added in drops. It is stirred for one hour at −70° C., and then 152 ml of N,N-dimethylformamide, dissolved in 50 ml of tetrahydrofuran, is added in drops at this temperature. After another hour of stirring at −70° C., 380 ml of hydrochloric acid (w=10%) is added in drops. In this case, the batch slowly comes to room temperature. After stirring overnight at room temperature, methyl tert-butyl ether is added, and the organic phase is separated after vigorous stirring. The aqueous phase is extracted two more times with methyl tert-butyl ether. The combined organic extracts are washed with brine and dried. After the desiccant is filtered off, the solvent is spun off, and the residue is chromatographed on silica gel (mobile solvent ethyl acetate/hexane). 25.66 g (69.2%) of the desired compound is isolated.

$^1$H-NMR (300 MHz, CDCl$_3$): δ=3.95 (3H), 7.13-7.26 (2H), 7.38-7.45 (1H), 10.4 (1H).

2-Fluoro-3-methoxybenzyl alcohol 25.66 g (166.47 mmol) of 2-fluoro-3-methoxybenzaldehyde is dissolved in 140 ml of ethanol and mixed in portions at 0° C. with 3.15 g (83.35 mmol) of sodium borohydride. After one hour of stirring at room temperature, the reaction mixture is mixed with water and extracted three times with methyl tert-butyl ether. The combined organic extracts are shaken with water and brine, dried, the desiccant is suctioned off, and the solvent is spun off. The remaining residue is chromatographed on silica gel (mobile solvent ethyl acetate/hexane). 24.79 g (95.3%) of the desired compound is obtained.

$^1$H-NMR (300 MHz, CDCl$_3$): δ=3.90 (3H), 4.78 (2H), 6.87-7.10 (3H).

2-Fluoro-3-methoxybenzyl chloride 24.79 g (158.75 mmol) of 2-fluoro-3-methoxybenzyl alcohol is dissolved in 35 ml of dichloromethane. While being cooled slightly, 58.4 ml of thionyl chloride is added in drops, and the batch is then stirred overnight at room temperature. The reaction mixture is spun in until a dry state is reached, the residue is dissolved in methyl tert-butyl ether, and it is shaken twice with semi-saturated potassium carbonate solution. The aqueous phase is extracted once with methyl tert-butyl ether. The combined organic extracts are worked up as usual. The residue that is obtained is incorporated in crude form into the next stage.

$^1$H-NMR (300 MHz, CDCl$_3$): δ=3.90 (3H), 4.65 (2H), 6.90-7.10 (3H).

2-Fluoro-3-methoxybenzyl cyanide 24.89 g (142.56 mmol) of 2-fluoro-3-methoxybenzyl chloride is stirred in 200 ml of DMSO with 8.38 g (171.07 mmol) of sodium cyanide for three hours at 90° C. The reaction mixture is poured into water and extracted four times with methyl tert-butyl ether. The combined organic phases are washed with brine, dried, the desiccant is suctioned off, and the solvent is spun off. First, only a portion of the residue (21.43 g) is incorporated in crude form into the next stage.

$^1$H-NMR (300 MHz, CDCl$_3$): δ=3.77 (2H), 3.90 (3H), 6.89-7.07 (2H), 7.08-7.15 (1H).

2-(2-Fluoro-3-methoxyphenyl)-2-methylpropanenitrile 4 g (24.22 mmol) of 2-fluoro-3-methoxybenzyl cyanide is dissolved in 38 ml of N,N-dimethylformamide and mixed with 6.87 g (48.35 mmol) of methyl iodide. At 0° C., 2.11 g (48.35 mmol) of sodium hydride (55%) is added in portions within 45 minutes. After 20 hours of stirring at room temperature, the batch is poured into ice water and extracted three times with 200 ml each of diethyl ether. The organic phases are washed with water and brine and dried. After the desiccant is filtered off and after the solvent is spun off, the residue is chromatographed on silica gel (mobile solvent ethyl acetate/hexane). 4.66 g (99.5%) of the desired compound is isolated.

$^1$H-NMR (300 MHz, CDCl$_3$): δ=1.80 (6H), 3.90 (3H), 92-7.02 (1H), 7.02-7.11 (2H).

2-(2-Fluoro-3-methoxyphenyl)-2-methylpropanal 4.66 g (24.12 mmol) of 2-(2-fluoro-3-methoxyphenyl)-2-methylpropanenitrile is dissolved in 96 ml of toluene. At −65° C. to −60° C., 30 ml (36.18 mmol) of a 1.2 molar solution of DIBAH in toluene is added in drops. After three and one-half hours of stirring at −65° C., 276 ml of a 10% L(+)-tartaric acid solution is added in drops at this temperature. In this case, the temperature rises to 0° C. The cold bath is removed, and the batch is stirred vigorously at room temperature for one hour. The reaction mixture is extracted three times with 300 ml each of diethyl ether. The combined organic extracts are treated as usual (water, brine, drying). After the solvent is spun off, 4.78 g (slightly above 100%) of the desired compound remains.

$^1$H-NMR (300 MHz, CDCl$_3$): δ=1.46 (6H), 3.89 (3H), 6.85-6.7.00 (2H), 7.08-7.15 (1H), 9.65 (1H).

E/Z-4-(2-Fluoro-3-methoxyphenyl)-4-methylpent-2-enoic acid methyl ester 20.26 g (111.26 mmol) of phosphonoacetic acid trimethyl ester is introduced into 68 ml of tetrahydrofuran. At 0° C., 61 ml of a 2 M solution of LDA in THF/heptane/ethylbenzene is added in drops. After 45 minutes of stirring, 21.83 g (111.26 mmol) of 2-(2-fluoro-3-methoxyphenyl)-2-methylpropanal, dissolved in 68 ml of tetrahydrofuran, is added in drops at 0° C. After stirring overnight, the reaction mixture is mixed with water while being cooled in an ice bath, and it is extracted three times with methyl tert-butyl ether. The combined organic extracts are treated as usual, and the residue that is obtained is chromatographed on silica gel (mobile solvent ethyl acetate/hexane). 23.30 g (75.8%) of the desired compound is isolated.

$^1$H-NMR (300 MHz, CDCl$_3$): δ=1.50 (6H), 3.73 (3H), 3.88 (3H), 5.74 (1H), 5.80 (1H), 6.80-7.10 (3H).

4-(2-Fluoro-3-methoxyphenyl)-4-methylpentanoic acid methyl ester 23.30 g (84.33 mmol) of E/Z-4-(2-fluoro-3-methoxyphenyl)-4-methylpent-2-enoic acid methyl ester is mixed in 310 ml of ethanol with 1.2 g of palladium on carbon, and it is stirred under hydrogen atmosphere overnight at room temperature. The catalyst is removed by filtration through a glass-fiber filter, and the residue that remains after concentration by evaporation is chromatographed on silica gel (mobile solvent ethyl acetate/hexane). 19.58 g (83.4%) of the desired compound is isolated.

$^1$H-NMR (300 MHz, CDCl$_3$): δ=1.48 (6H), 2.00-2.18 (4H), 3.60 (3H), 3.90 (3H), 6.78-7.03 (3H).

4-(2-Fluoro-3-methoxyphenyl)-2-hydroxy-4-methyl-pentanoic acid methyl ester 19.58 g (77 mmol) of 4-(2-fluoro-3-methoxyphenyl)-4-methylpentanoic acid methyl ester is introduced into 245 ml of tetrahydrofuran, and the reaction mixture is cooled to −70° C. Within one hour, 220.7 ml of a 0.5 molar solution of potassium-bis-(trimethylsilylamide) in toluene is added in drops, and the reaction mixture is then stirred for 45 more minutes at −70° C. 28.3 g (107.79 mmol) of Davis reagent, dissolved in 245 ml of tetrahydrofuran, is now added in drops within 40 minutes. After two hours of stirring at −70° C., 250 ml of saturated ammonium chloride solution is slowly added in drops, and in this case, the batch is brought to room temperature. After extraction with methyl tert-butyl ether, the combined organic extracts are treated as usual with water and brine. After the solvent is spun off, the residue is chromatographed several times on silica gel (mobile solvent ethyl acetate/hexane). 12.14 g (58.3%) of the desired compound is ultimately isolated.

$^1$H-NMR (300 MHz, CDCl$_3$): δ=1.45 (3H), 1.49 (3H), 1.90-2.01 (1H), 2.38-2.50 (2H), 3.70 (3H), 3.90 (3H), 3.92-4.03 (1H), 6.80-7.08 (3H).

Methyl-4-(2-fluoro-3-methoxyphenyl)-4-methyl-2-oxopentananoate 11.14 g (41.22 mmol) of methyl 4-(2-fluoro-3-methoxyphenyl)-2-hydroxy-4-methyl-pentanoate is added in 260 ml of dichloromethane and 71.3 ml of dimethyl sulfoxide. After 20.8 g (205.78 mmol) of triethylamine is added, the batch is mixed with 13 g (81.71) of SO$_3$/pyridine complex and then stirred overnight at room temperature. The reaction mixture is mixed with 100 ml of saturated ammonium chloride solution while being cooled slightly, and it is stirred vigorously. After 3× extraction with methyl tert-butyl ether, the combined organic phases are treated as usual. The residue that remains after the solvent is spun off is chromatographed together with the residue, which results from a sample batch (1 g), on silica gel (mobile solvent ethyl acetate/hexane). 10.03 g (83.2%, from both batches) of the desired compound is isolated.

$^1$H-NMR (300 MHz, CDCl$_3$): δ=1.49 (6H), 3.39 (2H), 3.73 (3H), 3.89 (3H), 6.80-6.91 (2H), 6.95-7.07 (1H).

Methyl-4-(2-fluoro-3-methoxyphenyl)-4-methyl-2-(trifluoromethyl)-2-(trimethylsilyloxy)-pentanoate 10.03 g (37.39 mmol) of methyl-4-(2-fluoro-3-methoxyphenyl)-4-methyl-2-oxopentanoate is dissolved in 63 ml of tetrahydrofuran, mixed with 5.68 g (39.98 mmol) of (trifluoromethyl)-trimethylsilane and then with 82.3 mg of tetrabutylammonium fluoride. After stirring overnight at room temperature, the batch is added to ice water, extracted with methyl tert-butyl ether, and the combined organic extracts are treated as usual. After the solvent is spun off, the residue is chromatographed on silica gel (mobile solvent ethyl acetate/ hexane). In addition to 6.94 g (45.2%) of the desired product, 2.75 g of starting material (contaminated) is isolated, which is again subjected to the same procedure. As a result, another 1.91 g of methyl-4-(2-fluoro-3-methoxyphenyl)-4-methyl-2-(trifluoromethyl)-2-(trimethylsilyloxy)-pentanoate is included.

MS (CI): 428 (100%), 395 (67%).

4-(2-Fluoro-3-methoxyphenyl)-4-methyl-2-(trifluoromethyl)-2-(trimethylsilyloxy)pentan-1-ol and 4-(2-Fluoro-3-methoxyphenyl)-4-methyl-2-(trifluoromethyl)-1-(trimethylsilyloxy)pentan-2-ol 8.85 g (21.56 mmol) of methyl-4-(2-fluoro-3-methoxyphenyl)-4-methyl-2-(trifluoromethyl)-2-(trimethylsilyloxy)-pentanoate is dissolved in 77 ml of diethyl ether. 1.64 g (43.12 mmol) of lithium aluminum hydride is added to this solution in portions at 0° C. After four hours of stirring at room temperature, it is cooled again to 0° C. and about 80 ml of saturated sodium bicarbonate solution is carefully added in drops. Then, it is vigorously stirred at room temperature for one hour. The batch is extracted several times with methyl tert-butyl ether. The combined organic extracts are washed with water and then with brine. After drying on sodium sulfate, the desiccant is suctioned off, the solvent is spun in, and the residue (7.36 g; mixture of the two regioisomeric silyl ethers) is incorporated in crude form into the next stage.

4-(2-Fluoro-3-methoxyphenyl)-4-methyl-2-(trifluoromethyl)pentane-1,2-diol 7.36 g (19.24 mmol) of the mixture of the two silyl ethers is dissolved in 108 ml of tetrahydrofuran, mixed with 6.07 g (19.24 mmol) of tetrabutylammonium fluoride-trihydrate and stirred overnight at room temperature. The reaction mixture is diluted with methyl tert-butyl ether, washed with water and brine, and then the organic solvent is spun off after drying. After chromatography on silica gel (mobile solvent ethyl acetate/hexane), 5.3 g (88.8%) of the desired compound is obtained.

$^1$H-NMR (300 MHz, CDCl$_3$): δ=1.45 (3H), 1.58 (3H), 2.20 (1H), 2.38 (2H), 2.93 (1H), 3.30-3.40 (1H), 3.50-3.60 (1H), 3.89 (3H), 6.85-6.98 (2H), 6.98-7.09 (1H).

4-(2-Fluoro-3-methoxyphenyl)-2-hydroxy-2-(trifluoromethyl)-pentanal 2.5 g (8.06 mmol) of rac-4-(2-fluoro-3-methoxyphenyl)-4-methyl-2-(trifluoromethyl)pentane-1,2-diol is introduced into a mixture that consists of 52 ml of dichloromethane, 14 ml of dimethyl sulfoxide and 4.08 g (40.29 mmol) of triethylamine. At room temperature, 2.57 g (16.11 mmol) of SO$_3$/pyridine complex is added, and the batch is stirred overnight at this temperature. The reaction mixture is mixed with saturated ammonium chloride solution and stirred vigorously. After additional common working-up, 2.11 g (85%) of the desired aldehyde is obtained.

$^1$H-NMR (300 MHz, CDCl$_3$): δ=1.45 (3H), 1.50 (3H), 2.30 (1H), 3.12 (1H), 3.62 (1H), 3.89 (3H), 6.75 (1H), 6.90 (1H), 7.00 (1H), 9.15 (1H).

4-{[5-Fluoro-2-hydroxy-6-methoxy-4,4-dimethyl-2-(trifluoromethyl)-1,2,3,4-tetrahydronaphthalen-1-yl]amino}-2,3-dihydroisoindol-1-one 150 mg (0.487 mmol) of 4-(3-fluoro-2-methoxyphenyl)-2-hydroxy-2-trifluoromethyl-pentanal is mixed in 0.9 ml of glacial acetic acid with 72.7 mg (0.487 mmol) of 4-amino-2,3-dihydroisoindol-1-one, and it is stirred for two days at room temperature. The batch is spun in until a dry state is reached, and the residue is chromatographed (Flashmaster). 119.8 mg (56.2%) of the desired cyclic compound is isolated.

$^1$H-NMR (300 MHz, CDCl$_3$): δ=1.50 (3H), 1.65 (3H), 2.05 (1H), 2.20 (1H), 3.83 (3H), 4.29 (2H), 4.40 (1H), 5.00 (1H), 6.79 (1H), 6.93 (1H), 7.00-7.12 (2H), 7.21 (1H), 7.35 (1H).

4-{[5-Fluoro-2,6-dihydroxy-4,4-dimethyl-2-(trifluoromethyl)-1,2,3,4-tetrahydronaphthalen-1-yl]amino}-2,3-dihydroisoindol-1-one 109.8 mg (0.250 mmol) of (rac.) 4-{[5-fluoro-2-hydroxy-6-methoxy-4,4-dimethyl-2-(trifluoromethyl)-1,2,3,4-tetrahydronaphthalen-1-yl]amino}-2,3-dihydroisoindol-1-one is mixed with 3.4 ml of a 1 M solution of BBr$_3$ in dichloromethane and stirred for four hours at room temperature. The batch is mixed at 0° C. with saturated sodium bicarbonate solution and extracted twice with ethyl acetate. The combined organic extracts are dried on sodium sulfate. After the desiccant is filtered off, and after the solvent is spun off, the residue is chromatographed on a Flashmaster. 15.6 mg (14.7%) of the final product is isolated.

$^1$H-NMR (300 MHz, CD$_3$OD): δ=1.53 (3H), 1.67 (3H), 2.03-2.20 (2H), 4.28-4.43 (2H), 5.13 (1H), 6.78 (1H), 6.90 (2H), 7.18 (1H), 7.38 (1H).

Example 6

4-{[7-Bromo-2,5-dihydroxy-4,4-dimethyl-2-(trifluoromethyl)-1,2,3,4-tetrahydronaphthalen-1-yl]amino}-1,3-dihydroindol-2-one 4-Amino-1,3-dihydroindol-2-one Dimethyl-2-(2,6-dinitrophenyl)-malonate 42.95 g (311.03 mmol) of dimethyl malonate is dissolved in 300 ml of N,N-dimethylformamide and mixed in portions with 35.15 g (296.22 mmol) of potassium-tert. butylate. After the tert-butanol that was produced has been distilled off, the reaction mixture is cooled to 20° C. 30 g (148.11 mmol) of 2,6-dichlorobenzene is quickly added in portions to the mixture. After three hours of stirring at 90° C., it is stirred overnight at room temperature. The reaction mixture is added to 800 ml of 1% NaOH solution (ice-cooled) and extracted three times with methyl tert-butyl ether. The combined ether phases are discarded according to TLC monitoring. The aqueous phase is carefully acidified with concentrated nitric acid (w=65%) while being cooled in an ice bath. 6× extraction with methyl tert-butyl ether, common working-up of the combined organic extracts (water, brine, drying, filtering and spinning-off of solvent) yields a residue that is chromatographed on silica gel (mobile solvent ethyl acetate/hexane). 12.09 g (27.09%) of the desired compound is isolated.

$^1$H-NMR (300 MHz, CDCl$_3$): δ=3.82 (6H), 5.39 (1H), 7.75 (1H), 8.27 (2H).

Methyl-(2,6-Dinitrophenyl)-acetate 10.08 g (33.8 mmol) of dimethyl-2-(2,6-dinitrophenyl)-malonate is mixed in 54 ml of glacial acetic acid with 2.7 ml of perchloric acid and refluxed at 125° C. In this case, the ethyl acetate that is produced is distilled off. After 90 minutes, the reaction is brought to a halt, since starting material is no longer present according to TLC. The reaction mixture is poured into ice water and extracted three times with ethyl acetate. The combined organic extracts are shaken with 5% sodium bicarbonate solution, with water and with brine. After the organic phase is dried, the desiccant is filtered off and the solvent is spun off, a residue remains that is chromatographed on silica gel (mobile solvent ethyl acetate/hexane). 4.69 g of the (2,6-dinitrophenyl)-acetic acid, which then is esterified with methanol (16 ml) and concentrated sulfuric acid (0.4 ml), is isolated. To this end, the acid and the reagents are refluxed for seven hours. The methanol is spun off, and the residue is worked up in the usual way. After chromatography on silica gel (mobile solvent ethyl acetate/hexane), 4.43 g (89%) of the desired ester is obtained.

$^1$H-NMR (300 MHz, CDCl$_3$): δ=3.75 (3H), 4.20 (2H), 7.69 (1H), 8.19 (2H).

4-Amino-1,3-dihydroindol-2-one 4.43 g (18.45 mmol) of methyl-(2,6-dinitrophenyl)-acetate is added in 38.8 ml of glacial acetic acid and 11 ml of water and mixed with 3.75 g of iron powder and stirred for four more hours. In this case, heating to 40 to 60° C. takes place. The reaction mixture is added to ice water, mixed with ethyl acetate and vigorously stirred for ten minutes. The mixture is filtered through a glass-fiber filter, the organic phase is separated, and the aqueous phase is extracted twice more with ethyl acetate. The combined organic extracts are washed with brine, dried, and the solvent is spun off after the desiccant is filtered off. The residue is chromatographed on silica gel (mobile solvent methanol/dichloromethane). 2.38 g of 4-nitro-indol-2-one is isolated. The nitro compound is mixed again in glacial acetic acid/water with 2.7 g of iron powder, and the above-described cycle is passed through another time. 1.63 g of the desired amine is isolated.

$^1$H-NMR (300 MHz, DMSO-d$_6$): δ=3.19 (2H), 5.03 (2H), 6.08 (1H), 6.22 (1H), 6.85 (1H), 10.10 (1H).

4-(4-Bromo-2-methoxyphenyl)-4-methyl-2-(trifluoromethyl)-pentane-1,2-diol 2.55 g (6.17 mmol) of 4-(4-bromo-2-methoxyphenyl)-2-hydroxy-4-methyl-2-(trifluoromethyl)-pentanoic acid ethyl ester (synthesized in two stages starting from 4-(4-bromo-2-methoxyphenyl)-2-oxopentanoic acid, WO 98/54159) is dissolved in 102 ml of diethyl ether, mixed in portions at 0 to −5° C. with 351.3 mg (9.256 mmol) of lithium aluminum hydride and stirred for three and one-half hours at room temperature. The reaction mixture is mixed drop by drop with saturated sodium bicarbonate solution while being cooled in an ice bath and stirred for 15 minutes at 5° C. and then for one hour at room temperature. The deposited precipitate is suctioned off, rewashed with diethyl ether, and the filtrate is concentrated by evaporation in a rotary evaporator. The residue is chromatographed on silica gel (mobile solvent ethyl acetate/hexane). In addition to 308 mg of the aldehyde (see next stage), 2.025 g (88.4%) of the diol is obtained.

4-(4-Bromo-2-methoxyphenyl)-2-hydroxy-4-methyl-2-(trifluoromethyl)-pentanal 2.03 g (5.442 mmol) of 4-(4-bromo-2-methoxyphenyl)-4-methyl-2-(trifluoromethyl)-pentane-1,2-diol is oxidized to aldehyde according to Swern as described in Example 3. 1.839 g (91.4%) of the desired compound is isolated.

$^1$H-NMR (300 MHz, CDCl$_3$): δ=1.39 (3H), 1.45 (3H), 2.23 (1H), 3.35 (1H), 3.58 (1H), 3.90 (3H), 6.93-7.09 (3H), 9.03 (1H).

4-{[4-(4-Bromo-2-methoxyphenyl)-2-hydroxy-4-methyl-2-(trifluoromethyl)-pentylidene]amino}-1,3-dihydroindol-2-one 300 mg (0.812 mmol) of 4-(4-bromo-2-methoxyphenyl)-2-hydroxy-4-methyl-2-trifluoromethyl-pentanal is stirred in 1.5 ml of glacial acetic acid with 120.4 mg (0.812 mmol) of 4-amino-1,3-dihydroindol-2-one over a weekend at room temperature. The reaction mixture is evaporated until a dry state is reached, and the residue is put on a Flashmaster column. 235.9 mg (58.1%) of the desired imine is isolated.

$^1$H-NMR (300 MHz, CDCl$_3$): δ=1.35 (3H), 1.53 (3H), 2.20 (1H), 3.30 (1H), 3.42 (2H), 3.85 (3H), 4.71 (1H), 6.05 (1H), 6.78 (1H), 6.80-6.90 (2H), 6.98 (1H), 7.19 (1H), 7.45 (1H), 8.25 (1H).

4-{[7-Bromo-2,5-dihydroxy-4,4-dimethyl-2-(trifluoromethyl)-1,2,3,4-tetrahydronaphthalen-1-yl)amino}-], 3-dihydroindol-2-one 235.9 mg of 4-{[4-(4-bromo-2-methoxyphenyl)-2-hydroxy-4-methyl-2-(trifluoromethyl)pentylidene]amino}-1,3-dihydroindol-2-one is mixed at 0° C. with 6.42 ml of a 1 M solution of BBr$_3$ in dichloromethane and stirred for four hours at room temperature. At 0° C., saturated sodium bicarbonate solution is carefully added in drops. After 3× extraction with ethyl acetate, the organic phases are dried on sodium sulfate. The desiccant is suctioned off, and the solvent is spun off. The residue is chromatographed on a Flashmaster. 125.4 mg (54%) of the desired compound is isolated.

$^1$H-NMR (300 MHz, CD$_3$OD): δ=1.52 (3H), 1.65 (3H), 1.98-2.18 (2H), 3.25-3.49 (2H), 4.98 (1H), 6.37 (1H), 6.47 (1H), 6.87 (1H), 7.02 (1H), 7.11 (1H).

Example 7

(+)-4-({7-Hydroxy-9,9-dimethyl-7-(trifluoromethyl)-6,7,8,9-tetrahydronaphtho[1,2-d]-1,3-dioxol-6-yl}amino)-2,3-dihydroisoindol-1-one and (−)-4-({7-Hydroxy-9,9-dimethyl-7-(trifluoromethyl)-6,7,8,9-tetrahydronaphtho[1,2-d]-1,3-dioxol-6-yl}amino)-2,3-dihydroisoindol-1-one 1,3-Benzodioxole-4-carboxylic acid-methyl ester 50 g of 2,3-dihydroxybenzoic acid in 450 ml of methanol is mixed drop by drop with 50 ml of thionyl chloride at room temperature. Then, the solution is heated for five hours to 60° C. and still stirred overnight at room temperature. The solvent is completely removed in a vacuum, and the remaining oil is taken up in diethyl ether and extracted with saturated sodium bicarbonate solution. After washing with brine, drying with sodium sulfate and removal of the solvent in a vacuum, 46 g of 2,3-dihydroxybenzoic acid-methyl ester is obtained. The latter is mixed in 575 ml of DMF and 20.2 ml of dibromomethane with 56.7 g of potassium carbonate, and it is heated for five hours under argon to 100° C. Then, it is stirred overnight at room temperature. After mixing with water, it is extracted three times with ethyl acetate. The organic phase is washed several times with water and dried on sodium sulfate. The solvent is removed in a vacuum, and 50.2 g of 1,3-benzodioxole-4-carboxylic acid-methyl ester is obtained as a brown solid.

Melting point: 55-57° C.

4-(1,3-Benzodioxol-4-yl)-4-methyl-2-oxopentanoic acid ethyl ester 4.76 g of 1,3-benzodioxole-4-carboxylic acid-methyl ester in 65 ml of dry THF is added in drops at room temperature to a solution of 21 ml of 3 M methylmagnesium chloride in THF under argon. The reaction mixture is stirred for three hours and then slowly mixed with 1N hydrochloric acid. After extraction with ethyl acetate and after the organic phase is washed with water, it is dried with sodium sulfate, and the solvent is removed in a vacuum. 5 g of 1-(1,3-benzodioxol-4-yl)-1-methylethanol is obtained as a brown oil. The tertiary alcohol (27.17 mmol) is mixed together with 7.8 g (41.6 mmol) of 2-(trimethylsilyloxy)-acrylic acid ethyl ester in 100 ml of dichloromethane at −70° C. with 5.4 g (20.8 mmol) of tin tetrachloride. After 15 minutes of stirring at −70° C., the solution is poured onto semi-saturated sodium carbonate solution, mixed with ethyl acetate and stirred vigorously. The phases are separated, and the aqueous phase is extracted twice with ethyl acetate. The organic phase is washed with brine, dried with sodium sulfate, and the solvent is removed in a vacuum. 7.15 g of a yellow oil that is distilled together with the products from several batches of a similar order of magnitude is obtained.

4-(1,3-Benzodioxol-4-yl)-2-hydroxy-4-methyl-2-trifluoromethyl-pentanoic acid ethyl ester 6.1 g (21.91 mmol) of 4-(1,3-benzodioxol-4-yl)-4-methyl-2-oxopentanoic acid ethyl ester, dissolved in 130 ml of tetrahydrofuran, is reacted with 9.5 ml (65.7 mmol) of (trifluoromethyl)trimethylsilane and 4.42 ml of a 1 M solution of tetrabutylammonium fluoride in tetrahydrofuran. Carrying out and working up the reaction are carried out as described in Example 3. The crude product that is obtained is purified together with one batch of a similar order of magnitude [9.19 g (33.02 mmol) of 4-(1,3-benzodioxol-4-yl)-4-methyl-2-oxopentanoic acid ethyl ester as a starting material] by chromatography on silica gel (mobile solvent ethyl acetate/hexane). 16.45 g (86%) of the desired product is isolated from the two batches.

4-(1,3-Benzodioxol-4-yl)-4-methyl-2-(trifluoromethyl)pentane-1,2-diol 12.5 g (36.03 mmol) of 4-(1,3-benzodioxol-4-yl)-2-hydroxy-4-methyl-2-(trifluoromethyl)-pentanoic acid ethyl ester is introduced into 430 ml of diethyl ether and mixed in portions with 2.05 g (54.1 mmol) of lithium aluminum hydride at 0° C. After stirring overnight at room temperature, the batch is carefully added to sodium bicarbonate solution. It is filtered by means of diatomaceous earth and extracted three times with ethyl acetate. The combined organic extracts are washed with brine, dried, and the solvent is spun off after the desiccant is filtered off. Chromatography of the residue on silica gel (mobile solvent ethyl acetate/hexane) yields 6.7 g (61%) of the desired alcohol.

4-(1,3-Benzodioxol-4-yl)-2-hydroxy-4-methyl-2-(trifluoromethyl)pentanal 2.26 g (7.38 mmol) of 4-(1,3-benzodioxol-4-yl)-4-methyl-2-(trifluoromethyl)pentane-1,2-diol is oxidized to aldehyde as described in Example 3 according to Swern. After the conventional working-up, the residue is chromatographed on a Flashmaster. 1.85 g (82.3%) of the desired aldehyde is obtained.

$^1$H-NMR (300 MHz, CDCl$_3$): δ=1.39 (3H), 1.48 (3H), 2.27 (1H), 3.10 (1H), 3.67 (1H), 5.92-6.02 (2H), 6.60-6.70 (1H), 6.70-6.88 (2H), 9.06 (1H).

(+)-4-({7-Hydroxy-9,9-dimethyl-7-(trifluoromethyl)-6,7,8,9-tetrahydronaphtho[1,2-d]-1,3-dioxol-6-yl}amino)-2,3-dihydroisoindol-1-one and

(−)-4-({7-Hydroxy-9,9-dimethyl-7-(trifluoromethyl)-6,7,8,9-tetrahydronaphtho[1,2-d]-1,3-dioxol-6-yl}amino)-2,3-dihydroisoindol-1-one 800 mg (2.63 mmol) of 4-(1,3-benzodioxol-4-yl)-2-hydroxy-4-methyl-2-(trifluoromethyl)pentanal is stirred in 5.2 ml of glacial acetic acid with 389 mg (2.63 mmol) of 4-amino-2,3-dihydroisoindol-1-one overnight at room temperature. The reaction mixture is spun in until a dry state is reached, and the residue is chromatographed on a Flashmaster. 725 mg (62.8%) of the desired compound is isolated as a racemate. Racemate cleavage (Chiralpak AD 20μ; mobile solvent: hexane/ethanol/diethylamine) yields 279.2 mg of the (+)-enantiomer {[α]$_D$=+20.7 (c=1.03, methanol)} and 297.5 mg of the (−)-enantiomer {[α]$_D$=−23.4 (c=1.02, methanol)}

Example 8

5-{[8-Chloro-2,5-dihydroxy-4,4-dimethyl-2-(trifluoromethyl)-1,2,3,4-tetrahydronaphthalen-1-yl]amino}-isoquinolin-1(2H)-one

4-(5-Chloro-2-methoxyphenyl)-2-hydroxy-4-methyl-2-(trifluoromethyl)pentanal 2 g (6.12 mmol) of 4-(5-chloro-2-methoxyphenyl)-hydroxy-4-methyl-2-trifluoromethyl-pentan-1-ol is oxidized with 854.6 mg (6.733 mmol) of oxalyl chloride and 1.05 ml (14.812 mmol) of DMSO as described in Example 2 according to Swern. After the working-up, 1.95 g (98.4%) of the desired aldehyde is obtained, which is incorporated in crude form into the next stage.

$^1$H-NMR (300 MHz, CDCl$_3$): δ=1.39 (3H), 1.49 (3H), 2.27 (1H), 3.32 (1H), 3.59 (1H), 3.88 (3H), 6.78 (1H), 7.10 (1H), 7.20 (1H), 9.09 (1H).

5-{[4-(5-Chloro-2-methoxyphenyl)-2-hydroxy-4-methyl-2-trifluoromethyl)-pentylidene]amino}isoquinolin-1(2H)-one 300 mg (0.924 mmol) of 4-(5-chloro-2-methoxyphenyl)-2-hydroxy-4-methyl-2-(trifluoromethyl)-pentanal is stirred with 148 mg (0.924 mmol) of 5-amino-isoquinolin-1-one in 1.33 ml of glacial acetic acid for four days at room temperature. The mixture is drawn off three times with toluene and evaporated in a rotary evaporator until a dry state is reached. The residue is chromatographed on silica gel (mobile solvent ethyl acetate/hexane). 345.8 mg (80.1%) of the desired compound is isolated.

$^1$H-NMR (300 MHz, CDCl$_3$): δ=1.39 (3H), 1.57 (3H), 2.29 (1H), 3.49 (1H), 3.83 (3H), 4.82 (1H), 6.57-6.65 (2H), 6.72 (1H), 6.89 (1H), 7.03 (1H), 7.18-7.29 (1H), 7.36 (1H), 7.40 (1H), 8.32 (1H), 10.98 (1H).

5-{[8-Chloro-2,5-dihydroxy-4,4-dimethyl-2-(trifluoromethyl)-1,2,3,4-tetrahydronaphthalen-1-yl]amino}-isoquinolin-1(2H)-one 50 mg (0.107 mmol) of the compound 5-{[4-(5-chloro-2-methoxyphenyl)-2-hydroxy-4-methyl-2-(trifluoromethyl)pentylidene]amino}2,3-isoquinolin-1-one that is described in the paragraph above is mixed at −20° C. with 2.1 ml of a 1 M solution of boron tribromide in dichloromethane, and it is stirred for two and one-half hours in a temperature range of between −20° C. and 0° C. The reaction mixture is mixed drop by drop at −20° C. with saturated sodium bicarbonate solution. After dilution with ethyl acetate, the cold bath is removed, and the batch is stirred for 15 minutes at room temperature. It is extracted twice with 30 ml each of ethyl acetate. The combined organic extracts are washed with water and saturated NaCl solution. After being dried on sodium sulfate, the solvent is spun off, and the remaining residue is chromatographed on silica gel (mobile solvent ethyl acetate/hexane). 16.5 mg (33%) of the desired compound is isolated.

MS (ES+): 453, 455

Example 9

8-Bromo-1-[(1H-indazol-4-yl)amino]-4,4-dimethyl-2-(trifluoromethyl)-1,2,3,4-tetrahydronaphthalene-2,5-diol)

4-(5-Bromo-2-methoxyphenyl)-2-hydroxy-4-methyl-2-(trifluoromethyl)pentanoic acid ethyl ester 34.45 g (258.91 mmol) of aluminum trichloride is introduced into 354.35 g (237.02 mmol) of 4-bromoanisole. 38.95 g (172.19 mmol) of 2-hydroxy-4-methylene-2-(trifluoromethyl)pentanoic acid ethyl ester is added in drops to this mixture within one hour. After stirring overnight at room temperature, the batch is added to ice water and made acidic with 10% hydrochloric acid. After 3× extraction with ethyl acetate, the combined organic extracts are washed with 1N hydrochloric acid and brine. After drying on magnesium sulfate, the solvent is spun off. Most of the excess 4-bromoanisole is distilled off (10 mbar; bath temperature 110° C.). After chromatography on silica gel (mobile solvent ethyl acetate/hexane), 36.87 g (51.8%) of the desired compound is obtained.

$^1$H-NMR (300 MHz, CDCl$_3$): δ=1.39 (3H), 1.46 (3H), 2.49 (1H), 2.85 (1H), 3.48 (1H), 3.62-3.75 (1H), 3.85 (3H), 4.02-4.15 (1H), 6.73 (1H), 7.23-7.33 (2H).

4-(5-Bromo-2-methoxyphenyl)-2-hydroxy-4-methyl-2-(trifluoromethyl)pentan-1-ol 3 g (7.25 mmol) of 4-(5-bromo-2-methoxyphenyl)-2-hydroxy-4-methyl-2-(trifluoromethyl)pentanoic acid ethyl ester is dissolved in 120 ml of diethyl ether, and the reaction mixture is cooled to 0° C. 426.5 mg (10.89 mmol) of lithium aluminum hydride is added in portions. After two hours of stirring at room temperature, starting material is no longer present. The batch is mixed with saturated sodium bicarbonate solution while being cooled in an ice bath, the precipitate is suctioned off, and it is washed with diethyl ether. After spinning-in, the residue is chromatographed on a Flashmaster. In addition to 540.5 mg of 4-(5-bromo-2-methoxyphenyl)-2-hydroxy-4-methyl-2-(trifluoromethyl)pentanal, 1.14 g of the desired alcohol (which, however, also contains the Desbrom compound) is isolated.

4-(5-Bromo-2-methoxyphenyl)-2-hydroxy-4-methyl-2-(trifluoromethyl)pentanal 1.13 g (3.06 mmol) of 4-(5-bromo-2-methoxyphenyl)-2-hydroxy-4-methyl-2-(trifluoromethyl)pentan-1-ol is added in 20 ml of dichloromethane and 5.4 ml of DMSO. After mixing with 1.55 g (15.32 mmol) of triethylamine and 975.28 mg (6.13 mmol) of SO$_3$/pyridine complex, the batch is stirred overnight at room temperature. After TLC, another spatula tip full of SO$_3$/pyridine complex is added, and it is further stirred for several hours. The reaction mixture is mixed with saturated ammonium chloride solution and shaken out three times with methyl tert-butyl ether. The combined organic extracts are washed with water and brine. After the solvent is dried and spun off, the residue is chromatographed on a Flashmaster. 902.7 mg (79.81%) of the desired aldehyde (together with the Desbrom compound) is isolated.

$^1$H-NMR (300 MHz, CDCl$_3$): δ=1.40 (3H), 1.50 (3H), 2.28 (1H), 3.30 (1H), 3.87 (3H), 6.73 (1H), 7.22 (1H), 7.35 (1H), 9.09 (1H).

1,1,1-Trifluoro-4-(5-bromo-2-methoxyphenyl)-2-[(1H-indazol-4-yl)iminomethyl]-4-methylpentan-2-ol 300 mg (0.813 mmol) of 4-(5-bromo-2-methoxyphenyl)-2-hydroxy-4-methyl-2-(trifluoromethyl)pentanal is mixed in 1.19 ml of glacial acetic acid with 108.2 mg (0.813 mmol) of 4-aminoindazole, and it is stirred for four days at room temperature. The batch is spun in until a dry state is reached, and the residue is drawn off three times with toluene. Chromatography on silica gel (mobile solvent ethyl acetate/hexane) yields 352.5 mg (89.5%) of the desired imine (together with the imine of the Desbrom compound).

$^1$H-NMR (300 MHz, CDCl$_3$): δ=1.48 (3H), 1.55 (3H), 2.28 (1H), 3.44 (1H), 3.80 (3H), 4.98 (1H), 6.35 (1H), 6.53 (1H), 6.99 (1H), 7.30 (1H), 7.29-7.40 (1H), 7.55 (1H), 7.99 (1H), 10.28 (1H).

8-Bromo-5-methoxy-1-[(1H-indazol-4-yl)amino]-4,4-dimethyl-2-(trifluoromethyl)-1,2,3,4-tetrahydronaphthalen-2-ol 100 mg (0.206 mmol) of 1,1,1-trifluoro-4-(5-bromo-2-methoxyphenyl)-2-[(1H-indazol-4-yl)iminomethyl]-4-methylpentan-2-ol is dissolved in one milliliter of dichloromethane, and the reaction mixture is cooled to −30° C. Four milliliters of a 1 M solution of BBr$_3$ in dichloromethane is added in drops within 15 minutes, and the batch is then stirred for 45 more minutes at −30° C. At −30° C., about 10 ml of a saturated sodium bicarbonate solution is carefully added in drops. After dilution with ethyl acetate, it is stirred for ten minutes and then extracted twice with 50 ml each of ethyl acetate. The combined organic extracts are washed with water and brine. The residue that is obtained after the solvent is dried and spun off is chromatographed several times on silica gel (mobile solvent ethyl acetate/dichloromethane). 21 mg of the desired compound (together with the corresponding Desbrom compound) is isolated.

$^1$H-NMR (300 MHz, CD$_3$OD): δ=1.55 (3H), 1.67 (3H), 2.10 (1H), 2.43 (1H), 3.89 (3H), 5.25 (1H), 6.72 (1H), 6.83 (1H), 6.90 (1H), 7.22 (1H), 7.49 (1H), 8.25 (1H).

8-Bromo-1-[(1H-indazol-4-yl)amino]-4,4-dimethyl-2-(trifluoromethyl)-1,2,3,4-tetrahydronaphthalene-2,5-diol 21 mg (0.043 mmol) of 8-bromo-5-methoxy-1-[(1H-indazol-4-yl)amino]-4,4-dimethyl-2-(trifluoromethyl)-1,2,3,4-tetrahydronaphthalen-2-ol is mixed at room temperature with 0.4 ml of a 1 M BBr$_3$ solution and stirred for 19 hours at room temperature. After the reaction mixture is mixed with ice, saturated sodium bicarbonate solution is added drop by drop, and it is diluted with ethyl acetate. The organic phases are washed neutral as usual, and the residue that remains after the solvent is spun in is chromatographed on silica gel (mobile solvent methanol/dichloromethane). 17.1 mg (83.8%) of the desired compound (together with the Desbrom compound) is isolated.

$^1$H-NMR (300 MHz, CD$_3$OD): δ=1.59 (3H), 1.71 (3H), 2.10 (1H), 2.42 (1H), 5.25 (1H), 6.64-6.78 (2H), 6.83 (1H), 7.20-7.34 (2H), 8.25 (1H).

Example 10

1-[(1H-Indazol-4-yl)amino]-4,4-dimethyl-2-(trifluoromethyl)-1,2,3,4-tetrahydronaphthalen-2-ol 2-Hydroxy-4-methyl-4-phenyl-2-(trifluoromethyl)pentanal 10.4 g of 4-methyl-2-oxo-4-phenylpentanoic acid (WO98/54159) in 250 ml of dimethylformamide is mixed at −5° C. with 4.1 ml of thionyl chloride and after 15 minutes, it is mixed with 4 ml of methanol. After 15 hours at room temperature, the batch is diluted with water, and extracted with ethyl acetate. The organic extracts are washed with water, dried ($Na_2SO_4$) and concentrated by evaporation, whereby 9.3 g of 4-methyl-2-oxo-4-phenylpentanoic acid-methyl ester is obtained. The latter is mixed in 558 ml of DMF at −5° C. with 15.5 ml (104.63 mmol) of (trifluoromethyl)trimethylsilane and 20.5 g (63.28 mmol) of cesium carbonate, and it is stirred for 16 hours at room temperature. Water is added, it is extracted with ethyl acetate, the organic phase is washed with water and dried ($Na_2SO_4$). The intermediate product that is concentrated by evaporation is taken up in 200 ml of THF, and 50 ml of a 1 M solution of tetrabutylammonium fluoride in THF is added. It is stirred for 2 hours, water is added, it is extracted with ethyl acetate, the organic phase is washed with water and dried ($Na_2SO_4$). After chromatography on silica gel with hexane-ethyl acetate (0-30%), 8.35 g of 2-hydroxy-4-methyl-4-phenyl-2-(trifluoromethyl)pentanoic acid-methyl ester is obtained. The ester (8.3 g, 28.59 mmol) is dissolved in 180 ml of THF, and over a period of 2.5 hours, 1.52 g (36.20 mmol) of lithium aluminum hydride is added in small portions. After complete conversion, 5 ml of ethyl acetate is added in drops, and after another 10 minutes, 10 ml of water is carefully added. Formed precipitate is filtered out, and it is washed carefully with ethyl acetate. After chromatography on silica gel with hexane-ethyl acetate (0-35%), 5.40 g of 4-methyl-4-phenyl-2-(trifluoromethyl)pentane-1,2-diol is obtained. 5.7 ml (40.3 mmol) of triethylamine is added to 2.5 g (9.53 mmol) of diol in 75 ml of dichloromethane and 28 ml of DMSO, and 5 g of pyridine/$SO_3$ complex is added in portions over 20 minutes. It is stirred over 2 hours, and 40 ml of saturated ammonium chloride solution is added. The mixture is stirred for another 15 minutes, the phases are separated, and it is extracted with dichloromethane. It is washed with water, and dried on sodium sulfate. The solvent is removed in a vacuum, and 3 g of product is obtained.

$^1$H-NMR (300 MHz, $CDCl_3$): δ=1.34 (s, 3H), 1.44 (s, 3H), 2.34 (d, 2H), 2.66 (d, 1H), 3.64 (s, 1H), 7.03-7.41 (m, 4H), 8.90 (s, 1H).

1,1,1-Trifluoro-4-phenyl-2-[(1H-indazol-4-yl)iminomethyl]-4-methylpentan-2-ol 130 mg (0.50 mmol) of 2-hydroxy-4-methyl-4-phenyl-2-(trifluoromethyl)-pentanal is dissolved in 15 ml of toluene and mixed with 73 mg (0.55 mmol) of 4-amino-indazole and with 0.22 ml of titanium tetraethylate and stirred at 100° C. for 2.5 hours under argon. For working-up, the reaction solution is mixed with 1 ml of saturated sodium chloride solution, and it is stirred for 30 minutes. The suspension is then suctioned off over Celite and washed with 200 ml of ethyl acetate. The organic phase is washed with saturated sodium chloride solution, dried with sodium sulfate and concentrated by evaporation in a vacuum: 246 mg. Column chromatography on silica gel with pentane-ethyl acetate yields 190 mg of the product.

$^1$H-NMR (300 MHz, DMSO-$d_6$): δ=1.35 (s, 3H), 1.47 (s, 3H), 2.26 (d, 1H), 2.73 (d, 1H), 6.13 (s, 1H), 6.24 (d, 1H), 6.94 (t, 1H), 7.06 (t, 2H), 7.23 (t, 1H), 7.34-7.40 (m, 3H), 7.56 (s, 1H), 8.00 (s, 1H), 13.17 (s, 1H).

1-[(1H-Indazol-4-yl)amino]-4,4-dimethyl-2-(trifluoromethyl)-1,2,3,4-tetrahydronaphthalen-2-ol 190 mg (0.51 mmol) of 1,1,1-trifluoro-4-phenyl-2-[(1H-indazol-4-yl)iminomethyl]-4-methylpentan-2-ol is dissolved in 100 ml of dichloromethane and cooled to −70° C. The solution is mixed over 10 minutes with 9 ml of titanium tetrachloride solution (1 mol in dichloromethane), and it is stirred for 1 hour at −70° C. Then, the cold solution is poured into 200 ml of saturated sodium bicarbonate solution and stirred for 15 minutes. For working-up, the mixture is extracted with dichloromethane, the organic phase is washed with saturated sodium chloride solution, dried with sodium sulfate and concentrated by evaporation in a vacuum: 208 mg. Column chromatography with dichloromethane-methanol yields 53 mg (28%) of the desired product.

$^1$H-NMR (300 MHz, DMSO-$d_6$): δ=1.36 (s, 3H), 1.51 (s, 3H), 2.08 (d, 2H), 5.35 (d, 1H), 5.93 (s, 1H), 6.24 (d, 1H), 6.32 (d, 1H), 6.74 (d, 1H), 7.05-7.12 (m, 2H), 7.21-7.28 (m, 2H), 7.43 (d, 1H), 8.15 (s, 1H), 12.81 (s, 1H).

Example 11

1-[(2-Methylbenzothiazol-7-yl)amino]-4,4-dimethyl-2-(trifluoromethyl)-1,2,3,4-tetrahydronaphthalen-2-ol 1,1,1-Trifluoro-4-phenyl-2-[(2-methylbenzothiazolyl-7-yl)iminomethyl]-4-methylpentan-2-ol $^1$H-NMR (300 MHz, DMSO-$d_6$): δ=1.33 (s, 3H), 1.47 (s, 3H), 2.24 (d, 1H), 2.71 (d, 1H), 2.82 (s, 3H), 6.19, (s, 1H), 6.54 (d, 1H), 6.91 (t, 1H), 7.02 (t, 2H), 7.31-7.40 (m, 3H), 7.51 (s, 1H), 7.78 (d, 1H).

1-[(2-Methylbenzothiazol-7-yl)amino]-4,4-dimethyl-2-(trifluoromethyl)-1,2,3,4-tetrahydronaphthalen-2-ol $^1$H-NMR (300 MHz, DMSO-$d_6$): δ=1.34 (s, 3H), 1.47 (s, 3H), 1.99-2.12 (m, 2H), 2.78 (s, 3H), 5.38 (d, 1H), 5.68 (d, 1H), 6.10 (s, 1H), 6.78 (dd, 1H), 7.07-7.16 (m, 2H), 7.20-7.28 (m, 3H), 7.41 (d, 1H).

Example 12

6-[(1H-Indazol-4-yl)amino]-9,9-dimethyl-7-(trifluoromethyl)-6,7,8,9-tetrahydro-naphtho[1,2-d]-1,3-dioxol-7-ol 4-(1,3-Benzodioxol-4-yl)-1,1,1-trifluoro-2-[1H-indazoly-4-yl)iminomethyl]-4-methylpentan-2-ol $^1$H-NMR (300 MHz, DMSO-$d_6$): δ=1.34 (s, 3H), 1.48 (s, 3H), 2.28 (d, 1H), 2.93 (d, 1H), 5.90 (s, 2H), 6.15 (s, 1H), 6.29 (d, 1H), 6.45 (t, 1H), 6.56 (dd, 1H), 6.62 (d, 1H), 7.23 (t, 1H), 7.40 (d, 1H), 7.74 (s, 1H), 8.00 (s, 1H), 13.17 (s, 1H).

6-[(1H-Indazol-4-yl)amino]-9,9-dimethyl-7-(trifluoromethyl)-6,7,8,9-tetrahydro-naphtho[1,2-d]-1,3-dioxol-7-ol $^1$H-NMR (300 MHz, DMSO-$d_6$): δ=1.43 (s, 3H), 1.55 (s, 3H), 2.04-2.12 (m, 2H), 5.26 (d, 1H), 5.95 (s, 1H), 6.00 (s, 2H), 6.19 (d, 1H), 6.29 (d, 1H), 6.70-6.78 (m, 3H), 7.07 (t, 1H), 8.12 (s, 1H), 12.81 (s, 1H).

Example 13

1-[(2-Methylquinolin-5-yl)amino]-4,4-dimethyl-2-(trifluoromethyl)-1,2,3,4-tetrahydronaphthalen-2-ol 1,1,1-Trifluoro-4-phenyl-2-[(2-methylquinolin-5-yl)iminomethyl]-4-methylpentan-2-ol 120 mg of 2-hydroxy-4-methyl-4-phenyl-2-(trifluoromethyl)pentanal, 67 mg of 5-amino-2-methylquinoline and 163 µl of titanium tetraethylate are stirred in 8 ml of toluene for 2 hours at 100° C. After cooling, the batch is mixed with 2 ml of water, stirred for 15 minutes at room temperature, and concentrated by evaporation in a vacuum. Column chromatography on silica gel with cyclohexane-ethyl acetate yields 111 mg of product.

$^1$H-NMR (300 MHz, CDCl$_3$): δ=1.35 (s, 3H), 1.55 (s, 3H), 2.45 (d, 1H), 2.75 (s, 3H), 2.80 (d, 1H), 5.00 (s, 1H), 6.15 (d, 1H), 6.9-7.1 (m, 3H), 7.30 (m, 3H), 7.35 (d, 1H), 7.45 (t, 1H), 7.90 (d, 1H), 8.35 (d, 1H).

1-[(2-Methylquinolin-5-yl)amino]-4,4-dimethyl-2-(trifluoromethyl)-1,2,3,4-tetrahydronaphthalen-2-ol 5.1 ml of a 1 M titanium tetrachloride-CH$_2$Cl$_2$ solution is added in drops to a solution of 111 mg of 1,1,1-trifluoro-4-phenyl-2-[(2-methylquinolin-5-yl)iminomethyl]-4-methylpentan-2-ol in 84 ml of CH$_2$Cl$_2$ at –78° C. After 1 hour at –78° C., the batch is mixed with saturated NaHCO$_3$ and heated to room temperature. The phases are separated, the aqueous phase is extracted with CH$_2$Cl$_2$, the combined organic phases are dried (Na$_2$SO$_4$) and concentrated by evaporation in a vacuum. Column chromatography on silica gel with cyclohexane-ethyl acetate yields 94 mg of product.

$^1$H-NMR (300 MHz, CDCl$_3$): δ=1.45 (s, 3H), 1.60 (s, 3H), 2.15 (d, 1H), 2.20 (d, 1H), 2.75 (s, 3H), 3.05 (br., 1H), 4.85 (br. d, 1H), 5.20 (d, 1H), 6.85 (d, 1H), 7.10 (t, 1H), 7.20 (d, 1H), 7.30 (t, 1H), 7.40 (d, 1H), 7.50 (d, 1H), 7.55 (t, 1H), 8.05 (d, 1H).

Example 14

1-[(Quinolin-5-yl)amino]-4,4-dimethyl-2-(trifluoromethyl)-1,2,3,4-tetrahydronaphthalen-2-ol 1,1,1-Trifluoro-4-phenyl-2-[(quinolin-5-yl)iminomethyl]-4-methylpentan-2-ol Analogously to Example 13, 120 mg of 2-hydroxy-4-methyl-4-phenyl-2-trifluoromethylpentanal and 61 mg of 5-aminoquinoline are converted into 95 mg of product.

$^1$H-NMR (300 MHz, CDCl$_3$): δ=1.35 (s, 3H), 1.60 (s, 3H), 2.45 (d, 1H), 2.80 (d, 1H), 5.00 (s, 1H), 6.20 (d, 1H), 6.95-7.1 (m, 3H), 7.30 (m, 2H), 7.50 (m, 2H), 8.00 (d, 1H), 8.45 (d, 1H), 8.95 (m, 1H).

1-[(Quinolin-5-yl)amino]-4,4-dimethyl-2-(trifluoromethyl)-1,2,3,4-tetrahydronaphthalen-2-ol Analogously to Example 13, 95 mg of 1,1,1-trifluoro-4-phenyl-2-[(quinolin-5-yl)iminomethyl]-4-methylpentan-2-ol is converted into 90 mg of product.

$^1$H-NMR (300 MHz, CDCl$_3$): δ=1.45 (s, 3H), 1.60 (s, 3H), 2.15 (d, 1H), 2.20 (d, 1H), 3.25 (br., 1H), 4.95 (br. d, 1H), 5.20 (d, 1H), 6.90 (dd, 1H), 7.10 (t, 1H), 7.25-7.35 (m, 4H), 7.40 (d, 1H), 7.60 (m, 2H), 8.15 (d, 1H), 8.90 (m, 1H).

Example 15

5-{[2-Hydroxy-4,4-dimethyl-2-(trifluoromethyl)-1,2,3,4-tetrahydronaphthalen-1-yl]amino}-quinolin-2(1H)-one 5-{[2-Hydroxy-4-methyl-4-phenyl-2-(trifluoromethyl)pentylidene]amino}quinolin-2(1H)-one Analogously to Example 13, 600 mg of 2-hydroxy-4-methyl-4-phenyl-2-(trifluoromethyl)pentanal and 337 mg of 5-aminoquinolin-2(1H)-one (52313) are converted into 570 mg of product.

$^1$H-NMR (300 MHz, CDCl$_3$): δ=1.35 (s, 3H), 1.55 (s, 3H), 2.40 (d, 1H), 2.80 (d, 1H), 4.70 (br. s, 1H), 5.80 (d, 1H), 6.75 (d, 1H), 7.05 (t, 1H), 7.15 (t, 2H), 7.30 (m, 4H), 8.00 (d, 1H), 9.05 (br. s, 1H).

5-{[2-Hydroxy-4,4-dimethyl-2-(trifluoromethyl)-1,2,3,4-tetrahydronaphthalen-1-yl]amino}-quinolin-2(1H)-one Analogously to Example 13, 23 mg of 5-{[2-hydroxy-4-methyl-4-phenyl-2-(trifluoromethyl)pentylidene]amino}quinolin-2(1H)-one is converted into 11 mg of product.

$^1$H-NMR (300 MHz, DMSO-d$_6$): δ=1.35 (s, 3H), 1.50 (s, 3H), 2.00 (d, 1H), 2.10 (d, 1H), 5.35 (d, 1H), 6.05 (s, 1H), 6.20 (d, 1H), 6.40 (d, 1H), 6.55 (t, 1H), 7.25 (m, 2H), 7.45 (d, 1H), 8.20 (d, 1H), 11.60 (br.s, 1H).

Example 16

1-[(2-Methoxyquinolin-5-yl)amino]-4,4-dimethyl-2-(trifluoromethyl)-1,2,3,4-tetrahydronaphthalen-2-ol 1,1,1-Trifluoro-4-phenyl-2-[(2-methoxyquinolin-5-yl)iminomethyl]-4-methylpentan-2-ol Analogously to Example 13, 200 mg of 2-hydroxy-4-methyl-4-phenyl-2-(trifluoromethyl)pentanal and 122 mg of 5-amino-2-methoxyquinoline are converted into 190 mg of product.

$^1$H-NMR (300 MHz, CDCl$_3$): δ=1.35 (s, 3H), 1.55 (s, 3H), 2.45 (d, 1H), 2.80 (d, 1H), 4.10 (s, 3H), 5.00 (s, 1H), 6.10 (d, 1H), 6.90 (d, 1H), 6.95 (t, 1H), 7.05 (t, 2H), 7.30 (d, 2H), 7.35 (t, 1H), 7.70 (d, 1H), 8.30 (d, 1H).

1-[(2-Methoxyquinolin-5-yl)amino]-4,4-dimethyl-2-(trifluoromethyl)-1,2,3,4-tetrahydronaphthalen-2-ol Analogously to Example 13, 185 mg of 1,1,1-trifluoro-4-phenyl-2-[(2-methoxyquinolin-5-yl)iminomethyl]-4-methylpentan-2-ol is converted into 127 mg of product.

$^1$H-NMR (300 MHz, CDCl$_3$): δ=1.45 (s, 3H), 1.60 (s, 3H), 2.15 (d, 1H), 2.20 (d, 1H), 3.10 (s, 1H), 4.10 (s, 3H), 4.75 (br. d, 1H), 5.20 (d, 1H), 6.75 (d, 1H), 6.85 (d, 1H), 7.1 (t, 1H), 7.25-7.45 (m, 4H), 7.50 (t, 1H), 8.00 (d, 1H).

Example 17

1-[(Phenylamino]-4,4-dimethyl-2-(trifluoromethyl)-1,2,3,4-tetrahydronaphthalen-2-ol 1,1,1-Trifluoro-4-phenyl-2-[(phenyl)iminomethyl]-4-methylpentan-2-ol Analogously to Example 1, 200 mg of 2-hydroxy-4-methyl-4-phenyl-2-(trifluoromethyl)pentanal and 64 µl of aniline are converted into 180 mg of product.

$^1$H-NMR (300 MHz, CDCl$_3$): δ=1.35 (s, 3H), 1.50 (s, 3H), 2.35 (d, 1H), 2.70 (d, 1H), 5.05 (s, 1H), 6.65 (d, 2H), 7.05 (t, 1H), 7.15-7.30 (m, 7H).

1-[(Phenylamino]-4,4-dimethyl-2-(trifluoromethyl)-1,2,3,4-tetrahydronaphthalen-2-ol 9.6 ml of a 1 M titanium tetrachloride-CH$_2$Cl$_2$ solution is added in drops to a solution of 175 mg of 1,1,1-trifluoro-4-phenyl-2-[(phenyl)iminomethyl]-4-methylpentan-2-ol in 160 ml of CH$_2$Cl$_2$ at −78° C. First, it is stirred for 1 hour at −78° C., and after another 10 ml of titanium tetrachloride-CH$_2$Cl$_2$ solution is added, it is stirred for 60 hours at room temperature.

The batch is mixed with saturated NaHCO$_3$, the phases are separated, the aqueous phase is extracted with CH$_2$Cl$_2$, the combined organic phases are dried (Na$_2$SO$_4$) and concentrated by evaporation in a vacuum. Column chromatography on silica gel with cyclohexane-ethyl acetate yields 45 mg of product.

$^1$H-NMR (CDCl$_3$): δ=1.40 (s, 3H), 1.50 (s, 3H), 2.00 (d, 1H), 2.20 (d, 1H), 3.40 (s, 1H), 3.80 (d, 1H), 4.95 (d, 1H), 6.80 (d, 2H), 6.85 (t, 1H), 7.15 (m, 1H), 7.20-7.30 (m, 4H), 7.40 (d, 1H).

Example 18

4-{[2-Hydroxy-4,4-dimethyl-2-(trifluoromethyl)-1,2,3,4-tetrahydronaphthalen-1-yl]amino}-2-(trifluoromethyl)benzonitrile 1,1,1-Trifluoro-4-phenyl-2-[(4-cyano-3-(trifluoromethyl)phenyl)iminomethyl]-4-methylpentan-2-ol Analogously to Example 13, 120 mg of 2-hydroxy-4-methyl-4-phenyl-2-(trifluoromethyl)pentanal and 78 mg of 4-cyano-3-(trifluoromethyl)aniline are converted into 71 mg of product.

$^1$H-NMR (300 MHz, CDCl$_3$): δ=1.35 (s, 3H), 1.55 (s, 3H), 2.40 (d, 1H), 2.75 (d, 1H), 4.55 (s, 1H), 6.75 (dd, 1H), 6.95 (d, 1H), 7.10 (t, 1H), 7.20 (m, 3H), 7.30 (m, 2H), 7.70 (d, 1H).

4-{[2-Hydroxy-4,4-dimethyl-2-(trifluoromethyl)-1,2,3,4-tetrahydronaphthalen-1-yl]amino}-2-(trifluoromethyl)benzonitrile Analogously to Example 13, 71 mg of 1,1,1-trifluoro-4-phenyl-2-[(4-cyano-3-(trifluoromethyl)phenyl)iminomethyl]-4-methylpentan-2-ol is converted into 58 mg of product.

$^1$H-NMR (300 MHz, CDCl$_3$): δ=1.40 (s, 3H), 1.50 (s, 3H), 2.15 (s, 2H), 2.60 (s, 1H), 5.05 (d, 1H), 5.10 (d, 1H), 6.85 (dd, 1H), 7.00 (d, 1H), 7.20 (s, 2H), 7.35 (m, 1H), 7.40 (d, 1H), 7.60 (d, 1H).

Example 19

5-{[5-Bromo-2-hydroxy-4,4-dimethyl-2-(trifluoromethyl)-1,2,3,4-tetrahydronaphthalen-1-yl]amino}-isoquinolin-1(2H)-one (2-Bromophenyl)-acetonitrile 25 g (100 mmol) of 2-bromobenzyl bromide is mixed in 100 ml of N,N-dimethylformamide and 64 ml of water with 9.75 g (150 mmol) of potassium cyanide and stirred overnight at room temperature. The reaction mixture is poured into ice water. After 3× extraction with methyl-tert butyl ether, the combined organic extracts are washed with brine, dried, and the solvent is spun off. The residue is chromatographed on silica gel (mobile solvent ethyl acetate/hexane). 18.9 g (96.4%) of the desired compound is obtained.

$^1$H-NMR (300 MHz, CDCl$_3$): δ=3.85 (2H), 7.23 (1H), 7.48 (1H), 7.55 (1H), 7.62 (1H).

2-(2-Bromophenyl)-2-methyl-propionitrile 18.9 g (96.41 mmol) of (2-bromophenyl)-acetonitrile and 31.41 g (221.74 mmol) of methyl iodide are dissolved in 150 ml of N,N-dimethylformamide. At 0° C., 8.87 g (221.74 mmol) of sodium hydride (as 60% suspension in oil) is added in portions, and the batch is stirred overnight at room temperature. The reaction mixture is poured into ice water and worked up as usual. Since the compound that is isolated after chromatography (20.9 g) still contains 2-(2-bromophenyl)-propionitrile in addition to the desired product, the entire amount is reacted another time with the same amounts of reagent. This reaction also yields only material that still contains mono-methyl compound. After another alkylation with 15 g of methyl iodide and 4.45 g of sodium hydride in 150 ml of N,N-dimethylformamide, 18.57 g of the desired compound is isolated.

$^1$H-NMR (300 MHz, CDCl$_3$): δ=1.91 (6H), 7.20 (1H), 7.35 (1H), 7.49 (1H), 7.68 (1H).

2-(2-Bromophenyl)-2-methyl-propanal 18.57 g (82.21 mmol) of 2-(2-bromophenyl)-2-methyl-propionitrile is reduced in 325 ml of toluene with 102.72 ml of a 1.2 M DIBAH solution in toluene, specifically as described in Example 3. After working-up, 18.17 g (97.34%) of the desired aldehyde is isolated, which is incorporated in crude form into the next stage.

$^1$H-NMR (300 MHz, CDCl$_3$): δ=1.51 (6H), 7.20 (1H), 7.33-7.45 (2H), 7.61 (1H), 9.8 (1H).

(E/Z)-4-(2-Bromophenyl)-4-methylpent-2-enoic acid ethyl ester 18.17 g (80.02 mmol) of 2-(2-bromophenyl)-2-methyl-propanal is subjected analogously to the Horner-Wittig reaction that is described in Example 3. After the working-up and subsequent chromatography on silica gel (mobile solvent ethyl acetate/hexane) described there, 22.3 g (81.67%) of the desired product is isolated.

(E/Z)-4-(2-Bromophenyl)-4-methylpent-2-enoic acid 22.3 g (65.349 mmol) of (E/Z)-4-(2-bromophenyl)-4-methylpent-2-enoic acid ethyl ester is saponified with 650 ml of sodium hydroxide solution (1N in ethanol/water 2:1) as described in Example 3. After the working-up, 14.32 g (69.9%) of the desired acid is isolated.

4-(2-Bromophenyl)-4-methyl-2-oxo-pentanoic acid 14.32 g (45.72 mmol) of (E/Z)-4-(2-bromophenyl)-4-methylpent-2-enoic acid is reacted with the aid of sulfuric acid in glacial acetic acid, as described in Example 3, to form the desired ketocarboxylic acid. 13 g (99.6%) is isolated.
$^1$H-NMR (300 MHz, CDCl$_3$): δ=1.60 (6H), 3.91 (2H), 7.09 (1H), 7.30 (1H), 7.49 (1H), 7.57 (1H).

4-(2-Bromophenyl)-4-methyl-2-oxo-pentanoic acid ethyl ester 13 g (45.59 mmol) of 4-(2-bromophenyl)-4-methyl-2-oxo-pentanoic acid is reacted with ethanol and concentrated sulfuric acid to form ester. After implementation and working-up (see Example 3), 13.01 g (91.1%) of the desired compound is obtained after chromatography on silica gel.
$^1$H-NMR (300 MHz, CDCl$_3$): δ=1.30 (3H), 1.60 (6H), 3.72 (2H), 4.17 (2H), 7.05 (1H), 7.27 (1H), 7.47 (1H), 7.57 (1H).

4-(2-Bromophenyl)-4-methyl-2-(trifluoromethyl)-pentane-1,2-diol 13 g (41.5 mmol) of 4-(2-bromophenyl)-4-methyl-2-oxo-pentanoic acid ethyl ester is reacted with Rupperts reagent, as described in Example 3. After working-up and chromatography on silica gel (mobile solvent ethyl acetate/hexane), 16.15 g (85.6%) of the desired compound is isolated.

73.6 ml (88.39 mmol) of a DIBAH solution (1.2 M in toluene) is added in drops (35 minutes) to a solution of 6.1 g (35.45 mmol) of the above-described trifluoromethyl alcohol in 148 ml of toluene at −10° C. After 30 minutes of stirring at a temperature of between −10° C. and −5° C., 24.2 ml of isopropanol and then water are carefully added in drops at −10° C. After two hours of vigorous stirring at room temperature, the precipitate that is produced is suctioned off on a G4 frit, washed with ethyl acetate, and the filtrate is spun in until a dry state is reached. The residue (regioisomeric mixture of the two silyl ethers; 14.5 g=95.4%=35.08 mmol) is reacted with tetrabutylammonium fluoride-trihydrate in tetrahydrofuran at room temperature as described in Example 3. After the conventional working-up and chromatography, 5.26 g of the desired compound is isolated.
$^1$H-NMR (300 MHz, CDCl$_3$): δ=1.62 (3H), 1.70 (3H), 2.19 (1H), 2.90-3.01 (2H), 3.27-3.89 (1H), 3.59 (1H), 7.09 (1H), 7.30 (1H), 7.53 (1H), 7.60 (1H).

4-(2-Bromophenyl)-2-hydroxy-4-methyl-2-trifluoromethyl-pentanal 2 g (5.86 mmol) of 4-(2-bromophenyl)-2-hydroxy-4-methyl-2-trifluoromethyl-pentan-1-ol is oxidized with SO$_3$-pyridine complex, as described in Example 1. 1.72 g (86.8 mmol) of the desired aldehyde is isolated.
$^1$H-NMR (300 MHz, CDCl$_3$): δ=1.60 (6H), 2.29 (1H), 3.65 (1H), 3.78 (1H), 7.09 (1H), 7.25 (1H), 7.34 (1H), 7.58 (1H), 9.20 (1H).

4-{[4-(2-Bromophenyl)-2-hydroxy-4-methyl-2-(trifluoromethyl)pentylidene]-amino}}isoquinolin-1 (2H)-one 200 mg (0.589 mmol) of 4-(2-bromophenyl)-2-hydroxy-4-methyl-2-trifluoromethyl-pentanal is stirred for five days at room temperature with 94.3 mg (0.589 mmol) of 5-aminoisoquinolin-1(2H)-one (Example 2) in 0.86 ml of glacial acetic acid. After the conventional working-up and chromatography on silica gel (mobile solvent ethyl acetate/hexane), 170.8 mg (60.2%) of the desired compound is isolated.
$^1$H-NMR (300 MHz, CDCl$_3$): δ=1.59 (3H), 1.70 (3H), 2.29 (1H), 3.86 (1H), 4.89 (1H), 6.58 (1H), 6.70-6.90 (3H), 7.15-7.37 (3H), 7.48 (1H), 7.59 (1H), 8.30 (1H), 11.00 (1H).

5-{[5-Bromo-2-hydroxy-4,4-dimethyl-2-(trifluoromethyl)-1,2,3,4-tetrahydronaphthalen-1-yl]amino}-isoquinolin-1(2H)-one 50 mg (0.104 mmol) of 4-{[4-(2-bromophenyl)-2-hydroxy-4-methyl-2-(trifluoromethyl)pentylidene]amino}}isoquinolin-1(2H)-one is mixed with one milliliter of a 1 M solution of BBr$_3$ in dichloromethane and stirred for one and three quarters hours at room temperature. After the conventional working-up (see Example 2) and after chromatography on silica gel (mobile solvent methanol/dichloromethane), 49.2 mg (98.4%) of the desired compound is obtained.
$^1$H-NMR (300 MHz, DMSO-d$_6$): δ=1.67 (3H), 1.79 (3H), 2.09 (1H), 2.21 (1H), 5.48 (1H), 6.02 (1H), 6.26 (1H), 6.81 (1H), 7.00-7.30 (5H), 7.49-7.62 (2H), 11.25 (1H).

With use of the corresponding starting aldehydes and amines that are described in the examples above, the following cyclic compounds are produced via the imines.

Example 20

5-Bromo-1-[(1H-indazol-4-yl)amino]-4,4-dimethyl-2-(trifluoromethyl)-1,2,3,4-tetrahydronaphthalen-2-ol The product is obtained after cyclization, as described in Example 19.
$^1$H-NMR (300 MHz, CD$_3$OD): δ=1.73 (3H), 1.88 (3H), 2.10-2.30 (2H), 5.30 (1H), 6.39 (1H), 6.85 (1H), 7.01 (1H), 7.24 (1H), 7.48 (1H), 7.58 (1H), 8.13 (1H).

Example 21

5-Bromo-4,4-dimethyl-1-propylamino-2-(trifluoromethyl)-1,2,3,4-tetrahydronaphthalen-2-ol The product is obtained after cyclization, as described in Example 19.
$^1$H-NMR (300 MHz, CD$_3$OD): δ=0.90-1.02 (3H), 1.48-1.60 (2H), 1.63 (3H), 1.70 (3H), 1.91 (1H), 2.15 (1H), 2.65-2.78 (2H), 2.91-3.05 (1H), 7.12 (1H), 7.45 (1H), 7.56 (1H).

Example 22

5-Bromo-1-[(3-hydroxypropyl)amino]-4,4-dimethyl-2-(trifluoromethyl)-1,2,3,4-tetrahydronaphthalen-2-ol The product is obtained after cyclization, as described in Example 19.
$^1$H-NMR (300 MHz, CD$_3$OD): δ=1.63 (3H), 1.71 (3H), 1.94 (1H), 1.99-2.11 (2H), 2.17 (1H), 2.84-2.98 (1H), 3.09-3.20 (1H), 3.55 (2H), 7.13 (1H), 7.49 (1H), 7.59 (1H).

Example 23

5-{[8-Fluoro-2,5-dihydroxy-4,4-dimethyl-2-(trifluoromethyl)-1,2,3,4-tetrahydronaphthalen-1-yl]amino}-isoquinolin-1(2H)-one The product is obtained after cyclization, as described in Example 19.
MS (ES+, ACN/H$_2$O+0.01% TFA): 437 (100%)

Example 24

4-{[7-Chloro-2,5-dihydroxy-4,4-dimethyl-2-(trifluoromethyl)-1,2,3,4-tetrahydronaphthalen-1-yl]amino}-6-fluoro-2,3-dihydroisoindol-1-one The product is obtained after cyclization, as described in Example 19.
$^1$H-NMR (300 MHz, CD$_3$OD): δ=1.58 (3H), 1.65 (3H), 2.01-2.10 (2H), 4.20-4.45 (2H), 5.10 (1H), 6.70-6.89 (4H).

Example 25

5-{[6-Fluoro-2-hydroxy-5-methoxy-4,4-dimethyl-2-(trifluoromethyl)-1,2,3,4-tetrahydronaphthalen-1-yl]amino}-isoquinolin-1(2H)-one The product is obtained after cyclization, as described in Example 3.
$^1$H-NMR (300 MHz, CD$_3$OD): δ=1.53 (3H), 1.58 (3H), 2.14 (2H), 3.99 (3H), 5.15 (1H), 6.84 (1H), 6.95 (1H), 7.00-7.10 (2H), 7.18 (1H), 7.39 (1H), 7.69 (1H).

The product that is obtained is separated into its enantiomers (Chiralpak AD 20µ; mobile solvent hexane/ethanol/DEA), and the latter is then used in the ether cleavage (analogously to Example 3):

5-{[6-Fluoro-2,5-dihydroxy-4,4-dimethyl-2-(trifluoromethyl)-1,2,3,4-tetrahydronaphthalen-1-yl]amino}-isoquinolin-1(2H)-one (cis, Enantiomer A)

$^1$H-NMR (300 MHz, CD$_3$OD): δ=1.62 (3H), 1.72 (3H), 2.04-2.21 (2H), 5.13 (1H), 6.75-6.92 (3H), 7.05 (1H), 7.18 (1H), 7.39 (1H), 7.69 (1H).

5-{[6-Fluoro-2,5-dihydroxy-4,4-dimethyl-2-(trifluoromethyl)-1,2,3,4-tetrahydronaphthalen-1-yl]amino}-isoquinolin-1(2H)-one (cis, Enantiomer B)

$^1$H-NMR (300 MHz, CD$_3$OD): δ=1.62 (3H), 1.72 (3H), 2.04-2.21 (2H), 5.13 (1H), 6.75-6.92 (3H), 7.05 (1H), 7.18 (1H), 7.39 (1H), 7.69 (1H).

Example 26

4-{[6-Fluoro-2,5-dihydroxy-4,4-dimethyl-2-(trifluoromethyl)-1,2,3,4-tetrahydronaphthalen-1-yl]amino}-2,3-dihydroisoindol-1-one The product is obtained after cyclization and ether cleavage, as described in Example 3.
$^1$H-NMR (300 MHz, CD$_3$OD): δ=1.60 (3H), 1.69 (3H), 1.99-2.20 (2H), 4.23-4.45 (2H), 5.13 (1H), 6.80-7.03 (3H), 7.18 (1H), 7.39 (1H).

Example 27

6-Chloro-1-[(1H-indazol-4-yl)amino]-4,4-dimethyl-2-(trifluoromethyl)-1,2,3,4-tetrahydronaphthalene-2,5-diol 3-Chloro-2-methoxybenzylcyanide 39.4 g (221.3 mmol) of NBS and 100 mg of benzoyl peroxide are added to 31.6 g (201.7 mmol) of 3-chloro-2-methoxytoluene in 500 ml of CCl$_4$. It is refluxed over 16 hours, allowed to cool and filtered. Solvent is removed from the filtrate, and the filtrate is dissolved in 214 ml of N,N-dimethylformamide and 142 ml of water. 20.9 g (322.1 mmol) of potassium cyanide is added at 0° C. and stirred over 16 hours. The reaction mixture is diluted with water and extracted several times with tert-butyl-methyl ether. The organic phase is washed several times with saturated sodium chloride solution and dried on sodium sulfate. The solvent is removed in a vacuum and after chromatographic purification on silica gel (hexane/ethyl acetate 20%), 29.7 g of product is obtained.
$^1$H-NMR (CDCl$_3$): δ=3.76 (s, 2H), 3.95 (s, 3H), 7.08 (t, 1H), 7.31 (d, 1H), 7.37 (d, 1H).

4-(3-Chloro-2-methoxy-phenyl)-4-methyl-2-(trifluoromethyl)-pentane-1,2-diol 29.7 g (163.7 mmol) of 4-chloro-2-methoxybenzylcyanide and 46.5 g (327.4 mmol) of methyl iodide in 260 ml DMF are mixed at 0° C. in portions with 13.2 g (327.4 mmol) of sodium hydride (60% in oil). It is stirred overnight and then mixed with water and ethyl acetate. The phases are separated, and the aqueous phase is extracted several times with ethyl acetate. It is washed with water and saturated sodium chloride solution, dried with sodium sulfate, and concentrated by evaporation in a vacuum. After chromatography on silica gel (hexane/ethyl acetate 95:5), 32.4 g of 2-(4-chloro-2-methoxy-phenyl)-2-methylpropionitrile is obtained as a colorless oil. 7 g (33.4 mmol) of the nitrile is slowly mixed in toluene at −78° C. with 41.6 ml (50.1 mmol) of diisobutylaluminum hydride solution (20% in toluene), and after 3 hours at −78° C., 5.55 ml of isopropanol is added in drops. It is allowed to heat to −5° C., and 380 ml of a 10% aqueous tartaric acid solution is added. After dilution with ether, it is stirred vigorously, the organic phase is separated, and the aqueous phase is extracted several times with ether. It is washed with brine, dried with sodium sulfate and concentrated by evaporation in a vacuum. After chromatography on silica gel (hexane/ethyl acetate 95:5), 7.1 g of 2-(4-chloro-methoxy-phenyl)-2-methylpropanal is obtained as a colorless oil. A solution of 8.95 g (33.4 mmol) of 2-diethylphosphono-2-ethoxyacetic acid-ethyl ester in 30 ml of tetrahydrofuran is mixed while being cooled with ice within 20 minutes with 19 ml (38 mmol) of a 2 M solution of lithium diisopropylamide in tetrahydrofuran-heptane-toluene, and it is stirred for 15 minutes at 0° C. Within 30 minutes, a solution of 7.1 g (33.4 mmol) of 2-(3-chloro-2-methoxyphenyl)-2-methylpropanal in 27 ml of tetrahydrofuran is added in drops at 0° C. After 20 hours at room temperature, water is added, and it is extracted several times with ether and ethyl acetate. It is washed with saturated ammonium chloride solution, dried (Na$_2$SO$_4$) and concentrated by evaporation. The crude product is purified by column chromatography on silica gel (hexane/ethyl acetate 10%), and 8.5 g of 4-(3-chloro-2-methoxy-phenyl)-4-methyl-3-ethoxy-2-ene-valeric acid ethyl ester is obtained. The intermediate product is saponified with 80 ml of 3 M sodium hydroxide solution/160 ml of ethanol. 5.3 g of acid, which is stirred with 80 ml of 2N sulfuric acid at 90° C. over 16 hours, is obtained. After cooling, it is made basic with potassium carbonate, washed with ether, and acidified with hydrochloric acid. After extraction with ethyl acetate, washing with saturated sodium chloride solution and removal of the solvent, 4.0 g of 4-(3-chloro-2-methoxyphenyl)-4-methyl-2-oxo-valeric acid is obtained. 6.6 g (24.3 mmol) of 4-(3-chloro-2-methoxy-phenyl)-4-methyl-2-oxo-valeric acid and 2.74 ml (51.4 mmol) of sulfuric acid (96%) are refluxed in 150 ml of ethanol for 5 hours. The batch is concentrated by evaporation in a vacuum, and the residue is taken up in saturated sodium bicarbonate solution. It is extracted several times with ethyl acetate, washed with saturated sodium bicarbonate solution, dried (sodium sulfate) and concentrated by evaporation in a vacuum. After chromatographic purification on silica gel (hexane/ethyl acetate 10%), 5.9 g of 4-(3-chloro-2-methoxy-phenyl)-4-methyl-2-oxo-valeric acid-ethyl ester is obtained. This ester and 3.4 g (23.8 mmol) of (trifluoromethyl)-trimethylsilane in 34 ml of THF are mixed with 49 mg of tetrabutylammonium fluoride at 0° C. It is stirred for 16 hours at room temperature, and then the reaction mixture is added to water. It is extracted several times with ethyl acetate, washed with saturated sodium chloride solution, dried with sodium sulfate, and concentrated by evaporation in a vacuum. 2.96 g of 4-(3-chloro-2-methoxy-phenyl)-2-hydroxy-4-methyl-2-trifluoromethyl-valeric acid-ethyl ester is obtained as a yellow oil. This oil is mixed in 24 ml of diethyl ether at 0° C. with 510 mg of lithium aluminum hydride and stirred for 4 more hours at room temperature. 20 ml of saturated sodium bicarbonate solution is carefully added to the batch at 0° C., and it is vigorously stirred for 1 more hour. It is extracted several times with methyl tert-butyl ether, washed with water and saturated sodium chloride solution, dried with sodium sulfate and concentrated by evaporation in a vacuum. The crude product is mixed in 33 ml of THF with 1.83 (5.79 mmol) of tetrabutylammonium fluoride trihydrate, and it is stirred for 16 hours. It is poured into ice water, extracted several times with methyl tert-butyl ether, washed with saturated sodium chloride solution, dried with sodium sulfate and concentrated by evaporation in a vacuum. After chromatographic purification on silica gel (hexane/ethyl acetate 25%), 1.81 g of 4-(3-chloro-2-methoxy-phenyl)-4-methyl-2-trifluoromethyl-pentane-1,2-diol is obtained.

$^1$H-NMR (300 MHz, CDCl$_3$): δ=1.47 (s, 3H), 1.56 (s, 3H), 2.21 (d, 1H), 2.54 (d, 1H), 2.91 (s, 1H), 3.31 (dd, 1H), 3.42 (d, 1H), 4.01 (s, 3H), 7.00 (t, 1H), 7.20-7.35 (m, 2H)

4-(3-Chloro-2-methoxy-phenyl)-2-hydroxy-4-methyl-2-(trifluoromethyl)-pentanal 1.87 g (18.5 mmol) of triethylamine and, in portions over 10 minutes, 1.17 g (7.4 mmol) of pyridine SO$_3$ complex are added to 1.2 g (3.7 mmol) of diol in 24 ml of dichloromethane and 6.4 ml of DMSO. It is stirred over 5 hours, and 30 ml of saturated ammonium chloride solution is added. The mixture is stirred for another 15 minutes, the phases are separated, and it is extracted with methyl tert-butyl ether. It is washed with water and dried on sodium sulfate. The solvent is removed in a vacuum, and after chromatographic purification on silica gel (hexane/ethyl acetate, 0-50%), 0.98 g of product is obtained.

$^1$H-NMR (CDCl$_3$): δ=1.44 (s, 3H), 1.50 (s, 3H), 2.29 (d, 2H), 3.28 (d, 1H), 3.55 (s, 1H), 4.01 (s, 3H), 6.95 (t, 1H), 7.07 (dd, 1H), 7.30 (dd, 1H), 8.90 (s, 1H).

1,1,1-Trifluoro-4-(3-chloro-2-methoxyphenyl)-2-[(1H-indazol-4-yl)iminomethyl]-4-methylpentan-2-ol 125 mg (0.385 mmol) of 4-(3-chloro-2-methoxy-phenyl)-2-hydroxy-4-methyl-2-(trifluoromethyl)-pentanal is mixed in 0.7 ml of glacial acetic acid with 51.3 mg (0.385 mmol) of 4-aminoindazole, and it is stirred overnight at room temperature. After concentration by evaporation until a dry state is reached, it is chromatographed on a Flashmaster. 11.9 mg (74.1%) of the desired compound is isolated.

6-Chloro-1-[(1H-indazol-4-yl)amino]-5-methoxy-4,4-dimethyl-2-(trifluoromethyl)-1,2,3,4-tetrahydronaphthalen-2-ol 116.9 mg (0.285 mmol) of imine is dissolved in 2.6 ml of dichloromethane and mixed at −25° C. with 1.13 ml of a 1 M solution of titanium tetrachloride in dichloromethane. After six more hours of stirring between −20° C. and +10° C., it is mixed with saturated sodium bicarbonate solution and extracted with ethyl acetate. After drying with sodium sulfate, the organic phases are spun in until a dry state is reached. Chromatography of the residue on the Flashmaster yields 91.9 mg (78.6%) of the desired cyclic compound (together with the Deschloro compound).

6-Chloro-1-[(1H-indazol-4-yl)amino]-4,4-dimethyl-2-(trifluoromethyl)-1,2,3,4-tetrahydronaphthalene-2,5-diol 69.9 mg (0.159 mmol) of 6-chloro-1-[(1H-indazol-4-yl)amino]-5-methoxy-4,4-dimethyl-2-(trifluoromethyl)-1,2,3,4-tetrahydronaphthalen-2-ol is mixed with 1.45 ml of a one-molar solution of BBr$_3$ in dichloromethane, and it is stirred for five hours at room temperature. After the conventional working-up, the residue is chromatographed on a Flashmaster. 28.1 mg (41.5%) of the desired compound is isolated.

Melting point: 112-120° C.

Example 28 cis-7-Chloro-1-[(2-methylquinazolin-5-yl)amino]-4,4-dimethyl-2-(trifluoromethyl)-1,2,3,4-tetrahydronaphthalen-2-ol 4-(4-Chlorophenyl)-2-hydroxy-4-methyl-2-trifluoromethyl-pentanal 2-(4-Chlorophenyl)-2-methylpropanal 10 g of 4-chlorobenzyl cyanide and 14.3 ml of methyl iodide in 140 ml of DMF are mixed at 0° C. in portions with sodium hydride (60% in oil). It is stirred overnight and then mixed with water and ethyl acetate. The phases are separated, and the aqueous phase is extracted with ethyl acetate.

It is thoroughly extracted with water, washed with brine, dried with sodium sulfate and concentrated by evaporation in a vacuum. After chromatography on silica gel (hexane/ethyl acetate 95:5), 11.73 g of 2-(4-chlorophenyl)-2-methylpropionitrile is obtained as a colorless oil. The latter is slowly mixed in toluene at −78° C. with 55.4 ml of diisobutylaluminum hydride solution (20% in toluene), and after 4 hours at −78° C., 50 ml of ethyl acetate was added in drops. It is stirred overnight while being heated to room temperature, and water is added. After filtration through diatomaceous earth, the phases are separated, and the aqueous phase is extracted with ethyl acetate. It is washed with water and brine, dried with sodium sulfate, and concentrated by evaporation in a vacuum. After chromatography on silica gel (hexane/ethyl acetate 95:5), 10.2 g of 2-(4-chlorophenyl)-2-methylpropanal is obtained as a colorless oil.

$^1$H-NMR (300 MHz, CDCl$_3$), δ=1.46 (s, 6H), 7.20 (d, 1H), 7.29-7.43 (m, 3H), 9.48 (s, 1H)

4-(4-Chlorophenyl)-4-methyl-2-oxo-valeric acid

A solution of 15.04 g of 2-diethylphosphono-2-ethoxyacetic acid-ethyl ester in 50 ml of tetrahydrofuran is mixed with 30 ml of a 2 M solution of lithium diisopropylamide in tetrahydrofuran-heptane-toluene while being cooled with ice within 20 minutes, and it is stirred for 15 minutes at 0° C. Within 30 minutes, a solution of 10.2 g of 2-(4-chlorophenyl)-2-methylpropanal in 50 ml of tetrahydrofuran is added thereto at 0° C. After 20 hours at room temperature, 2N sulfuric acid is added, it is extracted with ethyl acetate, dried (Na$_2$SO$_4$) and concentrated by evaporation. The crude product is saponified with 200 ml of 2 M sodium hydroxide solution/400 ml of ethanol. 13.8 g of acid, which is refluxed for 3 hours with 300 ml of 2N sulfuric acid and 100 ml of glacial acetic acid while being stirred vigorously, is obtained. After extraction with ethyl acetate and washing with water, 10.9 g of 4-(4-chlorophenyl)-4-methyl-2-oxo-valeric acid is obtained as a red oil.

$^1$H-NMR (300 MHz, CDCl$_3$), δ=1.47 (s, 6H), 3.28 (s, 2H), 7.28 (m, 4H), 7.73 (bs, 1H)

4-(4-Chlorophenyl)-4-methyl-2-(trifluoromethyl)-pentane-1,2-diol

Analogously to the synthesis of 4-(3-chloro-2-methoxyphenyl)-2-hydroxy-4-methyl-2-trifluoromethyl-pentanal (Example 27), 4.22 g of 4-(4-chlorophenyl)-4-methyl-2-(trifluoromethyl)pentane-1,2-diol is obtained as a colorless oil by esterification of 10.9 g of 4-(4-chlorophenyl)-4-methyl-2-oxo-valeric acid in ethanol/sulfuric acid, reaction of the product with (trifluoromethyl)trimethylsilane and tetrabutylammonium fluoride and reduction of the formed hydroxy ester with lithium aluminum hydride.

$^1$H-NMR (CDCl$_3$), δ (ppm)=1.39 (s, 3H), 1.49 (s, 3H), 2.07 (d, 1H), 2.19 (d, 1H), 2.83 (bs, 1H), 3.27 (d, 1H), 3.41 (d, 1H), 7.26-7.38 (m, 4H).

4-(4-Chlorophenyl)-2-hydroxy-4-methyl-2-(trifluoromethyl)-pentanal 6.8 ml (33.3 mmol) of triethylamine and, in portions over 20 minutes, 1.5 g of pyridine SO$_3$ complex are added to 2 g (6.7 mmol) of diol in 50 ml of dichloromethane and 22 ml of DMSO. It is stirred over 5 hours, and 40 ml of saturated ammonium chloride solution is added. The mixture is stirred for another 15 minutes, the phases are separated, and it is extracted with dichloromethane. It is washed with water and dried on sodium sulfate. The solvent is removed in a vacuum, and after chromatography on silica gel (hexane/ethyl acetate 0-30%), 1.27 g of product is obtained.

$^1$H-NMR (300 MHz, CDCl$_3$): δ=1.34 (s, 3H), 1.44 (s, 3H), 2.34 (d, 2H), 2.66 (d, 1H), 3.64 (s, 1H), 7.23-7.31 (m, 4H), 8.90 (s, 1H).

7-Chloro-1-[(2-methylquinazolin-5-yl)amino]-4,4-dimethyl-2-(trifluoromethyl)-1,2,3,4-tetrahydronaphthalen-2-ol Starting from the above-described aldehyde, the desired compound is synthesized via the imine as described in Example 83.

$^1$H-NMR (300 MHz, CDCl$_3$): δ=1.45 (s, 3H), 1.63 (s, 3H), 2.19 (d, 1H), 2.31 (d, 1H), 2.87 (s, 3H), 5.05 (d, 1H), 5.98 (d, 1H), 6.78 (d, 1H), 7.28-7.37 (m, 4H), 7.76 (t, 1H), 9.36 (s, 1H).

Example 29

5,8-Difluoro-1-[(2-methylquinazolin-5-yl)amino]-4,4-dimethyl-2-(trifluoromethyl)-1,2,3,4-tetrahydronaphthalen-2-ol 4-(2,5-Difluorophenyl)-4-methyl-2-trifluoromethyl-pentane-1,2-diol 5.4 g (15.5 mmol) of 4-(2,5-difluorophenyl)-2-hydroxy-4-methyl-2-trifluoromethyl-valeric acid ethyl ester (WO 02/10143) is dissolved at 0° C. in diethyl ether and mixed within 20 minutes with 1.76 g (46.5 mmol) of lithium aluminum hydride. It is allowed to stir at room temperature for 4 hours, and then enough saturated NaHCO$_3$ solution is carefully added until no more gas generation can be observed. The mixture is diluted with ethyl acetate, stirred for 15 more minutes, and then the formed precipitate is filtered off. It is concentrated by evaporation and chromatographed on silica gel with hexane/ethyl acetate (50%). 2.45 g of 2,5-difluorophenyl)-4-methyl-2-trifluoromethyl-pentane-1,2-diol is obtained as a weakly yellowish crystallizing oil.

4-(2,5-Difluorophenyl)-2-hydroxy-4-methyl-2-trifluoromethyl-pentanal 800 mg (2.8 mmol) of 4-(2,5-difluorophenyl)-4-methyl-2-trifluoromethyl-pentane-1,2-diol is introduced into 20 ml of dichloromethane, and at 0° C., 9.5 ml of DMSO and 1.95 ml of triethylamine are added. The solution is slowly mixed with 1.34 g (8.4 mmol) of SO$_3$-pyridine complex, and it is stirred for 2 hours at 0° C. The mixture is dispersed between saturated ammonium chloride solution and MTBE, the phases are separated, and the aqueous phase is extracted with MTBE. The combined organic phases are washed with water and saturated NaCl solution and dried with NaSO$_4$. It is concentrated by evaporation and chromatographed on silica gel with hexane/ethyl acetate (30%). 710 mg of the desired product is obtained.

$^1$H-NMR (300 MHz, CDCl$_3$): δ=1.41 (s, 3H), 1.48 (s, 3H), 2.39 (d, 2H), 3.02 (d, 1H), 3.61 (s, 1H), 6.84-7.18 (m, 3H), 9.23 (s, 1H).

5,8-Difluoro-1-[(2-methylquinazolin-5-yl)amino]-4,4-dimethyl-2-(trifluoromethyl)-1,2,3,4-tetrahydronaphthalen-2-ol The desired compound is synthesized via the imine (diastereomer A).

$^1$H-NMR (300 MHz, CDCl$_3$): δ=1.51 (s, 3H), 1.68 (s, 3H), 2.11 (d, J=15 Hz, 1H), 2.23 (d, J=15 Hz, 1H), 2.84 (s, 3H), 4.23 (s, br, 1H), 4.84 (d, J=8 Hz, 1H), 5.32 (d, J=8 Hz, 1H), 6.80-6.90 (m, 1H), 6.95-7.02 (m, 1H), 7.05 (d, J=8 Hz, 1H), 7.39 (d, J=8 Hz, 1H), 7.77 (dd, J=8 Hz/8 Hz, 1H), 9.19 (s, 1H).

Example 30

5-{[4,4-Dimethyl-6-fluoro-2-hydroxy-5-methoxy-2-trifluoromethyl-1,2,3,4-tetrahydronaphthalen-1-yl]amino}-quinolin-2(1H)-one

5-Aminoquinolin-2(1H)-one 4.5 g of 5-nitroquinolin-2(1H)-one (Chem. Pharm. Bull. (1981), 29, pp. 651-56) is hydrogenated in 200 ml of ethyl acetate and 500 ml of methanol in the presence of 450 mg of palladium on activated carbon as a catalyst under normal pressure with hydrogen until the reaction is completed. The catalyst is removed by filtration through diatomaceous earth, and the reaction solution is concentrated by evaporation in a vacuum. 3.8 g of the title compound is obtained as a yellow solid.

$^1$H-NMR (DMSO): δ=5.85 (bs, 2H), 6.27 (d, 1H), 6.33 (d, 1H), 6.43 (d, 1H), 7.10 (t, 1H), 8.07 (d, 1H), 11.39 (bs, 1H)

5-{[4,4-Dimethyl-6-fluoro-2-hydroxy-5-methoxy-2-trifluoromethyl-1,2,3,4-tetrahydronaphthalen-1-yl]amino}-quinolin-2(1H)-one Analogously to Example 3, the corresponding imine is produced starting from 500 mg of 4-(3-fluoro-2-methoxyphenyl)-2-hydroxy-4-methyl-2-trifluoromethyl-pentanal and 260 mg of 5-aminoquinolin-2(1H)-one. By reaction of 80 mg of the imine with 0.5 ml of titanium tetrachloride (1 M in dichloromethane), 20 mg of the title compound is obtained.

Examples 31 and 32

5-{[4,4-Dimethyl-2-hydroxy-5-methoxy-2-trifluoromethyl-1,2,3,4-tetrahydronaphthalen-1-yl]amino}-quinolin-2(1H)-one, Diastereomer B

5-{[2,5-Dihydroxy-4,4-dimethyl-2-trifluoromethyl-1,2,3,4-tetrahydronaphthalen-1-yl]amino}-quinolin-2(1H)-one, Diastereomer A

4-(2-Methoxyphenyl)-2-hydroxy-4-methyl-2-(trifluoromethyl)pentanal 19.3 g of 4-(2-methoxyphenyl)-4-methyl-2-oxo-pentanoic acid ethyl ester (WO 00/32584) in 630 ml of diethyl ether is mixed in portions at 0° C. with 3.3 g of lithium aluminum hydride. After stirring for 10 hours, it is added to saturated bicarbonate solution and filtered through diatomaceous earth. The phases are separated, and the aqueous phase is extracted with ethyl acetate. The organic phase is washed with water and brine, dried (Na$_2$SO$_4$) and concentrated by evaporation. After chromatography on silica gel (hexane/ethyl acetate 0->10%), 16.3 g of diol is obtained as a yellow oil.

2.0 g of diol, 5.2 ml of triethylamine and 5.12 g of sulfur trioxide-pyridine complex in 24 ml of DMSO are stirred at room temperature for 48 hours. It is added to 0.5N hydrochloric acid and extracted with ethyl acetate. The organic phase is washed with water and brine, dried (Na$_2$SO$_4$) and concentrated by evaporation in a vacuum. After chromatography on silica gel (hexane/ethyl acetate 0->3%), 1.44 g of 4-(2-methoxyphenyl)-2-hydroxy-4-methyl-2-(trifluoromethyl)pentanal is obtained as a yellow oil.

$^1$H-NMR (300 MHz, CDCl$_3$), δ=1.40 (s, 3H), 1.47 (s, 3H), 2.2 (d, 1H), 3.46 (d, 1H), 3.60 (s, 1H), 3.88 (s, 3H), 6.83-6.94 (m, 2H), 7.13 (dd, 1H), 7.24 (dt, 1H), 8.94 (s, 1H)

5-{[4,4-Dimethyl-2-hydroxy-5-methoxy-2-trifluoromethyl-1,2,3,4-tetrahydronaphthalen-1-yl]amino}-quinolin-2(1H)-one, Diastereomer B and 5-{[2,5-Dihydroxy-4,4-dimethyl-2-trifluoromethyl-1,2,3,4-tetrahydronaphthalen-1-yl]amino}-quinolin-2(1H)-one, Diastereomer A:

Analogously to Example 2, the corresponding imine is produced starting from 1.0 g of 4-(2-methoxyphenyl)-2-hydroxy-4-methyl-2-(trifluoromethyl)-pentanal and 553 mg of 5-aminoquinolin-2(1H)-one. 21 mg of 5-{[4,4-dimethyl-2-hydroxy-5-methoxy-2-trifluoromethyl-1,2,3,4-tetrahydronaphthalen-1-yl]amino}-quinolin-2(1H)-one as fraction 1 and 5 mg of 5-{[2,5-dihydroxy-4,4-dimethyl-2-trifluoromethyl-1,2,3,4-tetrahydronaphthalen-1-yl]amino}-quinolin-2(1H)-one as fraction 2 are obtained by reaction of 50 mg of the imine with 0.22 ml of BBr$_3$ (1N in dichloromethane).

Fraction 1: $^1$H-NMR (300 MHz, CD$_3$OD): δ=1.50 (s, 3H), 1.63 (s, 3H), 2.04 (d, 1H), 2.12 (d, 1H), 3.83 (s, 3H), 5.17 (s, 1H), 6.48 (d, 1H), 6.60 (d, 1H), 6.67 (d, 1H), 6.90 (d, 1H), 6.92 (d, 1H), 7.10 (t, 1H), 7.35 (t, 1H), 8.20 (d, 1H)

Flash point=269-270° C.

Fraction 2: $^1$H-NMR (300 MHz, CD$_3$OD): δ=1.39 (s, 3H), 1.52 (s, 3H), 2.05 (d, 1H), 2.23 (d, 1H), 5.28 (s, 1H), 6.38 (d, 1H), 6.58 (d, 1H), 6.68 (d, 1H), 6.92 (d, 1H), 7.00 (d, 1H), 7.11 (t, 1H), 7.38 (t, 1H), 8.14 (d, 1H)

Examples 33 and 34

(−)-5-{[4,4-Dimethyl-2-hydroxy-5-methoxy-2-trifluoromethyl-1,2,3,4-tetrahydronaphthalen-1-yl]amino}-quinolin-2(1H)-one

(+)-5-{[4,4-Dimethyl-2-hydroxy-5-methoxy-2-trifluoromethyl-1,2,3,4-tetrahydronaphthalen-1-yl]amino}-quinolin-2(1H)-one Separation of (+/−)-5-{[4,4-dimethyl-2-hydroxy-5-methoxy-2-trifluoromethyl-1,2,3,4-tetrahydronaphthalen-1-yl]amino}-quinolin-2(1H)-one:

The enantiomer mixture is separated by chromatography on chiral carrier material (CHIRALPAK AD®, DAICEL Company) with hexane/ethanol (90:10, vvv). The (−)-enantiomer: MS (ESI): M$^+$+1=433, [α]$_D$−70.1° °(c=1.0, CHCl$_3$) and the (+)-enantiomer: MS (ESI): M$^+$+1=433, [α]$_D$+78.5° (c=1.0, CHCl$_3$) are thus obtained.

Example 35

(+)-5-{[2,5-Dihydroxy-4,4-dimethyl-2-trifluoromethyl-1,2,3,4-tetrahydronaphthalen-1-yl]amino}-quinolin-2(1H)-one, Diastereomer B Analogously to Example 3, 5 mg of the title compound is obtained by reaction of 50 mg of (+)-5-{[4,4-dimethyl-2-hydroxy-5-methoxy-2-trifluoromethyl-1,2,3,4-tetrahydronaphthalen-1-yl]amino}-quinolin-2(1H)-one and 0.22 ml of BBr$_3$ (1 M in dichloromethane).

$^1$H-NMR (300 MHz, CD$_3$OD): δ=1.56 (s, 3H), 1.68 (s, 3H), 2.06 (d, 1H), 2.15 (d, 1H), 5.15 (s, 1H), 6.51 (d, 1H), 6.62 (d, 1H), 6.68 (d, 1H), 6.70 (d, 1H), 6.81 (d, 1H), 6.95 (t, 1H), 7.37 (t, 1H), 8.23 (d, 1H)

Example 36

(−)-5-{[2,5-Dihydroxy-4,4-dimethyl-2-trifluoromethyl-1,2,3,4-tetrahydronaphthalen-1-yl]amino}-quinolin-2(1H)-one, Diastereomer B Analogously to Example 3, 32 mg of the title compound is obtained by reaction of 70 mg of (−)-5-{[4,4-dimethyl-2-hydroxy-5-methoxy-2-trifluoromethyl-1,2,3,4-tetrahydronaphthalen-1-yl]amino}--quinolin-2(1H)-one and 0.32 ml of BBr$_3$ (1 M in dichloromethane).

$^1$H-NMR (300 MHz, CD$_3$OD): δ=1.57 (s, 3H), 1.68 (s, 3H), 2.05 (d, 1H), 2.14 (d, 1H), 5.15 (s, 1H), 6.51 (d, 1H), 6.62 (d, 1H), 6.67 (d, 1H), 6.68 (d, 1H), 6.81 (d, 1H), 6.95 (t, 1H), 7.37 (t, 1H), 8.22 (d, 1H)

Example 37

5-{[7-Chloro-2,5-dihydroxy-4,4-dimethyl-2-trifluoromethyl-1,2,3,4-tetrahydronaphthalen-1-yl]amino}-quinolin-2(1H)-one Analogously to Example 2, the corresponding imine is produced starting from 1.0 g of 4-(4-chloro-2-methoxyphenyl)-2-hydroxy-4-methyl-2-(trifluoromethyl)pentanal and 492 mg of 5-aminoquinolin-2(1H)-one. 20 mg of the title compound is obtained by reaction of 300 mg of the imine with 3.2 ml of BBr$_3$ (1N in dichloromethane).

$^1$H-NMR (300 MHz, DMSO): δ=1.46 (s, 3H), 1.58 (s, 3H), 1.95 (d, 1H), 2.05 (d, 1H), 5.28 (s, 1H), 6.08 (s, 1H), 6.20 (d, 1H), 6.40 (d, 1H), 6.50-6.66 (m, 3H), 6.77 (s, 1H), 7.24 (t, 1H), 7.35 (t, 1H), 8.19 (d, 1H), 10.04 (bs, 1H), 11.57 (bs, 1H)

Example 38

5-{[2,5-Dihydroxy-4,4-dimethyl-6-fluoro-2-trifluoromethyl-1,2,3,4-tetrahydronaphthalen-1-yl]amino}-quinolin-2(1H)-one Analogously to Example 2, the corresponding imine is produced starting from 1.0 g of 4-(3-fluoro-2-methoxyphenyl)-2-hydroxy-4-methyl-2-(trifluoromethyl)pentanal (Example 3) and 520 mg of 5-aminoquinolin-2(1H)-one. 255 mg of the title compound is obtained by reaction of 300 mg of imine with 3.3 ml of BBr$_3$ (1N in dichloromethane).

$^1$H-NMR (300 MHz, CD$_3$OD): δ=1.58 (s, 3H), 1.70 (s, 3H), 2.07 (d, 1H), 2.15 (d, 1H), 5.13 (s, 1H), 6.51 (d, 1H), 6.60 (d, 1H), 6.68 (d, 1H), 6.74-6.95 (m, 2H), 7.36 (t, 1H), 8.22 (d, 1H)

Examples 39 and 40

(−)-5-{[2,5-Dihydroxy-4,4-dimethyl-6-fluoro-2-trifluoromethyl-1,2,3,4-tetrahydronaphthalen-1-yl]amino}-quinolin-2(1H)-one and (+)-5-{[2,5-Dihydroxy-4,4-dimethyl-6-fluoro-2-trifluoromethyl-1,2,3,4-tetrahydronaphthalen-1-yl]amino}-quinolin-2(1H)-one Separation of (+/−)-5-{[2,5-Dihydroxy-4,4-dimethyl-6-fluoro-2-trifluoromethyl-1,2,3,4-tetrahydronaphthalen-1-yl]amino}-quinolin-2(1H)-one The enantiomer mixture is separated by chromatography on chiral carrier material (CHIRALPAK AD®, DAICEL Company) with hexane/ethanol (90:10, vvv). The (−)-enantiomer: MS (EI): M$^+$=436, [α]$_D$−23.6° °(c=1.0, CHCl$_3$) and the (+)-enantiomer: MS (EI): M$^+$=436, [α]$_D$+25.0° °(c=1.0, CHCl$_3$) are thus obtained.

Example 41

5-{[4,4-Dimethyl-5-methoxy-7-methyl-2-trifluoromethyl-1,2,3,4-tetrahydronaphthalen-1-yl]amino}-quinolin-2(1H)-one, Diastereomer A 4-(2-Methoxy-4-methylphenyl)-4-methyl-2-oxopentanoic acid ethyl ester Analogously to Example 7,2-methoxy-4-methylbenzoic acid methyl ester is produced from 30 g of 2,4-cresotic acid and 58.6 ml of methyl iodide with 124.3 g of potassium carbonate in 643 ml of DMF. The ester is reacted by reaction with 141 ml of methylmagnesium chloride (3 M in THF) in 475 ml of THF to form 1-(2-methoxy-4-methylphenyl)-1-methylethanol. 5 g of the product that is obtained is reacted with 6.4 g of 2-(trimethylsilyloxy)-acrylic acid ethyl ester in 102 ml of dichloromethane at −70° C. with 2.3 ml of tin tetrachloride to form 4.84 g of the title compound.

$^1$H-NMR (300 MHz, CDCl$_3$): δ=1.44 (s, 6H), 2.31 (s, 3H), 3.38 (s, 2H), 3.81 (s, 3H), 6.66 (s, 1H), 6.72 (d, 1H), 7.12 (d, 1H)

4-(2-Methoxy-4-methylphenyl)-2-hydroxy-4-methyl-2-(trifluoromethyl)pentanal

Analogously to Example 7, 4.84 g of 4-(2-methoxy-4-methylphenyl)-4-methyl-2-oxopentanoic acid ethyl ester is reacted with 7 ml of trifluoromethyltrimethylsilane and 3 ml of tetrabutylammonium fluoride solution (1 M in THF) in 56 ml THF to form 4.14 g of 4-(2-methoxy-4-methylphenyl)-2-hydroxy-4-methyl-2-(trifluoromethyl)pentanoic acid ethyl ester. The product is reduced with 856 mg of lithium aluminum hydride in 170 ml of diethyl ether to 3.58 g of 4-(2-methoxy-4-methylphenyl)-2-hydroxy-4-methyl-2-(trifluoromethyl)pentanol. The oxidation of the diol is carried out analogously to Example 7 under Swern conditions with 1.1 ml of oxalyl chloride, 2.1 ml of DMSO and 8.0 ml of triethylamine to 3.01 g of the title compound.

$^1$H-NMR (300 MHz, CDCl$_3$): δ=1.38 (s, 3H), 1.43 (s, 3H), 2.18 (d, 1H), 3.45 (d, 1H), 3.87 (s, 3H), 6.67 (s, 1H), 6.70 (d, 1H), 6.98 (d, 1H), 8.92 (s, 1H)

5-{[4,4-Dimethyl-5-methoxy-7-methyl-2-trifluoromethyl-1,2,3,4-tetrahydronaphthalen-1-yl]amino}-quinolin-2(1H)-one Analogously to Example 2, the corresponding imine is produced starting from 280 mg of 4-(2-methoxy-4-methylphenyl)-2-hydroxy-4-methyl-2-(trifluoromethyl)pentanal and 156 mg of 5-aminoquinolin-2(1H)-one. The latter is stirred at room temperature with 93 mg of aluminum chloride for 2.5 hours. The batch is added to saturated bicarbonate solution and extracted with ethyl acetate. The organic phase is washed with water and brine, dried (Na$_2$SO$_4$) and concentrated by evaporation in a vacuum. After chromatography on silica gel (dichloromethane/2-propanol 0->5%), 24 mg of the title compound is obtained.

$^1$H-NMR (300 MHz, CD$_3$OD): δ=1.50 (s, 3H), 1.62 (s, 3H), 2.04 (d, 1H), 2.13 (d, 1H), 2.20 (s, 3H), 3.85 (s, 3H), 5.13 (s, 1H), 6.51 (d, 1H), 6.62 (d, 1H), 6.70 (d, 1H), 6.75 (s, 1H), 6.78 (s, 1H), 7.39 (t, 1H), 8.23 (d, 1H)

Example 42

5-{[4,4-Dimethyl-7-fluoro-2-hydroxy-5-methoxy-2-trifluoromethyl-1,2,3,4-tetrahydronaphthalen-1-yl]amino}-quinolin-2(1H)-one

4-(4-Fluoro-2-methoxyphenyl)-2-hydroxy-4-methyl-2-(trifluoromethyl)pentanal 16.8 g of 4-(4-fluoro-2-methoxyphenyl)-4-methyl-2-oxopentanoic acid ethyl ester (WO 00/32584) in 600 ml of diethyl ether is mixed in portions at 0° C. with 2.7 g of lithium aluminum hydride. After stirring for 10 hours, it is added to saturated bicarbonate solution and filtered through diatomaceous earth. The phases are separated and the aqueous phase is extracted with ethyl acetate. The organic phase is washed with water and brine, dried ($Na_2SO_4$) and concentrated by evaporation. After chromatography on silica gel (hexane/ethyl acetate 0->10%), 6.7 g of diol and 2.65 g of the title compound are obtained.

The production of the title compound from the diol that is obtained is carried out by reaction of 3.0 g of diol, 6.6 ml of triethylamine and 6.5 g of sulfur trioxide-pyridine complex in 34 ml of DMSO at room temperature in 48 hours of reaction time. It is added to 0.5N hydrochloric acid and extracted with ethyl acetate. The organic phase is washed with water and brine, dried ($Na_2SO_4$) and concentrated by evaporation in a vacuum. After chromatography on silica gel (hexane/ethyl acetate 0->15%), 2.7 g of the title compound is obtained as a yellow oil.

$^1$H-NMR (300 MHz, $CDCl_3$), δ=1.38 (s, 3H), 1.46 (s, 3H), 2.19 (d, 1H), 3.37 (d, 1H), 3.58 (s, 1H), 3.87 (s, 3H), 6.55-6.64 (m, 2H), 7.06 (dd, 1H), 8.97 (s, 1H)

5-{[4,4-Dimethyl-7-fluoro-2-hydroxy-5-methoxy-2-trifluoromethyl-1,2,3,4-tetrahydronaphthalen-1-yl]amino}-quinolin-2(1H)-one Analogously to Example 41, the corresponding imine is produced starting from 500 mg of 4-(4-fluoro-2-methoxyphenyl)-2-hydroxy-4-methyl-2-(trifluoromethyl)pentanal and 260 mg of 5-aminoquinolin-2(1H)-one. 10 mg of the title compound is obtained by reaction of 220 mg of imine with 197 mg of aluminum chloride.

$^1$H-NMR ($CD_3OD$): δ=1.51 (s, 3H), 1.63 (s, 3H), 2.07 (d, 1H), 2.14 (d, 1H), 5.15 (s, 1H), 6.53 (d, 1H), 6.58-6.77 (m, 4H), 7.40 (t, 1H), 8.23 (d, 1H)

Example 43

(+)-5-{[2,5-Dihydroxy-4,4-dimethyl-2-trifluoromethyl-1,2,3,4-tetrahydronaphthalen-1-yl]amino}-quinolin-2(1H)-one Analogously to Example 3, 5 mg of the title compound is obtained by reaction of 50 mg of (+)-5-{[4,4-dimethyl-2-hydroxy-5-methoxy-2-trifluoromethyl-1,2,3,4-tetrahydronaphthalen-1-yl]amino}-quinolin-2(1H)-one and 0.22 ml of $BBr_3$ (1 M in dichloromethane).

$^1$H-NMR (300 MHz, $CD_3OD$): δ=1.57 (s, 3H), 1.69 (s, 3H), 2.06 (d, 1H), 2.15 (d, 1H), 5.16 (s, 1H), 6.51 (d, 1H), 6.62 (d, 1H), 6.69 (d, 1H), 6.71 (d, 1H), 6.82 (d, 1H), 6.95 (t, 1H), 7.37 (t, 1H), 8.23 (d, 1H)

Example 44

4-{[2-Hydroxy-4,4-dimethyl-5-methoxy-2-trifluoromethyl-1,2,3,4-tetrahydronaphthalen-1-yl]amino}-phthalide Analogously to Example 10, the corresponding imine is produced starting from 600 mg of 4-(2-methoxyphenyl)-2-hydroxy-4-methyl-2-(trifluoromethyl)pentanal and 308 mg of 4-amino-phthalide (Bull. Soc. Sci. Bretagne 26, 1951, Special Edition 5, p. 7, 96). As in Example 2, 650 mg of the imine is reacted by reaction with 7.7 ml of $BBr_3$ (1 M in dichloromethane), and 165 mg of the title compound is obtained.

$^1$H-NMR (300 MHz, DMSO-$d_6$): δ=1.30 (s, 3H), 1.46 (s, 3H), 1.93 (d, 1H), 2.18 (d, 1H), 3.57 (s, 3H), 5.10 (d, 1H), 5.20 (d, 1H), 5.32 (d, 1H), 5.55 (d, 1H), 5.81 (s, 1H), 6.80 (d, 1H), 7.03 (d, 1H), 7.04 (d, 1H), 7.20 (d, 1H), 7.27 (t, 1H), 7.37 (t, 1H)

Example 45

7-Chloro-1-[(1H-indazol-4-yl)amino]-4,4-dimethyl-2-(trifluoromethyl)-1,2,3,4-tetrahydronaphthalene-2,5-diol Analogously to Example 2, the corresponding imine is produced starting from 410 mg of 4-(4-chloro-2-methoxyphenyl)-2-hydroxy-4-methyl-2-(trifluoromethyl)pentanal and 168 mg of 4-aminoindazole. 98 mg of the title compound is obtained by reaction of 200 mg of imine with 6.7 ml of $BBr_3$ (1N in dichloromethane).

$^1$H-NMR (300 MHz, DMSO-$d_6$): δ=1.48 (s, 3H), 1.59 (s, 3H), 1.97 (d, 1H), 2.07 (d, 1H), 5.27 (d, 1H), 5.95 (s, 1H), 6.21 (d, 1H), 6.31 (d, 1H), 6.72 (s, 1H), 6.74 (d, 1H), 6.76 (s, 1H), 7.08 (t, 1H), 8.13 (s, 1H), 9.94 (s, 1H), 12.83 (s, 1H)

Examples 46 and 47

(−)-7-Chloro-1-[(1H-indazol-4-yl)amino]-4,4-dimethyl-2-(trifluoromethyl)-1,2,3,4-tetrahydronaphthalene-2,5-diol

(+)-7-Chloro-1-[(1H-indazol-4-yl)amino]-4,4-dimethyl-2-(trifluoromethyl)-1,2,3,4-tetrahydronaphthalene-2,5-diol

Separation of (+/−)-7-Chloro-1-[(1H-indazol-4-yl)amino]-4,4-dimethyl-2-(trifluoromethyl)-1,2,3,4-tetrahydronaphthalene-2,5-diol The enantiomer mixture is separated by chromatography on chiral carrier material (CHIRALPAK AD®, DAICEL Company) with hexane/2-propanol (98:2, vvv). The (−)-enantiomer: MS (EI): $M^+$=425/427, $[α]_D$−3.0° °(c=1.0, $CHCl_3$) and the (+)-enantiomer: MS (EI): $M^+$=425/427, $[α]_D$+5.0° °(c=1.0, $CHCl_3$) are thus obtained.

Examples 48 and 49

7-Fluoro-1-[(1H-indazol-4-yl)amino]-4,4-dimethyl-5-methoxy-2-(trifluoromethyl)-1,2,3,4-tetrahydronaphthalen-2-ol

7-Fluoro-1-[(1H-indazol-4-yl)amino]-4,4-dimethyl-2-(trifluoromethyl)-1,2,3,4-tetrahydronaphthalene-2,5-diol Analogously to Example 2, the corresponding imine is produced starting from 1.8 g of 4-(4-chloro-2-methoxyphenyl)-2-hydroxy-4-methyl-2-(trifluoromethyl)pentanal and 780 mg of 4-aminoindazole. By reaction of 300 mg of the imine with 10.6 ml of $BBr_3$ (1N in dichloromethane), 13 mg of 7-fluoro-1-[(1H-indazol-4-yl)amino]-4,4-dimethyl-5-methoxy-2-(trifluoromethyl)-1,2,3,4-tetrahydronaphthalen-2-ol as fraction 1 and 30 mg of 7-fluoro-1-[(1H-indazol-4-yl)amino]-4,4-dimethyl-2-(trifluoromethyl)-1,2,3,4-tetrahydronaphthalene-2,5-diol as fraction 2 are obtained.

Fraction 1: $^1$H-NMR (300 MHz, $CDCl_3$): δ=1.48 (s, 3H), 1.62 (s, 3H), 2.05 (d, 1H), 2.16 (d, 1H), 3.85 (s, 3H), 4.62 (d, 1H), 5.07 (d, 1H), 6.43 (d, 1H), 6.55 (dd, 1H), 6.71 (dd, 1H), 6.92 (d, 1H), 7.27 (t, 1H), 8.01 (s, 1H)

Fraction 2: $^1$H-NMR (300 MHz, $CDCl_3$): δ=1.54 (s, 3H), 1.65 (s, 3H), 2.07 (d, 1H), 2.17 (d, 1H), 4.62 (d, 1H), 5.07 (d, 1H), 6.37-6.47 (m, 2H), 6.72 (dd, 1H), 6.94 (d, 1H), 7.28 (t, 1H), 8.02 (s, 1H)

Examples 50 and 51

(−)-7-Fluoro-1-[(1H-indazol-4-yl)amino]-4,4-dimethyl-2-(trifluoromethyl)-1,2,3,4-tetrahydronaphthalene-2,5-diol

(+)-7-Fluoro-1-[(1H-indazol-4-yl)amino]-4,4-dimethyl-2-(trifluoromethyl)-1,2,3,4-tetrahydronaphthalene-2,5-diol

Separation of (+/−)-7-Fluoro-1-[(1H-indazol-4-yl)amino]-4,4-dimethyl-2-(trifluoromethyl)-1,2,3,4-tetrahydronaphthalene-2,5-diol The enantiomer mixture is separated by chromatography on chiral carrier material (CHIRALPAK AD®, DAICEL Company) with hexane/2-propanol (98:2, vvv). The (−)-enantiomer: MS (EI): M$^+$=409, $[α]_D$−40.5° °(c=0.2, $CHCl_3$) and the (+)-enantiomer: MS (EI): M$^+$=409 are thus obtained.

Examples 52 and 53

5-Fluoro-1-[(1H-indazol-4-yl)amino]-4,4-dimethyl-2-(trifluoromethyl)-1,2,3,4-tetrahydronaphthalene-2,5-diol, Diastereomer A

5-Fluoro-1-[(1H-indazol-4-yl)amino]-4,4-dimethyl-2-(trifluoromethyl)-1,2,3,4-tetrahydronaphthalene-2,5-diol, Diastereomer B

4-(2-Fluoro-4-methoxyphenyl)-2-hydroxy-4-methyl-2-(trifluoromethyl)pentanal 4.12 g of 4-(2-fluoro-4-methoxyphenyl)-4-methyl-2-oxopentanoic acid ethyl ester in 140 ml of diethyl ether is mixed in portions at 0° C. with 666 mg of lithium aluminum hydride. After stirring for 10 hours, it is added to saturated bicarbonate solution and filtered through diatomaceous earth. The phases are separated, and the aqueous phase is extracted with ethyl acetate. The organic phase is washed with water and brine, dried ($Na_2SO_4$) and concentrated by evaporation. After chromatography on silica gel (hexane/ethyl acetate 0->10%), 2.74 g of diol and 416 mg of the title compound are obtained.

The production of the title compound from the diol that is obtained is carried out by reaction of 3.0 g of the diol, 6.6 ml of triethylamine, and 6.5 g of sulfur trioxide-pyridine complex in 34 ml of DMSO at room temperature in 48 hours of reaction time. It is added to 0.5N hydrochloric acid and extracted with ethyl acetate. The organic phase is washed with water and brine, dried ($Na_2SO_4$) and concentrated by evaporation in a vacuum. After chromatography on silica gel (hexane/ethyl acetate 0->15%), 1.73 g of the title compound is obtained as a yellow oil.

$^1$H-NMR (300 MHz, $CDCl_3$), δ=1.39 (s, 3H), 1.46 (s, 3H), 2.26 (d, 1H), 3.09 (d, 1H), 3.63 (s, 1H), 3.78 (s, 3H), 6.52-6.65 (m, 2H), 7.03 (t, 1H), 9.04 (s, 1H)

5-Fluoro-1-[(1H-indazol-4-yl)amino]-4,4-dimethyl-2-(trifluoromethyl)-1,2,3,4-tetrahydronaphthalene-2,5-diol, Diastereomer A and 5-Fluoro-1-[(1H-indazol-4-yl)amino]-4,4-dimethyl-2-(trifluoromethyl)-1,2,3,4-tetrahydronaphthalene-2,5-diol, Diastereomer B:

Analogously to Example 2, the corresponding imine is produced starting from 1.7 g of 4-(2-fluoro-4-methoxyphenyl)-2-hydroxy-4-methyl-2-(trifluoromethyl)pentanal and 736 mg of 4-aminoindazole. By reaction of 300 mg of imine with 10.6 ml of $BBr_3$ (1N in dichloromethane), 12 mg of 5-fluoro-1-[(1H-indazol-4-yl)amino]-4,4-dimethyl-2-(trifluoromethyl)-1,2,3,4-tetrahydronaphthalene-2,5-diol, Diastereomer B as fraction 1 and 90 mg of 5-fluoro-1-[(1H-indazol-4-yl)amino]-4,4-dimethyl-2-(trifluoromethyl)-1,2,3,4-tetrahydronaphthalene-2,5-diol, diastereomer A as fraction 2 are obtained.

Fraction 1: $^1$H-NMR (300 MHz, $CDCl_3$): δ=1.48 (s, 3H), 1.58 (s, 3H), 2.06 (d, 1H), 2.23 (d, 1H), 4.95 (d, 1H), 5.11 (d, 1H), 6.37 (d, 1H), 6.48 (dd, 1H), 6.64 (d, 1H), 6.75 (s, 1H), 7.25 (t, 1H), 7.48 (s, 1H)

Fraction 2: $^1$H-NMR (300 MHz, $CDCl_3$): δ=1.48 (s, 3H), 1.58 (s, 3H), 2.05 (d, 1H), 2.24 (d, 1H), 5.04 (d, 1H), 5.12 (d, 1H), 6.37 (d, 1H), 6.48 (dd, 1H), 6.58 (dd, 1H), 6.78 (d, 1H), 7.24 (t, 1H), 7.29 (s, 1H)

Example 54

1-[(1H-indazol-4-yl)amino]-4,4-dimethyl-5-methoxy-2-(trifluoromethyl)-1,2,3,4-tetrahydronaphthalen-2-ol, Diastereomer A Analogously to Example 41, the corresponding imine is produced starting from 850 mg of 4-(2-methoxyphenyl)-2-hydroxy-4-methyl-2-(trifluoromethyl)pentanal and 390 mg of 4-aminoindazole. 138 mg of the title compound is obtained by reaction of 500 mg of imine with 495 mg of aluminum chloride.

$^1$H-NMR (300 MHz, $CDCl_3$), δ=1.52 (s, 3H), 1.66 (s, 3H), 2.05 (d, 1H), 2.16 (d, 1H), 3.85 (s, 3H), 4.57 (d, 1H), 5.23 (d, 1H), 6.48 (d, 1H), 6.82 (d, 1H), 6.92 (d, 1H), 6.95 (d, 1H), 7.12 (t, 1H), 7.29 (t, 1H), 7.97 (s, 1H)

Example 55

1-[(1H-Indazol-4-yl)amino]-4,4-dimethyl-5-methoxy-2-(trifluoromethyl)-1,23,4-tetrahydronaphthalen-2-ol, Diastereomer B Analogously to Example 2, 300 mg of the imine that is obtained in Example 54 is reacted with 11 ml of BBr$_3$ (1N in dichloromethane) to form 24 mg of the title compound.

$^1$H-NMR (300 MHz, CD$_3$OD), δ=1.42 (s, 3H), 1.55 (s, 3H), 2.08 (d, 1H), 2.23 (d, 1H), 3.33 (s, 3H), 5.33 (s, 1H), 6.63 (d, 1H), 6.72 (d, 1H), 6.88 (d, 1H), 7.06 (d, 1H), 7.20-7.31 (m, 2H), 8.17 (s, 1H)

Example 56

1-[(1H-Indazol-4-yl)amino]-4,4-dimethyl-2-(trifluoromethyl)-1,2,3,4-tetrahydronaphthalene-2,5-diol 100 mg of the compound of Example 54 is reacted analogously to Example 1 with 3.7 ml of BBr$_3$ (1N in dichloromethane) to form 47 mg of the title compound.

$^1$H-NMR (300 MHz, CD$_3$OD), δ=1.40 (s, 3H), 1.54 (s, 3H), 2.10 (d, 1H), 2.25 (d, 1H), 5.36 (s, 1H), 6.60 (d, 1H), 6.94 (d, 1H), 7.12 (t, 1H), 7.18-7.33 (m, 3H), 8.20 (s, 1H)

Example 57

7-Chloro-1-[(1H-indazol-4-yl)amino]-4,4-dimethyl-2-(trifluoromethyl)-1,2,3,4-tetrahydronaphthalen-2-ol Analogously to Example 2, the corresponding imine is produced starting from 350 mg of 4-(4-chlorophenyl)-2-hydroxy-4-methyl-2-(trifluoromethyl)pentanal and 158 mg of 4-aminoindazole. By reaction of 50 mg of imine with 1.8 ml of BBr$_3$ (1N in dichloromethane), 29 mg of the title compound is obtained.

$^1$H-NMR (300 MHz, CDCl$_3$), δ=1.41 (s, 3H), 1.54 (s, 3H), 2.10 (d, 1H), 2.19 (d, 1H), 4.63 (d, 1H), 5.14 (d, 1H), 6.43 (d, 1H), 6.95 (d, 1H), 7.23-7.37 (m, 4H), 8.03 (s, 1H)

Example 58

1-[(1-Methyl-indazol-4-yl)amino]-4,4-dimethyl-5-methoxy-2-(trifluoromethyl)-1,2,3,4-tetrahydronaphthalen-2-ol 4-Amino-1-methylindazole:

6.5 g of 4-nitroindazole (Chem. Ber. (1904), 37, 2583), 1.9 ml of methyl iodide and 14.4 g of cesium carbonate in 110 ml of DMF are stirred for 2 hours at 0° C. and then for 12 hours at room temperature. It is added to water and extracted with ethyl acetate. The organic phase is washed with water and brine, dried (Na$_2$SO$_4$) and concentrated by evaporation. The residue is recrystallized from ethyl acetate/hexane. 2.49 g of 1-methyl-4-nitroindazole is obtained. The latter is hydrogenated in 70 ml of THF with 420 mg of palladium on activated carbon under normal pressure with hydrogen. The batch is filtered through diatomaceous earth and completely concentrated by evaporation. 2.1 g of the title compound is obtained.

$^1$H-NMR (300 MHz, CD$_3$OD), δ=3.96 (s, 3H), 6.35 (d, 1H), 6.75 (d, 1H), 7.16 (d, 1H), 8.06 (s, 1H)

1-[(1-Methyl-indazol-4-yl)amino]-4,4-dimethyl-5-methoxy-2-(trifluoromethyl)-1,2,3,4-tetrahydronaphthalen-2-ol Analogously to Example 3, the corresponding imine is produced starting from 296 mg of 4-(2-methoxyphenyl)-2-hydroxy-4-methyl-2-(trifluoromethyl)pentanal and 150 mg of 4-amino-1-methylindazole. By reaction of 100 mg of the imine with 0.5 ml of titanium tetrachloride, 100 mg of the title compound is obtained.

Melting point: 172-174° C.

Examples 59 and 60

7-Ethyl-1-[(1H-indazol-4-yl)amino]-4,4-dimethyl-5-methoxy-2-(trifluoromethyl)-1,2,3,4-tetrahydronaphthalen-2-ol 7-Ethyl-1-[(1H-indazol-4-yl)amino]-4,4-dimethyl-2-(trifluoromethyl)-1,2,3,4-tetrahydronaphthalen-2-ol 2-Hydroxy-4-(4-iodo-2-methoxyphenyl)-4-methyl-2-trifluoromethylvaleric acid methyl ester 3 g of 4-(4-iodo-2-methoxyphenyl)-4-methyl-2-oxovaleric acid (WO 98/54159) is added in a solution of 1.3 ml of thionyl chloride in 12 ml of methanol at 0° C. and stirred for 10 hours at room temperature. It is added to saturated bicarbonate solution and extracted with ethyl acetate. The organic phase is washed with bicarbonate solution and brine, dried (Na$_2$SO$_4$) and concentrated by evaporation. 3.2 g of 4-(4-iodo-2-methoxyphenyl)-4-methyl-2-oxovaleric acid methyl ester is obtained as a crude product. This ester is mixed with 4.5 ml of trifluoromethyltrimethylsilane in 70 ml of DMF and 1.63 g of cesium carbonate at 0° C. and stirred for 10 hours at room temperature. 20 mg of tetrabutylammonium fluoride is added, and it is stirred for another 30 minutes at room temperature. The batch is added to water and extracted with ethyl acetate. The organic phase is washed with water and brine, dried (Na$_2$SO$_4$) and concentrated by evaporation. After chromatography on silica gel (hexane/ethyl acetate 0->15%), 1.47 g of the title compound is obtained as a yellow oil.

$^1$H-NMR (300 MHz, CDCl$_3$), δ=1.34 (s, 3H), 1.42 (s, 3H), 2.30 (d, 1H), 2.97 (d, 1H), 3.36 (s, 3H), 3.84 (s, 3H), 6.88 (dd, 1H), 7.13 (dd, 1H), 7.23 (dd, 1H)

4-(4-Ethyl-2-methoxyphenyl)-2-hydroxy-4-methyl-2-trifluoromethylpentanal:

1 g of 2-hydroxy-4-(4-iodo-2-methoxyphenyl)-4-methyl-2-trifluoromethyl-valeric acid methyl ester, 860 mg of tributylvinyl tin, 103 mg of palladium-dibenzylidene acetone complex and 30 mg of triphenylphosphine in 17 ml of THF are refluxed under argon atmosphere for 57 hours. It is filtered through diatomaceous earth and completely concentrated by evaporation. After chromatography on silica gel (hexane/ethyl acetate 0->2%), 339 mg of 2-hydroxy-4-(2-methoxy-4-vinylphenyl)-4-methyl-2-trifluoromethylvaleric acid methyl ester is obtained. The latter is stirred with 56 mg of lithium aluminum hydride in 11 ml of diethyl ether at room temperature for 10 hours. It is added to saturated bicarbonate solution, filtered through diatomaceous earth and extracted with ethyl acetate. The organic phase is washed with bicarbonate solution and brine, dried (Na$_2$SO$_4$) and concentrated by evaporation. After chromatography on silica gel (hexane/ethyl acetate 0->10%), 148 mg of 2-hydroxy-4-(2-methoxy-4-vinylphenyl)-4-methyl-2-trifluoro-methylpentanol is obtained. The latter is hydrogenated in 4.3 ml of ethyl acetate with 14 mg of palladium on activated carbon under normal pressure with hydrogen. The batch is filtered through diatomaceous earth and completely concentrated by evaporation. 127 mg of 4-(4-ethyl-2-methoxyphenyl)-2-hydroxy-4-methyl-2-trifluoromethylpentanol is obtained. The diol that is obtained is reacted with 0.29 ml of triethylamine and 280 mg of sulfur trioxide-pyridine complex in 1.3 ml of DMSO at room temperature in 10 hours of reaction time. It is added to saturated ammonium chloride solution and extracted with ethyl acetate. The organic phase is washed with water and brine, dried ($Na_2SO_4$) and concentrated by evaporation in a vacuum. After chromatography on silica gel (hexane/ethyl acetate 0->3%), 94 mg of the title compound is obtained as a colorless oil.

$^1$H-NMR (300 MHz, $CDCl_3$), δ=1.24 (t, 3H), 1.38 (s, 3H), 1.44 (s, 3H), 2.17 (d, 1H), 2.62 (q, 2H), 3.46 (d, 1H), 3.88 (s, 3H), 6.68 (s, 1H), 6.72 (d, 1H), 7.02 (d, 1H), 8.91 (s, 1H)

7-Ethyl-1-[(1H-indazol-4-yl)amino]-4,4-dimethyl-5-methoxy-2-(trifluoromethyl)-1,2,3,4-tetrahydronaphthalen-2-ol and 7-Ethyl-1-[(1H-indazol-4-yl)amino]-4,4-dimethyl-2-(trifluoromethyl)-1,2,3,4-tetrahydronaphthalen-2-ol Analogously to Example 2, the corresponding imine is produced starting from 90 mg of 4-(4-ethyl-2-methoxyphenyl)-2-hydroxy-4-methyl-2-(trifluoromethyl)pentanal and 38 mg of 4-aminoindazole. By reaction of 68 mg of imine with 0.39 ml of $BBr_3$ (1N in dichloromethane), 16 mg of 7-ethyl-1-[(1H-indazol-4-yl)amino]-4,4-dimethyl-5-methoxy-2-(trifluoromethyl)-1,2,3,4-tetrahydronaphthalen-2-ol as fraction 1 and 7 mg of 7-ethyl-1-[(1H-indazol-4-yl)amino]-4,4-dimethyl-2-(trifluoromethyl)-1,2,3,4-tetrahydronaphthalen-2-ol as fraction 2 are obtained.

Fraction 1: $^1$H-NMR (300 MHz, $CDCl_3$), δ=1.24 (t, 3H), 1.42 (s, 3H), 1.51 (s, 3H), 2.03 (d, 1H), 2.14 (d, 1H), 2.63 (q, 2H), 3.18 (s, 3H), 3.74 (bd, 1H), 5.33 (bd, 1H), 6.48 (s, 1H), 6.70 (d, 1H), 6.85 (s, 1H), 6.98 (d, 1H), 7.32 (t, 2H), 7.89 (s, 1H)

Fraction 2: $^1$H-NMR (300 MHz, $CDCl_3$), δ=1.00 (t, 3H), 1.55 (s, 3H), 1.65 (s, 3H), 2.04 (d, 1H), 2.18 (d, 1H), 2.36 (q, 2H), 3.18 (s, 3H), 4.65 (bd, 1H), 5.09 (bd, 1H), 6.47 (d, 1H), 6.48 (s, 1H), 6.76 (s, 1H), 6.92 (d, 1H), 7.29 (t, 2H), 8.00 (s, 1H)

Example 61

1-[(1-Methyl-indazol-4-yl)amino]-4,4-dimethyl-2-(trifluoromethyl)-1,2,3,4-tetrahydronaphthalene-2,5-diol Analogously to Example 2, 163 mg of the imine that is described according to Example 58 with 0.97 ml of $BBr_3$ (1N in dichloromethane) is reacted to form 44 mg of the title compound.

$^1$H-NMR (300 MHz, $CD_3OD$), δ=1.56 (s, 3H), 1.68 (s, 3H), 2.05 (d, 1H), 2.14 (d, 1H), 4.02 (s, 3H), 5.15 (s, 1H), 6.34 (d, 1H), 6.67 (d, 1H), 6.78 (d, 1H), 6.82-6.98 (m, 2H), 7.25 (t, 2H), 8.07 (s, 1H)

Examples 62 and 63

5-{[7-Fluoro-2-hydroxy-4,4-dimethyl-5-methoxy-2-(trifluoromethyl)-1,2,3,4-tetrahydronaphthalen-1-yl]amino}-isoquinolin-1(2H)-one 5-{[7-Fluoro-2,5-dihydroxy-4,4-dimethyl-2-(trifluoromethyl)-1,2,3,4-tetrahydronaphthalen-1-yl]amino}-isoquinolin-1(2H)-one Analogously to Example 2, the corresponding imine is produced starting from 385 mg of 4-(4-fluoro-2-methoxyphenyl)-2-hydroxy-4-methyl-2-(trifluoromethyl)-pentanal and 200 mg of 5-aminoisoquinolin-1(2H)-one. By reaction of 300 mg of imine with 10.0 ml of $BBr_3$ (1N in dichloromethane), 10 mg of 5-{[7-fluoro-2-hydroxy-4,4-dimethyl-5-methoxy-2-(trifluoromethyl)-1,2,3,4-tetrahydronaphthalen-1-yl]amino}-isoquinolin-1(2H)-one as fraction 1 and 100 mg of 5-{[7-fluoro-2,5-dihydroxy-4,4-dimethyl-2-(trifluoromethyl)-1,2,3,4-tetrahydronaphthalen-1-yl]amino}-isoquinolin-1(2H)-one as fraction 2 are obtained.

Fraction 1: $^1$H-NMR (300 MHz, DMSO-$d_6$), δ=1.32 (s, 3H), 1.47 (s, 3H), 1.95 (d, 1H), 2.24 (d, 1H), 3.44 (s, 3H), 5.01-5.14 (m, 2H), 5.85 (s, 1H), 6.70 (dd, 1H), 6.78 (d, 1H), 6.86 (dd, 1H), 6.98 (dd, 1H), 7.22 (d, 1H), 7.31 (t, 1H), 7.52 (d, 1H), 11.10 (bd, 1H)

Fraction 2: $^1$H-NMR (300 MMHz, DMSO-$d_6$), δ=1.47 (s, 3H), 1.58 (s, 3H), 1.97 (d, 1H), 2.08 (d, 1H), 5.30 (d, 1H), 5.94 (d, 1H), 6.13 (s, 1H), 6.35 (dd, 1H), 6.54 (dd, 1H), 6.81 (d, 1H), 7.03 (d, 1H), 7.17 (dd, 1H), 7.25 (t, 1H), 7.51 (d, 1H), 9.98 (bs, 1H), 11.25 (bd, 1H)

Examples 64 and 65

(−)-5-{[7-Fluoro-2,5-dihydroxy-4,4-dimethyl-2-(trifluoromethyl)-1,2,3,4-tetrahydronaphthalen-1-yl]amino}-isoquinolin-1(2H)-one (+)-5-{[7-Fluoro-2,5-dihydroxy-4,4-dimethyl-2-(trifluoromethyl)-1,2,3,4-tetrahydronaphthalen-1-yl]amino}-isoquinolin-1(2H)-one Separation of (+/−)-5-{[7-fluoro-2,5-dihydroxy-4,4-dimethyl-2-(trifluoromethyl)-1,2,3,4-tetrahydronaphthalen-1-yl]amino}-isoquinolin-1(2H)-one The enantiomer mixture is separated by chromatography on chiral carrier material (CHIRALPAK AD®, DAICEL Company) with hexane/ethanol (90:10, vvv). The (−)-enantiomer: MS (EI): M$^+$=436, $[α]_D$−62.5° °(c=0.5, $CHCl_3$) and the (+)-enantiomer: MS (EI): M$^+$=436, $[α]_{D+}$75.6° °(c=0.8, $CHCl_3$) are thus obtained.

Example 66

5-{[6-Fluoro-2-hydroxy-4,4-dimethyl-5-methoxy-2-(trifluoromethyl)-1,2,3,4-tetrahydronaphthalen-1-yl]amino}-2-methylphthalazin-1-one, Diastereomer A 5-Amino-2-methyl-phthalazin-1-one 3-Bromo-4-nitro-phthalide 5.37 g of 4-nitrophthalide (Tetrahedron Lett. (2001), 42, pp. 1647-50), 8.04 g of N-bromosuccinimide and 196 mg of benzoyl peroxide are refluxed in 80 ml of benzotrifluoride and heated by exposure to light until the reaction is completed. It is added to water, extracted with dichloromethane, washed several times with water, dried, and the solvent is removed in a vacuum. 7.24 g of 3-bromo-4-nitro-phthalide is obtained as a solid.

$^1$H-NMR (300 MHz, CDCl$_3$), δ=7.26 (s, 1H), 7.88 (t, 1H), 8.3 (d, 1H), 8.56 (d, 1H)

5-Nitro-phthalazin-1-one 18.25 g of hydrazine sulfate and 14.88 g of sodium carbonate are stirred in 300 ml of DMF at 100° C. for 1 hour. Then, 7.24 g of 3-bromo-4-nitro-phthalide in 100 ml of DMF is added, and it is stirred for another 4 hours at 100° C. It is added to water, extracted several times with ethyl acetate, and the organic phase is washed with water and brine. It is dried, and the solvent is removed in a vacuum. After recrystallization from ethyl acetate, 2.35 g of 5-nitro-phthalazin-1-one is obtained as a solid.

$^1$H-NMR (300 MHz, DMSO-d$_6$), δ=8.05 (t, 1H), 8.57-8.66 (m, 2H), 8.73 (s, 1H), 13.13 (bs, 1H)

2-Methy-5-nitro-phthalazin-1-one 1.6 g of 5-nitro-phthalazin-1-one and 2.31 g of potassium carbonate are stirred for 10 minutes at room temperature in 60 ml of DMF. 1.1 ml of methyl iodide is added, and it is stirred overnight. It is added to water, extracted several times with ethyl acetate, and the organic phase is washed with water and brine. It is dried, and the solvent is removed in a vacuum. 1.57 g of 2-methyl-5-nitro-phthalazin-1-one is obtained as a yellow solid.

$^1$H-NMR (300 MHz, DMSO-d$_6$), δ=3.73 (s, 3H), 8.05 (t, 1H), 8.62 (d, 2H), 8.75 (s, 1H)

5-Amino-2-methyl-phthalazin-1-one 1.57 g of 2-methyl-5-nitro-phthalazin-1-one and 130 mg of palladium on activated carbon are suspended in 45 ml of ethyl acetate and hydrogenated with hydrogen under normal pressure. It is filtered through diatomaceous earth, and the solvent is removed in a vacuum. 1.26 g of 5-amino-2-methyl-phthalazin-1-one is obtained as a yellow solid.

$^1$H-NMR (300 MHz, CDCl$_3$), =3.81 (s, 3H), 7.0 (d, 1H), 7.5 (t, 1H), 7.8 (d, 1H), 8.16 (s, 1H)

5-{[6-Fluoro-2-hydroxy-4,4-dimethyl-5-methoxy-2-(trifluoromethyl)-1,2,3,4-tetrahydronaphthalen-1-yl]amino}-2-methylphthalazin-1-one Analogously to Example 10, the corresponding imine is produced starting from 200 mg of 4-(3-fluoro-2-methoxyphenyl)-2-hydroxy-4-methyl-2-(trifluoromethyl)pentanal and 114 mg of 5-amino-2-methyl-phthalazin-1-one. As in Example 3, 50 mg of imine is reacted by reaction with 0.23 ml of titanium tetrachloride, and 12 mg of the title compound is obtained.

Melting point: 262-263° C.

Example 67

5-{[6-Fluoro-2-hydroxy-4,4-dimethyl-5-methoxy-2-(trifluoromethyl)-1,2,3,4-tetrahydronaphthalen-1-yl]amino}-phthalazin-1(2H)-one 5-Amino-phthalazin-1-one 980 mg of 5-nitro-phthalazin-1-one (Example 66) and 100 mg of palladium on activated carbon are suspended in 50 ml of ethyl acetate and 1 ml of triethylamine, and it is hydrogenated with hydrogen under normal pressure. It is filtered through diatomaceous earth, and the solvent is removed in a vacuum. 830 g of 5-amino-phthalazin-1-one as a solid is obtained as a crude product.

$^1$H-NMR (300 MHz, DMSO-d$_6$), δ=6.26 (bs, 2H), 7.00 (d, 1H), 7.32 (d, 1H), 7.44 (t, 1H), 8.48 (s, 1H), 12.35 (bs, 1H)

5-{[6-Fluoro-2-hydroxy-4,4-dimethyl-5-methoxy-2-(trifluoromethyl)-1,2,3,4-tetrahydronaphthalen-1-yl]amino}-phthalazin-1(2H)-one Analogously to Example 10, the corresponding imine is produced starting from 200 mg of 4-(3-fluoro-2-methoxyphenyl)-2-hydroxy-4-methyl-2-(trifluoromethyl)-pentanal and 105 mg of 5-amino-phthalazin-1-one. As in Example 3, 50 mg of imine is reacted by reaction with 0.22 ml of titanium tetrachloride, and 36 mg of the title compound is obtained.

$^1$H-NMR (300 MHz, CD$_3$OD), δ=1.53 (s, 3H), 1.64 (s, 3H), 2.12 (s, 2H), 3.94 (d, 3H), 5.24 (s, 1H), 6.96 (dd, 1H), 7.03 (dd, 1H), 7.24 (dd, 1H), 7.58-7.65 (m, 2H), 8.55 (s, 1H)

Example 68

5-{[7-Chloro-2,5-dihydroxy-4,4-dimethyl-2-(trifluoromethyl)-1,2,3,4-tetrahydronaphthalen-1-yl]amino}-2-methylphthalazin-1-one Analogously to Example 10, the corresponding imine is produced starting from 200 mg of 4-(3-fluoro-2-methoxyphenyl)-2-hydroxy-4-methyl-2-(trifluoromethyl)-pentanal and 108 mg of 5-amino-2-methyl-phthalazin-1-one. As in Example 2, 225 mg of imine is reacted by reaction with 2.3 ml of BBr$_3$ (1 M in dichloromethane), and 12 mg of the title compound is obtained.

$^1$H-NMR (300 MHz, CD$_3$OD), δ=1.55 (s, 3H), 1.66 (s, 3H), 2.08 (d, 1H), 2.14 (d, 1H), 5.22 (s, 1H), 6.74 (s, 1H), 6.78 (s, 1H), 7.18-7.27 (m, 1H), 7.62-7.72 (m, 2H), 8.57 (s, 1H)

Example 69

5-{[6-Fluoro-2-hydroxy-4,4-dimethyl-5-methoxy-2-(trifluoromethyl)-1,2,3,4-tetrahydronaphthalen-1-yl]amino}-2-methylphthalazin-1-one, Diastereomer B Analogously to Example 10, the corresponding imine is produced starting from 200 mg of 4-(3-fluoro-2-methoxyphenyl)-2-hydroxy-4-methyl-2-(trifluoromethyl)-pentanal and 114 mg of 5-amino-2-methyl-phthalazin-1-one. As in Example 2, 112 mg of imine is reacted by reaction with 0.36 ml of BBr$_3$ (1 M in dichloromethane), and 38 mg of the title compound is obtained.

$^1$H-NMR (300 MHz, CDCl$_3$), δ=1.53 (s, 3H), 1.64 (s, 3H), 2.11 (d, 1H), 3.85 (s, 3H), 3.97 (d, 3H), 5.02 (d, 1H), 5.13 (d, 1H), 6.97 (d, 1H), 7.00 (dd, 1H), 7.08 (d, 1H), 7.61 (t, 1H), 7.83 (d, 1H), 8.15 (s, 1H)

Example 70

5-{[6-Fluoro-2,5-dihydroxy-4,4-dimethyl-2-(trifluoromethyl)-1,2,3,4-tetrahydronaphthalen-1-yl]amino}-2-methylphthalazin-1-one 29 mg of the compound of Example 69 is reacted analogously to Example 1 with 0.13 ml of BBr$_3$ (1N in dichloromethane) to form 18 mg of the title compound.

¹H-NMR (300 MHz, CD₃OD), δ=1.60 (s, 3H), 1.71 (s, 3H), 2.09 (d, 1H), 2.16 (d, 1H), 3.83 (s, 3H), 5.23 (s, 1H), 6.79 (dd, 1H), 6.90 (dd, 1H), 7.22 (dd, 1H), 7.59-7.68 (m, 2H), 8.56 (s, 1H)

Example 71

5-{[6-Fluoro-2,5-dihydroxy-4,4-dimethyl-2-(trifluoromethyl)-1,2,3,4-tetrahydronaphthalen-1-yl]amino}-phthalazin-1(2H)-one 80 mg of the compound of Example 67 is reacted analogously to Example 1 with 0.35 ml of BBr₃ (1N in dichloromethane) to form 15 mg of the title compound.

¹H-NMR (300 MHz, CD₃OD), δ=1.60 (s, 3H), 1.71 (s, 3H), 2.14 (d, 2H), 5.23 (s, 1H), 6.80 (dd, 1H), 6.90 (dd, 1H), 7.25 (dd, 1H), 7.58-7.68 (m, 2H), 8.56 (s, 1H)

Examples 72 and 73

5-{[2-Hydroxy-4,4-dimethyl-5-methoxy-2-(trifluoromethyl)-1,2,3,4-tetrahydronaphthalen-1-yl]amino}-phthalazin-1(2H)-one 5-{[2,5-Dihydroxy-4,4-dimethyl-2-(trifluoromethyl)-1,2,3,4-tetrahydronaphthalen-1-yl]amino}-phthalazin-1(2H)-one Analogously to Example 10, the corresponding imine is produced starting from 500 mg of 4-(2-methoxyphenyl)-2-hydroxy-4-methyl-2-(trifluoromethyl)pentanal and 277 mg of 5-amino-phthalazin-1-one. As in Example 2, 32 mg of 5-{[2-hydroxy-4,4-dimethyl-5-methoxy-2-(trifluoromethyl)-1,2,3,4-tetrahydronaphthalen-1-yl]amino}-phthalazin-1(2H)-one as fraction 1 and 35 mg of 5-{[2,5-dihydroxy-4,4-dimethyl-2-(trifluoromethyl)-1,2,3,4-tetrahydronaphthalen-1-yl]amino}-phthalazin-1(2H)-one as fraction 3 are obtained by reaction of 470 mg of imine with 5.4 ml of BBr₃ (1 M in dichloromethane).

Fraction 1: ¹H-NMR (300 MHz, DMSO-d₆), δ=1.32 (s, 3H), 1.50 (s, 3H), 1.96 (d, 1H), 2.23 (d, 1H), 3.47 (s, 3H), 5.17 (d, 1H), 5.93 (s, 1H), 6.06 (d, 1H), 6.78 (d, 1H), 7.04 (d, 1H), 7.27 (t, 1H), 7.37 (d, 1H), 7.44 (d, 1H), 7.62 (t, 1H), 8.67 (s, 1H), 12.39 (s, 1H)

Fraction 3: ¹H-NMR (300 MHz, CD₃OD), δ=1.57 (s, 3H), 1.69 (s, 3H), 2.07 (d, 1H), 2.15 (d, 1H), 5.24 (s, 1H), 6.72 (d, 1H), 6.81 (d, 1H), 6.96 (t, 1H), 7.24 (dd, 1H), 7.57-7.70 (m, 2H), 8.57 (s, 1H)

Examples 74, 75 and 76

5-{[2-Hydroxy-4,4-dimethyl-5-methoxy-2-(trifluoromethyl)-1,2,3,4-tetrahydronaphthalen-1-yl]amino}-2-methylphthalazin-1-one 5-{[2,5-Dihydroxy-4,4-dimethyl-2-(trifluoromethyl)-1,2,3,4-tetrahydronaphthalen-1-yl]amino}-2-methylphthalazin-1-one, Diastereomer A 5-{[2,5-Dihydroxy-4,4-dimethyl-2-(trifluoromethyl)-1,2,3,4-tetrahydronaphthalen-1-yl]amino}-2-methylphthalazin-1-one, Diastereomer B Analogously to Example 10, the corresponding imine is produced starting from 500 mg of 4-(2-methoxyphenyl)-2-hydroxy-4-methyl-2-(trifluoromethyl)pentanal and 302 mg of 5-amino-2-methylphthalazin-1-one. As in Example 2, 158 mg of 5-{[2-hydroxy-4,4-dimethyl-5-methoxy-2-(trifluoromethyl)-1,2,3,4-tetrahydronaphthalen-1-yl]amino}-2-methylphthalazin-1-one as fraction 1, 66 mg of 5-{[2,5-dihydroxy-4,4-dimethyl-2-(trifluoromethyl)-1,2,3,4-tetrahydronaphthalen-1-yl]amino}-2-methylphthalazin-1-one, diastereomer A as fraction 4, and 77 mg of 5-{[2,5-dihydroxy-4,4-dimethyl-2-(trifluoromethyl)-1,2,3,4-tetrahydronaphthalen-1-yl]amino}-2-methylphthalazin-1-one, diastereomer A as fraction 5 are obtained by reaction of 570 mg of imine with 6.4 ml of BBr₃ (1 M in dichloromethane).

Fraction 1: ¹H-NMR (300 MHz, CD₃OD), δ=1.42 (s, 3H), 1.58 (s, 3H), 2.08 (d, 1H), 2.26 (d, 1H), 3.47 (s, 3H), 3.77 (s, 3H), 5.33 (s, 1H), 6.76 (d, 1H), 7.07 (d, 1H), 7.29 (t, 1H), 7.52 (dd, 1H), 7.60-7.71 (m, 2H), 8.51 (s, 1H)

Fraction 4: ¹H-NMR (300 MHz, CD₃OD), δ=1.42 (s, 3H), 1.56 (s, 3H), 2.09 (d, 1H), 2.27 (d, 1H), 3.78 (s, 3H), 5.33 (s, 1H), 6.62 (d, 1H), 6.95 (d, 1H), 7.14 (t, 1H), 7.56 (dd, 1H), 7.59-7.70 (m, 2H), 8.54 (s, 1H)

Fraction 5: ¹H-NMR (300 MHz, CD₃OD), δ=1.57 (s, 3H), 1.68 (s, 3H), 2.07 (d, 1H), 2.14 (d, 1H), 3.77 (s, 3H), 5.33 (s, 1H), 6.71 (d, 1H), 6.80 (d, 1H), 6.96 (t, 1H), 7.22 (dd, 1H), 7.58-7.69 (m, 2H), 8.56 (s, 1H)

Examples 77 and 78

(−)-5-{[2-Hydroxy-4,4-dimethyl-5-methoxy-2-(trifluoromethyl)-1,2,3,4-tetrahydronaphthalen-1-yl]amino}-2-methylphthalazin-1-one (+)-5-{[2-Hydroxy-4,4-dimethyl-5-methoxy-2-(trifluoromethyl)-1,2,3,4-tetrahydronaphthalen-1-yl]amino}-2-methylphthalazin-1-one Separation of (+/−)-5-{[2-hydroxy-4,4-dimethyl-5-methoxy-2-(trifluoromethyl)-1,2,3,4-tetrahydronaphthalen-1-yl]amino}-2-methylphthalazin-1-one The enantiomer mixture is separated by chromatography on chiral carrier material (CHIRALPAK AD®, DAICEL Company) with hexane/ethanol (90:10, vvv). The (−)-enantiomer: MS (EI): M⁺=447, [α]$_D$−48.0° °(c=0.7, CHCl₃) and the (+)-enantiomer: MS (EI): M⁺=447, [α]$_D$+45.6° °(c=0.8, CHCl₃) are thus obtained.

Examples 79 and 80

(−)-5-{[2,5-Dihydroxy-4,4-dimethyl-2-(trifluoromethyl)-12,3,4-tetrahydronaphthalen-1-yl]amino}-2-methylphthalazin-1-one, Diastereomer A (+)-5-{[2,5-Dihydroxy-4,4-dimethyl-2-(trifluoromethyl)-1,2,3,4-tetrahydronaphthalen-1-yl]amino}-2-methylphthalazin-1-one, Diastereomer A Separation of (+/−)-5-{[2,5-dihydroxy-4,4-dimethyl-2-(trifluoromethyl)-1,2,3,4-tetrahydronaphthalen-1-yl]amino}-2-methylphthalazin-1-one, diastereomer A The enantiomer mixture is separated by chromatography on chiral carrier material (CHIRALPAK AD®, DAICEL Company) with hexane/ethanol (85:15, vvv). The (−)-enan- Examples 81 and 82

(−)-5-{[2,5-Dihydroxy-4,4-dimethyl-2-(trifluoromethyl)-1,2,3,4-tetrahydronaphthalen-1-yl]amino}-2-methylphthalazin-1-one, Diastereomer A (+)-5-{[2,5-Dihydroxy-4,4-dimethyl-2-(trifluoromethyl)-1.2,3,4-tetrahydronaphthalen-1-yl]amino}-2-methylphthalazin-1-one, Diastereomer A Separation of (+/−)-5-{[2,5-dihydroxy-4,4-dimethyl-2-(trifluoromethyl)-1,2,3,4-tetrahydronaphthalen-1-yl]amino}-2-methylphthalazin-1-one, diastereomer B The enantiomer mixture is separated by chromatography on chiral carrier material (CHIRALPAK AD®, DAICEL Company) with hexane/ethanol (90:10, vvv). The (−)-enantiomer: MS (EI): M$^+$=433, [α]$_D$−10.1° °(c=0.8, CHCl$_3$) and the (+)-enantiomer: MS (EI): M$^+$=433, [α]$_{D+}$5.8° °(c=0.9, CHCl$_3$) are thus obtained.

Example 83 cis-1-[(2-Methylquinazolin-5-yl)amino]-4,4-dimethyl-2-(trifluoromethyl)-1,2,3,4-tetrahydronaphthalen-2-ol (Markus Berger)

5-Amino-2-methylquinazoline 12.7 g (62 mmol) of 2-methyl-5-nitro-3H-quinazolin-4-one (M. T. Bogert, V. J. Chambers *J. Org Chem.* 1905, 649-658) and 37.5 g of phosphorus pentachloride are refluxed in 75 ml of phosphoryl chloride over 20 hours. After cooling, it is poured into saturated NaHCO$_3$ solution and extracted with ethyl acetate. The organic phase is dried, and the solvent is removed. 14 g of 4-chloro-2-methyl-5-nitroquinazoline, of which 4.5 g (20.2 mmol) in 225 ml of ethyl acetate and 22.5 ml of triethylamine are dissolved, is obtained. 2 g of palladium is added to carbon, and it is stirred while being cooled with ice for 4 hours under hydrogen atmosphere at normal pressure. Catalyst is removed from the solution by means of filtration through Celite, whereby it is rewashed with 200 ml of ethanol and concentrated by evaporation. After chromatography on silica gel with ethyl acetate-ethanol (0-10%), 530 mg of the product is obtained.

$^1$H-NMR (300 MHz, CDCl$_3$): δ=2.87 (s, 3H), 4.52 (br., 2H), 6.77 (d, 1H), 7.33 (d, 1H), 7.65 (t, 1H), 9.40 (s, 1H).

(rac)-1,1,1,-Trifluoro-4-phenyl-2-[(E/Z)-(2-methylquinazol-5-yl)iminomethyl]-4-methyl-pentan-2-ol 0.3 ml of titanium tetraethylate is added to 140 mg (0.54 mmol) of 2-hydroxy-4-methyl-4-phenyl-2-(trifluoromethyl)-pentanal and 100 mg (0.63 mmol) of 5-amino-2-methylquinazoline in 15 ml of toluene, and the mixture is heated for over 2 hours to 100° C. After cooling, it is poured into water, and vigorous stirring is continued. The suspension is filtered through Celite, and it is rewashed thoroughly with ethyl acetate. The phases of the filtrate are separated, and it is extracted again with ethyl acetate. It is dried on sodium sulfate, and the solvent is removed in a vacuum. After chromatographic purification on silica gel (hexane/ethyl acetate 0-60%), 123 mg of (rac)-1,1,1,-trifluoro-4-phenyl-2-[(E/Z)-(2-methyl-quinazol-5-yl)iminomethyl]-4-methyl-pentan-2-ol is obtained.

cis-1-[(2-Methylquinazolin-5-yl)amino]-4,4-dimethyl-2-(trifluoromethyl)-1,2,3,4-tetrahydronaphthalen-2-ol 82 mg (0.20 mmol) of imine is taken up in 7 ml of dichloromethane and cooled to −70° C. 0.8 ml (0.8 mmol) of a 1 M titanium tetrachloride solution in dichloromethane is added in drops over 10 minutes, and it is stirred for another 6 hours at −65° C. The solution is poured into a saturated sodium bicarbonate solution and stirred vigorously for 5 minutes. It is extracted with dichloromethane, washed with saturated sodium chloride solution and dried on sodium sulfate. After concentration by evaporation and chromatography on silica gel (hexane/ethyl acetate 0-65%), 46 mg of the desired product is obtained.

$^1$H-NMR (300 MHz, CDCl$_3$): δ=1.46 (s, 3H), 1.63 (s, 3H), 2.19 (d, 1H), 2.29 (d, 1H), 2.87 (s, 3H), 5.14 (d, 1H), 5.97 (d, 1H), 6.81 (d, 1H), 7.15 (t, 1H), 7.36-7.43 (m, 2H), 7.42 (d, 1H), 7.75 (t, 1H), 9.42 (s, 1H).

Example 84 trans-5-Methoxy-1-[(2-methylquinazolin-5-yl)amino]-4,4-dimethyl-2-(trifluoromethyl)-1,2,3,4-tetrahydronaphthalen-2-ol The compound was produced analogously to Example 83.

$^1$H-NMR (300 MHz, CDCl$_3$): δ=1.43 (s, 3H), 1.54 (s, 3H), 2.07 (d, 1H), 2.18 (d, 1H), 2.84 (s, 3H), 3.21 (s, 3H), 4.31 (d, 1H), 5.38 (d, 1H), 6.63 (d, 1H), 7.05 (d, 1H), 7.18 (d, 1H), 7.31 (t, 1H), 7.43 (d, 1H), 7.81 (t, 1H), 9.13 (s, 1H).

Example 85 cis-6-Chloro-5-methoxy-1-[(2-methylquinazolin-5-yl)amino]-4,4-dimethyl-2-(trifluoromethyl)-1,2,3,4-tetrahydronaphthalen-2-ol The compound was produced analogously to Example 83.

$^1$H-NMR (300 MHz, CDCl$_3$): δ=1.58 (s, 3H), 1.74 (s, 3H), 2.14 (d, 1H), 2.25 (d, 1H), 2.88 (s, 3H), 3.97 (s, 3H), 5.05 (d, 1H), 5.92 (d, 1H), 6.79 (d, 1H), 7.09 (d, 1H), 7.19 (d, 1H), 7.30 (d, 1H), 7.75 (t, 1H), 9.39 (s, 1H).

Example 86 cis-6-Fluoro-5-methoxy-1-[(2-methylquinazolin-5-yl)amino]-4,4-dimethyl-2-(trifluoromethyl)-1,2,3,4-tetrahydronaphthalen-2-ol The compound was produced analogously to Example 83.

$^1$H-NMR (CDCl$_3$): δ=1.57 (s, 3H), 1.74 (s, 3H), 2.13 (d, 1H), 2.26 (d, 1H), 2.88 (s, 3H), 3.97 (s, 3H), 5.02 (d, 1H), 5.85 (d, 1H), 6.79 (d, 1H), 6.93 (dd, 1H), 7.07 (dd, 1H), 7.29 (d, 1H), 7.74 (d, 1H), 9.33 (s, 1H).

Example 87 cis-6-[(2-Methylquinazolin-5-yl)amino]-9,9-dimethyl-7-(trifluoromethyl)-6,7,8,9-tetrahydro-naphtho[1,2-d]-1,3-dioxol-7-ol The compound is synthesized as described in Example 83.
$^1$H-NMR (300 MHz, CDCl$_3$): δ=1.52 (s, 3H), 1.66 (s, 3H), 2.10 (d, 1H), 2.26 (d, 1H), 2.88 (s, 3H), 5.04 (d, 1H), 5.94 (d, 1H), 5.99 (d, 2H), 6.65 (d, 1H), 6.80 (d, 1H), 6.86 (d, 1H), 7.76 (t, 1H), 9.52 (s, 1H).

Example 88 cis-6-Chloro-1-[(2-methylquinazolin-5-yl)amino]-4,4-dimethyl-2-(trifluoromethyl)-1,2,3,4-tetrahydronaphthalene-2,5-diol The compound is produced by ether cleavage as described in Example 3.
$^1$H-NMR (300 MHz, CDCl$_3$): δ=1.54 (s, 3H), 1.68 (s, 3H), 2.06 (d, 1H), 2.20 (d, 1H), 2.81 (s, 3H), 4.98 (d, 1H), 5.81 (d, 1H), 5.91 (br., 1H), 6.73 (d, 1H), 6.86 (d, 1H), 7.08 (d, 1H), 7.23 (d, 1H), 9.35 (s, 11H).

Example 89 cis-6-Fluoro-1-[(2-methylquinazolin-5-yl)amino]-4,4-dimethyl-2-(trifluoromethyl)-1,2,3,4-tetrahydronaphthalene-2,5-diol The compound is produced by ether cleavage as described in Example 3.
$^1$H-NMR (300 MHz, CDCl$_3$): δ=1.62 (s, 3H), 1.77 (s, 3H), 2.13 (d, 1H), 2.27 (d, 1H), 2.88 (s, 3H), 5.03 (d, 1H), 5.67 (br, 1H), 5.78 (d, 1H), 6.79 (d, 1H), 6.91 (d, 2H), 7.29 (d, 1H), 7.73 (t, 1H), 9.35 (s, 1H).

Example 90 cis-6-[(7-Fluoro-2-methylquinazolin-5-yl)amino]-9,9-dimethyl-7-(trifluoromethyl)-6,7,8,9-tetrahydro-naphtho[1,2-d]-1,3-dioxol-7-ol 5-Amino-7-fluoro-2-methyquinazoline 17 g (70.5 mmol) of 3,6-difluoro-2-N-pivaloylaminobenzaldehyde (L. Florvall, I. Fagervall, L.-G- Larsson, S. B. Ross, Eur. J. Med. Chem. 34 (1999) 137-151), 9.2 g of acetamidine hydrochloride, 13.4 g of potassium carbonate and 10.4 g of molecular sieve (4A) are combined in 70 ml of butyronitrile. It is heated while being stirred vigorously for 17 hours to 145° C., and the solvent is removed in a vacuum. After the residue is chromatographed on silica gel with hexane/ethyl acetate (0-70%), 4.5 g of 7-fluoro-5-N-pivaloylamino-2-methylquinazoline is obtained.

1 g (3.82 mmol) of 7-fluoro-5-N-pivaloylamino-2-methyquinazoline is dissolved in 74 ml of toluene and cooled to −70° C. 9.5 ml (11.4 mmol) of a 1.2 M diisobutylaluminum hydride solution in toluene is added in drops over 30 minutes. The reaction mixture is allowed to heat to −40° C. and stirred for 4 hours at −40° C. Water is slowly added, and it is stirred for 30 minutes at room temperature until a precipitate is formed that is removed by means of filtration through Celite. The phases are separated, washed with saturated sodium chloride solution and dried on sodium sulfate. After chromatography on silica gel with hexane-ethyl acetate (0-100%), 64 mg of the product is obtained.
$^1$H-NMR (300 MHz, CDCl$_3$): δ=2.83 (s, 3H), 4.67 (br., 2H), 6.50 (dd, 1H), 6.93 (dd, 1H), 9.23 (s, 1H).

0.1 ml of titanium tetraethylate is added to 60 mg (0.46 mmol) of rac. 4-(1,3-benzodioxol-4-yl)-2-hydroxy-4-methyl-2-(trifluoromethyl)-pentanal and 32 mg (0.18 mmol) of 5-amino-7-fluoro-2-methylquinazoline in 7 ml of toluene, and the mixture is heated over 2.5 hours to 100° C. After cooling, it is poured into water, and vigorous stirring is continued. The suspension is filtered through Celite, and it is thoroughly rewashed with ethyl acetate. The phases of the filtrate are separated, and it is extracted again with ethyl acetate. It is dried on sodium sulfate, and the solvent is removed in a vacuum. The 4-(1,3-benzodioxol-4-yl)-1,1,1-trifluoro-2-[(E/Z)-(7-fluoro-2-methylquinazolin-5-yl)iminomethyl]-4-methyl-pentan-2-ol that is thus obtained in crude form is taken up in 8 ml of dichloromethane and cooled to −70° C. 1.1 ml (1.1 mmol) of a 1 M titanium tetrachloride solution in dichloromethane is added in drops over 10 minutes, and it is stirred for another hour at −70° C. The solution is poured into a saturated sodium bicarbonate solution and vigorously stirred for 5 minutes. It is extracted with dichloromethane, washed with saturated sodium chloride solution and dried on sodium sulfate. After concentration by evaporation and chromatography on silica gel (hexane/ethyl acetate 0-75%), 26 mg of the desired product is obtained.
$^1$H-NMR (300 MHz, CDCl$_3$): δ=1.53 (s, 3H), 1.66 (s, 3H), 2.12 (d, 1H), 2.27 (d, 1H), 2.84 (s, 3H), 4.94 (d, 1H), 5.99 (s, 1H), 6.00 (s, 1H), 6.02 (d, 1H), 6.50 (dd, 1H), 6.68 (d, 1H), 6.83 (d, 1H), 6.89 (dd, 1H), 9.26 (s, 1H).

Example 91 trans-5-Methoxy-1-[(7-fluoro-2-methylquinazolin-5-yl)amino]-4,4-dimethyl-2-(trifluoromethyl)-1,2,3,4-tetrahydronaphthalen-2-ol The compound was produced analogously to Example 83.
$^1$H-NMR (300 MHz, CDCl$_3$): δ=1.42 (s, 3H), 1.55 (s, 3H), 2.07 (d, 1H), 2.17 (d, 1H), 2.80 (s, 3H), 3.33 (s, 3H), 4.57 (d, 1H), 5.31 (d, 1H), 6.66 (d, 1H), 6.88 (dd, 1H), 7.00 (d, 1H), 7.05 (d, 1H), 7.30 (t, 1H), 9.03 (s, 1H).

Example 92 cis-6-Chloro-1-[(7-fluoro-2-methylquinazolin-5-yl)amino]-4,4-dimethyl-2-(trifluoromethyl)-1,2,3,4-tetrahydronaphthalene-2,5-diol The compound is produced by ether cleavage as described in Example 3.
$^1$H-NMR (300 MHz, CDCl$_3$): δ=1.60 (s, 3H), 1.73 (s, 3H), 2.12 (d, 1H), 2.24 (d, 1H), 2.84 (s, 3H), 4.96 (d, 1H), 5.98 (d, 1H), 6.01 (s, 1H), 6.51 (dd, 1H), 6.88 (d, 1H), 6.91 (dd, 1H), 7.17 (d, 1H), 9.23 (s, 1H).

Example 93 cis-6-Fluoro-1-[(7-fluoro-2-methylquinazolin-5-yl)amino]-4,4-dimethyl-2-(trifluoromethyl)-1,2,3,4-tetrahydronaphthalene-2,5-diol The compound is produced by ether cleavage as described in Example 3.
$^1$H-NMR (300 MHz, CD$_3$OD): δ=1.61 (s, 3H), 1.72 (s, 3H), 2.15 (m, 2H), 2.78 (s, 3H), 5.30 (s, 1H), 6.72-6.82 (m, 3H), 6.92 (dd, 1H), 9.55 (s, 1H).

Example 94 trans-7-Fluoro-1-[(7-fluoro-2-methylquinazolin-5-yl)amino]-5-methoxy-4,4-dimethyl-2-(trifluoromethyl)-1,2,3,4-tetrahydronaphthalen-2-ol $^1$H-NMR (300 MHz, CD$_3$OD): δ=1.40 (s, 3H), 1.53 (s, 3H), 2.07 (d, 1H), 2.18 (d, 1H), 2.81 (s, 3H), 3.34 (s, 3H), 4.52 (d, 1H), 5.25 (d, 1H), 6.41 (dd, 1H), 6.74 (dd, 1H), 6.86 (dd, 1H), 7.01 (dd, 1H), 9.03 (s, 1H).

Example 95 cis-6-Chloro-1-[(8-fluoro-2-methylquinazolin-5-yl)amino]-4,4-dimethyl-2-(trifluoromethyl)-1,2,3,4-tetrahydronaphthalene-2,5-diol 5-Amino-8-fluoro-2-methylquinazoline A solution of 2.4 g (18.6 mmol) of 2,5-difluoroaniline in 11 ml of water and 1.6 ml of concentrated hydrochloric acid (37%) that is 50° C. is added to a solution of 3.35 g (20.25 mmol) of chloral hydrate and 21.27 g (149.7 mmol) of sodium sulfate in 72 ml of water, which was previously stirred at this temperature for 1 hour. It is stirred for another 30 minutes at room temperature, and after 4.09 g (58.9 mmol) of hydroxylammonium chloride in 19 ml of water is added, it is heated for 45 minutes to 125° C. and kept at this temperature for 5 minutes. After cooling and after another hour, the deposited light-brown precipitate is filtered off, washed with water and dried. 3.0 g (15.0 mmol) of the hydroxylimine is obtained as an intermediate product, which is dissolved in portions in 15 ml of concentrated sulfuric acid at 60° C. After the addition is completed, it is heated for 2 hours to 80° C. and for 4 hours to 90° C. It is allowed to cool off, and the solution is poured into 100 g of ice. It is extracted with ethyl acetate, the organic phase is washed with water, dried on sodium sulfate, and concentrated by evaporation. After chromatography on silica gel with hexane-ethyl acetate (0-45%), 1.2 g (7.1 mmol) of 4,7-difluorisatin is obtained. 1.8 ml of a 30% hydrogen peroxide solution is added in drops to isatin in 30 ml of a 1 molar sodium hydroxide solution over 10 minutes. After 2 hours of stirring at room temperature, it is cooled to 0° C. and 5 ml of a 4 molar hydrochloric acid is added and diluted with 50 ml of water. It is extracted with ethyl acetate, dried on sodium sulfate, concentrated by evaporation, and 1.27 g of 3,6-difluoroanthranilic acid, which is reacted without further purification, is thus quantitatively obtained.

The 3,6-difluoroanthranilic acid is heated in 8 ml of acetic acid anhydride for 45 minutes to 100° C. After cooling, the acetic acid that is produced and excess acetic acid anhydride are removed azeotropically with toluene in a vacuum. The residue is mixed with 40 ml of a 25% ammonia solution while being cooled with ice, and it is stirred for 72 hours. It is diluted with water and acidified with acetic acid. It is extracted with ethyl acetate, the organic phase is washed with water, dried on sodium sulfate and concentrated by evaporation. The thus obtained 1.03 g (5.25 mmol) of 5,8-difluoro-2-methyl-3H-quinazolin-4-one and 6 g of phosphorus pentachloride are heated in 20 ml of phosphoryl chloride over 12 hours to 125° C. After cooling, it is poured into saturated NaHCO$_3$ solution and extracted with ethyl acetate. The organic phase is dried, and the solvent is removed. 1.7 g of 4-chloro-5,8-difluoro-2-methylquinazoline, which is dissolved in 60 ml of ethyl acetate and 5 ml of triethylamine, is obtained quantitatively. 600 mg of palladium on carbon is added and shaken for 2 hours (480 ml of hydrogen absorption) under hydrogen atmosphere at normal pressure. Catalyst is removed from the solution by means of filtration over Celite, whereby it is rewashed with 100 ml of ethanol and concentrated by evaporation. After chromatography on silica gel with hexane-ethyl acetate-ethanol (0-40%), 550 mg of 5,8-difluoro-2-methylquinazoline is obtained. 890 mg (13.7 mmol) of sodium azide is added to 240 mg (1.3 mmol) of 5,8-difluoro-2-methylquinazoline, 300 mg (1.13 mmol) of 18-crown-6 in 10 ml of DMF, and the mixture is heated over 8 hours to 125° C. The solvent is removed in a vacuum, and it is chromatographed on silica gel with ethyl acetate, and 52 mg of product is obtained.

$^1$H-NMR (300 MHz, CDCl$_3$): δ=2.92 (s, 3H), 4.31 (br., 2H), 6.67 (dd, 1H), 7.38 (dd, 1H), 9.37 (s, 1H).

0.23 ml (1.1 mmol) of titanium tetraethylate is added to 140 mg (0.46 mmol) of 4-(3-chloro-2-methoxyphenyl)-2-hydroxy-4-methyl-2-(trifluoromethyl)-pentanal and 100 mg (0.56 mmol) of 5-amino-8-fluoro-2-methylquinazoline in 14 ml of toluene, and the mixture is heated over 2 hours to 100° C. After cooling, it is poured into water, and vigorous stirring is continued. The suspension is filtered through Celite, and it is thoroughly rewashed with ethyl acetate. The phases of the filtrate are separated, and it is extracted again with ethyl acetate. It is dried on sodium sulfate, and the solvent is removed in a vacuum. The 4-(3-chloro-2-methoxyphenyl)-1,1,1-trifluoro-2-[(E/Z)-(8-fluoro-2-methylquinazolin-5-yl)iminomethyl]-4-methyl-pentan-2-ol that is thus obtained in crude form is taken up in 23 ml of dichloromethane and cooled to −30° C. 7.8 ml (7.8 mmol) of a 1 M boron tribromide solution in dichloromethane is added in drops over 10 minutes, allowed to come to room temperature over 1 hour, and stirred for another 16 hours. The solution is poured into a mixture of ice and saturated sodium bicarbonate solution and vigorously stirred for 15 minutes. It is extracted with dichloromethane, washed with saturated sodium chloride solution and dried on sodium sulfate. After concentration by evaporation and chromatography on silica gel (hexane/ethyl acetate 0-50%), 64 mg of the desired product is obtained.

$^1$H-NMR (300 MHz, CDCl$_3$): δ=1.60 (s, 3H), 1.74 (s, 3H), 2.07 (d, 1H), 2.26 (d, 1H), 2.93 (s, 3H), 4.99 (d, 1H), 5.66 (d, 1H), 5.99 (br., 1H), 6.67 (dd, 1H), 6.91 (d, 1H), 7.16 (d, 1H), 7.49 (dd, 1H), 9.41 (s, 1H).

Example 96 cis-1-[(8-Fluoro-2-methylquinazolin-5-yl)amino]-4,4-dimethyl-2-(trifluoromethyl)-1,2,3,4-tetrahydronaphthalen-2-ol $^1$H-NMR (300 MHz, CDCl$_3$): δ=1.45 (s, 3H), 1.61 (s, 3H), 2.17 (d, 1H), 2.26 (d, 1H), 2.92 (s, 3H), 5.08 (d, 1H), 5.69 (d, 1H), 6.69 (dd, 1H), 7.16 (t, 1H), 7.35 (m, 2H), 7.42 (d, 1H), 7.49 (t, 1H), 9.44 (s, 1H).

Example 97 trans-8-Fluoro-1-[(8-fluoro-2-methylquinazolin-5-yl)amino]-5-methoxy-4,4-dimethyl-2-(trifluoromethyl)-1,2,3,4-tetrahydronaphthalen-2-ol $^1$H-NMR (300 MHz, CDCl$_3$): δ=1.50 (s, 3H), 1.63 (s, 3H), 2.14 (s, 2H), 2.89 (s, 3H), 3.21 (s, 3H), 4.25 (d, 1H), 5.21 (d, 1H), 6.59 (dd, 1H), 6.98 (dd, 1H), 7.04 (dd, 1H), 7.52 (dd, 1H), 9.21 (s, 1H).

Example 98 cis-7-Chloro-1-[(−8-fluoro-2-methylquinazolin-5-yl)amino]-4,4-dimethyl-2-(trifluoromethyl)-1,2,3,4-tetrahydronaphthalen-2-ol $^1$H-NMR (300 MHz, CDCl$_3$): δ=1.44 (s, 3H), 1.60 (s, 3H), 2.18 (d, 1H), 2.27 (d, 1H), 2.93 (s, 3H), 5.00 (d, 1H), 5.71 (d, 1H), 6.66 (dd, 1H), 7.28-7.37 (m, 3H), 7.50 (dd, 1H), 9.39 (s, 1H).

Example 99 cis-6-Chloro-1-[(8-fluoro-2-methylquinazolin-5-yl)amino]-5-methoxy-4,4-dimethyl-2-(trifluoromethyl)-1,2,3,4-tetrahydronaphthalen-2-ol $^1$H-NMR (300 MHz, CDCl$_3$): δ=1.57 (s, 3H), 1.72 (s, 3H), 2.12 (d, 1H), 2.22 (d, 1H), 2.93 (s, 3H), 3.97 (s, 3H), 4.99 (d, 1H), 5.65 (d, 1H), 6.67 (dd, 1H), 7.07 (d, 1H), 7.21 (d, 1H), 7.49 (dd, 1H), 9.39 (s, 1H).

Example 100 cis-6-Fluoro-1-[(8-fluoro-2-methylquinazolin-5-yl)amino]-5-methoxy-4,4-dimethyl-2-(trifluoromethyl)-1,2,3,4-tetrahydronaphthalen-2-ol $^1$H-NMR (300 MHz, CDCl$_3$): δ=1.56 (s, 3H), 1.71 (s, 3H), 2.11 (d, 1H), 2.22 (d, 1H), 2.93 (s, 3H), 3.97 (s, 3H), 4.97 (d, 1H), 5.60 (d, 1H), 6.67 (dd, 1H), 6.93 (dd, 1H), 7.06 (dd, 1H), 7.48 (dd, 1H), 9.37 (s, 1H).

Example 101 cis-6-[(8-Fluoro-2-methylquinazolin-5-yl)amino]-9,9-dimethyl-7-(trifluoromethyl)-6,7,8,9-tetrahydro-naphtho[1,2-d]-1,3-dioxol-7-ol $^1$H-NMR (300 MHz, CDCl$_3$): δ=1.52 (s, 3H), 1.67 (s, 3H), 2.10 (d, 1H), 2.27 (d, 1H), 2.94 (s, 3H), 4.96 (d, 1H), 5.67 (d, 1H), 5.99 (s, 1H), 6.01 (s, 1H), 6.67 (d, 1H), 6.68 (dd, 1H), 6.86 (d, 1H), 7.49 (dd, 1H), 9.44 (s, 1H).

Example 102 cis-6-Fluoro-1-[(8-fluoro-2-methylquinazolin-5-yl)amino]-4,4-dimethyl-2-(trifluoromethyl)-1,2,3,4-tetrahydronaphthalene-2,5-diol $^1$H-NMR (300 MHz, CD$_3$OD): δ=1.60 (s, 3H), 1.72 (s, 3H), 2.09 (d, 1H), 2.17 (d, 1H), 2.86 (s, 3H), 5.23 (s, 1H), 6.80-6.93 (m, 3H), 7.57 (dd, 1H), 9.66 (s, 1H).

Example 103 cis-6-[(2-Methylquinolin-5-yl)amino]-9,9-dimethyl-7-(trifluoromethyl)-6,7,8,9-tetrahydro-naphtho[1,2-d]-1,3-dioxol-7-ol $^1$H-NMR (300 MHz, CDCl$_3$): δ=1.50 (s, 3H), 1.60 (s, 3H), 2.08 (d, 1H), 2.20 (d, 1H), 2.73 (s, 3H), 4.85 (d, 1H), 5.09 (d, 1H), 5.98 (s, 1H), 5.99 (s, 1H), 6.62 (d, 1H), 6.81 (m, 2H), 7.22 (d, 1H), 7.50 (d, 1H), 7.56 (t, 1H), 8.09 (d, 1H).

Example 104 cis-6-[(2-Methyl-1,7-naphthyridin-5-yl)amino]-9,9-dimethyl-7-(trifluoromethyl)-6,7,8,9-tetrahydro-naphtho[1,2-d]-1,3-dioxol-7-ol $^1$H-NMR (300 MHz, CD$_3$OD): δ=1.48 (s, 3H), 1.57 (s, 3H), 2.02 (d, 1H), 2.17 (d, 1H), 2.76 (s, 3H), 5.06 (s, 1H), 5.96 (s, 2H), 6.61 (d, 1H), 6.82 (d, 1H), 7.50 (d, 1H), 7.90 (s, 1H), 8.33 (d, 1H), 8.69 (s, 1H)

Example 105

Rac.-5,8-Difluoro-1-[(1H-indazol-4-yl)amino]-4,4-dimethyl-2-(trifluoromethyl)-1,2,3,4-tetrahydronaphthalen-2-ol (Diastereomer B)

Melting point: 209-21 1° C.

Example 106

Rac.-5-Fluoro-1-[(2-methylquinazolin-5-yl)amino]-6-methoxy-4,4-dimethyl-2-(trifluoromethyl)-1,2,3,4-tetrahydronaphthalene-2-diol (Diastereomer B)

Melting point: 11 5° C.

Example 107

Rac.-5-Fluoro-1-[(2-methylquinazolin-5-yl)amino]-4,4-dimethyl-2-(trifluoromethyl)-1,2,3,4-tetrahydronaphthalene-2,5-diol (Diastereomer B)

$^1$H-NMR (300 MHz, CD$_3$OD): δ=1.51 (s, 3H), 1.66 (s, 3H), 2.08 (d, J=14 Hz, 1H), 2.18 (d, J=14 Hz, 1H), 2.82 (s, 3H), 5.21 (s, 1H), 6.71-6.93 (m, 3H), 7.19 (d, J=8 Hz, 1H), 7.77 (dd, J=9 Hz/8 Hz, 1H), 9.57 (s, 1H).)

Example 108

Rac.-5-Fluoro-1-[(2-methylquinazolin-5-yl)amino]-6-methoxy-4,4-dimethyl-2-(trifluoromethyl)-1,2,3,4-tetrahydronaphthalene-2-diol (Diastereomer A)

MS (ESI): 4590 (M+1)

Example 109

6-Fluoro-1-{[(2-hydroxymethyl)-quinolin-5-yl)amino]}-5-methoxy-4,4-dimethyl-2-(trifluoromethyl)-1,2,3,4-tetrahydronaphthalen-2-ol 5-[4-(3-Fluoro-2-methoxyphenyl)-2-hydroxy-4-methyl-2-trifluoromethyl-pentylidenamino]-quinoline-2-carboxylic acid methyl ester A solution that consists of 4-(3-fluoro-2-methoxyphenyl)-2-hydroxy-4-methyl-2-trifluoro-methylpentanal (872 mg, 2.84 mmol) and 5-aminoquinoline-2-carboxylic acid methyl ester (570 mg, 2.84 mmol) in 5.0 ml of concentrated acetic acid is allowed to stir for two days at room temperature. After repeated co-evaporation with toluene, the residue is purified on silica gel with hexane/ethyl acetate (0-100% ethyl acetate). 820 mg (59% of theory) of the product is obtained.

$^1$H-NMR (300 MHz, CDCl$_3$): δ=1.41 (s, 3H), 1.59 (s, 3H), 2.35 (d, 1H), 3.33 (d, 1H), 4.00 (d, 3H), 4.11 (s, 3H), 4.76 (d, 1H), 6.32-6.39 (m, 1H), 6.49-6.56 (m, 1H), 6.66 (d, 1H), 6.81 (d, 1H), 7.60-7.65 (m, 2H), 8.14-8.24 (m, 2H), 8.52 (d, 1H).

5-(6-Fluoro-2-hydroxy-5-methoxy-4,4-dimethyl-2-trifluoromethyl-1,2,3,4-tetrahydronaphthalen-1-ylamino)-quinoline-2-carboxylic acid methyl ester 5-[4-(3-Fluoro-2-methoxyphenyl)-2-hydroxy-4-methyl-2-trifluoromethyl-pentylidenamino]-quinoline-2-carboxylic acid methyl ester (120 mg, 0.243 mmol) is dissolved in 2.0 ml of dichloromethane. Titanium tetrachloride (1 M solution in dichloromethane, 0.73 ml, 0.73 mmol) is added in drops within 15 minutes at −30° C. Then, the reaction mixture is allowed to stir for 3 hours at −30° C. to −1 5° C. By adding saturated sodium bicarbonate solution at −30° C., the reaction is brought to a halt. It is extracted with ethyl acetate, the combined organic phases are washed with water and saturated sodium chloride solution. After drying on sodium sulfate and after the solvent is removed in a vacuum as well as subsequent purification on silica gel with dichloromethane/methanol (0-3% methanol), 70 mg (58% of theory) of the product is obtained.

$^1$H-NMR (300 MHz, CD$_3$OD): δ=1.56 (s, 3H), 1.68 (s, 3H), 2.16 (s, 2H), 3.96 (d, 3H), 4.08 (s, 3H), 5.28 (s, 1H), 6.91-6.99 (m, 2H), 7.03-7.09 (m, 1H), 7.57 (d, 1H), 7.68 (t, 1H), 8.12 (d, 1H), 8.72 (d, 1H).

6-Fluoro-1-{[(2-hydroxymethyl)-quinolin-5-yl)amino]}-5-methoxy-4,4-dimethyl-2-(trifluoromethyl)-1,2,3,4-tetrahydronaphthalen-2-ol 5-(6-Fluoro-2-hydroxy-5-methoxy-4,4-dimethyl-2-trifluoromethyl-1,2,3,4-tetrahydro-naphthalen-1-ylamino)-quinoline-2-carboxylic acid methyl ester (70 mg, 0.14 mmol) is dissolved in 5.0 ml of methanol and mixed with sodium borohydride (22 mg, 0.57 mmol). After one hour and after 2 hours, in each case the same amounts are added to sodium borohydride (total amounts: 66 mg, 0.171 mmol). By adding water, the reaction is brought to a halt. It is extracted with ethyl acetate, the combined organic phases are washed with saturated sodium chloride solution and dried on sodium sulfate. After the solvent is removed in a vacuum, the purification of the residue on silica gel is carried out with hexane/ethyl acetate (0-100% ethyl acetate). 21 mg (32% of theory) of the product is obtained.

$^1$H-NMR (300 MHz, DMSO-d$_6$): δ=1.48 (s, 3H), 1.61 (s, 3H), 2.01 (d, 1H), 2.14 (d, 1H), 3.88 (d, 3H), 4.70 (d, 2H), 5.40 (d, 1H), 5.51 (t, 1H), 6.19 (s, 1H), 6.35 (d, 1H), 6.83 (d, 1H), 6.91-6.96 (m, 1H), 7.04-7.11 (m, 1H), 7.21 (d, 1H), 7.48 (t, 1H), 7.58 (d, 1H), 8.64 (d, 1H).

Example 110

1-[(5-Chloro-1H-indazol-4-yl)amino]-6-fluoro-5-methoxy-4,4-dimethyl-2-(trifluoromethyl)-1,2,3,4-tetrahydronaphthalen-2-ol

5-Chloro-4-nitro-1H-indazole 2.24 g (12 mmol) of 4-chloro-2-methyl-3-nitrophenylamine, produced according to the literature (Mori et al., Chem. Pharm. Bull. 1986, 34, 4859 ff. as well as Brand and Zöller, Chem. Ber. 1907, 3324 ff.) is dissolved in 100 ml of acetic acid. At 10° C., 6.0 ml of a 2 molar aqueous sodium nitrite solution is added in drops. The suspension is then added to boiling acetic acid (150 ml) within 15 minutes, and the reaction mixture is allowed to reflux for 4 hours. After the acetic acid is removed in a vacuum, the residue is taken up in ethyl acetate and saturated sodium bicarbonate solution. The organic phase is washed with saturated sodium chloride solution and dried on sodium sulfate. After the solvent is removed in a vacuum, the crude product is further reacted (1.81 g, 76%).

$^1$H-NMR (300 MHz, DMSO-d$_6$): δ=7.65 (d, 1H), 7.97 (d, 1H), 8.32 (s, 1H), 13.97 (s, 1H).

5-Chloro-1H-indazol-4-ylamine

A solution that consists of 5-chloro-4-nitro-1H-indazole (872 mg, 4.41 mmol) is mixed with 150 mg of palladium on carbon (10%) and stirred under hydrogen atmosphere at room temperature. After 45 minutes, the catalyst is suctioned off on one frit and washed with methanol. The filtrate is concentrated by evaporation, and the residue is taken up in 200 ml of ethyl acetate and heated. After renewed suctioning-off and concentration by evaporation of the filtrate, the purification on silica gel is carried out with hexane/ethyl acetate (100-33% hexane). 296 mg (40% of theory) of the product is obtained.

$^1$H-NMR (300 MHz, DMSO-d$_6$): δ=5.97 (s, 2H), 6.66 (d, 1H), 7.05 (d, 1H), 8.19 (s, 1H), 12.83 (s, 1H).

2-[(5-Chloro-1H-indazol-4-ylimino)-methyl]-1,1,1-trifluoro-4-(3-fluoro-2-methoxyphenyl)-4-methyl-pentan-2-ol A solution that consists of 4-(3-fluoro-2-methoxyphenyl)-2-hydroxy-4-methyl-2-trifluoro-methylpentanal (278 mg, 0.9 mmol) and 5-chloro-1H-indazol-4-ylamine (121 mg, 0.72 mmol) in 20 ml of xylene is mixed with titanium(IV)ethylate (0.42 ml, 2.0 mmol) and refluxed for 10 hours. After cooling to room temperature, xylene is distilled off, and the residue is purified on silica gel with hexane/ethyl acetate (30-100% ethyl acetate). 123 mg (37% of theory) of the product is obtained.

$^1$H-NMR (400 MHz, CDCl$_3$): δ=1.43 (s, 3H), 1.57 (s, 3H), 2.38 (d, 1H), 3.22 (d, 1H), 3.94 (d, 3H), 4.91 (s, 1H), 6.41-6.52 (m, 2H), 6.90 (d, 1H), 7.28 (d, 1H), 7.38 (d, 1H), 7.56 (s, 1H), 7.72 (s, 1H), 10.26 (br, 1H).

1-(5-Chloro-1H-indazol-4-ylamino)-6-fluoro-5-methoxy-4,4-dimethyl-2-trifluoromethyl-1,2,3,4-tetrahydro-naphthalen-2-ol Analogously to Example 109, 27 mg (24% of theory) of the product is obtained in the reaction of 2-[(5-chloro-1H-indazol-4-ylimino)-methyl]-1,1,1-trifluoro-4-(3-fluoro-2-methoxyphenyl)-4-methyl-pentan-2-ol (111 mg, 0.24 mmol) with titanium tetrachloride (0.72 ml of a 1 M solution in dichloromethane, 0.72 mmol) in 2.0 ml of dichloromethane after purification by means of preparative thin-layer chromatography.

$^1$H-NMR (400 MHz, CDCl$_3$): δ=1.56 (s, 3H), 1.65 (s, 3H), 2.09-2.17 (2d, 2H), 3.97 (d, 3H), 5.34-5.36 (m, 2H), 6.87-6.95 (m, 2H), 7.15 (dd, 1H), 7.32 (d, 1H), 8.05 (s, 1H).

Example 111

1-(5-Methyl-1H-indazol-4-ylamino)-6-fluoro-4,4-dimethyl-2-trifluoromethyl-1,2,3,4-tetrahydro-naphthalene-2,5-diol

5-Methyl-1H-indazol-4-ylamine

In a solution that consists of 2,4-dimethylaniline (12.4 ml, 100 mmol) in 80 ml of concentrated sulfuric acid, it is mixed at 0° C. with 5.0 ml of fuming nitric acid and stirred for 20 minutes at 4° C., and then for 30 minutes at room temperature. The reaction mixture is poured into 600 ml of ice water, and set at a pH of 10 with 5N sodium hydroxide solution. The precipitate is suctioned off, washed with water and dried. 15.72 g (95% of theory) of 2,4-dimethylnitrophenylamine is obtained as a mixture of regioisomers.

Analogously to the production of 5-chloro-4-nitro-1H-indazole, 1.14 g (57% of theory) of the product was obtained as a mixture of the two regioisomers in the reaction of 2,4-dimethylnitrophenylamine (2.0 g, 12 mmol) with 6.0 ml of a 2 molar aqueous sodium nitrite solution in acetic acid (250 ml).

MS (ES+, acetonitrile/water 1:1+0.01% formic acid): m/z (%) 178 (M+1, 100).

Analogously to the production of 5-chloro-1H-indazol-4-ylamine, the regioisomeric mixture of the previous reaction (1.0 g, 5.64 mmol)) is reacted with 100 mg of palladium on carbon in methanol under hydrogen atmosphere for 16 hours at room temperature. After purification on silica gel with hexane/ethyl acetate (33% hexane, then 100% ethyl acetate), 53 mg (6% of theory) of 5-methyl-1H-indazol-4-ylamine is obtained.

$^1$H-NMR (300 MHz, DMSO-$d_6$): δ=2.12 (s, 3H), 5.41 (s, 2H), 6.57 (d, 1H), 6.90 (d, 1H), 8.10 (s, 1H), 12.5 (s, 1H).

1-(5-Methyl-1H-indazol-4-ylamino)-6-fluoro-4,4-dimethyl-2-(trifluoromethyl)-1,2,3,4-tetrahydronaphthalene-2,5-diol 4-(3-Fluoro-2-methoxyphenyl)-2-hydroxy-4-methyl-2-(trifluoromethyl)-pentanal (308 mg, 1.0 mmol) and 5-methyl-1H-indazol-4-ylamine (148 mg, 1.0 mmol) are introduced into 15.0 ml of xylene and mixed with titanium(IV)ethylate (0.42 ml, 2.0 mmol). After 3 hours under reflux, the reaction mixture is allowed to cool to room temperature. After ethyl acetate and saturated sodium chloride solution are added, it is stirred vigorously for 30 minutes at room temperature. The deposited precipitate is suctioned off, the aqueous phase is separated, and the organic phase is dried on sodium sulfate. The purification is carried out by means of chromatography on silica gel with hexane/ethyl acetate (30-40% ethyl acetate). 345 mg (79% of theory) of 1,1,1-trifluoro-4-(3-fluoro-2-methoxyphenyl)-4-methyl-2-[(5-methyl-1H-indazol-4-ylimino)methyl]-pentan-2-ol is obtained.

1,1,1-Trifluoro-4-(3-fluoro-2-methoxyphenyl)-4-methyl-2-[(5-methyl-1H-indazol-4-ylimino)-methyl]-pentan-2-ol (150 mg, 0.34 mmol) is mixed with boron tribromide (3.40 ml of a 1 M solution in dichloromethane, 3.4 mmol) at room temperature. After 4 hours at room temperature, the reaction mixture is allowed to stand overnight at −30° C., then saturated sodium bicarbonate solution and ethyl acetate are added. It is extracted with ethyl acetate, and the combined organic phases are washed with saturated sodium chloride solution and dried on sodium sulfate. After the solvent is removed in a vacuum as well as purification by means of preparative thin-layer chromatography on silica gel with hexane/ethyl acetate (50% ethyl acetate), 56 mg (39% of theory) of the product is obtained.

$^1$H-NMR (300 MHz, CDCl$_3$): δ=1.61 (s, 3H), 1.68 (s, 3H), 2.09-2.14 (m, 4H), 2.24 (d, 1H), 4.24-4.33 (br, 1H), 5.22-5.23 (m, 1H), 6.84-6.91 (m, 3H), 7.14 (d, 1H), 8.04 (s, 1H).

MS (EI+): m/z(%)=423 (M+, 45), 147 (100).

Example 112

7-Bromo-1-[(1H-indazol-4-yl)amino]-5-methoxy-4,4-dimethyl-2-(trifluoromethyl)-1,2,3,4-tetrahydronaphthalen-2-ol (SL 4753-4)

$^1$H-NMR (300 MHz, CD$_3$OD): δ=1.52 (3H), 1.66 (3H), 2.00-2.22 (2H), 3.88 (3H), 5.18 (1H), 6.35 (1H), 6.89 (1H), 7.05 (1H), 7.15-7.29 (2H), 8.13 (1H).

Example 113

5-[(2-Hydroxy-4,4-pentamethylene-2-(trifluoromethyl)-1,2,3,4-tetrahydro-1-naphthyl)amino]-2-quinolone 5-[2-Hydroxy-4-phenyl-4,4-pentamethylene-2-trifluoromethylbutyl-1-imino]-2-quinolone Analogously to Example 15, 150 mg of 2-hydroxy-4-phenyl-4,4-pentamethylene-2-trifluoromethylbutyraldehyde is condensed with 88 mg of 5-aminoquinolone in the presence of 0.21 ml of titanium tetraethylate to form imine (102 mg).

$^1$H-NMR (300 MHz, CDCl$_3$): δ=1.40-2.05 (m, 10H), 2.40 (d, 1H), 2.65 (d, 1H), 4.80 (br. s, 1H), 6.15 (d, 1H), 6.80 (d, 1H), 6.85 (t, 1H), 7.00 (m, 2H), 7.20-7.35 (m, 4H), 8.20 (d, 1H), 12.00 (br. s, 1H).

5-[(2-Hydroxy-4,4-pentamethylene-2-(trifluoromethyl)-1,2,3,4-tetrahydro-1-naphthyl)amino]-2-quinolone Analogously to Example 15, 100 mg of imine is converted with 4 ml of a 1 M titanium tetrachloride-CH$_2$Cl$_2$ solution into 59 mg of product.

$^1$H-NMR (DMSO-$d_6$): δ=1.35-1.80 (m, 11H), 2.15 (m, 1H), 5.35 (d, 1H), 5.95 (s, 1H), 6.25 (d, 1H), 6.40 (d, 1H), 6.55 (t, 2H), 7.15 (m, 2H), 7.25 (t, 1H), 7.30 (m, 1H), 7.55 (d, 1H), 8.20 (d, 1H), 11.55 (br.s, 1H).

Example 114 cis-1-[(8-Fluoro-2-methylquinazolin-5-yl)amino]-2-(trifluoromethyl)-1,2,3,4-tetrahydronaphthalene-2-diol 200 mg (3.1 mmol) of potassium cyanide in 2 ml of water is added to 0.55 g (2.7 mmol) of 1,1,1-trifluoro-4-phenyl-butan-2-one (D. Yang; M-K. Wong; Z. Yan J. Org. Chem. (2000); 65; 4179-4184) in 4 ml of THF and 2 ml of water. It is cooled to 0° C., and 1 ml of a 25% sulfuric acid is added, allowed to heat to room temperature and stirred for 16 hours. Saturated sodium bicarbonate solution is added and extracted with ethyl acetate. After washing with saturated sodium chloride solution and drying on sodium sulfate, the crude cyanide, which is dissolved in 15 ml of diethyl ether and cooled to −70° C., is obtained quantitatively. 4.6 ml (5.5 mmol) of a 1.2 M DIBAL solution in toluene is added in drops over 10 minutes. It is allowed to heat for 2 hours to room temperature, quenched with 10% tartaric acid solution, and vigorous stirring is continued. After extraction with ethyl acetate, 5 g of silica gel and 10 ml of a 1 M sulfuric acid are added. It is stirred vigorously for 12 hours and filtered through Celite. The phases are separated, and it is extracted again with ethyl acetate. After chromatography on silica gel (hexane/ethyl acetate 30%), 300 mg of still contaminated 2-hydroxy-4-phenyl-2-(trifluoromethyl)-butanal is obtained.

0.5 ml (2.4 mmol) of titanium tetraethylate is added to the thus obtained aldehyde and 200 mg (1.13 mmol) of 5-amino-8-fluoro-2-methylquinazoline in 15 ml of toluene, and the mixture is heated for 2 hours to 100° C. After the cooling, it is poured into water, and vigorous stirring is continued. The suspension is filtered through Celite and thoroughly rewashed with ethyl acetate. The phases of the filtrate are separated, and it is extracted again with ethyl acetate. It is dried on sodium sulfate, and the solvent is removed in a vacuum. After chromatography on silica gel (hexane/ethyl acetate 30%), 100 mg of 1-(8-fluoro-2-methylquinazolin-5-ylimino)-4-phenyl-2-(trifluoromethyl)butan-2-ol is obtained. The imine is taken up in 5 ml of dichloromethane and cooled to −70° C. 1 ml (1 mmol) of a 1 M titanium tetrachloride solution in dichloromethane is added in drops over 10 minutes and stirred for one hour. The solution is poured into saturated sodium bicarbonate solution and stirred vigorously for 15 minutes. It is extracted with ethyl acetate, washed with saturated sodium chloride solution, and dried on sodium sulfate. After concentration by evaporation and chromatography on silica gel (hexane/ethyl acetate 50%), 44 mg of the desired product is obtained.

$^1$H-NMR (300 MHz, CDCl$_3$): δ=2.25-2.32 (m, 2H), 2.91 (ddd, 1H), 2.92 (s, 3H), 3.19 (ddd, 1H), 5.09 (d, 1H), 5.26 (d, 1H), 6.78 (dd, 1H), 7.15-7.29 (m, 4H), 7.49 (dd, 1H), 9.34 (s, 1H).

Example 115 cis-1-[(8-Fluoro-2-methylquinazolin-5-yl)amino]-4,4-dimethyl-2-(trifluoromethyl)-1,2,3,4-tetrahydronaphthalene-2,5-diol $^1$H-NMR (300 MHz, CDCl$_3$): δ=1.59 (s, 3H), 1.72 (s, 3H), 2.11 (d, 1H), 2.21 (d, 1H), 2.93 (s, 3H), 5.05 (d, 1H), 5.28 (br, 1H), 5.40 (d, 1H), 6.66 (d, 1H), 6.71 (dd, 1H), 6.94 (d, 1H), 7.03 (t, 1H), 7.47 (dd, 1H), 9.37 (s, 1H).

Example 116 cis-1-[(7,8-Difluoro-2-methylquinazolin-5-yl)amino]-4,4-dimethyl-2-(trifluoromethyl)-1,2,3,4-tetrahydronaphthalen-2-ol 5-Amino-7,8-difluoro-2-methyquinazoline 156 ml (391 mmol) of a 2.5 M butyllithium solution in hexane is added in drops to 41.7 g (180 mmol) of 2,2-dimethyl-N-(3,4,5-trifluorphenyl)-propionamide in 385 ml of THF at −70° C. It is allowed to stir for one hour, and then 38.6 ml of DMF in 90 ml of THF is added in drops, and the solution may heat to −60° C. It is stirred for another hour at −70° C., and then the cold reaction solution is poured into a mixture of 2 kg of ice and 400 ml of concentrated hydrochloric acid. It is stirred vigorously and extracted after one hour several times with diethyl ether. The organic phase is washed neutral with water and dried on sodium sulfate. After concentration by evaporation, 49.3 g (188 mmol) of crude 4,5,6-trifluoro-2-N-pivaloylaminobenzaldehyde is obtained, which is added together with 26 g (275 mmol) of acetamidine hydrochloride, 38.3 g (277 mmol) of potassium carbonate and 30 g of molecular sieve (4A) in 206 ml of butyronitrile. It is heated while being stirred vigorously for 18 hours to 145° C., and the solvent is removed in a vacuum. After the residue is chromatographed on silica gel with hexane/ethyl acetate (0-100%), 9.1 g of 7,8-difluoro-5-N-pivaloylamino-2-methylquinazoline is obtained.

2.0 g (7.2 mmol) of 7,8-difluoro-5-N-pivaloylamino-2-methyquinazoline is dissolved in 140 ml of toluene and cooled to −70° C. 24 ml (28.8 mmol) of a 1.2 M diisobutyl aluminum hydride solution in toluene is added in drops over 30 minutes. The reaction mixture is allowed to heat to −25° C. over 2 hours and stirred for 2 hours at −25° C. Isopropanol and then water are slowly added and stirred for 12 hours at room temperature until a precipitate, which is removed by means of filtration through Celite, is formed. It is rewashed well with a methylene chloride/methanol mixture and concentrated by evaporation. The residue is vigorously stirred in 200 ml of ethyl acetate and 50 ml of methanol together with 100 g of silica gel and 20 g of manganese dioxide. It is filtered through Celite, rewashed well with a methylene chloride-methanol mixture and concentrated by evaporation. After chromatography on silica gel with hexane-ethyl acetate (0-100%), 370 mg of the product is obtained.

$^1$H-NMR (300 MHz, CD$_3$OD): δ=2.81 (s, 3H), 6.64 (dd, 1H), 9.52 (s, 1H).

cis-1-[(7,8-Difluoro-2-methylquinazolin-5-yl)amino]-4,4-dimethyl-2-(trifluoromethyl)-1,2,3,4-tetrahydronaphthalen-2-ol $^1$H-NMR (300 MHz, CDCl$_3$): δ=1.46 (s, 3H), 1.61 (s, 3H), 2.20 (d, 1H), 2.24 (d, 1H), 2.91 (s, 3H), 5.00 (d, 1H), 5.86 (d, 1H), 6.56 (dd, 1H), 6.71 (dd, 1H), 7.18 (t, 1H), 7.29 (d, 1H), 7.32 (t, 1H), 7.43 (d, 1H), 9.28 (s, 1H).

Example 117 cis-1-[(7,8-Difluoro-2-methylquinazolin-5-yl)amino]-4,4-dimethyl-6-fluoro-5-methoxy-2-(trifluoromethyl)-1,2,3,4-tetrahydronaphthalen-2-ol $^1$H-NMR (300 MHz, CDCl$_3$): δ=1.59 (s, 3H), 1.70 (s, 3H), 2.12 (d, 1H), 2.22 (d, 1H), 2.91 (s, 3H), 3.98 (s, 3H), 4.90 (d, 1H), 5.80 (d, 1H), 6.56 (dd, 1H), 6.94 (dd, 1H), 7.00 (dd, 1H), 9.24 (s, 1H).

Example 118

5-{[2-Hydroxy-4,4-dimethyl-2,5-bis(trifluoromethyl)-1,2,3,4-tetrahydronaphthalen-1-ylamino}-quinolin-2(1H)-one The production is performed as described in Example 15 (13). The cyclization of the imine to the product is carried out in trifluoroacetic acid under reflux, however, instead of with TiCl$_4$ in toluene.

$^1$H-NMR (300 MHz, CDCl$_3$): δ=1.55 (s, 3H), 1.65 (s, 3H), 2.05 (d, 1H), 2.30 (d, 1H), 5.10 (d, 1H), 5.30 (d, 1H), 6.35 (d, 1H), 6.60 (d, 1H), 6.70 (d, 1H) 7.25 (m, 1H), 7.30 (t, 1H), 7.55 (d, 1H), 7.75 (d, 1H), 7.95 (d, 1H), 10.85 (br.s, 1H).

MS (ES): MH$^+$: 471.

Example 119

5-{[6-Chloro-2-hydroxy-4,4-dimethyl-2-(trifluoromethyl)-1,2,3,4-tetrahydronaphthalen-1-yl]aminoquinolin-2(1H)-one The synthesis is carried out as described in Example 15.

$^1$H-NMR (300 MHz, CDCl$_3$): δ=1.40 (s, 3H), 1.60 (s, 3H), 2.10 (d, 1H), 2.20 (d, 1H), 5.05 (br., 1H), 5.70 (br., 1H), 6.50 (d, 1H), 6.60 (m, 2H), 7.05 (dd, 1H), 7.20 (d, 1H), 7.35 (m, 2H), 8.30 (d, 1H), 10.40 (br., 1H)

MS (ES): MH+: 437/439 (3:1). .

Example 120

5-{[2-Hydroxy-4,4-dimethyl-2-(trifluoromethyl)-1,2,3,4-tetrahydronaphthalen-1-yl]amino}-1-methylquinolin-2(1H)-one $^1$H-NMR (300 MHz, CDCl$_3$): δ=1.40 (s, 3H), 1.60 (s, 3H), 2.10 (d, 1H), 2.20 (d, 1H), 3.60 (s, 3H), 5.15 (d, 1H), 5.45 (d, 1H), 6.60 (d, 1H), 6.65 (d, 1H), 6.75 (d, 1H), 7.10 (t, 1H), 7.30 (m, 1H), 7.40 (m, 2H), 8.00 (d, 1H).
MS (ES): MH$^+$: 417.

Example 121

5-{[2-Hydroxy-4,4-dimethyl-2-(trifluoromethyl)-5,6-trimethylene-1,2,3,4-tetrahydronaphthalen-1-yl]amino}-quinolin-2(1H)-one $^1$H-NMR (300 MHz, CDCl$_3$): δ=1.45 (s, 3H), 1.65 (s, 3H), 1.95-2.15 (m, 3H), 2.20 (d, 1H), 2.80 (m, 2H), 3.15 (m, 2H), 5.10 (d, 1H), 5.25 (d, 1H), 6.55 (m, 3H), 7.00 (d, 11H), 7.10 (d, 1H), 7.30 (t, 11H), 8.00 (d, 1H), 10.10 (br., 1H).
MS (ES): MH$^+$: 443.

Enantiomer separation is carried out by chiral HPLC (Chiralpak AD 20μ column with hexane-ethanol 95:5 as an eluant); the (−)-enantiomer is eluted at 11.4 minutes, the (+)-enantiomer at 14.1 minutes.

Example 122

5-{[6-Chloro-2-hydroxy-4,4-dimethyl-5-methoxy-2-(trifluoromethyl)-1,2,3,4-tetrahydronaphthalen-1-yl]amino}-quinolin-2(1H)-one $^1$H-NMR (300 MHz, CDCl$_3$): δ=1.55 (s, 3H), 1.70 (s, 3H), 2.10 (d, 1H), 2.20 (d, 1H), 3.95 (s, 3H), 5.05 (d, 1H), 5.35 (d, 1H), 6.55 (m, 3H), 7.00 (d, 1H), 7.15 (d, 1H), 7.35 (t, 1H), 8.05 (d, 1H), 9.95 (br., 1H).
MS (ES): MH$^+$: 467/469 (3/1).

Example 123

5-{[6-Chloro-2,5-dihydroxy-4,4-dimethyl-2-(trifluoromethyl)-1,2,3,4-tetrahydronaphthalen-1-yl]amino}-quinolin-2(1H)-one $^1$H-NMR (300 MHz, CDCl$_3$): δ=1.60 (s, 3H), 1.70 (s, 3H), 2.05 (d, 1H), 2.20 (d, 1H), 4.20 (br., 1H), 5.05 (d, 1H), 5.40 (d, 1H), 5.95 (br.s, 1H), 6.55 (m, 3H), 6.85 (d, 1H), 7.10 (d, 1H), 7.35 (t, 1H), 8.10 (d, 1H), 9.75 (br., 1H).
MS (ES): MH$^+$: 453/455 (3/1).

Enantiomer separation is carried out by chiral HPLC (Chiracel OD 20μ column with hexane-ethanol 85:15 as an eluant); the (+)-enantiomer is eluted at 10.4 minutes, the (−)-enantiomer at 14.8 minutes.

(+)-Enantiomer:
$^1$H-NMR ([D]$_6$-DMSO): δ=1.50 (s, 3H), 1.65 (s, 3H), 1.95 (d, 1H), 2.10 (d, 1H), 5.30 (d, 1H), 6.05 (s, 1H), 6.20 (d, 1H), 6.40 (d, 1H), 6.55 (m, 2H), 6.70 (d, 1H), 7.20 (m, 2H), 8.20 (d, 1H), 9.05 (s, 1H), 11.55 (s, 1H).

(−)-Enantiomer:
$^1$H-NMR ([D]$_6$-DMSO): δ=1.50 (s, 3H), 1.65 (s, 3H), 1.95 (d, 1H), 2.10 (d, 1H), 5.30 (d, 1H), 6.05 (s, 1H), 6.20 (d, 1H), 6.40 (d, 1H), 6.55 (m, 2H), 6.70 (d, 1H), 7.20 (m, 2H), 8.20 (d, 1H), 9.05 (s, 1H), 11.55 (s, 1H).

Example 124

5-{[5-Bromo-2-hydroxy-4,4-dimethyl-2-(trifluoromethyl)-1,2,3,4-tetrahydronaphthalen-1-yl]amino}-quinolin-2(1H)-one The cyclization of the imine precursor to the product is carried out in trifluoroacetic acid under reflux instead of with TiCl$_4$ in toluene.

$^1$H-NMR (300 MHz, CDCl$_3$): δ=1.70 (s, 3H), 1.85 (s, 3H), 2.10 (d, 1H), 2.25 (d, 1H), 5.10 (d, 1H), 5.40 (d, 1H), 6.50 (d, 1H), 6.55 (d, 1H), 6.60 (d, 1H), 6.90 (t, 1H), 7.30 (d, 1H), 7.35 (t, 1H), 7.55 (d, 1H), 8.05 (d, 1H), 10.40 (br. s, 1H).
MS (ES): MH$^+$: 481/483 (1/1).

Example 125

5-{[6-Chloro-2-hydroxy-5-methoxy-2-(trifluoromethyl)-4,4-trimethylene-1,2,3,4-tetrahydronaphthalen-1-yl]amino}-quinolin-2(1H)-one $^1$H-NMR (300 MHz, CDCl$_3$): δ=2.05-2.40 (m, 5H), 2.60 (d, 1H), 2.85 (m, 2H), 4.10 (s, 3H), 4.95 (d, 1H), 5.05 (d, 1H), 6.55 (m, 2H), 6.65 (d, 1H), 6.70 (d, 1H), 6.95 (d, 1H), 7.15 (d, 1H), 7.35 (t, 1H), 7.90 (d, 1H), 10.50 (br., 1H).
MS (ES): MH$^+$: 478/480 (3/1).

Example 126

5-{[6-Chloro-2,5-dihydroxy-2-(trifluoromethyl)-4,4-trimethylene-1,2,3,4-tetrahydronaphthalen-1-yl]amino}-quinolin-2(1H)-one $^1$H-NMR ([D]$_6$-DMSO): δ=1.80 (m, 1H), 2.05 (m, 2H), 2.20 (d, 1H), 2.30 (m, 1H), 2.60 (d, 1H), 2.90 (q, 1H), 3.25 (q, 1H), 5.30 (d, 1H), 5.90 (s, 1H), 6.10 (d, 1H), 6.35 (d, 1H), 6.55 (d, 2H), 6.70 (d, 1H), 7.20 (d, 1H), 7.25 (t, 1H), 8.15 (d, 1H), 9.30 (s, 1H), 11.55 (br.S, 1H).
MS (ES): MH$^+$: 465/467 (3/1).

Enantiomer separation is carried out by chiral HPLC (Chiralpak AD 20μ column with hexane-ethanol as an eluant); the (−)-enantiomer is first eluted.

$^1$H-NMR ([D]$_6$-DMSO): δ=1.80 (m, 1H), 2.05 (m, 2H), 2.20 (d, 1H), 2.30 (m, 1H), 2.60 (d, 1H), 2.90 (q, 1H), 3.25 (q, 1H), 5.30 (d, 1H), 5.90 (s, 1H), 6.10 (d, 1H), 6.35 (d, 1H), 6.55 (d, 2H), 6.70 (d, 1H), 7.20 (d, 1H), 7.25 (t, 1H), 8.15 (d, 1H), 9.30 (s, 1H), 11.55 (br. S, 1H).

(+)-Enantiomer:
$^1$H-NMR ([D]$_6$-DMSO): δ=1.80 (m, 1H), 2.05 (m, 2H), 2.20 (d, 1H), 2.30 (m, 1H), 2.60 (d, 1H), 2.90 (q, 1H), 3.25 (q, 1H), 5.30 (d, 1H), 5.90 (s, 1H), 6.10 (d, 1H), 6.35 (d, 1H), 6.55 (d, 2H), 6.70 (d, 1H), 7.20 (d, 1H), 7.25 (t, 1H), 8.15 (d, 1H), 9.30 (s, 1H), 11.55 (br. S, 1H).

Example 127

5-{[5-Difluoromethoxy-2-hydroxy-4,4-dimethyl-2-(trifluoromethyl)-1,2,3,4-tetrahydronaphthalen-1-yl]amino}-quinolin-2(1H)-one The cyclization of the imine to the product is carried out in trifluoroacetic acid under reflux instead of with TiCl$_4$ in toluene.

¹H-NMR ([D]₆-DMSO): δ=1.45 (s, 1H), 1.60 (s, 1H), 2.00 (d, 1H), 2.15 (d, 1H), 5.40 (d, 1H), 6.15 (s, 1H), 6.20 (d, 1H), 6.40 (d, 1H), 6.55 (d, 1H0, 6.60 (d, 1H), 7.05 (m, 2H), 7.20 (t, 1H), 7.30 (t, $CHF_2$, $J_{HF}$=75 Hz), 8.20 (d, 1H), 11.55 (s, 1H).
MS (ES): MH⁺: 469.

Example 128

4-{[6-Chloro-2-hydroxy-4,4-dimethyl-5-methoxy-2-(trifluoromethyl)-1,2,3,4-tetrahydronaphthalen-1-yl]amino}-indazole ¹H-NMR (300 MHz, CDCl₃): δ=1.40 (s, 3H), 1.55 (s, 3H), 2.05 (d, 1H), 2.20 (d, 1H), 5.15 (br., 2H), 6.40 (d, 1H), 6.90 (d, 1H), 7.05 (dd, 1H), 7.25-7.35 (m, 4H), 8.55 (br., 1H).
MS (ES): MH⁺=410/412 (3:1);

Example 129

5-(6-Chloro-2-hydroxy-7-methoxy-4,4 dimethyl-2-(trifluoromethyl)-1,2,3,4-tetrahydronaphthalen-1-ylamino)-1H-quinolin-2-one 4-(3-Chloro-4-methoxyphenyl)-2-hydroxy-4-methyl-2-(trifluoromethyl)-pentanal 75 ml of methylmagnesium chloride (22% in THF) is introduced into 200 ml of THF and at 0° C., a solution of 9.17 g (45.7 mmol) of methyl-3-chloro-4-methoxybenzoate in 200 ml of THF is added in drops within 1 hour. After the conversion is completed, the reaction is ended by the addition of 30 ml of saturated ammonium chloride solution, and the mixture is dispersed between ethyl acetate and water. The aqueous phase is extracted with ethyl acetate, the combined organic phases are washed with water and saturated sodium chloride solution, dried with sodium sulfate, and concentrated by evaporation in a rotary evaporator.

4.5 g (22.4 mmol) of the crude product (yield 98%) is introduced into 100 ml of dichloromethane and first 6.0 g (42.7 mmol) of 2-trimethylsilanyloxy-acrylic acid ethyl ester, and then 1.85 ml of tin tetrachloride are added in drops at –70° C. After 10 minutes, the reaction mixture is added to saturated potassium carbonate solution. The aqueous phase is extracted with dichloromethane, the combined organic phases are washed with 1 M hydrochloric acid solution, water and saturated sodium chloride solution, dried with sodium sulfate and concentrated by evaporation in a rotary evaporator. After column chromatography (silica gel, hexane/ethyl acetate 9:1), 2.0 g (29%) of the desired intermediate products is obtained.

1.5 g (5.0 mmol) of this ketoester is mixed in THF at –70° C. with 2.1 ml of trimethyl-trifluoromethylsilane and 620 µl of tetrabutylammonium fluoride (1 M solution in THF). It is allowed to thaw to room temperature and to stir for 18 hours, then the mixture is mixed at 0° C. with 6 ml of tetrabutylammonium fluoride (1 M solution in THF). After another 10 minutes, the mixture is dispersed between ethyl acetate and 1 M hydrochloric acid solution. The aqueous phase is extracted with ethyl acetate, the combined organic phases are washed with 1 M hydrochloric acid solution, water and saturated sodium chloride solution, dried with sodium sulfate, and concentrated by evaporation in a rotary evaporator. 1.81 g of the desired intermediate product, which, dissolved in 15 ml of diethyl ether, is added in drops at 0° C. to a suspension of 0.40 g of lithium aluminum hydride in diethyl ether, is obtained. After 1 hour at 0° C. and 18 hours at room temperature, the reaction is completed by adding 25 ml of saturated sodium bicarbonate solution. The precipitate that is formed is filtered off, rewashed with ethyl acetate, and the filtrate is washed with saturated sodium chloride solution, dried with sodium sulfate and concentrated by evaporation in a rotary evaporator. After column chromatography (silica gel, hexane/ethyl acetate 8:2), 1.04 g (65%) of the desired diol intermediate product is obtained.

109 µl (1.12 mmol) of oxalyl chloride is introduced into dichloromethane, and first 190 µl (2.68 mmol) of DMSO and, after 15 minutes of stirring, a solution of 366 mg (1.12 mmol) of the diol intermediate stage in dichloromethane are added in drops at –75° C. After another 15 minutes, 830 µl (5.62 mmol) of triethylamine is added in drops (at –50°). It is allowed to slowly thaw and stirred for another 18 hours. The reaction is completed by adding saturated ammonium chloride solution, the phases are separated, and the aqueous phase is extracted with dichloromethane. The combined organic phases are washed with 1 M hydrochloric acid solution, water and saturated NaCl solution and dried with NaSO₄. It is concentrated by evaporation and chromatographed on silica gel with hexane/ethyl acetate (4:1). 302 mg (84%) of the desired 4-(3-chloro-4-methoxy-phenyl)-2-hydroxy-4-methyl-2-trifluoromethyl-pentanal is obtained.

¹H-NMR (CDCl₃): δ=1.34 (s, 3H), 1.40 (s, 3H), 2.30 (d, 1H), 2.62 (d, 1H), 3.66 (s, 1H), 3.90 (s, 3H), 6.84 (d, 1H), 7.13 (dd, 1H), 7.31 (d, 1H), 8.90 (s, 1H).

5-(6-Chloro-2-hydroxy-7-methoxy-4,4 dimethyl-2-(trifluoromethyl)-1,2,3,4-tetrahydronaphthalen-1-ylamino)-1H-quinolin-2-one 100 mg (0.31 mmol) of 4-(3-chloro-4-methoxy-phenyl-2-hydroxy-4-methyl-2-trifluoromethyl-pentanal and 50 mg (0.31 mmol) of 5-amino-1H-quinolin-2-one are introduced into 30 ml of toluene and 0.16 ml of titanium tetraethylate is added in drops. The mixture is stirred for 1 hour at a bath temperature of 100° C. After cooling, the solution is added to ice, several ml of saturated sodium bicarbonate solution is added, it is filtered off on diatomaceous earth and rewashed with ethyl acetate and water. The phases are separated, the aqueous phase is extracted with ethyl acetate, the combined organic phases are washed with water and saturated sodium chloride solution, dried with sodium sulfate and concentrated by evaporation in a rotary evaporator. The imine (30%) that is obtained after chromatographic purification (silica gel, hexane/ethyl acetate 95:5 to 25:75) is taken up again in dichloromethane and mixed at –50° C. with 3.6 ml of titanium tetrachloride (1 M in toluene). It is allowed to thaw, and the mixture is added to ice after 18 hours of stirring, the phases are separated, extracted with dichloromethane, washed with saturated sodium chloride solution and dried with sodium sulfate. After concentration by evaporation in a rotary evaporator, the crude product is chromatographed on silica gel (eluant: 2% methanol in dichloromethane). The product that is obtained is recrystallized from hexane/diethyl ether (yield: 28%).

Melting point: 182° C.;
¹H-NMR (CD₃OD): δ=1.28 (s, 3H), 1.42 (s, 3H), 1.95 (d, 1H), 2.07 (d, 1H), 3.54 (s, 3H), 4.88 (s, 1H), 6.42-6.48 (m, 2H), 6.58 (d, 1H), 6.82 (s, 1H), 7.25-7.30 (m, 2H), 7.97 (d, 1H).

Example 130

5-(6-Chloro-2-hydroxy-7-methoxy-4,4-dimethyl-2-(trifluoromethyl)-1,2,3,4-tetrahydronaphthalen-1-ylamino)-2H-isoquinolin-1-one This compound was produced with use of the aldehyde that is described in Example 129 above and the corresponding amine.
Melting point: 85° C., MS (ESI): 47 (M+1).

Example 131

5-(6-Chloro-2-hydroxy-7-methoxy-4,4-dimethyl-2-(trifluoromethyl)-12,4-tetrahydronaphthalen-1-ylamino)-2H-phthalazin-1-one Example 131 was produced as described in Example 129 with use of the corresponding starting materials.
$^1$H-NMR (CD$_3$OD): δ=1.39 (s, 3H), 1.53 (s, 3H), 2.16 (dd, 2H), 3.12 (s, 3H), 5.30 (s, 1H), 6.94 (s, 1H), 7.31 (dd, 1H), 7.42 (s, 1H), 7.64-7.71 (m, 2H), 8.59 (s, 1H).

Example 132

6-Chloro-7-methoxy-4,4-dimethyl-1-(2-methylquinolin-5-ylamino)-2-(trifluoromethyl)-1,2,3,4-tetrahydronaphthalen-2-ol Example 132 was synthesized with use of the corresponding starting materials as described in Example 129.
$^1$H-NMR (CDCl$_3$): δ=1.39 (s, 3H), 1.52 (s, 3H), 2.15 (dd, 2H), 2.73 (s, 3H), 3.49 (s, 3H), 4.97 (d, 1H), 5.10 (d, 1H), 6.80-6.84 (m, 2H), 7.24 (d, 1H), 7.36 (s, 1H), 7.49 (d, 1H), 7.55 (dd, 1H), 8.08 (d, 1H).

Example 133

6-Chloro-1-(8-fluoro-2-methylquinazolin-5-ylamino)-7-methoxy-4,4-dimethyl-2-(trifluoromethyl-1,2,3,4-tetrahydronaphthalen-2-ol The compound was produced analogously to Example 129.
$^1$H-NMR (CDCl$_3$): δ=1.42 (s, 3H), 1.56 (s, 3H), 2.19 (dd, 2H), 3.62 (s, 3H), 4.31 (s, br, 1H), 5.01 (d, 1H), 5.56 (d, 1H), 6.70 (dd, 1H), 6.90 (s, 1H), 7.39 (s, 1H), 7.46-7.52 (m, 1H), 9.39 (s, 1H).

Example 134

5-(6-Chloro-2,7-dihydroxy-4,4-dimethyl-2-(trifluoromethyl)-1,2,3,4-tetrahydronaphthalen-1-ylamino)-1H-quinolin-2-one 20 mg of 5-[4-(3-chloro-4-methoxyphenyl)-2,2-dihydroxy-4-methylpentylamino]-1H-quinolin-2-one (43 μmol) is introduced into dichloromethane, mixed with 0.86 mmol of boron tribromide (1 M solution in dichloromethane), and stirred for 3 hours at room temperature. The reaction is completed with saturated sodium bicarbonate solution. It is extracted with dichloromethane, the organic phases are washed with saturated sodium chloride solution and dried with sodium sulfate and concentrated by evaporation. The crude product is recrystallized from hexane/diethyl ether. 9 mg (40%) of the desired product is obtained.
Melting point: 158° C.; MS (ESI): 453 (M+1).

Example 135

1-(8-Fluoro-2-methylquinazolin-5-ylamino)-7-methoxy-4,4-dimethyl-2-(trifluoromethyl)-1,2,3,4-tetrahydronaphthalen-2-ol 2-Hydroxy-4-(4-methoxyphenyl)-4-methyl-2-(trifluoromethyl)-pentanal The aldehyde was produced from 4-methoxybenzyl cyanide as described in Example 5.
$^1$H-NMR (CDCl$_3$): δ=1.34 (s, 3H), 1.43 (s, 3H), 2.30 (d, 1H), 2.69 (d, 1H), 3.66 (s, 1H), 3.80 (s, 3H), 6.85 (d, 2H), 7.21 (d, 2H), 8.76 (s, 1H).

1-(8-Fluoro-2-methylquinazolin-5-ylamino)-7-methoxy-4,4-dimethyl-2-(trifluoromethyl)-1,2,3,4-tetrahydronaphthalen-2-ol The above compound was produced with use of the corresponding starting materials, as described in Example 129.
Melting point 97° C.; MS (ESI): 450 (M+1).

Example 136

5-(2-Hydroxy-7-methoxy-4,4-dimethyl-2-(trifluoromethyl)-1,2,3,4-tetrahydronaphthalen-1-ylamino)-1H-quinolin-2-one The production was carried out as described in Example 129 with use of the 2-hydroxy-4-(4-methoxyphenyl-4-methyl-2-(trifluoromethyl)-pentanal and the corresponding amine.
Melting point 128° C.; MS (ESI): 433 (M+1).

Example 137

5-(2-Hydroxy-7-methoxy-4,4-dimethyl-2-(trifluoromethyl)-1,2,3,4-tetrahydronaphthalen-1-ylamino)-2H-isoquinolin-1-one The production was carried out as described in Example 129 with use of the 2-hydroxy-4-(4-methoxyphenyl)-4-methyl-2-(trifluoromethyl)-pentanal and the corresponding amine.
Melting point 112° C.; MS (ESI): 433 (M+1).

Example 138

5-(2-Hydroxy-7-methoxy-4,4-dimethyl-2-(trifluoromethyl)-1,2,3,4-tetrahydronaphthalen-1-ylamino)-2H-phthalazin-1-one The production was carried out as described in Example 129 with use of the 2-hydroxy-4-(4-methoxyphenyl)-4-methyl-2-(trifluoromethyl)-pentanal and the corresponding amine.
Melting point 197° C.; MS (ESI): 434 (M+1).

Example 139

7-Methoxy-4,4-dimethyl-1-(2-methylquinolin-5-ylamino)-2-(trifluoromethyl)-1,2,3,4-tetrahydronaphthalen-2-ol The production was carried out as described in Example 129 with use of 2-hydroxy-4-(4-methoxyphenyl)-4-methyl-2-(trifluoromethyl)-pentanal and the corresponding amine.

Melting point 84° C.; MS (ESI): 431 (M+1).

The racemate was separated into the enantiomers with the aid of chiral HPLC.

Analytic HPLC: Chiralpak AD 10μ, 250×4.6 mm, 1 ml min$^{1}$, hexane/ethanol 90/10

(+)-Enantiomer: $R_t$=7.0 minutes; melting point 84° C.; MS (ESI); 431 (M+1);

(−)-Enantiomer: $R_t$=17.8 minutes; melting point 85° C.; MS (ESI): 431 (M+1); specific optical rotation: −5.9 (c=0.14, CHCl$_3$).

Example 140

4,4-Dimethyl-1-(2-methylquinolin-5-ylamino)-2-(trifluoromethyl)-1,2,3,4-tetrahydronaphthalene-2,7-diol The ether that is described in Example 139 was subjected to ether cleavage with BBr$_3$ analogously to Example 134.

Melting point 127° C.; MS (ESI): 417 (M+1).

Example 141

5-(2,7-Dihydroxy-4,4-dimethyl-2-(trifluoromethyl)-1,2,3,4-tetrahydronaphthalen-1-ylamino)-2H-phthalazin-1-one The ether that is described in Example 138 was subjected to ether cleavage with BBr$_3$ analogously to Example 134.

Melting point 116° C.; MS (ESI): 420 (M+1).

Example 142

1-(8-Fluoro-2-methylquinazolin-5-ylamino)-4,4-dimethyl-2-(trifluoromethyl)-1,2,3,4-tetrahydronaphthalene-2.7-diol.

The ether that is described in Example 135 was subjected to ether cleavage with BBr$_3$ analogously to Example 134.

$^1$H-NMR (CD$_3$OD): δ=1.41 (s, 3H), 1.54 (s, 3H), 2.02 (d, 1H), 2.17 (d, 1H), 2.82 (d, 3H), 4.32 (s, 1H), 6.93 (dd, 1H), 7.01 (d, 1H), 7.32-7.43 (m, 2H), 7.52-7.66 (m, 3H); MS (ESI): 436 (M+1).

Example 143

5-(2,7-Dihydroxy-4,4-dimethyl-2-(trifluoromethyl)-1,2,3,4-tetrahydronaphthalen-1-ylamino)-1H-quinolin-2-one The ether that is described in Example 136 was subjected to ether cleavage with BBr$_3$ analogously to Example 134.

$^1$H-NMR (CD$_3$OD): δ=1.38 (s, 3H), 1.52 (s, 3H), 2.13 (dd, 2H), 5.17 (s, 1H), 6.53 (d, 1H), 6.62 (d, 1H), 6.68-6.78 (m, 2H), 7.26 (d, 1H), 7.39 (dd, 1H), 8.26 (d, 1H); MS (ESI): 419 (M+1).

Example 144

5-(2-Hydroxy-5-methoxy-2-(trifluoromethyl)-1,2,3,4-tetrahydronaphthalen-1-ylamino)-1H-quinolin-2-one The compound above was produced as described in Example 129 with use of 2-hydroxy-4-(2-methoxyphenyl)-4-methyl-2-(trifluoromethyl)-pentanal and the corresponding amine.

Melting point 228° C.; MS (ESI): 405 (M+1)

Example 145

1-(8-Fluoro-2-methylquinazolin-5-ylamino)-5-methoxy-2-(trifluoromethyl)-1,2,3,4-tetrahydro-naphthalen-2-ol The compound above was produced as described in Example 129 with use of 2-hydroxy-4-(2-methoxyphenyl)-4-methyl-2-(trifluoromethyl)-pentanal and the corresponding amine.

Melting point 132° C.; MS (ESI): 422 (M+1)

Example 146

7-Chloro-1-(8-fluoro-2-methylquinazolin-5-ylamino)-4,4-dimethyl-2-(trifluoromethyl)-1,2,3,4-tetrahydronaphthalene-2,6-diol

2-Chloro-5-methylanisole 50 g (350.65 mmol) of 2-chloro-5-methylphenol is dissolved in 450 ml of acetone and mixed with 96.5 g (701.3 mmol) of potassium carbonate under nitrogen. After 43.6 ml of methyl iodide (2 equivalents) is added, it is refluxed for three hours. After cooling, the reaction mixture is filtered, the filter residue is washed with acetone, and the filter is spun in until a dry state is reached (bath temperature 30° C.). Since the residue still contains potassium carbonate, it is taken up in a little diethyl ether and filtered again. After the solvent is spun off, 57 g (103.8%) of the desired compound is obtained, which is used as crude product in the next stage.

$^1$H-NMR (300 MHz, CDCl$_3$): δ=2.35 (3H), 3.90 (3H), 6.68-6.79 (2H), 7.22 (1H).

4-Chloro-3-methoxybenzylbromide 57 g (363.96 mmol) of 2-chloro-5-methylanisole is dissolved in 800 ml of carbon tetrachloride and mixed at room temperature with 69.9 g (393.08 mmol) of N-bromosuccinimide. After 174.6 mg of benzoyl peroxide is added, it is refluxed for five hours (bath temperature 105° C.). The reaction mixture is suctioned off through a glass-pleated filter, rewashed, and the solution is spun in a rotary evaporator. 83.6 g (97.5%) of the desired product (COntains traces of starting material and dibromide) is obtained, which is incorporated in crude form into the next stage.

$^1$H-NMR (300 MHz, CDCl$_3$): δ=3.91 (3H), 4.48 (2H), 6.90-6.98 (2H), 7.32 (1H).

4-Chloro-3-methoxybenzylcyanide 83.6 g (354.97 mmol) of the crude bromide is dissolved in 255 ml of DMF and mixed with 266 ml of water. After 34.7 g (532.45 mmol) of potassium cyanide is added (heating), the mixture is stirred for three hours at room temperature. The reaction mixture is poured into one liter of ice water and extracted three times with 500 ml each of diethyl ether. The combined organic extracts are washed with water and brine. After drying on sodium sulfate, it is filtered, and the solvent is spun off. The residue is chromatographed on silica gel (mobile solvent ethyl acetate/hexane). 44.7 g (69.4%) of the desired compound is obtained.

$^1$H-NMR (300 MHz, CDCl$_3$): δ=3.75 (2H), 3.94 (3H), 6.80-6.91 (2H), 7.38 (1H).

2-(4-Chloro-3-methoxyphenyl)-2-methylpropanenitrile 44.7 g (246.1 mmol) of the above-described nitrile is dissolved in 380 ml of DMF and mixed with 69.8 g (492.2 mmol) of methyl iodide. After cooling to 0° C., 21.5 g (492.2 mmol) of NaH (55% suspension) is added in portions to the reaction mixture within three and V$_2$ hours. After 18 hours at room temperature, the batch is poured into 600 ml of ice water and extracted three times with 500 ml each of diethyl ether. The combined organic phases are washed with water and brine. After drying on sodium sulfate, the desiccant is filtered of, and the solvent is spun off in a rotary evaporator. After chromatography on silica gel (mobile solvent ethyl acetate/hexane), 42.37 g (81.1%) of the desired compound is obtained.

$^1$H-NMR (300 MHz, CDCl$_3$): δ=1.75 (6H), 3.96 (3H), 6.97 (1H), 7.07 (1H), 7.49 (1H).

2-(4-Chloro-3-methoxyphenyl)-2-methylpropanal 25 g (119.23 mmol) of the above-described nitrile is dissolved in 475 ml of toluene. At −65° C. to −60° C., 149 ml of a 1.2 molar solution of DIBAH in toluene is added in drops within 60 minutes. After two hours of stirring at this temperature, the dropwise addition of 681 ml of a 20% L-(+)-tartaric acid solution is begun. After 200 milliliters, the temperature is increased to −10° C. The remainder of the tartaric acid solution is quickly added, and the batch is vigorously stirred for 16 hours at room temperature. The reaction mixture is shaken twice with 600 ml each of diethyl ether. The combined organic extracts are shaken with water and brine, dried, and the solvent is spun off. The residue that is obtained (25 g=98.8%) is incorporated in crude form into the next stage.

$^1$H-NMR (300 MHz, CDCl$_3$): δ=1.48 (6H), 3.90 (3H), 6.70-6.88 (2H), 7.37 (1H), 9.49 (1H).

Ethyl-E-4-(4-chloro-3-methoxyphenyl)-4-methylpent-2-enoate 25.6 g (114.3 mmol) of triethylphosphonacetate is introduced into 148 ml of tetrahydrofuran. At 0° C., 60.8 ml of a 2 M solution of LDA in THF/heptane/ethylbenzene is added in drops (one and one-fourth hours). After one hour of stirring, 22.1 g (103.91 mmol) of 2-(4-chloro-3-methoxyphenyl)-2-methylpropanal, dissolved in 100 ml of tetrahydrofuran, is added in drops at 0° C. After five days of stirring at room temperature, the reaction mixture is poured into 200 ml of dilute ammonium chloride solution and extracted twice with 300 ml each of diethyl ether. The combined organic extracts are treated as usual, and the residue that is obtained is chromatographed on silica gel (mobile solvent ethyl acetate/hexane). 24.1 g (82%) of the desired compound is isolated.

$^1$H-NMR (300 MHz, CDCl$_3$): δ=1.30 (3H), 1.47 (6H), 3.90 (3H), 4.20 (2H), 5.80 (1H), 6.80-6.88 (2H), 7.09 (1H), 7.29 (1H).

Ethyl-4-(4-chloro-3-methoxyphenyl)-4-methylpentanoate 24.1 g (85.23 mmol) of ethyl-E-4-(4-chloro-3-methoxyphenyl)-4-methylpent-2-enoate is mixed in 228 ml of ethyl acetate with 2.41 g of palladium on carbon (10%), and it is stirred overnight at room temperature under hydrogen atmosphere. The catalyst is removed by filtration through a glass-fiber filter, and the residue that remains after concentration by evaporation (24.1 g=99.1%) is incorporated in crude form into the next stage.

$^1$H-NMR (300 MHz, CDCl$_3$): δ=1.21 (3H), 1.34 (6H), 1.90-2.10 (4H), 3.92 (3H), 4.10 (2H), 6.82-6.90 (2H), 7.29 (1H).

Ethyl-4-(4-chloro-3-methoxyphenyl)-2-hydroxy-4-methylpentanoate 24.1 g (84.63 mmol) of ethyl-4-(4-chloro-3-methoxyphenyl)-4-methylpentanoate is dissolved in 296 ml of tetrahydrofuran, and the reaction mixture is cooled to −70° C. to −65° C. Within 1¾ hours, 236.9 ml of a 0.5 molar solution of potassium-bis-(trimethylsilylamide) in toluene is added in drops, and the reaction mixture then is stirred for 75 more minutes at −70° C. 30.9 g (118.48 mmol) of Davis reagent, dissolved in 296 ml of tetrahydrofuran, is now added in drops within 60 minutes. After two hours of stirring at −70° C., 152 ml of saturated ammonium chloride solution is slowly added in drops, the cold bath is removed, and it is vigorously stirred for 30 minutes. After extraction with diethyl ether, the combined organic extract are treated as usual with water and brine. After the solvent is spun off, the residue is chromatographed on silica gel (mobile solvent ethyl acetate/hexane). 21.4 g (84.2%) of the desired compound is isolated (easily contaminated).

Ethyl-4-(4-chloro-3-methoxyphenyl)-4-methyl-2-oxopentanoate 6.15 g (20.45 mmol) of ethyl 4-(4-chloro-3-methoxyphenyl)-2-hydroxy-4-methyl-pentanoate is dissolved in 213 ml of dichloromethane and mixed with 71 ml of dimethyl sulfoxide. After 10.3 g (102.23 mmol) of triethylamine is added, the batch is mixed in portions with 8.1 g (51.12 mmol) of SO$_3$/pyridine complex and then stirred overnight at room temperature. The reaction mixture is mixed while being cooled slightly with 81 ml of saturated ammonium chloride solution and vigorously stirred. After 2× extraction with diethyl ether, the combined organic phases are treated as usual. The residue that remains after the solvent is spun off is chromatographed on silica gel (mobile solvent ethyl acetate/hexane) together with the residue that results from another batch (15.27 g). 15.46 g (72.9%, from the two batches) of the desired compound is isolated.

$^1$H-NMR (300 MHz, CDCl$_3$): δ=1.25 (3H), 1.48 (6H), 3.16 (2H), 3.90 (3H), 4.12 (2H), 6.83-6.94 (2H), 7.28 (1H).

(rac.) Ethyl-4-(4-chloro-3-methoxyphenyl)-4-methyl-2-(trifluoromethyl-2-(trimethylsilyloxy)-pentanoate 15.46 g (51.75 mmol) of ethyl-4-(4-chloro-3-methoxyphenyl)-4-methyl-2-oxopentanoate is dissolved in 85 ml of tetrahydrofuran and mixed at 0° C. with 8.83 g (62.09 mmol) of (trifluoromethyl)-trimethylsilane. After 126.8 mg of tetrabutylammonium fluoride is added, it SEQ ID No: stirred for two hours at 0 to 5° C. The batch is added to 150 ml of ice water, extracted twice with diethyl ether, and the combined organic extracts are treated as usual. After the solvent is spun off, the residue is chromatographed on silica gel (mobile solvent ethyl acetate/hexane). 14.11 g (61.8%) of the desired product (COntaminated), which is incorporated into the next stage, is isolated.

MS (CI): 458 (100%).

Ethyl-4-(4-chloro-3-methoxyphenyl)-4-methyl-2-(trifluoromethyl-2-hydroxy-pentanoate 8.9 g (20.18 mmol) of contaminated ethyl-4-(4-chloro-3-methoxyphenyl)-4-methyl-2-(trifluoromethyl-2-(trimethyl-silyloxy)-pentanoate is dissolved in 116 ml of tetrahydrofuran and mixed at room temperature with 6.37 g (20.18 mmol) of tetrabutylammonium fluoride trihydrate and stirred for one hour at room temperature. The reaction mixture is mixed with water and extracted twice with 250 ml each of diethyl ether. The combined organic extracts are washed with water and with brine. After drying on sodium sulfate, the desiccant is filtered off, the solvent is spun off, and the remaining residue is chromatographed on silica gel (mobile solvent ethyl acetate/hexane). 4.03 g (54.2%) of the desired compound is isolated. Other preparations are performed analogously.

$^1$H-NMR (300 MHz, CDCl$_3$): δ=1.19 (3H), 1.39 (3H), 1.49 (3H), 2.28 (1H), 2.49 (1H), 3.60-3.71 (2H), 3.93 (3H), 3.98-4.10 (1H), 6.82-6.93 (2H), 7.28 (1H).

4-(4-Chloro-3-methoxyphenyl)-2-hydroxy-2-(trifluoromethyl)-pentanal 5.25 g (14.24 mmol) of (rac.) ethyl-4-(4-chloro-3-methoxyphenyl)-4-methyl-2-(trifluoromethyl)-2-hydroxy-pentanoate is dissolved in 53 ml of diethyl ether and mixed at 0° C. with 405.2 mg (10.68 mmol) of lithium aluminum hydride within 30 minutes. The reaction mixture is stirred for 1¼ more hours at 0° C. For hydrolysis, the mixture is mixed drop by drop with 12.5 ml of saturated sodium bicarbonate solution while being cooled in an ice bath. It is stirred vigorously for 30 minutes while being cooled in an ice bath and for 60 minutes at room temperature. The precipitate is suctioned off and washed with diethyl ether. The filtrate is concentrated by evaporation in a rotary evaporator, and the residue is chromatographed on silica gel (mobile solvent ethyl acetate/hexane). 3.29 g (71.2%) of the desired aldehyde, which still contains some starting ester and 54.7 mg of the corresponding diol, is isolated.

$^1$H-NMR (300 MHz, CDCl$_3$): δ=1.39 (3H), 1.48 (3H), 2.34 (1H), 2.69 (1H), 3.69 (1H), 3.92 (3H), 6.80-6.93 (2H), 7.30 (1H), 8.90 (1H).

4-(4-Chloro-3-methoxy-phenyl)-1,1,1-trifluoro-2-{[(E)-8-fluoro-2-methyl-quinazolin-5-ylimino]-methyl}-4-methyl-pentan-2-ol 350 mg (1.08 mmol) of (rac.)-4-(4-chloro-3-methoxyphenyl)-2-hydroxy-2-(trifluoromethyl)-pentanal is mixed in 5.8 ml of o-xylene with 190.9 mg (1.08 mmol) of 5-amino-8-fluoro-2-methylquinazoline. After 0.64 ml (2.16) titanium (IV) isopropylate is added, it is refluxed for three hours (bath temperature 120° C.). After cooling, the batch is added to saturated sodium chloride solution and stirred vigorously for 20 minutes. After 2× extraction with ethyl acetate, the combined organic extracts are washed with brine. After drying on sodium sulfate, and after the desiccant is suctioned off and the solvent is spun off, the residue is chromatographed on silica gel (mobile solvent ethyl acetate/hexane). 327.5 mg (62.8%) of the desired imine is isolated.

$^1$H-NMR (300 MHz, CDCl$_3$): δ=1.38 (3H), 1.58 (3H), 2.45 (1H), 2.71 (1H), 2.99 (3H), 3.69 (3H), 4.75 (1H), 6.28 (1H), 6.79-6.90 (2H), 7.08 (1H), 7.37-7.49 (2H), 9.63 (1H).

7-Chloro-1-(8-fluoro-2-methylquinazolin-5-ylamino)-6-methoxy-4,4-dimethyl-2-(trifluoromethyl)-1,2,3,4-tetrahydronaphthalen-2-ol 80 mg (0.165 mmol) of imine is dissolved in 1.2 ml of dichloromethane, mixed drop by drop with 0.5 ml of titanium tetrachloride at 0° C. and stirred for 1¾ hours at this temperature. The reaction mixture is mixed drop by drop with saturated sodium bicarbonate solution at 0° C. and mixed with ethyl acetate. The cold bath is removed, and the batch is stirred vigorously for 20 minutes. After extraction with ethyl acetate, the combined organic extracts are worked up as usual. After chromatography on silica gel (mobile solvent methanol/dichloromethane), 60.7 mg (75.8%) of the desired compound is obtained.

$^1$H-NMR (300 MHz, DMSO-d$_6$): δ=1.40 (3H), 1.56 (3H), 1.99-2.15 (2H), 2.78 (3H), 3.90 (3H), 5.40 (1H), 6.18 (1H), 6.72-6.90 (2H), 7.10-7.20 (2H), 7.60 (1H), 9.79 (1H).

7-Chloro-1-(8-fluoro-2-methylquinazolin-5-ylamino)-4,4-dimethyl-2-(trifluoromethyl)-1,2,3,4-tetrahydronaphthalene-2,6-diol 35 mg (0.072 mmol) of the compound that is described in the preceding section is mixed with 0.7 ml of a one-molar solution of boron tribromide in dichloromethane while being cooled in an ice bath, and it is stirred for two hours while being cooled in an ice bath. The reaction mixture is mixed drop by drop at −30° C. with saturated sodium bicarbonate solution, specifically to pH 8. The cold bath is removed, and the batch is stirred vigorously for 15 minutes at room temperature. After 2× extraction with ethyl acetate, the organic extracts are worked up as usual. After chromatography on silica gel (mobile solvent methanol/dichloromethane), 17.7 mg (52.2 mg) of the desired compound is ultimately isolated.

$^1$H-NMR (300 MHz, CD$_3$OD): δ=1.40 (3H), 1.56 (3H), 2.07-2.20 (2H), 2.89 (3H), 5.23 (1H), 6.83 (1H), 6.99 (1H), 7.20 (1H), 7.59 (1H), 9.69 (1H).

Example 147

5-(7-Chloro-2,6-dihydroxy-4,4-dimethyl-2-(trifluoromethyl)-1,2,3,4-tetrahydronaphthalen-1-ylamino-2H-isoquinolin-1-one

5-[4-(4-Chloro-3-methoxyphenyl)-2-hydroxy-4-methyl-2-(trifluoromethyl)-pentylidenamino)-2H-isoquinolin-1-one 400 mg (1.232 mmol) of the 4-(4-chloro-3-methoxyphenyl)-2-hydroxy-2-(trifluoromethyl)-pentanal that is described in the example above is reacted with 197.3 mg (1.232 mmol) of 5-amino-2H-isoquinolin-1-one to form imine. After the reaction, conventional working-up and chromatography, 332.9 mg (57.9%) of the desired imine is obtained.

$^1$H-NMR (300 MHz, CDCl$_3$): δ=1.38 (3H), 1.56 (3H), 2.43 (1H), 2.72 (1H), 3.70 (3H), 4.95 (1H), 6.41 (1H), 6.75-6.98 (3H), 7.08-7.31 (2H), 7.31-7.48 (2H), 11.2 (1H).

5-(7-Chloro-2-hydroxy-6-methoxy-4,4-dimethyl-2-(trifluoromethyl-1,2,3,4-tetrahydronaphthalen-1-ylamino-2H-isoquinolin-1-one 100 mg (0.214 mmol) of imine is reacted with titanium tetrachloride as described in Example 146. 36.9 mg (36.9%) of the desired cyclic compound is isolated, specifically as a diastereomer mixture in a 65:35 ratio.
MS (ES+): 467 (100%)

5-(7-Chloro-2,6-dihydroxy-4,4-dimethyl-2-(trifluoromethyl)-1,2,3,4-tetrahydronaphthalen-1-ylamino-2H-isoquinolin-1-one 27 mg (0.058 mmol) of the ether that is described in the section above is reacted with boron tribromide as described in Example 146. After the reaction is carried out and after the conventional working-up, 19.9 mg (75.9%) of the desired compound is obtained, specifically as a uniform diastereomer.
$^1$H-NMR (300 MHz, CD$_3$OD): δ=1.29 (3H), 1.43 (3H), 1.98-2.09 (2H), 5.00 (1H), 6.75 (1H), 6.86 (1H), 6.93 (1H), 7.00-7.10 (2H), 7.29 (1H), 7.59 (1H).

Example 148

5-(7-Chloro-2,6-dihydroxy-4,4-dimethyl-2-(trifluoromethyl)-1,2,3,4-tetrahydronaphthalen-1-ylamino-2-methyl-2H-phthalazin-1-one

5-[4-(4-Chloro-3-methoxyphenyl)-2-hydroxy-4-methyl-2-(trifluoromethyl)-pentylidenamino)-2-methyl-2H-phthalazin-1-one 350 mg (1.078 mmol) of the above-described 4-(4-chloro-3-methoxyphenyl)-2-hydroxy-2-(trifluoromethyl)-pentanal is reacted with 251.8 mg (1.078 mmol) of 5-amino-2-methyl-2H-phthalazin-1-one to form imine. After the reaction, conventional working-up and chromatography, 328.4 mg (63.2%) of the desired imine is obtained.
$^1$H-NMR (300 MHz, CDCl$_3$): δ=1.38 (3H), 1.58 (3H), 2.43 (1H), 2.72 (1H), 3.70 (3H), 3.89 (3H), 4.70 (1H), 6.51 (1H), 6.80-6.89 (2H), 7.10 (1H), 7.40 (1H), 7.63 (1H), 8.33 (1H), 8.42 (1H).

5-(7-Chloro-2-hydroxy-6-methoxy-4,4-dimethyl-2-(trifluoromethyl)-1,2,3,4-tetrahydronaphthalen-1-ylamino-2-methyl-2H-phthalazin-1-one 100 mg (0.207 mmol) of imine is cyclized with titanium tetrachloride in dichloromethane as described in Example 146. 30.5 mg (30.5%) of the desired compound is isolated, specifically as a diastereomer mixture.
MS (ES+): 482 (100%)

5-(7-Chloro-2,6-dihydroxy-4,4-dimethyl-2-(trifluoromethyl)-1,2,3,4-tetrahydronaphthalen-1-ylamino-2-methyl-2H-phthalazin-1-one 24 mg (0.049 mmol) of the ether that is described in the section above is reacted with boron tribromide as described in Example 146. After the reaction is performed and after the conventional working-up, 18.7 mg (75.9%) of the desired compound is obtained, specifically as a diastereomer mixture.
MS (ES+): 468 (100%)

Example 149

5-(7-Chloro-2,6-dihydroxy-4,4-dimethyl-2-(trifluoromethyl)-1,2,3,4-tetrahydronaphthalen-1-ylamino-1H-quinolin-2-one

5-[4-(4-Chloro-3-methoxyphenyl)-2-hydroxy-4-methyl-2-(trifluoromethyl)-pentylidenamino)-1H-quinolin-2-one 350 mg (1.078 mmol) of the 4-(4-chloro-3-methoxyphenyl)-2-hydroxy-2-(trifluoromethyl)-pentanal that is described in the example above is reacted with 172.6 mg (1.078 mmol) of 5-amino-1H-quinolin-2-one to form imine. After reaction, conventional working-up and chromatography, 319.4 mg (6349%) of the desired imine is obtained.
$^1$H-NMR (300 MHz, CDCl$_3$): δ=1.34 (3H), 1.55 (3H), 2.43 (1H), 2.70 (1H), 3.70 (3H), 4.85 (1H), 6.00 (1H), 6.70-6.90 (3H), 7.13 (1H), 7.29-745 (3H), 8.17 (1H), 12.30 (1H).

5-(7-Chloro-2,6-dihydroxy-4,4-dimethyl-2-(trifluoromethyl)-1,2,3,4-tetrahydronaphthalen-1-ylamino-1H-quinolin-2one 106 mg (0.227 mmol) of imine is mixed at −20° C. with 2.3 ml of a 1 M solution of boron tribromide in dichloromethane, and it is stirred for two hours at −20° C. to 0° C. The reaction mixture is brought to pH 8 with saturated sodium bicarbonate solution and worked up as usual. After chromatography on silica gel (mobile solvent methanol/dichloromethane), 55.1 mg (53.5%) of the desired cyclic compound is isolated as a free phenol.
$^1$H-NMR (300 MHz, CD$_3$OD): δ=1.41 (3H), 1.55 (3H), 2.05-2.20 (2H), 5.12 (1H), 6.49-6.64 (2H), 6.73 (1H), 6.98 (1H), 7.16 (1H), 7.40 (1H), 8.25 (1H).

Example 150

7-Chloro-1-(2-methylquinazolin-5-ylamino)-4,4-dimethyl-2-(trifluoromethyl)-1,2,3,4-tetrahydronaphthalene-2,6-diol

4-(4-Chloro-3-methoxyphenyl)-1,1,1-trifluoro-2-[(2-methylquinazolin-5-ylamino)-methyl]-4-methyl-pentan-2-ol 200 mg (0.616 mmol) of (rac.)-4-(4-chloro-3-methoxyphenyl)-2-hydroxy-2-(trifluoromethyl)-pentanal are reacted with 98.1 mg (0.616 mmol) of 5-amino-2-methylquinazoline, as described in Example 146, to form imine. After the conventional working-up and purification, 184.3 mg (64.2%) of the desired imine is isolated.
$^1$H-NMR (300 MHz, CDCl$_3$): δ=1.36 (3H), 1.59 (3H), 2.45 (1H), 2.73 (1H), 2.93 (3H), 3.68 (3H), 4.82 (1H), 6.30 (1H), 6.78-6.90 (2H), 7.08 (1H), 7.48 (1H), 7.71 (1H), 7.84 (1H), 9.60 (1H).

7-Chloro-1-(2-methylquinazolin-5-ylamino)-6-methoxy-4,4-dimethyl-2-(trifluoromethyl)-1,2,3,4-tetrahydronaphthalen-2-ol 180 mg (0.386 mmol) of imine is cyclized as described with the aid of titanium tetrachloride. 165.6 mg (92%) of the desired cyclic compound is isolated.
$^1$H-NMR (300 MHz, CD$_3$OD): δ=1.49 (3H), 1.61 (3H), 2.10-2.25 (2H), 2.84 (3H), 3.93 (3H), 5.31 (1H), 6.95 (1H), 7.10 (1H), 7.19-7.27 (2H), 7.81 (1H), 9.65 (1H).

7-Chloro-1-(2-methylquinazolin-5-ylamino)-4,4-dimethyl-2-(trifluoromethyl)-1,2,3,4-tetrahydronaphthalene-2,6-diol 50 mg (0.107 mmol) of the derivative that is described in the section above is reacted with the aid of boron tribromide to form the corresponding phenol. 30.2 mg (66.1%) of the desired compound is isolated.

$^1$H-NMR (300 MHz, DMSO-d$_6$): δ=1.33 (3H), 1.48 (3H), 1.95-2.13 (2H), 2.72 (3H), 5.39 (1H), 6.15 (1H), 6.80-6.95 (2H), 6.95-7.13 (3H), 7.69 (1H), 9.72 (1H), 10.03 (1H).

Example 151

7-Chloro-1-(7-fluoro-2-methylquinazolin-5-ylamino)-4,4-dimethyl-2-(trifluoromethyl)-1,2,3,4-tetrahydronaphthalene-2,6-diol 4-(4-Chloro-3-methoxyphenyl)-1,1,1-trifluoro-2-[(7-fluoro-2-methylquinazolin-5-ylimino)-methyl]-4-methyl-pentan-2-ol 200 mg (0.616 mmol) of aldehyde is reacted with 109.1 mg (0.616) of 5-amino-7-fluoro-2-methylquinazoline as already described several times. 173 mg (58.1%) of the desired imine is isolated.

$^1$H-NMR (300 MHz, CDCl$_3$): δ=1.39 (3H), 1.58 (3H), 2.47 (1H), 2.73 (1H), 2.90 (3H), 3.72 (3H), 4.64 (1H), 6.17 (1H), 6.80-6.90 (2H), 7.09 (1H), 7.40-7.50 (2H), 9.49 (1H).

7-Chloro-1-(7-fluoro-2-methylquinazolin-5-ylamino)-6-methoxy-4,4-dimethyl-2-(trifluoromethyl)-1,2,3,4-tetrahydronaphthalen-2-ol 170 mg (0.351 mmol) of the above-described imine is cyclized with 1.05 ml (1.053 mmol) of titanium tetrachloride in dichloromethane. After the conventional working-up and subsequent chromatography, 168.4 mg (99%) of the desired cyclic compound is isolated as an ether.

$^1$H-NMR (300 MHz, CD$_3$OD): δ=1.49 (3H), 1.61 (3H), 2.20 (2H), 2.80 (3H), 3.93 (3H), 5.33 (1H), 6.70-6.85 (2H), 7.10 (1H), 7.20 (1H), 9.57 (1H).

7-Chloro-1-(7-fluoro-2-methylquinazolin-5-ylamino)-4,4-dimethyl-2-(trifluoromethyl)-1,2,3,4-tetrahydronaphthalene-2,6-diol 50 mg (0.103 mmol) of the ether that is described in the section above is subjected as usual to ether cleavage with boron tribromide. After the working-up and the conventional chromatography on silica gel (mobile solvent methanol/dichloromethane), 32.2 mg (66.4%) of the desired compound is isolated.

$^1$H-NMR (300 MHz, DMSO-d$_6$): δ=1.32 (3H), 1.49 (3H), 1.95-2.13 (2H), 2.70 (3H), 5.48 (1H), 6.15 (1H), 6.79 (1H), 6.88 (1H), 6.95-7.16 (2H), 9.68 (1H), 10.03 (1H).

Example 152

7-Chloro-1-(7,8-difluoro-2-methylquinazolin-5-ylamino)-4,4-dimethyl-2-(trifluoromethyl)-1,2,3,4-tetrahydronaphthalene-2,6-diol 4-(4-Chloro-3-methoxyphenyl)-1,1,1-trifluoro-2-[(7,8-difluoro-2-methylquinazolin-5-ylimino)-methyl]-4-methyl-pentan-2-ol 200 mg (0.616 mmol) of aldehyde is reacted with 120 mg (0.616) of 5-amino-7,8-difluoro-2-methylquinazoline as already described several times. 201.3 mg (65.1%) of the desired imine is isolated.

$^1$H-NMR (300 MHz, CDCl$_3$): δ=1.38 (3H), 1.58 (3H), 2.46 (1H), 2.72 (1H), 2.96 (3H), 3.72 (3H), 4.59 (1H), 6.28 (1H), 6.80-6.90 (2H), 7.10 (1H), 7.46 (1H), 9.53 (1H).

7-Chloro-1-(7,8-difluoro-2-methylquinazolin-5-ylamino)-6-methoxy-4,4-dimethyl-2-(trifluoromethyl)-1,2,3,4-tetrahydronaphthalen-2-ol 200 mg (0.398 mmol) of the above-described imine is cyclized with 1.19 ml (1.194 mmol) of titanium tetrachloride in dichloromethane. After the conventional working-up and subsequent chromatography, 163.6 mg (81.8%) of the desired cyclic compound is isolated.

$^1$H-NMR (300 MHz, CD$_3$OD): δ=1.48 (3H), 1.61 (3H), 2.19 (2H), 2.86 (3H), 3.93 (3H), 5.30 (1H), 6.88 (1H), 7.09 (1H), 7.21 (1H), 9.62 (1H).

7-Chloro-1-(7,8-difluoro-2-methylquinazolin-5-ylamino)-4,4-dimethyl-2-(trifluoromethyl)-1,2,3,4-tetrahydronaphthalene-2,6-diol 50 mg (0.099 mmol) of the compound that is described in the section above is subjected as usual to ether cleavage with boron tribromide. After working-up and purification on flash chromatography (mobile solvent methanol/dichloromethane), 29.5 mg (60.7) of the desired compound is isolated.

$^1$H-NMR (300 MHz, DMSO-d$_6$): 1.32 (3H), 1.47 (3H), 1.95-2.12 (2H), 2.78 (3H), 5.45 (1H), 6.13 (1H), 6.92-7.18 (4H), 9.73 (1H), 10.02 (1H).

Example 153

4-(7-Chloro-2,6-dihydroxy-4,4-dimethyl-2-(trifluoromethyl)-1,2,3,4-tetrahydronaphthalen-1-ylamino)-1,3-dihydroindol-2-one 4-[4-(4-Chloro-3-methoxyphenyl)-2-hydroxy-4-methyl-2-(trifluoromethyl)-pentylidenamino]-1,3-dihydroindol-2-one 150 mg (0.462 mmol) of aldehyde is boiled with 102.7 mg (0.693 mmol) of 4-amino-1,3-dihydroindol-2-one in xylene after addition of titanium tetraisopropylate to the water separator as already described in the examples above. After conventional working-up and chromatography, 119.3 mg (56.7%) of the desired imine is isolated.

$^1$H-NMR (300 MHz, CDCl$_3$): δ=1.35 (3H), 1.50 (3H), 2.49 (1H), 2.66 (1H), 3.35-3.59 (2H), 3.75 (3H), 4.89 (1H), 5.98 (1H), 6.70-6.90 (3H), 7.02-7.22 (2H), 7.33 (1H), 8.22 (1H).

4-(7-Chloro-2-hydroxy-6-methoxy-4,4-dimethyl-2-(trifluoromethyl)-,1,2,3,4-tetrahydronaphthalen-1-ylamino)-1,3-dihydroindol-2-one 119 mg (0.261 mmol) of the above-described imine is cyclized as usual in dichloromethane with 0.78 ml of titanium tetrachloride. After working-up and chromatography, 78.1 mg (65.6%) of the desired compound is obtained.

$^1$H-NMR (300 MHz, CD$_3$OD): δ=1.42 (3H), 1.59 (3H), 2.00-2.20 (2H), 3.23-3.49 (2H), 3.91 (3H), 5.03 (1H), 6.37 (1H), 6.48 (1H), 7.03 (1H), 7.10 (1H), 7.29 (1H).

4-(7-Chloro-2,6-dihydroxy-4,4-dimethyl-2-(trifluoromethyl)-1,2,3,4-tetrahydronapthalen-1-ylamino)-1,3-dihydroindol-2-one 65 mg (0.143 mmol) of the ether that is described in the section above is mixed with 1.4 boron tribromide in dichloromethane. After working-up and chromatography, 45.4 mg (72.1%) of the desired phenol is obtained.

$^1$H-NMR (300 MHz, CD$_3$OD): δ=1.39 (3H), 1.51 (3H), 1.98-2.20 (2H), 3.25-3.50 (2H), 5.00 (1H), 6.37 (1H), 6.46 (1H), 6.93 (1H), 7.10 (1H), 7.21 (1H).

Example 154

8,8-Dimethyl-5-(naphthalen-1-ylamino)-6-(trifluoromethyl)-5,6,7,8-tetrahydronaphthalene-1,6-ol 1,1,1-Trifluoro-4-(2-methoxyphenyl)-4-methyl-2-(naphthalen-1-yliminomethyl)-pentan-2-ol 150 mg (0.517 mmol) of 2-hydroxy-4-(2-methoxyphenyl)-4-methyl-2-(trifluoromethyl)-pentanal is converted into imine with 74 mg (0.517 mmol) of 1-naphthylamine in toluene with the aid of titanium tetraisopropylate. After working-up and chromatography, 166.7 mg (77.7%) of the desired imine is isolated.

$^1$H-NMR (300 MHz, CDCl$_3$): δ=1.42 (3H), 1.59 (3H), 2.29 (1H), 3.57 (1H), 3.88 (3H), 5.09 (1H), 6.10 (1H), 6.48 (1H), 6.79 (1H), 7.00 (1H), 7.10 (1H), 7.22 (1H), 7.40 (1H), 7.47-7.58 (2H), 7.69 (1H), 7.80 (1H), 8.05 (1H).

8,8-Dimethyl-5-(naphthalen-1-ylamino-6-(trifluoromethyl-5,6,7,8-tetrahydronaphthalene-1,6-diol 160.9 mg (0.387 mmol) of the above-described imine is treated as usual with boron tribromide at 0° C., and after conventional working-up and chromatography on a Flashmaster, 100.9 mg (62.7%) of the desired cyclic phenol is produced.

$^1$H-NMR (300 MHz, CDCl$_3$): δ=1.60 (3H), 1.73 (3H), 2.00-2.28 (2H), 3.09 (1H), 4.79 (1H), 5.02 (1H), 5.20 (1H), 6.62 (1H), 6.85-7.02 (3H), 7.30-7.58 (4H), 7.73-7.90 (3H).

Example 155

8,8-Dimethyl-5-(naphthalen-2-ylamino)-6-(trifluoromethyl)-5,6,7,8-tetrahydronaphthalene-1,6-diol 1,1,1-Trifluoro-4-(2-methoxyphenyl-4-methyl-2-(naphthalen-2-yliminomethyl)-pentan-2-ol 150 mg (0.517 mmol) of 2-hydroxy-4-(2-methoxyphenyl)-4-methyl-2-(trifluoromethyl)-pentanal is converted into imine with 74 mg (0.517 mmol) of 2-naphthylamine in toluene with the aid of titanium tetraisopropylate. After working-up and chromatography, 192.8 mg (89.8%) of the desired imine is isolated.

$^1$H-NMR (300 MHz, CDCl$_3$): δ=1.40 (3H), 1.58 (3H), 2.20 (1H), 3.58 (1H), 3.89 (3H), 5.09 (1H), 6.69 (1H), 6.80-6.90 (2H), 6.95 (1H), 7.05-7.18 (2H), 7.38-7.53 (3H), 7.63-7.85 (3H).

8,8-Dimethyl-5-(naphthalen-2-ylamino)-6-(trifluoromethyl)-5,6,7,8-tetrahydronaphthalene-1,6-diol 173.0 mg (0.416 mmol) of the above-described imine is treated as usual with boron tribromide at 0° C., and after conventional working-up and chromatography on a Flashmaster, 132.6 mg (76.6%) of the desired cyclic phenol is produced.

$^1$H-NMR (300 MHz, CDCl$_3$): δ=1.60 (3H), 1.66 (3H), 2.00-2.24 (2H), 3.04 (1H), 5.00 (1H), 5.09 (1H), 6.62 (1H), 6.92-7.10 (4H), 7.28 (1H), 7.40 (1H), 7.60-7.78 (3H).

Example 156

2-Chloro-5-(6-hydroxynaphthalen-1-ylamino)-8,8-dimethyl-6-(trifluoromethyl)-5,6,7,8-tetrahydronaphthalene-1,6-diol 5-(4-(3-Chloro-2-methoxyphenyl)-2-hydroxy-4-methyl-2-(trifluoromethyl)-pentylideneamino]-naphthalen-2-ol 200 mg (0.616 mmol) of 2-hydroxy-4-(3-chloro-2-methoxyphenyl)-4-methyl-2-(trifluoromethyl)-pentanal is reacted as usual with 98.1 mg (0.616 mmol) of 5-amino-2-naphthol to form imine. 185.1 mg (64.5%) of the desired compound is isolated.

$^1$H-NMR (300 MHz, CDCl$_3$): δ=1.47 (3H), 1.62 (3H), 2.40 (1H), 3.23 (1H), 4.00 (3H), 4.99 (1H), 5.15 (1H), 6.39 (1H), 6.49 (1H), 6.83 (1H), 7.00 (1H), 7.05-7.20 (2H), 7.23-7.32 (2H), 7.52-7.63 (2H), 7.95 (1H).

2-Chloro-5-(6-hydroxynaphthalin-1-ylamino)-8,8-dimethy-6-(trifluoromethyl)-5,6,7,8-tetrahydro-naphthalene-1,6-diol 185.1 mg (0.397 mmol) of imine is cyclized with boron tribromide, as already described several times. 146.9 mg (81.8%) of the desired phenol is isolated.

$^1$H-NMR (300 MHz, CDCl$_3$): δ=1.59 (3H), 1.70 (3H), 2.02-2.28 (2H), 3.00 (1H), 4.75 (1H), 5.10-5.19 (2H), 5.95 (1H), 6.73 (1H), 6.88 (1H), 7.00-7.12 (2H), 7.12-7.22 (2H), 7.34 (1H), 7.70 (1H).

Example 157

2-Chloro-5-(5-hydroxynaphthalen-1-ylamino)-8,8-dimethyl-6-(trifluoromethyl)-5,6,7,8-tetrahydronaphthalene-1,6-diol 5-(4-(3-Chloro-2-methoxyphenyl)-2-hydroxy-4-methyl-2-(trifluoromethyl)-pentylideneamino]-naphthalen-1-ol 200 mg (0.616 mmol) of 2-hydroxy-4-(3-chloro-2-methoxyphenyl)-4-methyl-2-(trifluoromethyl)-pentanal is reacted as usual with 98.1 mg (0.616 mmol) of 5-amino-1-naphthol to form imine. 145.0 mg (50.5%) of the desired compound is isolated.

$^1$H-NMR (300 MHz, CDCl$_3$): δ=1.45 (3H), 1.62 (3H), 2.40 (1H), 3.25 (1H), 4.01 (3H), 5.01 (1H), 5.39 (1H), 6.46 (1H), 6.53 (1H), 6.80-6.91 (2H), 7.02 (1H), 7.30-7.40 (2H), 7.59 (1H), 7.64 (1H), 8.10 (1H).

2-Chloro-5-(5-hydroxynaphthalen-1-ylamino)-8,8-dimethyl-6-(trifluoromethyl)-5,6,7,8-tetrahydro-naphthalene-1,6-diol 145.0 mg (0.311 mmol) of imine is cyclized with boron tribromide, as already described several times. 87.6 mg (62.3%) of the desired phenol is isolated.

¹H-NMR (300 MHz, CDCl₃): δ=1.58 (3H), 1.70 (3H), 2.05-2.28 (2H), 3.00 (1H), 4.78 (1H), 5.15 (1H), 5.49 (1H), 5.95 (1H), 6.80-6.93 (3H), 7.10 (1H), 7.29 (1H), 7.32-7.45 (2H), 7.68 (1H).

Example 158

3-Chloro-5-(6-hydroxynaphthalen-1-ylamino)-8,8-dimethyl-6-(trifluoromethyl)-5,6,7,8-tetrahydronaphthalene-1,6-diol 5-(4-(4-Chloro-2-methoxyphenyl)-2-hydroxy-4-methyl-2-(trifluoromethyl)-pentylideneamino]-naphthalen-2-ol 200 mg (0.616 mmol) of 2-hydroxy-4-(4-chloro-2-methoxyphenyl)-4-methyl-2-(trifluoromethyl)-pentanal are reacted as usual with 98.1 mg (0.616 mmol) of 5-amino-2-naphthol to form imine. 113.0 mg (39.4%) of the desired compound is isolated.

¹H-NMR (300 MHz, CDCl₃): δ=1.38 (3H), 1.58 (3H), 2.30 (1H), 3.40 (1H), 3.85 (3H), 5.00 (1H), 5.15 (1H), 6.06 (1H), 6.50 (1H), 6.75 (1H), 6.99 (1H), 7.05-7.20 (2H), 7.28 (1H), 7.45 (1H), 7.58 (1H), 7.93 (1H).

3-Chloro-5-(6-hydroxynaphthalen-1-ylamino)-8,8-dimethyl-6-(trifluoromethyl)-5,6,7,8-tetrahydronaphthalene-1,6-diol 113.0 mg (0.243 mmol) of imine is cyclized with boron tribromide, as already described several times. 85.7 mg (78.2%) of the desired compound is isolated.

¹H-NMR (300 MHz, CDCl₃): δ=1.55 (3H), 1.65 (3H), 2.01-2.23 (2H), 2.95 (1H), 4.80 (1H), 5.10 (1H), 5.20 (1H), 5.48 (1H), 6.60-6.75 (2H), 6.93 (1H), 7.09 (1H), 7.10-7.23 (2H), 7.35 (1H), 7.74 (1H).

Example 159

2-Chloro-8,8-dimethyl-5-(pyridin-3-ylamino)-6-(trifluoromethyl)-5,6,7,8-tetrahydronaphthalene-1,6-diol 4-(3-Chloro-2-methoxyphenyl)-1,1,1-(trifluoromethyl)-4-methyl-(pyridin-3-yliminomethyl)-pentan-2-ol 200 mg (0.616 mmol) of 2-hydroxy-4-(3-chloro-2-methoxyphenyl)-4-methyl-2-(trifluoromethyl)-pentanal is reacted as usual with 57.9 mg (0.616 mmol) of 3-aminopyridine to form imine. 197.2 mg (79.9%) of the desired compound is isolated.

¹H-NMR (300 MHz, CDCl₃): δ=1.43 (3H), 1.60 (3H), 2.28 (1H), 3.25 (1H), 3.98 (3H), 4.70 (1H), 6.75 (1H), 6.95 (1H), 7.00-7.15 (2H), 7.23 (1H), 7.58 (1H), 8.12 (1H), 8.49 (1H).

6-Chloro-5-methoxy-4,4-dimethyl-1-(pyridin-3-ylamino)-2-(trifluoromethyl)-1,2,3,4-tetrahydronaphthalen-2-ol 190.0 mg (0.474 mmol) of imine is cyclized with titanium tetrachloride as already described several times. 184.0 mg (96.8%) of the desired cyclic compound is isolated as ether.

¹H-NMR (300 MHz, CD₃OD): δ=1.54 (3H), 1.62 (3H), 2.11 (2H), 3.95 (3H), 5.05 (1H), 7.11 (1H), 7.15-7.28 (3H), 7.83 (1H), 8.09 (1H).

2-Chloro-8,8-dimethyl-5-(pyridin-3-ylamino)-6-(trifluoromethyl)-5,6,7,8-tetrahydronaphthalene-1,6-diol 100 mg (0.249 mmol) of the above-described ether is treated as usual with boron tribromide. After the conventional working-up and chromatography, 85.8 mg (88.9%) of the desired compound is isolated.

¹H-NMR (300 MHz, CD₃OD): δ=1.58 (3H), 1.69 (3H), 2.00-2.20 (2H), 5.00 (1H), 6.89 (1H), 7.10-7.30 (3H), 7.81 (1H), 8.06 (1H).

Example 160

1,6-Dihydroxy-8,8-dimethyl-5-(pyridin-3-ylamino)-6-(trifluoromethyl)-5,6,7,8-tetrahydronaphthalene-2-carbonitrile 50 mg of the 2-chloro-8,8-dimethyl-5-(pyridin-3-ylamino)-6-(trifluoromethyl)-5,6,7,8-tetrahydronaphthalene-1,6-diol that is described in Example 159 is dissolved in 0.12 ml of 1-methy-2-pyrrolidinone and mixed with 12.6 mg (0.258 mmol) of sodium cyanide and 28.2 mg (0.129 mmol) of nickel(II) bromide. The reaction mixture is brought to reaction in the microwave as described in the literature (J. Org. Chem. 68, 9122 (2003) (200° C., 20 bar). After cooling, the reaction mixture is diluted with ethyl acetate and then a small amount of water is added. The mixture is filtered over Extrelut (mobile solvent ethyl acetate). The solvent is spun off, and the residue is chromatographed on silica gel (mobile solvent methanol/dichloromethane). 9.4 mg (19.2%) of the desired nitrile is isolated.

MS (CI): 378 (100%); IR (KBr): 2228.

Example 161

2-Chloro-8,8-dimethyl-5-(pyridin-4-ylamino)-6-(trifluoromethyl)-5,6,7,8-tetrahydronaphthalene-1,6-diol 4-(3-Chloro-2-methoxyphenyl)-1,1,1-(trifluoromethyl)-4-methyl-(pyridin-4-yliminomethyl)-pentan-2-ol 200 mg (0.616 mmol) of 2-hydroxy-4-(3-chloro-2-methoxyphenyl)-4-methyl-2-(trifluoromethyl)-pentanal is reacted as usual with 57.9 mg (0.616 mmol) of 4-aminopyridine to form imine. 167.9 mg (68.0%) of the desired compound is isolated.

¹H-NMR (300 MHz, CDCl₃): δ=1.43 (3H), 1.60 (3H), 2.29 (1H), 3.26 (1H), 4.00 (3H), 4.55 (1H), 6.59-6.65 (2H), 6.80 (1H), 7.01 (1H), 7.11 (1H), 7.55 (1H), 8.46-8.55 (2H).

6-Chloro-5-methoxy-4,4-dimethyl-1-(pyridin-4-ylamino)-2-(trifluoromethyl)-1,2,3,4-tetrahydronaphthalen-2-ol 160.0 mg (0.399 mmol) of imine is cyclized with titanium tetrachloride as already described several times. 45.2 mg (28.2%) of the desired cyclic compound is isolated as ether.

¹H-NMR (300 MHz, CD₃OD): δ=1.55 (3H), 1.69 (3H), 2.12 (2H), 3.98 (3H), 5.28 (1H), 6.80-6.93 (2H), 6.99 (1H), 7.28 (1H), 7.98-8.20 (2H).

2-Chloro-8,8-dimethyl-5-(pyridin-4-ylamino)-6-(trifluoromethyl)-5,6,7,8-tetrahydronaphthalene-1,6-diol 37 mg (0.092 mmol) of the above-described ether is treated as usual with boron tribromide. After the conventional working-up and chromatography, 13.8 mg (38.6%) of the desired compound is isolated.

$^1$H-NMR (300 MHz, CD$_3$OD): δ=1.58 (3H), 1.70 (3H), 2.00-2.20 (2H), 5.19 (1H), 6.70-6.89 (3H), 7.19 (1H), 7.90-8.20 (2H).

Example 162

5-(2,5-Dihydroxy-6-isopropyl-4,4-dimethyl-2-(trifluoromethyl)-1,2,3,4-tetrahydronaphthalen-1-ylamino)-2H-isoquinolin-1-one

Methyl-3-isopropyl-2-methoxybenzoate 28 g (156.25 mmol) of 2-hydroxy-3-isopropylbenzoic acid is dissolved in 280 ml of DMF and added in drops to a mixture of 47.5 g of potassium carbonate in 274 ml of DMF. After one more hour of stirring at room temperature, 21.4 ml (343.76 mmol) of iodomethane is added in drops, and the mixture is stirred for one day at room temperature. After acidification with 10% sulfur acid to pH 3-4 (ice bath cooling), the reaction mixture is extracted four times with 500 ml each of methyl tert-butyl ether. The combined organic extracts are washed with water and with brine and dried on sodium sulfate. After the desiccant is filtered off, the solvent is spun off, and the residue is chromatographed several times on silica gel (mobile solvent methyl tert-butyl ether/hexane). 25.59 g (79.02%) of the desired compound is isolated.

$^1$H-NMR (300 MHz, CDCl$_3$): δ=1.26 (6H), 3.42 (1H), 3.85 (3H), 3.96 (3H), 7.15 (1H), 7.43 (1H), 7.65 (1H).

2-(3-Isopropyl-2-methoxyphenyl)-propan-2-ol 25.59 g (142.81 mmol) of methyl-3-isopropyl-2-methoxybenzoate is dissolved in 250 ml of tetrahydrofuran and added in drops to 114.25 ml (342.74 mmol) of methylmagnesium bromide (3M in diethyl ether). In this case, the temperature increases to 46° C. After three hours of stirring at room temperature, 625 ml of saturated ammonium chloride solution is added in drops to the reaction mixture. After 3× extraction with methyl tert-butyl ether, the combined organic extracts are washed with water and brine and dried (sodium sulfate). The desiccant is filtered off, the solvent is spun off, and the residue (28.16 g=95.15%) is incorporated in crude form into the next stage.

$^1$H-NMR (300 MHz, CDCl$_3$): δ=1.25 (6H), 1.63 (6H), 3.31 (1H), 3.90 (3H), 4.78 (1H), 7.00-7.23 (3H).

Ethyl-4-(3-isopropyl-2-methoxyphenyl)-4-methyl-2-oxo-pentanoate 15.3 ml (129.71 mmol) of tin tetrachloride is added in drops to a mixture, cooled to −72° C., that consists of 28.16 g (135.19 mmol) of 2-(3-isopropyl-2-methoxyphenyl)-propan-2-ol and 50.9 g (270.38 mmol) of 2-trimethylsilanyloxyacrylic acid ethyl ester in 420 ml of dichloromethane. In this case, the temperature increased to −65° C. After 30 minutes of stirring in this temperature interval, the reaction mixture is poured into a mixture that consists of saturated sodium carbonate solution and dichloromethane (in each case 250 ml). After 30 minutes of stirring at room temperature, the batch is transferred into a spherical separating funnel and a 1:1 mixture that consists of water and dichloromethane is added until a phase separation takes place. After the organic phase is shaken with sodium carbonate, 1N HCl and water, it is dried with sodium sulfate. According to the conventional procedure, the residue is chromatographed on silica gel (mobile solvent ethyl acetate/hexane). 20.44 g (48.35%) of the desired compound is obtained.

$^1$H-NMR (300 MHz, CDCl$_3$): δ=1.15-1.34 (9H), 3.28 (1H), 3.38 (2H), 3.78 (3H), 4.09-4.21 (2H), 7.05 (1H), 7.10-7.19 (2H).

Ethyl-2-hydroxy-4-(3-isopropyl-2-methoxyphenyl)-4-methyl-2-(trifluoromethyl)-pentanoate 11.82 g (38.58 mmol) of ethyl-4-(3-isopropyl-2-methoxyphenyl)-4-methyl-2-oxopentanoate and 6.58 g (46.29 mmol) of (trifluoromethyl)trimethylsilane are dissolved in 70 ml of tetrahydrofuran and mixed with 50 mg of tetrabutylammonium fluoride trihydrate (slight temperature increase). Since after three hours, no complete reaction has yet taken place, the same amount of tetrabutylammonium fluoridetrihydrate is added once more. After stirring overnight, 12.17 g of tetrabutylammonium fluoride trihydrate is added to cleave the silyl ether that is produced and thus to obtain directly free hydroxyl compound. The reaction mixture is diluted with methyl tert-butyl ether, and the organic extract is washed with water and brine. After drying (sodium sulfate), and after the desiccant is filtered off and the solvent is filtered off, the residue is chromatographed several times on silica gel (mobile solvent ethyl acetate/hexane). 11.04 g (76%) of the desired compound is isolated.

$^1$H-NMR (300 MHz, CDCl$_3$): δ=1.13-1.32 (9H), 1.40-1.48 (6H), 2.48 (1H), 2.72 (1H), 3.32 (1H), 3.57 (1H), 3.65-3.78 (1H), 3.85 (3H), 4.08-4.20 (1H), 6.96-7.09 (2H), 7.18 (1H).

4-(3-Isopropyl-2-methoxyphenyl)-4-methyl-2-(trifluoromethyl)-pentane-1,2-diol 11.04 g (29.33 mmol) of the ester that is described in the section above is dissolved in 90 ml of diethyl ether and mixed at 2° C. in portions with 2.23 g (58.66 mmol) of lithium aluminum hydride. After stirring overnight at room temperature, 50 ml of saturated sodium bicarbonate solution is carefully added in drops while being cooled in an ice bath. After one hour of vigorous stirring at room temperature, it is extracted three times with methyl tert-butyl ether. The combined organic extracts are worked up as usual, and the residue that remains after the solvent is spun off is chromatographed on silica gel (mobile solvent ethyl acetate/hexane). 7.15 g (72.9%) of the desired diol is isolated.

$^1$H-NMR (300 MHz, CDCl$_3$): δ=1.25 (3H), 1.29 (3H), 1.50 (3H), 1.58 (3H), 1.80 (1H), 2.23 (1H), 2.61 (1H), 2.83 (1H), 3.23-3.49 (3H), 3.89 (3H), 7.09 (1H), 7.17-7.26 (2H).

2-Hydroxy-4-(3-isopropyl-2-methoxyphenyl)-4-methyl-2-(trifluoromethyl)-pentanal 3.17 g (25.04 mmol) of oxalyl chloride is introduced into 83 ml of dichloromethane and cooled to −78° C. At this temperature, 3.9 g (50.08 mmol) of dimethyl sulfoxide, dissolved in 10 ml of dichloromethane, is added in drops. After five minutes of stirring, 7.15 g (21.38 mmol) of 4-(3-isopropyl-2-methoxyphenyl)-4-methyl-2-(trifluoromethyl)pentane-1,2-diol, dissolved in 21.4 ml of dichloromethane, is added. Then, the reaction mixture is stirred for two hours at this low temperature. 10.8 g (106.9 mmol) of triethylamine is carefully added in drops, and the batch is then stirred vigorously at room temperature for one hour. After water is added and after stirring is done for another ten minutes, it is extracted twice with dichloromethane. The combined organic extracts are washed with 1% sulfuric acid, saturated sodium bicarbonate solution and brine. After drying, and after the solvent is spun off, the residue is chromatographed on silica gel (mobile solvent ethyl acetate/hexane). Finally, 5.93 g (83.44%) of the desired aldehyde is obtained.

$^1$H-NMR (300 MHz, CDCl$_3$): δ=1.20 (3H), 1.32 (3H), 1.40-1.54 (6H), 2.22 (1H), 3.30 (1H), 3.40 (1H), 3.59 (1H), 3.83 (3H), 6.95-7.07 (2H), 7.20 (1H), 8.91 (1H).

5-[2-Hydroxy-4-(3-isopropyl-2-methoxyphenyl)-4-methyl-2-(trifluoromethyl)-pentylidenamino]-2H-isoquinolin-1-one 147.3 mg (0.443 mmol) of the aldehyde that is described in the section above is stirred overnight at room temperature with 71 mg (0.443 mmol) of 5-amino-2H-isoquinolin-1-one in 1.3 ml of glacial acetic acid. The reaction mixture is drawn off three times with toluene, and the residue is chromatographed on a Flashmaster. 157 mg (75%) of the desired imine is isolated.

$^1$H-NMR (300 MHz, DMSO-d$_6$): δ=0.93 (3H), 1.19 (3H), 1.43 (3H), 1.55 (3H), 2.18 (1H), 3.18 (1H), 3.29 (1H, half under the water of the DMSO), 3.75 (3H), 6.19 (1H), 6.33 (1H), 6.63 (1H), 6.77 (1H), 6.89-6.99 (2H), 7.16-7.32 (3H), 8.03 (1H), 11.33 (1H).

5-(2-Hydroxy-6-isopropyl-5-methoxy-4,4-dimethyl-2-(trifluoromethyl)-1,2,3,4-tetrahydronaphthalen-1-ylamino)-2H-isoquinolin-1-one 157 mg of imine (0.331 mmol) is dissolved in 2.5 ml of dichloromethane and mixed drop by drop at 0° C. with 0.95 ml (0.993 mmol) of titanium(IV) chloride. After one hour of stirring at 0° C., the reaction mixture is mixed drop by drop with saturated sodium bicarbonate solution and diluted with ethyl acetate. The cold bath is removed, and the batch is stirred vigorously for 30 minutes at room temperature. After 2× extraction with ethyl acetate, the organic extracts are treated as usual. After the residue is chromatographed on a Flashmaster, 108 mg (68.98%) of the desired cyclic compound is obtained as a racemate.

$^1$H-NMR (300 MHz, CD$_3$OD): δ=1.10-1.30 (6H), 1.55 (3H), 1.70 (3H), 2.13 (2H), 3.39 (1H, under the signal of CH$_3$OH), 3.80 (3H), 5.19 (1H), 6.86 (1H), 6.99-7.20 (4H), 7.39 (1H), 7.70 (1H).

5-(2,5-Dihydroxy-6-isopropyl-4,4-dimethyl-2-(trifluoromethyl)-1,2,3,4-tetrahydronaphthalen-1-ylamino)-2H-isoquinolin-1-one 70 mg (0.147 mmol) of the above-described cyclic ether is mixed at room temperature with 1.5 ml of a 1 M solution of boron tribromide in dichloromethane, and it is stirred for five hours at room temperature. The reaction mixture is mixed with pieces of ice. Saturated sodium bicarbonate solution is carefully added in drops, specifically up to pH 8. After the mixture is diluted with ethyl acetate, it is vigorously stirred. After 2× extraction with ethyl acetate, the combined organic extracts are washed with water and brine and dried (sodium sulfate). After the solvent is filtered and spun off, the remaining residue is chromatographed on silica gel (mobile solvent methanol/dichloromethane). 43.2 mg (63.6%) of the desired compound is isolated.

$^1$H-NMR (300 MHz, DMSO-d$_6$): δ=0.96-1.20 (6H), 1.52 (3H), 1.68 (3H), 1.90-2.11 (2H), 3.30 (1H, half under the signal of the water), 5.29 (1H), 5.91 (1H), 6.00 (1H), 6.70 (1H), 6.81 (1H), 6.97 (1H), 7.05 (1H), 7.17 (1H), 7.25 (1H), 7.49 (1H), 8.09 (1H), 11.20 (1H).

Example 163

5-(2,5-Dihydroxy-6-isopropyl-4,4-dimethyl-2-(trifluoromethyl)-1,2,3,4-tetrahydronaphthalen-1-ylamino)-1H-quinolin-2-one 5-[2-Hydroxy-4-(3-isopropyl-2-methoxyphenyl)-4-methyl-(trifluoromethyl)-pentylideneamino]-1H-quinolin-2-one 300 mg (0.903 mmol) of the 2-hydroxy-4-(3-isopropyl-2-methoxyphenyl)-4-methyl-2-(trifluoromethyl)-pentanal that is described in Example 162 is reacted with 5-amino-1H-quinolin-2-one and worked up as described in the example above. After chromatography on a Flashmaster, 372 mg (86.91%) of the desired imine is isolated.

$^1$H-NMR (300 MHz, DMSO-d$_6$): δ=0.90 (3H), 1.18 (3H), 1.40 (3H), 1.54 (3H), 2.15 (1H), 3.15 (1H), 3.29 (1H, half under the water of the DMSO), 3.75 (3H), 5.90 (1H), 6.20 (1H), 6.53 (1H), 6.64 (1H), 6.85-6.98 (2H), 7.13 (1H), 7.22-7.36 (2H), 8.09 (1H), 11.77 (1H).

5-(2-Hydroxy-6-isopropyl-5-methoxy-4,4-dimethyl-2-(trifluoromethyl)-1,2,3,4-tetrahydro-naphthalen-1-ylamino)-1H-quinolin-2-one 120 mg (0.253 mmol) of the described imine is cyclized with titanium(IV) chloride in dichloromethane as described in Example 162. After working-up and chromatography, 64.3 mg (53.6%) of the desired cyclic compound is obtained.

$^1$H-NMR (300 MHz, CDCl$_3$): δ=1.10-1.30 (6H), 1.58 (3H), 1.71 (3H), 2.00-2.20 (2H), 3.31 (1H), 3.80 (3H), 4.01 (1H), 5.09 (1H), 5.25 (1H), 6.50-6.70 (3H), 7.00-7.12 (2H), 7.35 (1H), 8.01 (1H), 10.78 (1H).

5-(2,5-Dihydroxy-6-isopropyl-4,4-dimethyl-2-(trifluoromethyl)-1,2,3,4-tetrahydronaphthalen-1-ylamino)-1H-quinolin-2-one 114 mg (0.240 mmol) of the described imine is cooled to −20° C. and mixed with 2.4 ml of a 1 M boron tribromide solution in dichloromethane. First, it is stirred for two hours at −20° C. to 0° C. and then for 30 minutes at room temperature. The reaction mixture is mixed drop by drop at −20° C. with saturated sodium bicarbonate solution until a pH of 8 is reached. The cold bath is removed, and the batch is stirred vigorously at room temperature for 10 minutes. After the extraction with ethyl acetate, the combined organic extracts are shaken as usual. After the solvent is spun off, 48 mg of a mixture that consists of cyclic ether and the cyclic phenol is obtained. To obtain the uniform ether-cleaved compound, the mixture is treated once again with 1.2 ml of boron tribromide solution, but this time at room temperature (3½ hours of stirring). After the conventional working-up already described, and after chromatography on silica gel, 52.6 mg (92.9%) of the desired compound is obtained.

$^1$H-NMR (300 MHz, CD$_3$OD): δ=1.10-1.30 (6H), 1.60 (3H), 1.72 (3H), 2.00-2.20 (2H), 3.25 (1H), 5.15 (1H), 6.51 (1H), 6.63 (1H), 6.70 (1H), 6.88 (1H), 7.01 (1H), 7.39 (1H), 8.24 (1H).

Example 164

5-(7-Fluoro-2-methylquinazolin-5-ylamino)-2-isopropyl-8,8-dimethyl-6-(trifluoromethyl)-5,6,7,8-tetrahydronaphthalene-1 6-diol

1,1,1-Trifluoro-2-[(7-fluoro-2-methylquinazolin-5-ylimino)-methyl-]-4-(3-isopropyl-2-methoxy-phenyl)-4-methyl-pentan-2-ol 150 mg (0.451 mmol) of the aldehyde that is described in Example 162 is reacted with 79.9 mg (0.451 mmol) of 7-fluoro-2-methylquinazolin-5-ylamine in xylene with the aid of titanium(IV) isopropylate to form imine. After conventional working-up, 207.8 mg (93.6%) of the desired compound is obtained.

$^1$H-NMR (300 MHz, CDCl$_3$): δ=0.83 (3H), 1.20 (3H), 1.41 (3H), 1.62 (3H), 2.25 (1H), 2.90 (3H), 3.20 (1H), 3.68 (1H), 3.83 (3H), 4.61 (1H), 5.95 (1H), 6.54 (1H), 6.80 (1H), 6.99 (1H), 7.30-7.42 (2H), 9.30 (1H).

1-(7-Fluoro-2-methylquinazolin-5-ylamino)-6-isopropyl-5-methoxy-4,4-dimethyl-2-(trifluoromethyl-1,2,3,4-tetrahydronaphthalen-2-ol 207.8 mg (0.422 mmol) of the imine that is described in the section above is cyclized with 1.26 ml of titanium(IV) chloride in dichloromethane. According to the process that is described in Example 162, 194.4 mg (93.5%) of the desired compound is isolated.

$^1$H-NMR (300 MHz, CDCl$_3$): δ=1.10-1.30 (6H), 1.60 (3H), 1.75 (3H), 2.10-2.28 (2H), 2.87 (3H), 3.33 (1H), 3.80 (3H), 4.99 (1H), 6.09 (1H), 6.20 (1H), 6.54 (1H), 6.90 (1H), 7.06-7.19 (2H), 9.20 (1H).

(−)1-(7-Fluoro-2-methylquinazolin-5-ylamino)-6-isopropyl-5-methoxy-4,4-dimethyl-2-(trifluoromethyl)-1,2,3,4-tetrahydronaphthalen-2-ol

(+)-1-(7-Fluoro-2-methylquinazolin-5-ylamino)-6-isopropyl-5-methoxy-4,4-dimethyl-2-(trifluoromethyl)-1,2,3,4-tetrahydronaphthalen-2-ol 94 mg of the racemic compound is separated in the ether stage on a chiral column to obtain the two enantiomers. 36 mg of the (−)-enantiomer and 32 mg of the (+)-enantiomer are isolated.

(−)-Enantiomer: [α]$_D$=−34.4° (c=1, CH$_3$OH); (+)-Enantiomer: [α]$_D$=+31.77° (c=1, CH$_3$OH)

5-(7-Fluoro-2-methylquinazolin-5-ylamino)-2-isopropyl-8,8-dimethyl-6-(trifluoromethyl)-5,6,7,8-tetrahydronaphthalene-1,6-diol 100 mg (0.203 mmol) of 1-(7-fluoro-2-methylquinazolin-5-ylamino)-6-isopropyl-5-methoxy-4,4-dimethyl-2-(trifluoromethyl)-1,2,3,4-tetrahydronaphthalene-2-diol is treated with BBr$_3$ in dichloromethane as already described several times. After working-up and chromatography, 18.5 mg (19.1%) of the desired phenol is obtained.

$^1$H-NMR (300 MHz, CD$_3$OD): δ=1.05-1.30 (6H), 1.65 (3H), 1.74 (3H), 2.28 (2H), 2.79 (3H), 3.27 (1H), 5.30 (1H), 6.65-6.90 (2H), 6.93-7.17 (2H), 9.55 (1H).

(−)-5-(7-Fluoro-2-methylquinazolin-5-ylamino)-2-isopropyl-8,8-dimethyl-6-(trifluoromethyl)-5,6,7,8-tetrahydronaphthalene-1,6-diol

(+)-5-(7-Fluoro-2-methylquinazolin-5-ylamino)-2-isopropyl-8,8-dimethyl-6-(trifluoromethyl)-5,6,7,8-tetrahydronaphthalene-1,6-diol The enantiomer-pure ethers that are described above are converted into the enantiomer-pure phenols as described for the racemate. 10.4 mg (43.5) of the phenol is obtained from 247 mg of ether ((−)-enantiomer). 5.1 mg (19.6%) of the phenol is isolated from 26.7 mg of ether ((+)-enantiomer).

Example 165

5-(7,8-Difluoro-2-methylquinazolin-5-ylamino)-2-isopropyl-8,8-dimethyl-6-(trifluoromethyl)-5,6,7,8-tetrahydronaphthalene-1 6-diol

1,1,1-Trifluoro-2-[(7,8-difluoro-2-methylquinazolin-5-ylimino)-methyl]-4-(3-isopropyl-2-methoxy-phenyl)-4-methyl-pentan-2-ol 150 mg (0.451 mmol) of the aldehyde that is described in Example 162 is reacted with 88 mg (0.451 mmol) of 7,8-difluoro-2-methylquinazolin-5-ylamine in xylene with the aid of titanium(IV) isopropylate to form imine. After the conventional working-up, 208.6 mg (90.7%) of the desired compound is obtained.

$^1$H-NMR (300 MHz, CDCl$_3$): δ=0.90 (3H), 1.23 (3H), 1.43 (3H), 1.63 (3H), 2.23 (1H), 2.98 (3H), 3.22 (1H), 3.69 (1H), 3.83 (3H), 4.58 (1H), 5.99 (1H), 6.58 (1H), 6.88 (1H), 6.99 (1H), 7.39 (1H), 9.39 (1H).

1-(7,8-Difluoro-2-methylquinazolin-5-ylamino)-6-isopropyl-5-methoxy-4,4-dimethyl-2-(trifluoromethyl)-1,2,3,4-tetrahydronaphthalen-2-ol 208.6 mg (0.409 mmol) of the imine that is described in the section above is cyclized with 1.23 ml of titanium(IV) chloride in dichloromethane. According to the process that is described in Example 162, 198 mg (95.9%) of the desired compound is isolated.

$^1$H-NMR (300 MHz, CDCl$_3$): δ=1.10-1.30 (6H), 1.63 (3H), 1.76 (3H), 2.09-2.25 (2H), 2.91 (3H), 3.32 (1H), 3.80 (3H), 4.94 (1H), 5.40 (1H), 5.82 (1H), .6.58 (1H), 7.03-7.19 (2H), 9.27 (1H).

(−)-(7,8-Difluoro-2-methylquinazolin-5-ylamino)-6-isopropyl-5-methoxy-4,4-dimethyl-2-(trifluoromethyl)-1,2,3,4-tetrahydronaphthalen-2-ol

(+)-1-(7,8-Difluoro-2-methylquinazolin-5-ylamino)-6-isopropyl-5-methoxy-4,4-dimethyl-2-(trifluoromethyl)-1,2,3,4-tetrahydronaphthalen-2-ol 80 mg of the racemic compound is separated in the ether stage on a chiral column to obtain the two enantiomers. 38.1 mg of (−)-enantiomer and 35.5 mg of (+)-enantiomer are obtained.

(−)-Enantiomer: [α]$_D$=−38.5° (c=1, CH$_3$OH); (+)-Enantiomer: [α]D+$^{37\prime}$ (c=1, CH$_3$OH)

5-(7,8-Difluoro-2-methylquinazolin-5-ylamino)-2-isopropyl-8,8-dimethyl-6-(trifluoromethyl-5,6,7,8-tetrahydronaphthalene-1,6-diol 100 mg (0.196 mmol) of 1-(7,8-difluoro-2-methylquinazolin-5-ylamino)-6-isopropyl-5-methoxy-4,4-dimethyl-2-(trifluoromethyl)-1,2,3,4-tetrahydronaphthalen-2-ol is treated with $BBr_3$ in dichloromethane as already described several times. After working-up and chromatography, 33 mg (33.9%) of the desired phenol is obtained.

$^1$H-NMR (300 MHz, $CD_3OD$): δ=1.05-1.30 (6H), 1.63 (3H), 1.74 (3H), 2.12 (2H), 2.83 (3H), 3.26 (1H), 5.38 (1H), 6.73-6.90 (2H), 7.03 (1H), 9.59 (1H).

(−)-5-(7,8-Difluoro-2-methylquinazolin-5-ylamino)-2-isopropyl-8,8-dimethyl-6-(trifluoromethyl)-5,6,7,8-tetrahydronaphthalene-1,6-diol

(+)-5-(7,8-Difluoro-2-methylquinazolin-5-ylamino)-2-isopropyl-8,8-dimethyl-6-(trifluoromethyl-5,6,7,8-tetrahydronaphthalene-1,6-diol The above-described enantiomer-pure ethers are converted into the enantiomer-pure phenols as described for the racemate. 6.6 mg (22.9%) of the phenol is obtained from 29.7 mg of ether ((−)-enantiomer). 10.7 mg (40.6%) of the phenol is isolated from 27.1 mg of ether ((+)-enantiomer).

Example 166

5-(8-Fluoro-2-methylquinazolin-5-ylamino)-2-isopropyl-8,8-dimethyl-6-(trifluoromethyl)-5,6,7,8-tetrahydronaphthalene-1,6-diol

1,1,1-Trifluoro-2-[(8-fluoro-2-methylquinazolin-5-ylimino)-methyl-]-4-(3-isopropyl-2-methoxy-phenyl)-4-methyl-pentan-2-ol 150 mg (0.451 mmol) of the aldehyde that is described in Example 162 is reacted with 79.9 mg (0.451 mmol) of 8-fluoro-2-methylquinazolin-5-ylamine in xylene with the aid of titanium(IV) isopropylate to form imine. After conventional working-up, 176 mg (79.3%) of the desired compound is obtained.

$^1$H-NMR (300 MHz, $CDCl_3$): δ=0.82 (3H), 1.20 (3H), 1.45 (3H), 1.62 (3H), 2.25 (1H), 3.00 (3H), 3.20 (1H), 3.63 (1H), 3.83 (3H), 4.69 (1H), 6.20 (1H), 6.47 (1H), 6.70 (1H), 6.98 (1H), 7.28-7.40 (2H), 9.48 (1H).

1-(8-Fluoro-2-methylquinazolin-5-ylamino)-6-isopropyl-5-methoxy-4,4-dimethyl-2-(trifluoromethyl)-1,2,3,4-tetrahydronaphthalen-2-ol 176 mg (0.358 mmol) of the imine that is described in the section above is cyclized with 1.1 ml of titanium(IV) chloride in dichloromethane. According to the working-up and chromatography described in Example 162, 147.3 mg (83.6%) of the desired compound is isolated.

$^1$H-NMR (300 MHz, $CDCl_3$): δ=1.10-1.35 (6H), 1.60 (3H), 1.75 (3H), 2.05-2.25 (2H), 2.93 (3H), 3.33 (1H), 3.80 (3H), 4.88 (1H), 5.02 (1H), 5.52 (1H), 6.70 (1H), 7.00-7.18 (2H), 7.49 (1H), 9.35 (1H).

5-(8-Fluoro-2-methylquinazolin-5-ylamino)-2-isopropyl-8,8-dimethyl-6-(trifluoromethyl)-5,6,7,8-tetrahydronaphthalene-1,6-diol 50 mg (0.102 mmol) of 1-(8-fluoro-2-methylquinazolin-5-ylamino)-6-isopropyl-5-methoxy-4,4-dimethyl-2-(trifluoromethyl-1,2,3,4-tetrahydronaphthalen-2-ol is treated with $BBr_3$ in dichloromethane as already described several times. After working-up and chromatography, 13.7 mg (28.2%) of the desired phenol is obtained.

$^1$H-NMR (300 MHz, $CD_3OD$): δ=1.05-1.30 (6H), 1.65 (3H), 1.76 (3H), 2.00-2.20 (2H), 2.88 (3H), 3.27 (1H), 5.25 (1H), 6.77-6.94 (2H), 7.00 (1H), 7.59 (1H), 9.68 (1H).

Example 167

4-(2,5-Dihydroxy-6-isopropyl-,4-dimethyl-2-(trifluoromethyl)-1,2,3,4-tetrahydronaphthalen-1-ylamino-1 3-dihydro-indol-2-one

4-[2-Hydroxy-4-(3-isopropyl-2-methoxyphenyl)-4-methyl-2-(trifluoromethyl)-pentylidenamino]-1,3-dihydro-indol-2-one 250 mg (0.903 mmol) of the 2-hydroxy-4-(3-isopropyl-2-methoxyphenyl)-4-methyl-2-(trifluoromethyl)-pentanal that is described in Example 162 is reacted with 4-amino-1,3-dihydro-indol-2-one as described in the example above and worked up. After chromatography, 334.9 mg (92.2%) of the desired imine is isolated.

$^1$H-NMR (300 MHz, $CDCl_3$): δ=0.99 (3H), 1.25 (3H), 1.46 (3H), 1.54 (3H), 2.20 (1H), 3.27 (1H), 3.42 (2H), 3.49 (1H), 3.84 (3H), 4.79 (1H), 5.90 (1H), 6.68-6.82 (2H), 6.90-7.09 (3H), 8.28 (1H).

4-(2-Hydroxy-6-isopropyl-5-methoxy-4,4-dimethyl-2-(trifluoromethyl-1,2,3,4-tetrahydronaphthalen-1-ylamino)-1,3-dihydro-indol-2-one 230 mg (0.497 mmol) of the described imine is cyclized with titanium(IV) chloride in dichloromethane as described in Example 162. After working-up and chromatography, 208.3 mg (90.5%) of the desired cyclized compound is obtained.

$^1$H-NMR (300 MHz, $CD_3OD$): δ=1.10-1.30 (6H), 1.51 (3H), 1.66 (3H), 1.96-2.16 (2H), 3.38 (3H, are below the methanol signal), 3.79 (3H), 5.03 (1H), 6.33 (1H), 6.49 (1H), 7.00-7.20 (3H).

4-(2,5-Dihydroxy-6-isopropyl-4,4-dimethyl-2-(trifluoromethyl)-1,2,3,4-tetrahydronaphthalen-1-ylamino)-1,3-dihydro-indol-2-one 50 mg (0.108 mmol) of the described ether is treated with $BBr_3$ solution in dichloromethane. After the above-described working-up and chromatography, 35.6 mg (73.4%) of the desired compound is obtained.

$^1$H-NMR (300 MHz, $CD_3OD$): δ=1.10-1.30 (6H), 1.61 (3H), 1.70 (3H), 1.95-2.18 (2H), 3.27 (1H), 3.38 (2H, lie below the methanol signal), 5.01 (1H), 6.33 (1H), 6.49 (1H), 6.89 (1H), 6.95-7.15 (2H).

The following compounds are synthesized analogously from the corresponding aldehydes and amines.

Example 168 cis-6-Chloro-1-[(7,8-difluoro-2-methylquinazolin-5-yl)amino]-4,4-dimethyl-5-methoxy-2-(trifluoromethyl)-1,2,3,4-tetrahydronaphthalen-2-ol $^1$H-NMR (300 MHz, CDCl$_3$): δ=1.58 (s, 3H), 1.72 (s, 3H), 2.14 (d, 1H), 2.22 (d, 1H), 2.92 (s, 3H), 3.97 (s, 3H), 4.91 (d, 1H), 5.83 (d, 1H), 6.55 (dd, 1H), 7.03 (d, 1H), 7.23 (d, 1H), 9.24 (s, 1H).

Example 169 cis-1-[(8-Fluoro-2-methylquinazolin-5-yl)amino]-7-methoxy-2-(trifluoromethyl)-1,2,3,4-tetrahydronaphthalen-2-ol $^1$H-NMR (300 MHz, CDCl$_3$): δ=2.24-2.34 (m, 2H), 2.86 (ddd, 1H), 2.91 (s, 3H), 3.12 (ddd, 1H), 3.63 (s, 3H), 5.00 (d, 1H), 5.47 (d, 1H), 6.75 (dd, 1H), 6.79 (d, 1H), 6.84 (s, 1H), 7.11 (d, 1H), 7.49 (dd, 1H), 9.35 (s, 1H).

Example 170 cis-6-Chloro-1-[(7,8-difluoro-2-methylquinazolin-5-yl)amino]-4,4-dimethyl-2-(trifluoromethyl)-1,2,3,4-tetrahydronaphthalene-2,5-diol $^1$H-NMR (300 MHz, CD$_3$OD): δ=1.60 (s, 3H), 1.72 (s, 3H), 2.16 (s, 2H), 2.84 (s, 3H), 5.30 (s, 1H), 6.84 (d, 1H), 6.86 (dd, 1H), 7.17 (d, 1H), 9.60 (s, 1H).

Example 171 cis-1-[(7,8-Difluoro-2-methylquinazolin-5-yl)amino]-6-fluoro-4,4-dimethyl-2-(trifluoromethyl)-1,2,3,4-tetrahydronaphthalene-2,5-diol $^1$H-NMR (300 MHz, CD$_3$OD): δ=1.61 (s, 3H), 1.72 (s, 3H), 2.14 (s, 2H), 2.84 (s, 3H), 3.98 (s, 3H), 5.27 (s, 1H), 6.76-6.94 (m, 3H), 9.59 (s, 1H).

Example 172 cis-1-[(8-Fluoro-2-methylquinazolin-5-yl)amino]-2-(trifluoromethyl)-1,2,3,4-tetrahydronaphthalene-2,7-diol $^1$H-NMR (300 MHz, CD$_3$OD): δ=2.16-2.35 (m, 2H), 2.81 (ddd, 1H), 2.85 (s, 3H), 3.08 (ddd, 1H), 5.24 (s, 1H), 6.67 (dd, 1H), 6.78 (d, 1H), 6.89 (dd, 1H), 7.02 (d, 1H), 7.59 (dd, 1H), 9.67 (s, 1H).

Example 173

2-Hydroxy-3-(1-phenylcyclohexyl)-2-(trifluoromethyl)propanal 12.6 g (45.9 mmol) of ethyl-2-oxo-3-(1-phenylcyclohexyl)-propionate (WO9854159) and 19.9 ml (138 mmol) of (trifluoromethyl)-trimethylsilane in 215 ml of THF are cooled to −70° C. and mixed with 8.6 ml of a 1 molar tetrabutylammonium fluoride solution in THF. The reaction mixture is allowed to heat over 18 hours to room temperature and then poured into saturated sodium chloride solution. It is extracted several times with ethyl acetate, washed with saturated sodium chloride solution, dried with sodium sulfate and concentrated by evaporation in a vacuum. After chromatographic purification on silica gel (hexane/ethyl acetate 20%), 13.1 g of ethyl-2-hydroxy-3-(1-phenylcyclohexyl)-2-(trifluoromethyl)-propionate is obtained as a yellow oil. A solution of 3.33 g (87.7 mmol) of lithium aluminum hydride in 173 ml of THF is added in drops to 13.1 g (38.1 mmol) of ester in 174 ml of THF at 0° C., and it is stirred for 16 hours at room temperature. 20 ml of saturated ammonium chloride solution is carefully added to the batch at 0° C., and it is stirred vigorously for 15 more minutes. It is extracted several times with ethyl acetate, washed with saturated sodium chloride solution, dried with sodium sulfate and concentrated by evaporation in a vacuum. After chromatographic purification on silica gel (hexane/ethyl acetate 0%-33%), 6.1 g of 3-(1-phenylcyclohexyl)-2-(trifluoromethyl)-propane-1,3-diol is obtained. 15.7 ml (113 mmol) of triethylamine is added to 6.1 g (20.2 mmol) of diol in 245 ml of dichloromethane and 79 ml of DMSO, and 13.8 g (87 mmol) of pyridine SO$_3$ complex is added in portions over 10 minutes. It is stirred for 3 hours, and saturated ammonium chloride solution is added. The mixture is stirred for another 15 minutes, the phases are separated, and it is extracted with dichloromethane. It is washed with water and dried on sodium sulfate. The solvent is removed in a vacuum, and after chromatographic purification on silica gel (hexane/ethyl acetate, 0-33%), the desired product is obtained quantitatively.

$^1$H-NMR (CDCl$_3$): δ=1.17-1.78 (m, 9H), 1.98-2.05 (m, 1H), 2.41 (d, 1H), 3.46 (d, 1H), 3.66 (s, 1H), 7.18 (d, 2H), 7.24 (t, 2H), 7.31 (d, 1H), 8.55 (s, 1H).

cis-4'-[(8-Fluoro-2-methylquinazolin-5-yl)amino]-3',4'-dihydro-3'-(trifluoromethyl)-spiro[cyclohexane-[1,1'(2'H)-naphthalen]-3'-ol $^1$H-NMR (300 MHz, CDCl$_3$): δ=1.25-1.85 (m, 9H), 1.97 (d, 1H), 2.11 (d, 1H), 2.68 (d, 1H), 2.91 (s, 3H), 5.08 (d, 1H), 5.38 (d, 1H), 6.69 (dd, 1H), 7.18 (t, 1H), 7.34 (d, 1H), 7.35 (t, 1H), 7.47 (dd, 1H), 7.56 (d, 1H), 9.36 (s, 1H).

Example 174 dis-4'-[(7,8-Difluoro-2-methylquinazolin-5-yl)amino]-3',4'-dihydro-3'-(trifluoromethyl)-spiro[cyclohexane-[1,1'(2'H)-naphthalen]-3'-ol $^1$H-NMR (300 MHz, CDCl$_3$): δ=1.25-1.90 (m, 9H), 1.93 (d, 1H), 2.02 (d, 1H), 2.64 (d, 1H), 2.89 (s, 3H), 4.99 (d, 1H), 5.66 (d, 1H), 6.54 (dd, 1H), 7.18 (t, 1H), 7.29 (d, 1H), 7.36 (t, 1H), 7.54 (d, 1H), 9.25 (s, 1H).

Example 175 cis-1-[(7,8-Difluoro-2-methylquinazolin-5-yl)amino]-4,4-dimethyl-2-(trifluoromethyl)-1,2,3,4-tetrahydronaphthalene-2,5-diol $^1$H-NMR (300 MHz, CD$_3$OD): δ=1.58 (s, 3H), 1.70 (s, 3H), 2.13 (s, 2H), 2.84 (s, 3H), 5.28 (s, 1H), 6.71-6.87 (m, 3H), 6.99 (t, 1H), 9.59 (s, 2H).

Example 176

Trans-1-[(7,8-Difluoro-2-methylquinazolin-5yl)amino]-6-fluoro-4,4-dimethyl-2-(trifluoromethyl)-1,2,3,4-tetrahydronaphthalene-2,5-diol $^1$H-NMR (300 MHz, CDCl$_3$): δ=1.40 (s, 3H), 1.54 (s, 3H), 2.05 (d, 1H), 2.19 (d, 1H), 2.76 (s, 3H), 3.57 (br, 1H), 4.62 (d, 1H), 5.27 (d, 1H), 6.54 (br, 1H), 6.90-6.97 (m, 2H), 7.07 (dd, 1H), 9.10 (s, 1H).

Example 177 cis-5-{3',4'-Dihydro-3'-hydroxy-3'-(trifluoromethyl)-spiro]cyclohexane-1,1'(2'H)-naphthalen-4'-yl]amino}-quinolin-2(1H)-one $^1$H-NMR (300 MHz, CD$_3$OD): δ=0.91 (m, 1H), 1.12 (m, 3H), 1.89 (d, 1H), 2.44 (d, 1H), 5.29 (s, 1H), 6.51 (d, 1H), 6.67 (d, 1H), 6.71 (d, 1H), 6.79 (d, 1H), 7.09 (t, 1H), 7.21 (t, 1H), 7.24 (d, 1H), 7.39 (t, 1H), 8.24 (d, 1H).

Example 178 cis-4'-[(8-Fluoro-2-methylquinazolin-5-yl)amino]-3,4'-dihydro-3'-(trifluoromethyl)-spiro[cyclopropane-1,1'(2'H)-naphthalen]-3'-ol $^1$H-NMR (300 MHz, CD$_3$OD): δ=0.92-0.98 (m, 1H), 1.13-1.19 (m, 3H), 1.98 (d, 1H), 2.40 (d, 1H), 2.85 (s, 3H), 5.36 (s, 1H), 6.81 (d, 1H), 6.91 (dd, 1H), 7.10 (t, 1H), 7.23 (t, 1H), 7.28 (d, 1H), 7.59 (dd, 1H), 9.68 (s, 1H).

Example 179 cis-6-Chloro-1-[(8-fluoro-2-methyloquinazolin-5-yl)amino]-4,4-dimethyl-2-(pentafluoroethyl)-1,2,3,4-tetrahydronaphthalene-2,5-diol 4-(3-Chloro-2-methoxyphenyl-2-hydroxy-4-methyl-2-(trifluoroethyl)-pentanal 1.0 g (3.35 mmol) of ethyl-4-(3-chloro-2-methoxyphenyl)-4-methyl-2-oxovalerate and 0.96 (5.0 mmol) of (pentafluoroethyl)-trimethylsilane in 7 ml of THF are mixed with 62 mg (0.67 mmol) of tetramethylammonium fluoride at −40° C. It is stirred for 2 hours at −25° C., then 1 ml of 1N hydrochloric acid is added to the reaction mixture, and after 10 minutes, it is poured into water. It is extracted several times with ethyl acetate, washed with saturated sodium chloride solution, dried with sodium sulfate and concentrated by evaporation in a vacuum. 1.44 g of ethyl-4-(3-chloro-2-methoxyphenyl)-2-hydroxy-4-methyl-2-(pentafluoroethyl)-valerate, which is mixed in 14.5 ml of diethyl ether at 0° C. with 0.22 g (5.9 mmol) of lithium aluminum hydride, is obtained, and it is stirred for 2 hours at room temperature. The batch is poured into ice water, and it is vigorously stirred for 15 more minutes. It is filtered through Celite, extracted several times with diethyl ether, washed with saturated sodium chloride solution, dried with sodium sulfate and concentrated by evaporation in a vacuum. After chromatographic purification on silica gel (hexane/ethyl acetate 0%-20%), 0.77 g of 4-(3-chloro-2-methoxyphenyl)-2-(pentafluoroethyl)-4-methyl-propane-1,2-diol is obtained. 0.84 ml (6.1 mmol) of triethylamine and 388 mg (2.44 mmol) of pyridine SO$_3$ complex are added to 0.46 g (1.22 mmol) of diol in 9.5 ml of dichloromethane and 2.5 ml of DMSO. It is stirred for 2 hours, and then another 388 mg (2.44 mmol) of pyridine SO$_3$ complex is dosed in. After 1 hour of stirring, saturated ammonium chloride solution is added. The mixture is stirred for another 15 minutes, the phases are separated, and it is extracted with diethyl ether. It is washed with saturated ammonium chloride solution and dried on sodium sulfate. The solvent is removed in a vacuum, and after chromatographic purification on silica gel (hexane/ethyl acetate, 30%), 357 g of product is obtained.

$^1$H-NMR (CDCl$_3$): δ=1.43 (s, 3H), 1.48 (s, 3H), 2.34 (d, 1H), 3.29 (d, 1H), 3.58 (s, 1H), 4.01 (s, 3H), 6.95 (t, 1H), 7.05 (dd, 1H), 7.30 (dd, 1H), 9.10 (s, 1H).

cis-6-Chloro-1-[(8-fluoro-2-methylquinazolin-5-yl)amino]-4,4-dimethyl-2-(pentafluoroethyl)-1,2,3,4-tetrahydronaphthalene-2,5-diol $^1$H-NMR (300 MHz, CD$_3$OD): δ=1.61 (s, 3H), 1.74 (s, 3H), 2.14 (d, 1H), 2.20 (d, 1H), 2.86 (s, 3H), 5.34 (s, 1H), 6.84 (d, 1H), 6.86 (dd, 1H), 7.12 (d, 1H), 7.57 (dd, 1H), 9.65 (s, 1H).

Example 180

Cis-6-Chloro-1-[(7-fluoro-2-methylquinazolin-5-yl)amino]-4,4-dimethyl-2-(pentafluoroethyl)-1,2,3,4-tetrahydronaphthalene-2,5-diol $^1$H-NMR (300 MHz, CDCl$_3$): δ=1.58 (s, 3H), 1.72 (s, 3H), 2.17 (d, 1H), 2.26 (d, 1H), 2.84 (s, 3H), 3.95 (s, 3H), 5.05 (d, 1H), 6.07 (d, 1H), 6.51 (dd, 1H), 6.91 (dd, 1H), 7.04 (d, 1H), 7.18 (d, 1H), 9.17 (s, 1H).

Example 181

Trans-6-Chloro-1-[(7-fluoro-2-methylquinazolin-5-yl)amino]-4,4-dimethyl-2-(pentafluoroethyl)-1,2,3,4-tetrahydronaphthalene-2,5-diol $^1$H-NMR (300 MHz, CD$_3$OD): δ=1.45 (s, 3H), 1.61 (s, 3H), 2.29 (d, 1H), 2.37 (d, 1H), 2.74 (s, 3H), 3.65 (s, 3H), 5.58 (s, 1H), 6.83 (dd, 1H), 6.98 (dd, 1H), 7.30 (dd, 1H), 7.42 (d, 1H), 9.52 (s, 1H).

Example 182 cis-5-{[6-Chloro-2-hydroxy-5-methoxy-4,4-dimethyl-2-(pentafluoroethyl)-1,2,3,4-tetrahydronaphthalen-1-yl]amino}-quinolin-2(1H)-one $^1$H-NMR (300 MHz, CDCl$_3$): δ=1.55 (s, 3H), 1.72 (s, 3H), 2.07 (d, 1H), 2.20 (d, 1H), 3.96 (2, 3H), 5.12 (d, 1H), 5.46 (br, 1H), 5.81 (d, 1H), 6.44-6.53 (m, 3H), 6.95 (d, 1H), 7.06 (d, 1H), 7.32 (t, 1H), 8.28 (d, 1H), 9.92 (s, 1H).

Example 183 cis-5-{[2,5-Dihydroxy-4,4-dimethyl-2-(pentafluoroethyl)-1,2,3,4-tetrahydronaphthalen-1-yl]amino}-quinolin-2(1H)-one $^1$H-NMR (300 MHz, CDCl$_3$): δ=1.58 (s, 3H), 1.76 (s, 3H), 2.08 (d, 1H), 2.24 (d, 1H), 2.63 (s, 1H), 5.11 (d, 1H), 5.54 (s, 1H), 5.85 (d, 1H), 5.97 (s, 1H), 6.42 (d, 1H), 6.49 (d, 1H), 6.49 (d, 1H), 6.52 (d, 1H), 7.00 (dd, 1H), 7.31 (t, 1H), 8.31 (d, 1H), 9.77 (s, 1H).

Example 184 cis-7'-Fluoro-4'-[(8-fluoro-2-methylquinazolin-5-yl)-amino]-3',4'-dihydro-8'-methoxy-3'-(trifluoromethyl)-spiro[cyclohexane-1,1'(2'H)-naphthalen]-3'-ol 3-[1-(3-Fluoro-2-methoxyphenyl)-cyclohexyl]-2-hydroxy-2-(trifluoromethyl)propanal 385 ml of a 0.5 molar (182 mmol) solution of bis-(trimethylsilyl)-potassium amide in toluene is added in drops at 0° C. to 26.5 g (184 mmol) of 2,6-difluoroanisole and 24 ml (198 mmol) of cyclohexylcyanide in 500 ml of toluene. It is stirred for 18 hours at room temperature and mixed with water while being cooled with ice, and the solution is set at a pH of 4 with 4N hydrochloric acid.

The organic phase is separated, and the aqueous phase is extracted several times with diethyl ether. It is washed with brine, dried with sodium sulfate and concentrated by evaporation in a vacuum. After chromatographic purification on silica gel (hexane/ethyl acetate 5%-10%), 28.5 g of 1-(3-fluoro-2-methyoxyphenyl)-cyclohexylnitrile is obtained. 27.5 g (118 mmol) of nitrile is slowly mixed in 430 ml of toluene at −78° C. with 147 ml (176 mmol) of diisobutyl aluminum hydride solution (20% in toluene), and after 3 hours at −78° C., 35 ml of isopropanol was added in drops. It is allowed to heat to −5° C., and 600 ml of a 10% aqueous tartaric acid solution is added. After dilution with ether, it is vigorously stirred, the organic phase is separated, and the aqueous phase is extracted several times with ethyl acetate. It is washed with brine, dried with sodium sulfate and concentrated by evaporation in a vacuum. 27.5 g of aldehyde is obtained as a yellow oil. A solution of 5.7 g (21.2 mmol) of 2-diethylphosphono-2-ethoxyacetic acid ethyl ester in 25 ml of tetrahydrofuran is mixed with 13.6 ml (27.2 mmol) of a 2 M solution of lithium diisopropylamide in tetrahydrofuran-heptane-toluene within 15 minutes while being cooled with ice, and it is stirred for 20 minutes at 0° C. Within 30 minutes, a solution of 5 g (21.2 mmol) of 1-(3-fluoro-2-methoxyphenyl)-cyclohexylformanal in 5 ml of tetrahydrofuran is added in drops at 0° C. After 16 hours at room temperature, ice water is added, and it is extracted several times with ether. It is washed with saturated ammonium chloride solution, dried on sodium sulfate and concentrated by evaporation. The crude product is saponified with 6 g of sodium hydroxide in 100 ml of ethanol and 50 ml of water over 4 days at room temperature. 1.7 g of acid, which is stirred with 35 ml of 2N sulfuric acid and 7 ml of acetic acid at 90° C. over 30 hours, is obtained. After cooling, it is made basic with potassium carbonate, washed with ether and acidified with hydrochloric acid. After extraction with ethyl acetate, washing with saturated sodium chloride solution and removal of the solvent, 1.09 g of the crude keto acid is obtained. 1.09 g (3.7 mmol) of 3-{1-(3-fluoro-2-methoxyphenyl)-cyclopropyl]-2-oxopropionic acid and 0.45 ml of sulfuric acid (96%) are refluxed in 40 ml of ethanol for 2 hours. The batch is concentrated by evaporation in a vacuum, the residue is added in ice water, and it is made basic with saturated sodium bicarbonate solution. It is extracted several times with ethyl acetate, washed with saturated sodium chloride solution, dried (sodium sulfate) and concentrated by evaporation in a vacuum. After chromatographic purification on silica gel (hexane/ethyl acetate 20%), 1.05 g of ethyl-3-[1-(3-fluoro-2-methoxyphenyl)-cyclopropyl]-2-oxopropionate is obtained.

1.05 g (3.3 mmol) of ethyl-3-[1-(3-fluoro-2-methoxyphenyl)-cyclohexyl]-2-oxopropionate and 0.74 ml (5 mmol) of (trifluoromethyl)-trimethylsilane in 7 ml of THF are mixed with 62 mg of tetramethylammonium fluoride at −40° C. It is stirred for 2 hours at −25° C., and then another 0.35 ml (2.4 mmol) of (trifluoromethyl)-trimethylsilane and 62 mg of tetramethylammonium fluoride are added. After another 2 hours, 1 ml of 2N hydrochloric acid is added, and the reaction mixture is added to water. It is extracted several times with ethyl acetate, washed with saturated sodium chloride solution, dried with sodium sulfate, and concentrated by evaporation in a vacuum. After chromatographic purification on silica gel (hexane/ethyl acetate 10%-40%), 800 mg of ethyl-3-[1-(3-fluoro-2-methoxyphenyl)-cyclopropyl]-2-hydroxy-2-(trifluoromethyl)-propionate is obtained as a yellow oil. This oil is mixed in 40 ml of diethyl ether at 0° C. with 150 g (4 mmol) of lithium aluminum hydride, and it is stirred for 2.5 more hours at room temperature. 20 ml of saturated ammonium chloride solution is carefully added at 0° C. to the batch, and it is vigorously stirred for 15 more minutes. It is extracted several times with diethyl ether, washed with saturated sodium chloride solution, dried with sodium sulfate and concentrated by evaporation in a vacuum. After chromatographic purification on silica gel (hexane/ethyl acetate 10%-1 5%), 630 g of 3-[1-(3-fluoro-2-methoxyphenyl)-cyclopropyl]-2-(trifluoromethyl)-propane-1,2-diol is obtained.

$^1$H-NMR (CDCl$_3$): δ=1.44-1.87 (m, 10H), 2.19-2.38 (m, 4H), 3.15-3.42 (br, 2H), 3.96 (s, 3H), 6.9 (ddd, 1H), 7.01 (d, 1H), 7.16 (ddd, 1H).

1.6 ml (11 mmol) of triethylamine and, in portions over 10 minutes, 1.4 g (70 mmol) of pyridine SO$_3$ complex are added to 700 mg (2 mmol) of diol in 20 ml of dichloromethane and 7.8 ml of DMSO. It is stirred for 3 hours, and saturated ammonium chloride solution is added. The mixture is stirred for another 15 minutes, the phases are separated, and it is extracted with dichloromethane. It is washed with water and dried on sodium sulfate. The solvent is removed in a vacuum, and the desired aldehyde is obtained quantitatively.

cis-7'-Fluoro-4'-[(8-fluoro-2-methylquinazolin-5-yl)-amino]-3',4'-dihydro-8'-methoxy-3'-(trifluoromethyl)-spiro]cyclohexane-1,1'(2'H)-naphthalen]-3'-ol $^1$H-NMR (300 MHz, CDCl$_3$): δ=1.25-1.85 (m, 8H), 2.00 (d, 1H), 2.44 (ddd, 1H), 2.64 (ddd, 1H), 2.91 (s, 3H), 2.92 (d, 1H), 4.00 (s, 3H), 4.96 (d, 1H), 5.41 (d, 1H), 6.66 (dd, 1H), 6.93 (dd, 1H), 7.04 (dd, 1H), 7.47 (dd, 1H), 9.34 (s, 1H).

Example 185

Cis-7'-Fluoro-4'-[(8-fluoro-2-methylquinazolin-5-yl) amino]-3',4'-dihydro-3'-(trifluoromethyl)-spiro[cyclohexane-1,1'(2'H)-naphthalene]-3',8'-diol $^1$H-NMR (300 MHz, CD$_3$OD): δ=1.22-1.85 (m, 8H), 2.03 (d, 1H), 2.82 (ddd, 1H), 2.85 (s, 3H), 2.91 (d, 1H), 3.05 (ddd, 1H), 5.22 (s, 1H), 6.80-6.95 (m, 3H), 7.56 (dd, 1H), 9.65 (s, 1H).

Example 186 cis-7'-Fluoro-4'-[(7-fluoro-2-methylquinazolin-5-yl) amino]-3',4'-dihydro-8'-methoxy-3'-(trifluoromethyl)-spiro[cyclohexane-1,1° (2' H)-naphthalen]-3'-ol $^1$H-NMR (300 MHz, CDCl$_3$): δ=1.25-1.90 (m, 10H), 2.17 (d, 1H), 2.34 (d, 1H), 2.80 (s, 3H), 3.56 (s, 3H), 4.59 (d, 1H), 5.33 (d, 1H), 6.91 (dd, 1H), 7.00 (dd, 1H), 7.10 (dd, 1H), 7.17 (dd, 1H), 9.03 (s, 1H).

Example 187 cis-5-(7'-Fluoro-3',4'-dihydro-3'-hydroxy-8'-methoxy-3'-(trifluoromethyl)-spiro[cyclohexane-1,1'(2'H)-naphthalen-4'-yl]amino}-quinolin-2(1H)-one $^1$H-NMR (300 MHz, CDCl$_3$): δ=1.25-1.90 (m, 8H), 2.09 (d, 1H), 2.41 (ddd, 1H), 2.60 (ddd, 1H), 2.90 (d, 1H), 3.99 (s, 3H), 4.85 (s, 1H), 5.00 (d, 1H), 5.67 (d, 1H), 6.48-6.55 (m, 3H), 6.83 (dd, 1H), 6.96 (dd, 1H), 7.31 (t, 1H), 8.22 (d, 1H), 9.79 (s, 1H).

Example 188 cis-6-Chloro-1-[(7-fluoro-2-methylquinazolin-5-yl)amino]-4,4,-dimethyl-2-(pentafluoroethyl)-1,2,3,4-tetrahydronaphthalene-2,5-diol $^1$H-NMR (300 MHz, CD$_3$OD): δ=1.61 (s, 3H), 1.74 (s, 3H), 2.18 (s, 2H), 2.79 (s, 3H), 5.42 (s, 1H), 6.76-6.82 (m, 3H), 7.15 (d, 1H), 9.54 (s, 1H).

Example 189 cis-6-Chloro-1-[(2-methylquinazolin-5yl)amino]-4,4-dimethyl-2-(pentafluoroethyl)-1,2,3,4-tetrahydronaphthalene-2,5-diol $^1$H-NMR (300 MHz, CD$_3$OD): δ=1.61 (s, 3H), 1.74 (s, 3H), 2.18 (s, 2H), 2.82 (s, 3H), 5.40 (s, 1H), 6.84 (d, 1H), 6.95 (d, 1H), 7.10 (d, 1H), 7.20 (d, 1H), 7.79 (t, 1H), 9.62 (s, 1H).

Example 190 cis-5-{7'-Chloro-3,4'-dihydro-3',8'-dihydroxy-3'-(trifluoromethyl)-spiro[cyclohexane-1,1'(2'H)-naphthalen-4'-yl]-amino}-quinolin-2(1H)-one $^1$H-NMR (300 MHz, CD$_3$OD): δ=1.25-1.90 (m, 8H), 2.02 (d, 1H), 2.80 (ddd, 1H), 2.91 (d, 1H), 3.05 (ddd, 1H), 5.12 (d, 1H), 5.51 (d, 1H), 6.59 (d, 1H), 6.69 (d, 1H), 6.81 (dd, 1H), 6.986 (dd, 1H), 7.37 (t, 1H), 8.23 (d, 1H).

Example 191 cis-6-Fluoro-1-[(8-fluoro-2-methylquinazolin-5-yl)amino]-5-methoxy-4,4-dimethyl-2-(pentafluoroethyl)-1,2,3,4-tetrahydronaphthalen-2-ol 4-(3-Fluoro-2-methoxyphenyl)-2-hydroxy-4-methyl-2-(pentafluoroethyl)pentanal 1.0 g (3.54 mmol) of ethyl-4-(3-fluoro-2-methoxyphenyl)-2-oxo-4-methyl-valerate and 0.98 g (5.1 mmol) of (pentafluoroethyl)-trimethylsilane in 7 ml of THF are mixed with 65 mg (0.7 mmol) of tetramethylammonium fluoride at −40° C. The reaction mixture is heated to −25° C. and stirred at this temperature. After 4.5 hours, 1 ml of 2N hydrochloric acid is added, and the reaction mixture is added to water. It is extracted several times with ethyl acetate, washed with saturated sodium chloride solution, dried on sodium sulfate, and concentrated by evaporation in a vacuum. 1.65 g of ethyl-4-(3-fluoro-2-methoxyphenyl)-2-hydroxy-4-methyl-2-(pentafluoroethyl)valerate is obtained as a crude product. The ester is mixed in 80 ml of diethyl ether at 0° C. with 300 mg (8 mmol) of lithium aluminum hydride and stirred for 3.5 more hours at room temperature. A little water is carefully added to the batch at 0° C., and it is stirred vigorously for 15 minutes. It is filtered through Celite, and the precipitate is rewashed thoroughly with ethyl acetate. The filtrate is dried with sodium sulfate and concentrated by evaporation in a vacuum. After chromatographic purification on silica gel (hexane/ethyl acetate 10%-15%), 800 mg of 4-(3-fluoro-2-methoxyphenyl)-4-methyl-2-(pentafluoroethyl)pentane-1,2-diol is obtained. 1.8 ml (13 mmol) of triethylamine is added to 800 mg (2.2 mmol) of diol in 25 ml of dichloromethane and 8.9 ml of DMSO, and 1.6 g (10 mmol) of pyridine SO$_3$.complex is added in portions over 10 minutes. It is stirred over 2.5 hours, and saturated ammonium chloride solution is added. The mixture is stirred for another 15 minutes, the phases are separated, and it is extracted with dichloromethane. It is washed with water and dried on sodium sulfate. The solvent is removed in a vacuum, and the desired aldehyde is obtained quantitatively.

$^1$H-NMR (CDCl$_3$): δ=1.40 (s, 3H), 1.46 (s, 3H), 2.35 (d, 1H), 3.28 (d, 1H), 3.60 (s, 1H), 4.02 (s, 3H), 6.86 (dd, 1H), 6.91 (ddd, 1H), 7.01 (ddd, 1H), 9.14 (s, 1H).

cis-6-Fluoro-1-[(8-fluoro-2-methylquinazolin-5-yl)amino]-5-methoxy-4,4-dimethyl-2-(pentafluoroethyl)-1,2,3,4-tetrahydronaphthalen-2-ol $^1$H-NMR (300 MHz, CDCl$_3$): δ=1.55 (s, 3H), 1.69 (s, 3H), 2.13 (d, 1H), 2.20 (d, 1H), 2.92 (s, 3H), 3.97 (s, 3H), 5.08 (d, 1H), 5.41 (d, 1H), 6.70 (dd, 1H), 6.90 (dd, 1H), 7.0 (dd, 1H), 7.48 (dd, 1H), 9.33 (s, 1H).

Example 192 cis-1-[(7,8-Difluoro-2-methylquinazolin-5-yl)amino]-6-fluoro-5-methoxy-4,4-dimethyl-2-(pentafluoroethyl)-1,2,3,4-tetrahydronaphthalen-2-ol $^1$H-NMR (300 MHz, CD$_3$OD): δ=1.55 (s, 3H), 1.68 (s, 3H), 2.14 (d, 1H), 2.21 (d, 1H), 2.84 (s, 3H), 3.97 (s, 3H), 5.39 (s, 1H), 6.88 (dd, 1H), 6.98 (dd, 1H), 7.03 (dd, 1H), 9.59 (s, 1H).

Example 193 cis-1-[(7,8-Difluoro-2-methylquinazolin-5-yl)amino]-4,4-dimethyl-6-fluoro-2-(pentafluoroethyl)-1,2,3,4-tetrahydronaphthalene-2,5-diol $^1$H-NMR (300 MHz, CDCl$_3$): δ=1.61 (s, 3H), 1.72 (s, 3H), 2.15 (d, 1H), 2.22 (d, 1H), 2.91 (s, 3H), 5.00 (d, 1H), 5.61 (br, 1H), 5.71 (d, 1H), 6.56 (dd, 1H), 6.83 (dd, 1H), 6.92 (dd, 1H), 9.24 (s, 1H).

Example 194 cis-5-{[6-Fluoro-2-hydroxy-5-methoxy-4,4-dimethyl-2-(pentafluoroethyl)-1,2,3,4-tetrahydronaphthalen-1-yl]amino}-quinolin-2(1H)-one $^1$H-NMR (300 MHz, CDCl$_3$): δ=1.54 (s, 3H), 1.69 (s, 3H), 2.07 (d, 1H), 2.17 (d, 1H), 3.97 (s, 3H), 4.58 (br, 1H), 5.10 (d, 1H), 5.45 (d, 1H), 6.52-6.56 (m, 3H), 6.83 (dd, 1H), 6.94 (dd, 1H), 7.34 (t, 1H), 8.12 (d, 1H), 10.11 (s, 1H).

Example 195 cis-6-Fluoro-1-[(8-fluoro-2-methylquinazolin-5-yl) amino]-4,4-dimethyl-2-(pentafluoroethyl)-1,2,3,4-tetrahydronaphthalene-2,5-diol $^1$H-NMR (300 MHz, CDCl$_3$): δ=1.61 (s, 3H), 1.72 (s, 3H), 2.15 (d, 1H), 2.23 (d, 1H), 2.92 (s, 3H), 5.08 (d, 1H), 5.38 (d, 1H), 5.64 (br, 1H), 6.70 (dd, 1H), 6.85 (dd, 1H), 6.90 (dd, 1H), 7.48 (dd, 1H), 9.33 (s, 1H).

Example 196 cis-4'-[(7,8-Difluoro-2-methylquinazolin-5-yl) amino]-7'-fluoro-3',4'-dihydro-8'-methoxy-3'-(trifluoromethyl)-spiro[cyclopropane-1,1'(2'H)-naphthalen]-3'-ol

Ethyl-3-[1-(3-fluoro-2-methoxyphenyl)-cyclopropyl]-2-oxopropionate 396 ml of a 0.5 molar (198 mmol) solution of bis-(trimethylsilyl)potassium amide in toluene is added in drops at 0° C. over 40 minutes to 26 g (180 mmol) of 2,6-difluoroanisole and 14.6 ml (198 mmol) of cyclopropylcyanide in 500 ml of toluene. It is stirred for 18 hours at room temperature and mixed with water and 1 M sulfuric acid while being cooled with ice. The organic phase is separated, and the aqueous phase is extracted several times with ethyl acetate. It is washed with brine, dried with sodium sulfate and concentrated by evaporation in a vacuum. After chromatographic purification on silica gel (hexane/ethyl acetate 10%-20%), 12.7 g of 1-(3-fluoro-2-methoxyphenyl)-cyclopropylnitrile is obtained. 12.7 g (66.1 mmol) of the nitrile is slowly mixed in toluene at −78° C. with 82.7 ml (99.2 mol) of diisobutyl aluminum hydride solution (20% in toluene), and after 3 hours at −78° C., 11.1 ml of isopropanal is added in drops. It is allowed to heat to −5° C., and 150 ml of a 10% aqueous tartaric acid solution is added. After dilution with ether, it is vigorously stirred, the organic phase is separated, and the aqueous phase is extracted several times with ethyl acetate. It is washed with brine, dried with sodium sulfate, and concentrated by evaporation in a vacuum. 11.8 g of aldehyde is obtained as a yellow oil. A solution of 16.3 g (60.7 mmol) of 2-diethylphosphono-2-ethoxyacetic acid ethyl ester in 60 ml of tetrahydrofuran is mixed within 20 minutes with 33.4 ml (66.8 mmol) of a 2 M solution of lithium diisopropylamide in tetrahydrofuran-heptane-toluene while being cooled with ice, and it is stirred for 30 minutes at 0° C. Within 30 minutes, a solution of 11.8 g (60.7 mmol) of I in 61 ml of tetrahydrofuran is added in drops at 0° C. After 20 hours at room temperature, ice water is added and extracted several times with ether and ethyl acetate. It is washed with saturated ammonium chloride solution, dried on sodium sulfate and concentrated by evaporation. The crude product is saponified with 170 ml of 2 M sodium hydroxide solution in 170 ml of ethanol over 15 hours at room temperature. 13.9 g of acid, which is stirred with 87 ml of 2N sulfuric acid at 90° C. over 16 hours, is obtained. After cooling, it is made basic with potassium carbonate, washed with ether, and acidified with hydrochloric acid. After extraction with ethyl acetate, washing with saturated sodium chloride solution and removal of the solvent, 10.2 g of the crude keto acid is obtained. 10.2 g (40.6 mmol) of 3-[1-(3-fluoro-2-methoxyphenyl)-cyclopropyl]-2-oxopropionic acid and 4.5 ml (85.3 mmol) of sulfuric acid (96%) are refluxed in 200 ml of ethanol for 1 hour. The batch is concentrated by evaporation in a vacuum, the residue is added to ice water and made basic with saturated sodium bicarbonate solution. It is extracted several times with ethyl acetate, washed with saturated sodium chloride solution, dried (sodium sulfate) and concentrated by evaporation in a vacuum. After chromatographic purification on silica gel (hexane/ethyl acetate 20%), 9.6 g of ethyl-3-[1-(3-fluoro-2-methoxyphennyl)-cyclopropyl]-2-oxopropionate is obtained.

$^1$H-NMR (CDCl$_3$): δ=0.90 (m, 4H), 1.29 (t, 3H), 3.09 (s, 2H), 3.99 (d, 3H), 4.20 (q, 2H), 6.87 (ddd, 1H), 6.95 (dd, 1H), 7.07 (d, 1H), 9.26.

3-[(3-Fluoro-2-methoxyphenyl)-cyclopropyl]-2-hydroxy-2-(trifluoromethyl)propanal 9.6 g (34.3 mmol) of ethyl-3-[1-(3-fluoro-2-methoxyphenyl)-cyclopropyl]-2-oxopropionate and 34.5 ml (233 mmol) of (trifluoromethyl)-trimethylsilane in 343 ml of DMF are mixed with 46.9 g of cesium carbonate at 0° C. It is stirred for 2 hours at 0° C. and then the reaction mixture is added to water. It is extracted several times with ethyl acetate, washed with saturated sodium chloride solution, dried with sodium sulfate and concentrated by evaporation in a vacuum. After chromatographic purification on silica gel (hexane/ethyl acetate 10%-40%), 10.4 g of ethyl-3-[1-(3-fluoro-2-methoxyphenyl)-cyclopropyl]-2-hydroxy-2-(trifluoromethyl)-propionate is obtained as a yellow oil. This oil is mixed in 297 ml of diethyl ether at 0° C. with 2.25 g (59.4 mmol) of lithium aluminum hydride, and it is stirred for 1 more hour at room temperature. 20 ml of saturated ammonium chloride solution is carefully added to the batch at 0° C., and it is stirred vigorously for 15 more minutes. It is extracted several times with diethyl ether, washed with saturated sodium chloride solution, dried with sodium sulfate and concentrated by evaporation in a vacuum. After chromatographic purification on silica gel (hexane/ethyl acetate 10%-50%), 5.6 g of 3-[1-(3-fluoro-2-methoxyphenyl)-cyclopropyl]-2-(trifluoromethyl)-propane-1,2-diol is obtained. 12. 4 ml (89 mmol) of triethylamine is added to 5.6 g (18.1 mmol) of diol in 100 ml of dichloromethane and 61 ml of DMSO, and 11 g (70 mmol) of pyridine/SO$_3$ complex is added in portions over 10 minutes. It is stirred over 3 hours, and saturated ammonium chloride solution is added. The mixture is stirred for another 15 minutes, the phases are separated, and it is extracted with dichloromethane. It is washed with water and dried on sodium sulfate. The solvent is removed in a vacuum, and after chromatographic purification on silica gel (hexane/ethyl acetate, 0-50%), 5.9 g of product is obtained.

$^1$H-NMR (CDCl$_3$): δ=0.68-0.76 (m, 2H), 0.90-1.02 (m, 2H), 2.03 (d, 1H), 2.91 (d, 1H), 3.85 (s, 1H), 4.03 (s, 3H), 6.80 (d, 1H), 6.87 (ddd, 1H), 6.98 (dd, 1H), 9.26 (s, 1H).

cis-4'-[(7,8-Difluoro-2-methylquinazolin-5-yl) amino]-7'-fluoro-3',4'-dihydro-8'-methoxy-3'-(trifluoromethyl)-spiro[cyclopropane-1,1'(2'H)-naphthalen]-3'-ol $^1$H-NMR (300 MHz, CD$_3$OD): δ=0.83 (ddd, 1H), 0.99 (ddd, 1H), 1.42 (ddd, 1H), 1.89 (ddd, 1H), 2.01 (d, 1H), 2.15 (d, 1H), 2.84 (s, 3H), 3.85 (s, 3H), 5.19 (s, 1H), 6.65 (dd, 1H), 6.96 (dd, 1H), 7.04 (dd, 1H), 9.63 (s, 1H).

Example 197 cis-7'-Fluoro-3',4'-dihydro-8'-methoxy-4'-[(2-methylquinazolin-5-yl)amino]-3'-(trifluoromethyl)-spiro[cyclopropane-1,1'(2'H)-naphthalen]-3'-ol $^1$H-NMR (300 MHz, CDCl$_3$): δ=0.82 (ddd, 1H), 1.00 (ddd, 1H), 1.54 (ddd, 1H), 1.86 (ddd, 1H), 1.91 (d, 1H), 2.32 (d, 1H), 2.84 (s, 3H), 3.87 (s, 3H), 5.08 (d, 1H), 5.78 (d, 1H), 6.67 (d, 1H), 6.88 (dd, 1H), 7.05 (dd, 1H), 7.28 (d, 1H), 7.70 (t, 1H), 9.36 (s, 1H).

Example 198 cis-7'-Fluoro-3',4'-dihydro-4'-[(2-methylquinazolin-5-yl)amino]-3'-(trifluoromethyl)-spiro[cyclopropane-1,1'(2'H)-naphthalene-3',8'-diol $^1$H-NMR (300 MHz, CD$_3$OD): δ=0.67 (ddd, 1H), 0.90 (ddd, 1H), 1.77 (ddd, 1H), 1.93 (d, 1H), 2.12 (ddd, 1H), 2.21 (d, 1H), 2.81 (s, 3H), 5.28 (s, 1H), 6.75-6.88 (m, 3H), 7.18 (d, 1H), 7.78 (t, 1H), 9.65 (s, 1H).

Example 199 cis-4'-[(7,8-Difluoro-2-methylquinazolin-5-yl)amino]-7'-fluoro-3',4'-dihydro-3'-(trifluoromethyl)-spiro[cyclopropane-1,1'(2'H)-naphthalene]-3',8'-diol $^1$H-NMR (300 MHz, CDCl$_3$): δ=0.71 (ddd, 1H), 0.91 (ddd, 1H), 1.81 (d, 1H), 1.83-2.00 (m, 2H), 2.39 (d, 1H), 2.87 (s, 3H), 4.98 (d, 1H), 5.75 (d, 1H), 6.49 (dd, 1H), 6.78-6.89 (m, 2H), 9.28 (s, 1H).

Example 200 cis-1-[(7,8-Difluoro-2-methylquinazolin-5-yl)amino]-5-fluoro-6-methoxy-4,4-dimethyl-2-(trifluoromethyl)-1,2,3,4-tetrahydronaphthalen-2-ol $^1$H-NMR (300 MHz, CD$_3$OD): δ=1.53 (s, 3H), 1.65 (s, 3H), 2.17 (s, 2H), 2.84 (s, 3H), 3.85 (s, 3H), 5.32 (s, 1H), 6.87 (dd, 1H), 6.95 (dd, 1H), 7.07 (d, 1H), 9.61 (s, 1H).

Example 201 cis-1-[(7,8-Difluoro-2-methylquinazolin-5-yl)amino]-5-fluoro 4,4-dimethyl-2-(trifluoromethyl)-1,2,3,4-tetrahydronaphthalene-2,6-diol $^1$H-NMR (300 MHz, CD$_3$OD): δ=1.54 (s, 3H), 1.66 (s, 3H), 2.16 (s, 2H), 2.84 (s, 3H), 3.98 (s, 3H), 5.29 (s, 1H), 6.78 (dd, 1H), 6.86 (dd, 1H), 6.94 (dd, 1H), 9.60 (s, 1H).

Example 202 cis-7'-Fluoro-4'-[(8-fluoro-2-methylquinazolin-5-yl)amino]-3',4'-dihydro-3'-(trifluoromethyl)-spiro[cyclopropane-1,1'(2'H)-naphthalene]-3',8'-diol $^1$H-NMR (300 MHz, CDCl$_3$): δ=0.71 (ddd, 1H), 0.93 (ddd, 1H), 1.79 (d, 1H), 1.90-2.06 (m, 2H), 2.39 (d, 1H), 2.91 (s, 3H), 3.80 (br, 1H), 5.05 (d, 1H), 5.39 (d, 1H), 5.48 (br, 1H), 6.65 (dd, 1H), 6.80-6.90 (m, 2H), 7.46 (dd, 1H), 9.35 (s, 1H).

Example 203 cis-7'-Fluoro-4'-[(7-fluoro-2-methylquinazolin-5-yl)amino]-3',4'-dihydro-3'-(trifluoromethyl)-spiro[cyclohexane-1,1'(2'H)-naphthalene]-3',8'-diol $^1$H-NMR (300 MHz, CDCl$_3$): δ=1.20-2.10 (m, 10H), 2.10 (d, 1H), 2.47 (d, 1H), 2.68 (s, 3H), 4.66 (d, 1H), 5.33 (d, 1H), 6.91 (d, 2H), 7.03 (dd, 1H), 7.10 (dd, 1H), 9.01 (s, 1H).

Example 204 cis-6-Chloro-5-methoxy-1-[(2-methylquinolin-5-yl)amino]-4,4-dimethyl-2-(trifluoromethyl)-1,2,3,4-tetrahydronaphthalen-2-ol $^1$H-NMR (300 MHz, CD$_3$OD): δ=1.56 (s, 3H), 1.69 (s, 3H), 2.16 (s, 2H), 2.72 (s, 3H), 3.97 (s, 3H), 5.25 (s, 1H), 6.82 (d, 1H), 7.11 (d, 1H), 7.20 (d, 1H), 7.32 (d, 1H), 7.36 (d, 1H), 7.55 (t, 1H), 8.45 (d, 1H).

Example 205 cis-6-Chloro-1-[(2-methylquinolin-5-yl)amino]-4,4-dimethyl-2-(trifluoromethyl)-1,2,3,4-tetrahydronaphthalene-2,5-diol $^1$H-NMR (300 MHz, CD$_3$OD): δ=1.61 (s, 3H), 1.73 (s, 3H), 2.12 (d, 1H), 2.18 (d, 1H), 2.72 (s, 3H), 5.23 (s, 1H), 6.82 (d, 1H), 6.87 (d, 1H), 7.11 (d, 1H), 7.31 (d, 1H), 7.35 (d, 11H), 7.55 (t, 0.1H), 8.45 (d, 1H).

Example 206 cis-1-[(2-Methyl-1-quinolin-5-yl)amino]-4,4-dimethyl-2-(trifluoromethyl)-1,2,3,4-tetrahydronaphthalen-2-ol-N-oxide $^1$H-NMR (300 MHz, CD$_3$OD): δ=1.44 (s, 3H), 1.58 (s, 3H), 2.19 (s, 2H), 2.76 (s, 3H), 5.35 (s, 1H), 7.00 (dd, 1H), 7.12 (t, 1H), 7.27-7.34 (m, 2H), 7.45-7.52 (m, 2H), 7.71 (t, 1H), 7.96 (d, 1H), 8.29 (d, 1H).

Example 207 cis-6-Chloro-1-[(2-methylquinolin-5-yl)amino]-4,4-dimethyl-2-(trifluoromethyl)-1,2,3,4-tetrahydronaphthalene-2,5-diol N-oxide 75 mg of 70% meta-chloroperbenzoic acid is added to 84 mg (0.19 mmol) of cis-6-chloro-1-[(2-methylquinolin-5-yl)amino]-4,4-dimethyl-2-(trifluoromethyl)-1,2,3,4-tetrahydronaphthalene-2,5-diol in 8 ml of dichloromethane, and the solution is stirred over two hours. 50 mg of solid sodium bicarbonate is added, and after 30 minutes, it is poured into water. It is extracted with dichloromethane, washed with saturated sodium chloride solution and dried on sodium sulfate. After concentration by evaporation and chromatography on silica gel (hexane/ethyl acetate 0-100%), 58 mg of the title compound is obtained.

$^1$H-NMR (300 MHz, CD$_3$OD): δ=1.61 (s, 3H), 1.73 (s, 3H), 2.13 (d, 1H), 2.18 (d, 1H), 2.75 (s, 3H), 5.30 (s, 1H), 6.85 (d, 1H), 7.01 (d, 1H), 7.13 (d, 1H), 7.48 (d, 1H), 7.70 (t, 1H), 7.96 (d, 1H), 8.27 (d, 1H).

Example 208 cis-6-[(2-Methyl-quinolin-5-yl)amino]-9,9-dimethyl-7-(trifluoromethyl)-6,7,8,9-tetrahydro-naphthol[1,2-d]-1,3-dioxol-7-ol N-oxide $^1$H-NMR (300 MHz, CDCl$_3$): δ=1.49 (s, 3H), 1.58 (s, 3H), 2.06 (d, 1H), 2.20 (d, 1H), 2.61 (s, 3H), 5.08 (d, 1H), 5.62 (d, 1H), 5.99 (s, 2H), 6.64 (d, 1H), 6.83 (d, 1H), 6.85 (d, 1H), 7.13 (d, 1H), 7.55 (t, 1H), 7.96 (d, 1H), 8.03 (d, 1H).

Example 209 cis-7'-Fluoro-4'-[(7-fluoro-2-methylquinazolin-5-yl)amino]-3,4'-dihydro-3'-(trifluoromethyl)-spiro[cyclopropane-1,1'(2'H)-naphthalene]-3',8'-diol $^1$H-NMR (30 MHz, CD$_3$OD): δ=0.66 (ddd, 1H), 0.89 (ddd, 1H), 1.86 (ddd, 1H), 1.93 (d, 1H), 2.10 (ddd, 1H), 2.22 (d, 1H), 2.78 (s, 3H), 5.26 (s, 1H), 6.67 (dd, 1H), 6.75-6.82 (m, 2H), 6.87 (dd, 1H), 9.58 (s, 1H).

Example 210 cis-5-(7'-Fluoro-3' 4'-dihydro-3',8'-dihydroxy-3'-(trifluoromethyl)-spiro[cyclopropane-1,1° (2'H)-naphthalen-4'-yl]-amino}-quinolin-2(1H)-one $^1$H-NMR (300 MHz, CD$_3$OD): δ=0.66 (ddd, 1H), 0.90 (ddd, 1H), 1.71 (ddd, 1H), 1.88 (d, 1H), 2.09 (ddd, 1H), 2.20 (d, 2H), 5.15 (s, 1H), 6.51-6.54 (m, 2H), 6.70 (d, 1H), 6.79 (dd, 1H), 6.85 (dd, 1H), 7.36 (t, 1H), 8.25 (d, 1H).

Example 211

Cis-7'-Chloro-4'-[(7-fluoro-2-methylquinazolin-5-yl)amino]-3,4'-dihydro-3'-(trifluoromethyl)-spiro[cyclopropane-1,1'(2'H)-naphthalene]-3',8'-diol $^1$H-NMR (300 MHz, CDCl$_3$): δ=0.70 (ddd, 1H), 0.91 (ddd, 1H), 1.70 (ddd, 1H), 1.77 (d, 1H), 2.08 (ddd, 1H), 2.44 (d, 1H), 2.82 (d, 3H), 5.06 (d, 1H), 5.77 (s, 1H), 5.88 (d, 1H), 6.44 (dd, 1H), 6.88 (d, 1H), 6.91 (dd, 1H), 7.13 (d, 1H), 9.23 (s, 1H).

Example 212

Cis-7'-Chloro-3',4'-dihydro-4'-[(2-methylquinolin-5-yl)amino]-3'-(trifluoromethyl)-spiro[cyclopropane-1,1° (2'H)-naphthalene]-3',8'-diol $^1$H-NMR (300 MHz, CD$_3$OD): δ=0.68 (ddd, 1H), 0.91 (ddd, 1H), 1.69 (ddd, 1H), 1.91 (d, 1H), 2.11 (ddd, 1H), 2.22 (d, 1H), 2.72 (s, 3H), 5.20 (s, 1H), 6.70 (d, 1H), 6.78-6.85 (m, 2H), 7.30 (d, 1H), 7.36 (d, 1H), 7.53 (t, 1H), 8.47 (d, 1H).

Example 213 cis-7'-Chloro-3',4'-dihydro-4'-[(2-methyl-quinolin-5-yl)amino]-3'-(trifluoromethyl)-spiro[cyclopropane-1,1'(2'H)-naphthalene]-3',8'-diol N-oxide $^1$H-NMR (300 MHz, CD$_3$OD): δ=0.67 (ddd, 1H), 0.91 (ddd, 1H), 1.74 (ddd, 1H), 1.91 (d, 1H), 2.10 (ddd, 1H), 2.23 (d, 1H), 2.75 (s, 3H), 5.25 (s, 1H), 6.78 (dd, 1H), 6.84 (dd, 1H), 6.90 (d, 1H), 7.49 (d, 1H), 7.69 (t, 1H), 7.95 (d, 1H), 8.30 (d, 1H).

Example 214 cis-7'-Chloro-4'-[(7-fluoro-2-methylquinazolin-5-yl)amino]-3,4'-dihydro-8'-methoxy-3'-(trifluoromethyl)-spiro[cyclohexane-1,1'(2'H)-naphthalen]-3'-ol $^1$H-NMR (300 MHz, CDCl$_3$): 1.20-1.85 (m, 8H), 2.05 (d, 1H), 2.44 (ddd, 1H), 2.63 (ddd, 1H), 2.82 (s, 3H), 2.97 (d, 1H), 4.00 (s, 3H), 4.95 (d, 1H), 5.92 (d, 1H), 6.49 (dd, 1H), 6.91 (dd, 1H), 7.04 (d, 1H), 7.22 (d, 1H), 9.16 (s, 1H).

Example 215 cis-7'-Chloro-4'-[(7-fluoro-2-methylquinazolin-5-yl)amino]-3,4'-dihydro-3'-(trifluoromethyl)-spiro[cyclohexane-1.1' (2'H)-naphthalene]-3',8'-diol $^1$H-NMR (300 MHz, CDCl$_3$): δ=1.25-1.85 (m, 8H), 1.86 (d, 1H), 2.79 (ddd, 1H), 2.82 (s, 3H), 2.93 (ddd, 1H), 2.97 (d, 1H), 4.95 (d, 1H), 5.85 (d, 1H), 6.14 (s, 1H), 6.48 (dd, 1H), 6.89-6.93 (m, 2H), 7.19 (d, 1H), 9.19 (s, 1H).

Example 216 cis-7'-Chloro-3',4'-dihydro-4'-[(2-methylquinazolin-5-yl)amino]-3'-(trifluoromethyl)-spiro [cyclopropane-1,1' (2'H)-naphthalene-3',8'-diol $^1$H-NMR (300 MHz, CD$_3$OD): δ=0.69 (ddd, 1H), 0.92 (ddd, 1H), 1.71 (ddd, 1H), 1.95 (d, 1H), 2.13 (ddd, 1H), 2.20 (d, 1H), 2.81 (s, 3H), 5.29 (s, 1H), 6.85 (d, 2H), 7.10 (d, 1H), 7.19 (d, 1H), 7.78 (t, 1H), 9.65 (d, 1H).

Example 217

(−)-2-Chloro-5-(1H-indazol-4-ylamino)-8,8-dimethyl-6-(trifluoromethyl)-5,6,7,8-tetrahydro-naphthalene-1,6-diol and (+)-2-Chloro-5-(1H-indazol-4-ylamino)-8,8-dimethyl-6-(trifluoromethyl)-5,6,7,8-tetrahydro-naphthalene-1,6-diol (−)-6-Chloro-1-(1H-indazol-4-ylamino)-5-methoxy-4,4-dimethyl-2-(trifluoromethyl)-1,2,3,4-tetrahydronaphthalen-2-ol and (+)-6-Chloro-1-(1H-indazol-4-ylamino)-5-methoxy-4,4-dimethyl-2-(trifluoromethyl)-1,2,3,4-tetrahydronaphthalen-2-ol The racemic compound (324.2 mg) that was produced according to the process that is described in the examples above is separated into its enantiomers in the ether stage on a chiral column (Chiralpak AD 20μ, eluant hexane/ethanol). 122.8 mg of the (−)-enantiomer and 147.1 mg of the (+)-enantiomer are obtained.

(−)-Enantiomer: [α]$_D$=−0.8 (c=1, MeOH)

(+)-Enantiomer: [α]$_D$=+1.0 (c=1, MeOH)

(−)-2-Chloro-5-(1H-indazol-4-ylamino)-8,8-dimethyl-6-(trifluoromethyl)-5,6,7,8-tetrahydronaphthalene-1,6-diol and (+)-2-Chloro-5-(1H-indazol-4-ylamino)-8,8-dimethyl-6-(trifluoromethyl)-5,6,7,8-tetrahydronaphthalene-1,6-diol 24 mg (21.4%) of the phenol is obtained from 115.8 mg of the (−)-enantiomer ether by ether cleavage with $BBr_3$.

91.5 mg (66.9%) of the phenol is obtained from 141.2 mg of the (+)-enantiomer ether by ether cleavage with $BBr_3$.

Example 218

5-{[4,4-Dimethyl-2-hydroxy-5-methoxy-2-(pentafluoroethyl)-1,2,3,4-tetrahydronaphthalen-1-yl]amino}quinolin-2(1H)-one 4-(2-Methoxyphenyl)-2-hydroxy-4-methyl-2-(pentafluoroethyl)pentanal Analogously to Example 7, 687 mg of ethyl-4-(2-methoxyphenyl)-4-methyl-2-oxopentanoate (WO 00/32584) is reacted with 1 g of (pentafluoroethyl)trimethylsilane and 0.5 ml (tetrabutylammonium fluoride solution (1 M in THF)) in 18 ml of THF to form g of ethyl-4-(2-methoxyphenyl)-2-hydroxy-4-methyl-2-(pentafluoroethyl)-pentanoate. 450 mg of the obtained ester in 12 ml of diethyl ester is mixed in portions at 0° C. with 66 mg of lithium aluminum hydride. After stirring for 11 hours, it is added to saturated bicarbonate solution and filtered through diatomaceous earth. The phases are separated, and the aqueous phase is extracted with ethyl acetate. The organic phase is washed with water and brine, dried ($Na_2SO_4$) and concentrated by evaporation. 420 mg of diol is obtained as a yellow oil. 400 mg of the diol is oxidized to the corresponding aldehyde with 0.11 ml of oxalyl chloride, 0.21 ml of DMSO and 1 ml of triethylamine. It is washed with water and brine, dried with sodium sulfate and concentrated by evaporation in a vacuum. After chromatography on silica gel (hexane/ethyl acetate 0->5%), 268 mg of the title compound is obtained as a yellow oil.

$^1$H-NMR ($CDCl_3$): δ=1.39 (s, 3H), 1.46 (s, 3H), 2.26 (d, 1H), 3.46 (d, 1H), 3.88 (s, 3H), 6.77-6.95 (m, 2H), 7.11 (dd, 1H), 7.13-7.28 (m, 1H), 8.95 (s, 1H)

5-{[4,4-Dimethyl-2-hydroxy-5-methoxy-2-(pentafluoroethyl)-1,2,3,4-tetrahydronaphthlalen-1-yl]amino}-quinolin-2(1H)-one Analogously to Example 10, the corresponding imine is produced starting from 180 mg of 4-(2-methoxyphenyl)-2-hydroxy-4-methyl-2-(pentafluoroethyl)pentanal and 83 mg of 5-aminoquinolin-2-(1H)-one. 7 mg of the title compound is obtained by reaction of 70 mg of the imine with 58 mg of aluminum trichloride in 1.5 ml of dichloromethane.

$^1$H-NMR ($CD_3OD$): δ=1.52 (s, 3H), 1.66 (s, 3H), 2.09 (d, 1H), 2.15 (d, 1H), 3.85 (s, 3H), 5.27 (s, 1H), 6.51 (d, 1H), 6.62 (d, 1H), 6.70 (d, 1H), 6.92 (d, 2H), 7.11 (dd, 1H), 7.38 (t, 1H), 8.23 (d, 1H)

Example 219

5-{[6-Chloro-4,4-dimethyl-2-hydroxy-5-methoxy-2-(trifluoromethyl)-1,2,3,4-tetrahydronaphthalen-1-yl]amino}-6-methylquinolin-2(1H)-one 5-Amino-6-methylquinolin-2(1H)-one 4.12 g of 2-chloro-6-methylquinoline (J. Med. Chem. 1992, pp. 2761-2768) is added at 0° C. to a solution that consists of 15 ml of 100% nitric acid and 2 ml of 96% sulfuric acid. After 4 hours at 0° C., it is added to water, and the product is filtered off. 4.66 g of 2-chloro-6-methyl-5-nitroquinoline is obtained as a beige solid. The latter is reacted for 80 hours at 100° C. in 46 ml of glacial acetic acid and 26 ml of water. The thus obtained 6-methyl-5-nitroquinolin-2(1H)-one is filtered off from the reaction solution. The 3.45 g of product that is obtained is reacted with hydrogen under normal pressure in methanol to palladium on activated carbon to form aniline. 2.89 g of the title compound is obtained as a beige solid.

$^1$H-NMR (DMSO): δ=2.08 (s, 3H), 5.56 (s, 2H), 6.25 (d, 1H), 6.42 (d, 1H), 7.06 (d, 1H=, 8.18 (d, 1H), 11.32 (s, 1H)

5-{[6-Chloro-4,4-dimethyl-2-hydroxy-5-methoxy-2-(trifluoromethyl)-1,2,3,4-tetrahydronapthalen-1-yl]amino}-6-methylquinolin-2(1H)-one Analogously to Example 10, the corresponding imine is produced starting from 500 mg of 4-(3-chloro-2-methoxyphenyl)-2-hydroxy-4-methyl-2-(trifluoromethyl)pentanal and 300 mg of 5-amino-6-methylquinolin-2(1H)-one. 10 mg of the title compound is obtained by reaction of 80 mg of the imine with 2.5 ml of titanium tetrachloride solution (1 M in dichloromethane) in 4.3 ml of dichloromethane.

$^1$H-NMR (DMSO): δ=1.57 (s, 3H), 1.68 (s, 3H), 1.87 (d, 1H), 2.12 (d, 1H), 2.38 (s, 3H), 3.88 (s, 3H), 4.87 (d, 1H), 5.85 (d, 1H), 5.96 (d, 1H), 6.62 (d, 1H), 6.81 (d, 1H), 7.11 (d, 1H), 7.44 (d, 1H), 8.42 (s, 1H), 11.57 (s, 1H)

Example 220

5-{[2,5-Dihydroxy-2-(trifluoromethyl)-4,4,7-trimethyl-1,2,3,4-tetrahydronaphthalen-1-yl]amino}-quinolin-2(1)-one Analogously to Example 3, 19 mg of the title compound is obtained starting from 74 mg of the compound of Example 41 with 0.48 ml of $BBr_3$ solution (1 M in dichloromethane) at 40° C.

$^1$H-NMR ($CD_3OD$): δ=1.53 (s, 3H), 1.65 (s, 3H), 2.01 (d, 1H), 2.10 (s, 3H), 2.12 (d, 1H), 5.10 (s, 1H), 6.47-6.56 (m, 2H), 6.58-6.65 (m, 2H), 6.69 (d, 1H), 7.39 (t, 1H), 8.22 (d, 1H)

Example 221

5-{[2-Hydroxy-5-methoxy-2-(pentafluoroethyl)-4,4,7-trimethyl-1,2,3,4-tetrahydronaphthalen-1-yl]amino}-quinolin-2(11H)-one 4-(2-Methoxy-4-methylphenyl)-2-hydroxy-4-methyl-2-(pentafluoroethyl)pentanal Analogously to the synthesis of 4-(2-methoxyphenyl)-2-hydroxy-4-methyl-2-(pentafluoroethyl)-pentanal, 1.05 g of the title compound is obtained starting from 1.7 g of ethyl-4-

(2-methoxy-4-methylphenyl)-4-methyl-2-oxopentanoate (Example 41) with 1.4 g of (pentafluoroethyl)trimethylsilane, subsequent reduction with 344 mg of lithium aluminum hydride and ultimate oxidation under Swern conditions.

$^1$H-NMR (CDCl$_3$): δ=1.36 (s, 3H), 1.42 (s, 3H), 2.23 (d, 1H), 2.32 (s, 3H), 3.48 (d, 1H), 3.64 (s, 1H), 3.87 (s, 3H), 6.67 (s, 1H), 6.71 (d, 1H), 6.97 (d, 1H), 8.93 (s, 1H)

5-{[2-Hydroxy-5-methoxy-2-(pentafluoroethyl)-4,4,7-trimethyl-1,2,3,4-tetrahydronaphthalen-1-yl]amino}-quinolin-2(1H)-one Analogously to Example 10, the corresponding imine is produced starting from 200 mg of 4-(2-methoxy-4-methylphenyl)-2-hydroxy-4-methyl-2-(pentafluoroethyl)pentanal and 93 mg of 5-aminoquinolin-2(1H)-one. 2 mg of the title compound is obtained by reaction of 80 mg of the imine with 1.6 ml of titanium tetrachloride solution (1 M in dichloromethane) in 5 ml of dichloromethane.

$^1$H-NMR (CD$_3$OD): δ=1.48 (s, 3H), 1.62 (s, 3H), 2.05 (d, 1H), 2.12 (d, 1H), 2.16 (s, 3H), 3.83 (s, 3H), 5.21 (s, 1H), 6.52 (d, 1H), 6.62 (d, 1H), 6.71 (d, 1H), 6.75 (s, 2H), 7.40 (t, 1H), 8.23 (d, 1H)

Example 222

5-{[2-Hydroxy-5-methoxy-2-(trifluoromethyl)-4,4,6-trimethyl-1,2,3,4-tetrahydronaphthalen-1-yl]amino}-quinolin-2(1H)-one Ethyl-4-(2-methoxy-3-methylphenyl)-4-methyl-2-oxopentanoate Analogously to Example 7, methyl-2 methoxy-3-methylbenzoate is produced from 30 g of 3-methylsalicylic acid and 60 ml of methyl iodide with 125 g of potassium carbonate in 640 ml of DMF. The ester is reacted by reaction with 129 ml of methyl magnesium chloride (3 M in THF) in 435 ml of THF to form 1-(2-methoxy-4-methylphenyl)-1-methylethanol. 20.8 g of the product that is obtained is reacted with 27.1 g of 2-(trimethylsilyloxy)-acrylic acid ethyl ester in 410 ml of dichloromethane at 0° C. with 10.4 ml of tin tetrachloride to form 12.63 g of the title compound.

$^1$H-NMR (300 MHz, CDCl$_3$): δ=1.28 (t, 3H), 1.48 (s, 6H), 2.29 (s, 3H), 3.37 (s, 2H), 3.76 (s, 3H), 4.14 (q, 2H), 6.95 (t, 1H), 7.05 (d, 1H), 7.13 (d, 1H)

4-(2-Methoxy-4-methylphenyl)-2-hydroxy-4-methyl-2-(trifluoromethyl)pentanal

Analogously to Example 7, 14.68 g of ethyl-4-(2-methoxy-4-methylphenyl)-4-methyl-2-oxopentanoate is reacted with 21.6 ml (trifluoromethyl)trimethylsilane and 9.7 ml of tetrabutylammonium fluoride solution (1 M in THF) in 195 ml of THF to form 13.73 g of ethyl-4-(2-methoxy-4-methylphenyl)-2-hydroxy-4-methyl-2-(trifluoromethyl)pentanoate. The product is reduced with 2.84 g of lithium aluminum hydride in 560 ml of diethyl ether to form 11.62 g of 4-(2-methoxy-4-methylphenyl-2-hydroxy-4-methyl-2-(trifluoromethyl)pentanol. The oxidation of the diol is carried out analogously to Example 7 under Swern conditions with 3.8 ml of oxalyl chloride, 7.1 ml of DMSO and 26.5 ml of triethylamine to 5.91 g of the title compound.

$^1$H-NMR (CDCl$_3$): δ=1.44 (s, 3H), 1.48 (s, 3H), 2.22 (d, 1H), 3.36 (d, 1H), 3.83 (s, 3H), 6.90-7.12 (m, 3H), 8.93 (s, 1H)

5-{[2-Hydroxy-5-methoxy-2-(trifluoromethyl)-4,4,6-trimethyl-1,2,3,4-tetrahydronaphthalen-1-yl]amino}-quinolin-2(1H)-one Analogously to Example 10, the corresponding imine is produced starting from 600 mg of 4-(2-methoxy-4-methylphenyl)-2-hydroxy-4-methyl-2-(trifluoromethyl)pentanal and 315 mg of 5-aminoquinolin-2(1H)-one. 12 mg of the title compound is obtained by reaction of 370 mg of the imine with 8.3 ml of titanium tetrachloride (1 M in dichloromethane) in 20 ml of dichloromethane.

$^1$H-NMR (CD$_3$OD): δ=1.52 (s, 3H), 1.67 (s, 3H), 2.10 (s, 2H), 2.30 (s, 3H), 3.79 (s, 3H), 5.16 (s, 1H), 6.51 (d, 1H), 6.61 (d, 1H), 6.70 (d, 1H), 7.00 (s, 2H), 7.38 (t, 1H), 8.21 (d, 1H)

Examples 223 and 224

4-{[4,4-Dimethyl-2-hydroxy-5-methoxy-2-(trifluoromethyl)-1,2,3,4-tetrahydronaphthalen-1-yl]amino}-phthalide and 4-{[2,5-dihydroxy-4,4-dimethyl-2-(trifluoromethyl)-1,2,3,4-tetrahydronaphthalen-1-yl]amino}-phthalide Analogously to Example 10, the corresponding imine is produced starting from 600 mg of 4-(2-methoxyphenyl)-2-hydroxy-4-methyl-2-(trifluoromethyl)pentanal and 308 mg of 4-aminophthalide. By reaction of 640 mg of the imine with 7.7 ml of bromine tribromide solution (1 M in dichloromethane), 165 mg of 4-{[4,4-dimethyl-2-hydroxy-5-methoxy-2-(trifluoromethyl)-1,2,3,4-tetrahydronaphthalen-1-yl]amino}-phthalide is obtained as fraction 1, and 115 mg of 4-{[2,5-dihydroxy-4,4-dimethyl-2-(trifluoromethyl)-1,2,3,4-tetrahydronaphthalen-1-yl]amino}-phthalide is obtained as fraction 2.

Fraction 1: $^1$H-NMR (CDCl$_3$): δ=1.40 (s, 3H), 1.49 (s, 3H), 2.03 (d, 1H), 2.13 (d, 1H), 3.17 (d, 1H), 3.32 (s, 1H), 3.90 (s, 3H), 5.01 (d, 1H), 5.11-5.24 (m, 2H), 6.66 (d, 1H), 7.03 (d, 1H), 7.21-7.32 (m, 2H), 7.39-7.50 (m, 2H)

Fraction 2: $^1$H-NMR (CD$_3$OD): δ=1.55 (s, 3H), 1.67 (s, 3H), 2.04 (d, 1H), 2.12 (d, 1H), 5.15 (s, 1H), 5.21 (d, 1H), 5.32 (d, 1H), 6.70 (d, 1H), 6.84 (d, 1H), 6.96 (t, 1H), 7.07 (d, 1H), 7.18 (d, 1H), 7.42 (t, 1H)

Examples 225 and 226

(−)-4-[4,4-Dimethyl-2-hydroxy-5-methoxy-2-(trifluoromethyl)-1,2,3,4-tetrahydronaphthalen-1-yl]amino}-phthalide and (+)-4-{[4,4-dimethyl-2-hydroxy-5-methoxy-2-(trifluoromethyl)-1,2,3,4-tetrahydronaphthalen-1-yl]amino}-phthalide Separation of (+/−)4-{[4,4-dimethyl-2-hydroxy-5-methoxy-2-(trifluoromethyl)-1,2,3,4-tetrahydronaphthalen-1-yl]amino}-phthalide The enantiomer mixture is separated by chromatography on chiral carrier material (CHIRALPAK AD®, DAICEL Company) with hexane/ethanol (95:5, vvv). The (−)-enantiomer: MS (EI): M$^+$=421, [α]$_D$−79.3° (c=0.9, CHCl$_3$) and the (+)-enantiomer: MS (EI): M$^+$=421 are thus obtained.

Examples 227 and 228

(−)-4-{[2,5-Dihydroxy-4-4-dimethyl-2-(trifluoromethyl)-1,2,3,4-tetrahydronaphthalen-1-yl]amino}-phthalide and (+)-4-{[2,5-Dihydroxy-4-4-dimethyl-2-(trifluoromethyl)-1,2,3,4-tetrahydronaphthalen-1-yl]amino}-phthalide Separation of (+/−)-4-{[2,5-dihydroxy-4,4-dimethyl-2-(trifluoromethyl)-1,2,3,4-tetrahydronaphthalen-1-yl]amino}-phthalide The enantiomer mixture is separated by chromatography on chiral carrier material (CHIRALPAK AD®, DAICEL Company) with hexane/ethanol (90:10, vvv). The (−)-enantiomer: MS (EI): $M^+$=407, $[\alpha]_D$−66.0° (c=1.0, $CHCl_3$) and the (+)-enantiomer: MS (EI): $M^+$=407 are thus obtained.

Example 229

5-{[5-Methoxy-2-hydroxy-2-(trifluoromethyl)-4,4,7-trimethyl-1,2,3,4-tetrahydronaphthalen-1-yl]amino}-2-methylphthalazin-1-one Analogously to Example 10, the corresponding imine is produced starting from 500 mg of 4-(2-methoxy-4-methylphenyl)-2-hydroxy-4-methyl-2-(trifluoromethyl)-pentanal and 288 mg of 5-amino-2-methylphthalazin-1-one. As in Example 3, 90 mg of the imine is reacted by reaction with 0.4 ml of titanium tetrachloride (1 M in dichloromethane) in 5 ml of dichloromethane, and 25 mg of the title compound is obtained.

$^1$H-NMR (DMSO): δ=1.42 (s, 3H), 1.57 (s, 3H), 1.95 (d, 1H), 2.05 (d, 1H), 2.14 (s, 3H), 3.70 (s, 3H), 3.80 (s, 3H), 5.38 (d, 1H), 5.98 (s, 1H), 6.57 (d, 1H), 6.66 (s, 1H), 6.80 (s, 1H), 7.25 (d, 1H), 7.47 (d, 1H), 7.58 (t, 1H), 8.63 (s, 1H)

Examples 230 and 231

(−)-5-{[5-Methoxy-2-hydroxy-2-(trifluoromethyl)-4,4,7-trimethyl-1,2,3,4-tetrahydronaphthalen-1-yl]amino}-2-methylphthalazin-1-one and (+)-5-{[5-Methoxy-2-hydroxy-2-(trifluoromethyl)-4,4,7-trimethyl-1,2,3,4-tetrahydronaphthalen-1-yl]amino}-2-methylphthalazin-1-one Separation of (+/−)-5-{[5-methoxy-2-hydroxy-2-(trifluoromethyl)-4,4,7-trimethyl-1,2,3,4-tetrahydronaphthalen-1-yl]amino}-2-methylphthalazin-1-one The enantiomer mixture is separated by chromatography on chiral carrier material (CHIRALPAK AD®, DAICEL Company) with ethanol as an eluant. The
(−)-enantiomer: MS (EI): $M^+$=461, and the
(+)-enantiomer: MS (EI): $M^+$=461, $[\alpha]_D$+4.9° (c=0.7, $CHCl_3$) are thus obtained.

Example 232

5-{[6-Chloro-4,4-dimethyl-5-methoxy-2-hydroxy-2-(trifluoromethyl)-1,2,3,4-tetrahydronaphthalin-1-yl]amino}-2-methylphthalazin-1-one Analogously to Example 10, the corresponding imine is produced starting from 1.0 g of 4-(3-chloro-2-methoxyphenyl)-2-hydroxy-4-methyl-2-(trifluoromethyl)pentanal and 542 mg of 5-amino-2-methyl-phthalazin-1-one. As in Example 3, 840 mg of the imine is reacted by reaction with 43.6 ml of titanium tetrachloride (1 M in dichloromethane) in 40 ml of dichloromethane, and 114 mg of the title compound is obtained.

$^1$H-NMR (DMSO): δ=1.47 (s, 3H), 1.61 (s, 3H), 2.00 (d, 1H), 2.14 (d, 1H), 3.71 (s, 3H), 3.88 (s, 3H), 5.46 (d, 1H), 6.17 (s, 1H), 6.61 (d, 1H), 7.00 (d, 1H), 7.27 (d, 1H), 7.33 (d, 1H), 7.49 (d, 1H), 7.60 (t, 1H), 8.64 (s, 1H)

Examples 233 and 234

(−)-5-{[6-Chloro-4,4-dimethyl-5-methoxy-2-hydroxy-2-(trifluoromethyl)-1,2,3,4-tetrahydronaphthalen-1-yl]amino}-2-methylphthalazin-1-one and (+)-5-{[6-Chloro-4,4-dimethyl-5-methoxy-2-hydroxy-2-(trifluoromethyl)-1,2,3,4-tetrahydronaphthalen-1-yl]amino}-2-methylphthalazin-1-one Separation of (+/−)-5-{[6-chloro-4,4-dimethyl-5-methoxy-2-hydroxy-2-(trifluoromethyl)-1,2,3,4-tetrahydronaphthalen-1-yl]amino}-2-methylphthalazin-1-one The enantiomer mixture is separated by chromatography on chiral carrier material (CHIRALPAK AD®, DAICEL Company) with hexane/ethanol (90:10, vvv). The
(−)-Enantiomer: MS (EI): $M^+$=481/483 and the
(+)-Enantiomer: MS (EI): $M^+$=481/483, $[\alpha]_D$+10.6° (c=0.8 $CHCl_3$) are thus obtained.

Example 235

5-{[6-Chloro-2,5-dihydroxy-4,4-dimethyl-2-(trifluoromethyl)-1,2,3,4-tetrahydronaphthalen-1-yl]amino}-amino}-2-methylphthalazin-1-one Analogously to Example 3, 19 mg of the title compound is obtained starting from 20 mg of 5-{[6-chloro-4,4-dimethyl-5-methoxy-2-hydroxy-2-(trifluoromethyl)-1,2,3,4-tetrahydronaphthalen-1-yl]amino}-2-methylphthalazin-1-one with 0.13 ml of $BBr_3$ solution (1 M in dichloromethane) at 40° C.

$^1$H-NMR (DMSO): δ=1.52 (s, 3H), 1.65 (s, 3H), 2.00 (d, 1H), 2.11 (d, 1H), 3.70 (s, 3H), 5.42 (d, 1H), 6.07 (s, 1H), 6.58 (d, 1H), 6.74 (d, 1H), 7.20 (d, 1H), 7.26 (d, 1H), 7.47 (d, 1H), 7.58 (t, 1H), 8.63 (s, 1H), 9.09 (s, 1H)

Example 236

(−)-5-{[6-Chloro-2,5-dihydroxy-4,4-dimethyl-2-(trifluoromethyl)-1,2,3,4-tetrahydronaphthalen-1-yl]amino}-amino}-2-methylphthalazin-1-one Analogously to Example 3, 23 mg of the title compound is obtained starting from 26 mg of (−)-5-{[6-chloro-4,4-dimethyl-5-(methoxy-2-hydroxy-2-(trifluoromethyl)-1,2,3,4-tetrahydronaphthalen-1-yl]amino}-2-methylphthalazin-1-one with 0.5 ml of $BBr_3$ solution (1 M in dichloromethane) in 0.25 ml of dichloromethane at 40° C.

$^1$H-NMR (DMSO): δ=1.52 (s, 3H), 1.65 (s, 3H), 2.00 (d, 1H), 2.11 (d, 1H), 3.70 (s, 3H), 5.42 (d, 1H), 6.07 (s, 1H), 6.58

Example 237

(+)-5-{[6-Chloro-2,5-dihydroxy-4,4-dimethyl-2-(trifluoromethyl)-1,2,3,4-tetrahydronaphthalen-1-yl]amino}-amino}-2-methylphthalazin-1-one Analogously to Example 3, 12 mg of the title compound is obtained starting from 20 mg of (+)-5-{[6-chloro-4,4-dimethyl-5-methoxy-2-hydroxy-2-(trifluoromethyl)-1,2,3,4-tetrahydronaphthalen-1-yl]amino}-2-methylphthalazin-1-one with 0.4 ml of BBr$_3$ solution (1 M in dichloromethane) in 0.25 ml of dichloromethane at 40° C.

$^1$H-NMR (DMSO): δ=1.52 (s, 3H), 1.65 (s, 3H), 2.00 (d, 1H), 2.11 (d, 1H), 3.70 (s, 3H), 5.42 (d, 1H), 6.07 (s, 1H), 6.58 (d, 1H), 6.74 (d, 1H), 7.20 (d, 1H), 7.26 (d, 1H), 7.47 (d, 1H), 7.58 (t, 1H), 8.63 (s, 1H), 9.09 (s, 1H)

Example 238

(+)-5-{[2,5-Dihydroxy-2-(trifluoromethyl)-4,4,7-trimethyl-1,2,3,4-tetrahydronaphthalen-1-yl]amino}-amino}-2-methylphthalazin-1-one Analogously to Example 3, 19 mg of the title compound is obtained starting from 20 mg of 5-{[5-methoxy-2-hydroxy-2-(trifluoromethyl)-4,4,7-trimethyl-1,2,3,4-tetrahydronaphthalen-1-yl]amino}-2-methylphthalazin-1-one with 0.13 ml of BBr$_3$ solution (1 M in dichloromethane) at 40° C.

$^1$H-NMR (DMSO): δ=1.46 (s, 3H), 1.60 (s, 3H), 1.94 (d, 1H), 2.01 (d, 1H), 2.06 (s, 3H), 3.70 (s, 3H), 5.35 (d, 1H), 5.92 (s, 1H), 6.51 (s, 1H), 6.53-6.63 (m, 2H), 7.26 (d, 1H), 7.46 (d, 1H), 7.57 (t, 1H), 8.63 (s, 1H), 9.31 (s, 1H)

Example 239

5-{[5-Methoxy-2-hydroxy-2-(trifluoromethyl)-4,4,6-trimethyl-1,2,3,4-tetrahydronaphthalen-1-yl]amino}-2-methylphthalazin-1-one Analogously to Example 10, the corresponding imine is produced starting from 600 mg of 4-(3-methyl-2-methoxyphenyl)-2-hydroxy-4-methyl-2-(trifluoromethyl)pentanal and 316 mg of 5-amino-2-methylphthalazin-1-one. As in Example 3, 460 mg of the imine is reacted by reaction with 5.2 ml of titanium tetrachloride (1 M in dichloromethane) in 23 ml of dichloromethane, and 36 mg of title compound is obtained.

$^1$H-NMR (DMSO): δ=1.45 (s, 3H), 1.60 (s, 3H), 1.96 (d, 1H), 2.10 (d, 1H), 2.24 (s, 3H), 3.70 (s, 3H), 3.72 (s, 3H), 5.40 (d, 1H), 6.03 (s, 1H), 6.57 (d, 1H), 6.87 (d, 1H), 7.03 (d, 1H), 7.25 (d, 1H), 7.46 (d, 1H), 7.58 (t, 1H), 8.63 (s, 1H).

Example 240

5-{[6-Chloro-4,4-dimethyl-5-methoxy-2-hydroxy-2-(trifluoromethyl)-1,2,3,4-tetrahydronaphthalen-1-yl]amino}-phthalazin-1-one Analogously to Example 10, the corresponding imine is produced starting from 1.0 g of 4-(3-chloro-2-methoxyphenyl)-2-hydroxy-4-methyl-2-(trifluoromethyl)pentanal and 494 mg of 5-amino-phthalazin-1-one. As in Example 3, 775 mg of the imine is reacted by reaction with 24.9 ml of titanium tetrachloride (1 M in dichloromethane) in 46 ml of dichloromethane, and 483 mg of the title compound is obtained.

$^1$H-NMR (DMSO): δ=1.47 (s, 3H), 1.61 (s, 3H), 1.99 (d, 1H), 2.13 (d, 1H), 3.88 (s, 3H), 5.45 (d, 1H), 6.17 (s, 1H), 6.57 (d, 1H), 7.00 (d, 1H), 7.28 (d, 1H), 7.33 (d, 1H), 7.46 (d, 1H), 7.57 (t, 1H), 8.61 (s, 1H), 1.256 (s, 1H)

Examples 241 and 242

(−)-5-{[6-Chloro-4,4-dimethyl-5-methoxy-2-hydroxy-2-(trifluoromethyl)-1,2,3,4-tetrahydronaphthalin-1-yl]amino}-phthalazin-1-one and (+)-5-[6-Chloro-4,4-dimethyl-5-methoxy-2-hydroxy-2-(trifluoromethyl)-1,2,3,4-tetrahydronaphthalin-1-yl]amino}-phthalazin-1-one Separation of (+/−)-5-{[6-Chloro-4,4-dimethyl-5-methoxy-2-hydroxy-2-(trifluoromethyl)-1,2,3,4-tetrahydronaphthalen-1-yl]amino}-phthalazin-1-one The enantiomer mixture is separated by chromatography on chiral carrier material (CHIRALPAK AD®, DAICEL Company) with hexane/ethanol (90:10, vvv). The (−)-enantiomer: flash point=267-270° C., and the (+)-enantiomer: flash point=263-265° C., [α]$_D$+ 6.5° (c=1.2, CHCl$_3$) are thus obtained.

Example 243

5-{[6-Chloro-2,5-dihydroxy-4,4-dimethyl-2-(trifluoromethyl)-1,2,3,4-tetrahydronaphthalen-1-yl]amino}-amino}-phthalazin-1-one Analogously to Example 3, 19 mg of the title compound is obtained starting from 20 mg of 5-{[6-chloro-4,4-dimethyl-5-methoxy-2-hydroxy-2-(trifluoromethyl)-1,2,3,4-tetrahydronaphthalen-1-yl]amino}-phthalazin-1-one with 0.13 ml of BBr$_3$ solution (1 M in dichloromethane) at 40° C.

$^1$H-NMR (DMSO): δ=1.43 (s, 1H), 1.56 (s, 3H), 1.91 (d, 1H), 2.01 (d, 1H), 5.33 (d, 1H), 6.00 (s, 1H), 6.44 (d, 1H), 6.65 (d, 1H), 7.12 (d, 1H), 7.18 (d, 1H), 7.36 (d, 1H), 7.49 (t, 1H), 8.52 (s, 1H), 9.02 (s, 1H), 12.46 (s, 1H)

Example 244

(−)-5-{[6-Chloro-2,5-dihydroxy-4,4-dimethyl-2-(trifluoromethyl)-1,2,3,4-tetrahydronaphthalen-1-yl]amino}-amino}-2-methylphthalazin-1-one Analogously to Example 3, 94 mg of the title compound is obtained starting from 100 mg of (−)-5-{[6-chloro-4,4-dimethyl-5-methoxy-2-hydroxy-2-(trifluoromethyl)-1,2,3,4-tetrahydronaphthalen-1-yl]amino}-phthalazin-1-one with 2.1 ml of BBr$_3$ solution (1 M in dichloromethane) in 1 ml of dichloromethane at 40° C.

$^1$H-NMR (DMSO): δ=1.43 (s, 1H), 1.56 (s, 3H), 1.91 (d, 1H), 2.01 (d, 1H), 5.33 (d, 1H), 6.00 (s, 1H), 6.44 (d, 1H), 6.65 (d, 1H), 7.12 (d, 1H), 7.18 (d, 1H), 7.36 (d, 1H), 7.49 (t, 1H), 8.52 (s, 1H), 9.02 (s, 1H), 12.46 (s, 1H)

Example 245

(+)-5-{[6-Chloro-2,5-dihydroxy-4,4-dimethyl-2-(trifluoromethyl)-1,2,3,4-tetrahydronaphthalen-1-yl]amino}-amino}-phthalazin-1-one Analogously to Example 3, 82 mg of the title compound is obtained starting from 100 mg of (+)-5-{[6-chloro-4,4-dimethyl-5-methoxy-2-hydroxy-2-(trifluoromethyl)-1,2,3,4-tetrahydronapthalen-1-yl]amino}-phthalazin-1-one with 2.1 ml of BBr$_3$ solution (1 M in dichloromethane) in 1 ml of dichloromethane at 40° C.

$^1$H-NMR (DMSO): δ=1.43 (s, 1H), 1.56 (s, 3H), 1.91 (d, 1H), 2.01 (d, 1H), 5.33 (d, 1H), 6.00 (s, 1H), 6.44 (d, 1H), 6.65 (d, 1H), 7.12 (d, 1H), 7.18 (d, 1H), 7.36 (d, 1H), 7.49 (t, 1H), 8.52 (s, 1H), 9.02 (s, 1H), 12.46 (s, 1H)

Example 246

5-{[2-Hydroxy-5-methoxy-2-(trifluoromethyl)-4,4,7-trimethyl-1,2,3,4-tetrahydronaphthalen-1-yl]amino}-phthalazin-1-one Analogously to Example 10, the corresponding imine is produced starting from 500 mg of 4-(2-methoxy-4-methylphenyl)-2-hydroxy-4-methyl-2-(trifluoromethyl)pentanal and 287 mg of 5-amino-phthalazin-1-one. As in Example 3, 320 mg of the imine is reacted by reaction with 7.2 ml of titanium tetrachloride (1 M in dichloromethane) in 20 ml of dichloromethane, and 80 mg of the title compound is obtained.

$^1$H-NMR (DMSO): δ=1.43 (s, 1H), 1.57 (s, 3H), 1.95 (d, 1H), 2.06 (d, 1H), 2.15 (s, 3H), 3.80 (s, 3H), 5.38 (d, 1H), 5.99 (s, 1H), 6.53 (d, 1H), 6.66 (s, 1H), 6.79 (s, 1H), 7.25 (d, 1H), 7.44 (d, 1H), 7.57 (t, 1H), 8.61 (s, 1H), 12.54 (s, 1H)

Examples 247 and 248

(−)-5-{[2-Hydroxy-5-methoxy-2-(trifluoromethyl)-4,4,7-trimethyl-1,2,3,4-tetrahydronaphthalen-1-yl]amino}-phthalazin-1-one and (+)-5-{[2-Hydroxy-5-methoxy-2-(trifluoromethyl)-4,4,7-trimethyl-1,2,3,4-tetrahydronaphthalen-1-yl]amino}-2-methylphthalazin-1-one Separation of (+/−)-5-{[6-chloro-4,4-dimethyl-5-methoxy-2-hydroxy-2-(trifluoromethyl)-1,2,3,4-tetrahydronaphthalen-1-yl]amino}-2-methylphthalazin-1-one The enantiomer mixture is separated with ethanol as an eluant by chromatography on chiral carrier material (CHIRALPAK AD®, DAICEL Company). The (−)-enantiomer: MS (EI): M$^+$=447, [α]$_D$=3.4° °(c=0.7, CHCl$_3$) and the (+)-enantiomer: MS (EI): M$^+$=447, [α]$_D$=3.7° °(c=1.1, CHCl$_3$) are thus obtained.

Example 249

5-{[2-Hydroxy-5-methoxy-2-(pentafluoroethyl)-4,4,7-trimethyl-1,2,3,4-tetrahydronaphthalen-1-yl]amino}-phthalazin-1-one Analogously to Example 10, the corresponding imine is produced starting from 250 mg of 4-(2-methoxy-4-methylphenyl)-2-hydroxy-4-methyl-2-(pentafluoroethyl)pentanal and 118 mg of 5-amino-phthalazin-1-one. As in Example 3, 65 mg of the imine is reacted by reaction with 0.38 ml of titanium tetrachloride (1 M in dichloromethane) in 6 ml of dichloromethane, and 8 mg of the title compound is obtained.

$^1$H-NMR (CD$_3$OD): δ=1.40 (s, 1H), 1.55 (s, 3H), 2.19 (d, 1H), 2.29 (d, 1H), 2.33 (s, 3H), 3.47 (s, 3H), 5.46 (s, 1H), 6.61 (s, 1H), 6.90 (s, 1H), 7.54-7.63 (m, 2H), 7.63-7.73 (m, 2H), 8.43 (s, 1H)

Example 250

5-{[6-Chloro-4,4-dimethyl-2-hydroxy-5-methoxy-2-(trifluoromethyl)-1,2,3,4-tetrahydronaphthalen-1-yl]amino}-8-fluoro-quinolin-2(1H)-one 5-Amino-8-fluoroquinolin-2(1H)-one 10 g of 2,5-difluoroaniline and 6 g of pyridine in 350 ml of dichloromethane are mixed drop by drop at 0° C. with 12.9 g of cinnamic acid chloride and stirred until conversion is completed at 0° C. The batch is added to 2N hydrochloric acid, and it is extracted with dichloromethane. It is washed with water, dried with sodium sulfate and concentrated by evaporation in a vacuum. The solid that is obtained is mixed with 11.1 g of aluminum chloride and heated for 8 hours to 150° C. After chromatography on silica gel, 2.9 g of 5,8-difluoroquinolin-2(1H)-one is obtained. The latter is reacted in 100 ml of ethylene glycol in the presence of 780 mg of copper(II) oxide for 20 hours at 200° C. in ammonia atmosphere at 60 bar. After chromatography on silica gel, in this case 5-amino-8-fluoroquinolin-2(1H)-one is obtained as fraction A and 2,5-diamino-8-fluoroquinoline is obtained as fraction B.

Fraction A: $^1$H-NMR (DMSO): δ=5.73 (s, 2H), 6.28 (dd, 1H), 6.35 (d, 1H), 7.07 (dd, 1H), 8.08 (dd, 1H), 11.31 (s, 1H).

Fraction B: $^1$H-NMR (DMSO): δ=5.36 (s, 2H), 6.23 (dd, 1H), 6.47 (s, 2H), 6.63 (d, 1H), 6.96 (dd, 1H), 8.07 (dd, 1H).

5-{[6-Chloro-4,4-dimethyl-2-hydroxy-5-methoxy-2-(trifluoromethyl)-1,2,3,4-tetrahydronaphthalen-1-yl]amino}-8-fluoro-quinolin-2(1H)-one Analogously to Example 10, the corresponding imine is produced starting from 250 g of 4-(3-chloro-2-methoxyphenyl)-2-hydroxy-4-methyl-2-(trifluoromethyl)pentanal and 137 mg of 5-amino-8-fluoroquinolin-2(1H)-one. The title compound is obtained analogously to Example 3 by reaction of the imine that is formed with 1.4 ml of titanium tetrachloride solution (1 M in dichloromethane).

$^1$H-NMR (CD$_3$OD): δ=1.53 (s, 3H), 1.67 (s, 3H), 2.22 (s, 2H), 3.96 (s, 3H), 5.14 (s, 1H), 6.51-6.61 (m, 2H), 7.09 (d, 1H), 7.20 (d, 1H), 7.24 (dd, 1H), 8.21 (dd, 1H).

Example 251

2-Amino-5-{[6-chloro-4,4-dimethyl-2-hydroxy-5-methoxy-2-(trifluoromethyl)-1,2,3,4-tetrahydronaphthlen-1-yl]amino}-8-fluoro-quinoline Analogously to Example 10, the corresponding imine is produced starting from 250 g of 4-(3-chloro-2-methoxyphenyl)-2-hydroxy-4-methyl-2-(trifluoromethyl)-pentanal and 137 mg of 2,5-diamino-8-fluoroquinoline. The title compound is obtained analogously to Example 3 by reaction of the imine that is formed with 1.0 ml of titanium tetrachloride solution (1 M in dichloromethane).

$^1$H-NMR (CD$_3$OD): δ=1.54 (s, 3H), 1.67 (s, 3H), 2.20 (s, 2H), 3.94 (s, 3H), 5.11 (s, 1 h), 6.43 (dd, 1H), 6.81 (d, 1H), 7.11 (d, 1H), 7.15 (d, 1H), 7.20 (d, 1H), 8.18 (dd, 1H).

Examples 252 and 253

5-{[4,4-Dimethyl-6-fluoro-2-hydroxy-5-methoxy-2-(trifluoromethyl)-1,2,3,4-tetrahydronaphthalen-1-yl]amino}-8-fluoro-quinolin-2(1H)-one and 2-Amino-5-{[4,4-dimethyl-6-fluoro-2-hydroxy-5-methoxy-2-(trifluoromethyl)-1,2,3,4-tetrahydronaphthalen-1-yl]amino}-8-fluoro-quinoline Analogously to Example 10, a mixture of the corresponding imines is produced starting from 237 g of 4-(3-fluoro-2-methoxyphenyl)-2-hydroxy-4-methyl-2-(trifluoromethyl)pentanal and 137 mg of a mixture that consists of 5-amino-8-fluoroquinolin-2(1H)-one and 2,5-diamino-8-fluoroquinoline. Analogously to Example 3, the mixture of imines with 2.5 ml of titanium tetrachloride solution (1 M in dichloromethane) is reacted, and the two title compounds are obtained after chromatography on silica gel.

Fraction A: $^1$H-NMR (CD$_3$OD): δ=1.53 (s, 3H), 1.65 (s, 3H), 2.08 (d, 1H), 2.23 (d, 1H), 3.95 (d, 3H), 5.11 (s, 1H), 6.50-6.61 (m, 2H), 6.98 (dd, 1H), 7.06 (dd, 1H) 7.23 (dd, 1H), 8.22 (dd, 1H).

Fraction B: $^1$H-NMR (CD$_3$OD): δ=1.52 (s, 3H), 1.66 (s, 3H), 2.08 (d, 1H), 2.15 (d, 1H), 3.95 (d, 1H), 5.09 (s, 1H), 6.40-6.57 (m, 2H), 6.82 (d, 1H), 6.94 (dd, 1H), 7.02-7.20 (m, 2H), 8.18 (t, 1H).

Example 254

5-{[7-Fluoro-3-hydroxy-8-methoxy-3-(trifluoromethyl)-3,4-dihydro-2H-spiro(cyclobutane-1,1'-naphthalen-4-yl]amino}-quinolin-2(1H)-one 3-{([3-Fluoro-2-methoxyphenyl)-cyclobutyl}-2-hydroxy-2-(trifluoromethyl)-pentanal Analogously to the synthesis of 4-(3-fluoro-2-methoxyphenyl)-2-hydroxy-4-methyl-2-(trifluoromethyl)-pentanal in Example 3, 3-{(3-fluoro-2-methoxyphenyl)-cyclobutyl}-2-hydroxy-2-(trifluoromethyl)-pentanal is obtained starting from 2,6-difluoroanisole and cyclobutanecarbonitrile.

$^1$H-NMR (CDCl$_3$): δ=1.75-1.90 (m, 1H), 2.10-2.40 (m, 3H), 2.46-2.57 (m, 2H), 2.83 (d, 1H), 3.00 (d, 1H), 3.94 (d, 3H), 6.75 (dt, 1H), 6.83-7.02 (m, 2H), 8.94 (s, 1H).

5-{[7-Fluoro-3-hydroxy-8-methoxy-3-(trifluoromethyl)-3,4-dihydro-2H-spiro(cyclobutane-1,1'-naphthalen-4-yl]amino}-quinolin-2(1H)-one Analogously to Example 10, the corresponding imine is produced starting from 350 g of 3-{(3-fluoro-2-methoxyphenyl)cyclobutyl}-2-hydroxy-2-(trifluoromethyl)pentanal and 200 mg of 5-amino-quinolin-2(1H)-one. Analogously to Example 3, the imine is reacted with 1.6 ml of titanium tetrachloride solution (1 M in dichloromethane, and 35 mg of the title compound is obtained.

$^1$H-NMR (CD$_3$OD): δ=2.10-2.29 (m, 4H), 2.40-2.56 (m, 1H), 2.65-2.80 (m, 2H), 2.93-3.06 (m, 1H), 4.09 (d, 3H), 5.14 (s, 1H), 6.49 (d, 1H), 6.63 (d, 1H), 6.70 (d, 1H), 6.97 (d, 2H), 8.20 (d, 1H).

Example 255

5-{[3,8-Dihydroxy-7-fluoro-3-(trifluoromethyl)-3,4-dihydro-2H-spiro(cyclobutane-1,1'-naphthalen-4-yl]amino}-quinolin-2(1H)-one Analogously to Example 3, 12 mg of the title compound is obtained starting from 20 mg of 5-{[7-fluoro-3-hydroxy-8-methoxy-3-(trifluoromethyl)-3,4-dihydro-2H-spiro(cyclobutane-1,1'-naphthalen-4-yl]amino}-quinolin-2(1H)-one with 0.22 ml of BBr$_3$ solution (1 M in dichloromethane) at room temperature.

$^1$H-NMR (CD$_3$OD): δ=1.81-1.94 (m, 1H), 2.08-2.27 (m, 3H), 2.28-2.41 (m, 1H), 2.75 (d, 1H), 3.08 (q, 1H), 3.44 (q, 1H), 5.13 (s, 1H), 6.48 (d, 1H), 6.63 (d, 1H), 6.68 (d, 1H), 6.73 (dd, 1H), 6.90 (dd, 1H), 7.37 (t, 1H), 8.20 (d, 1H).

Example 256

5-{[7-Fluoro-3-hydroxy-8-methoxy-3-(trifluoromethyl)-3,4-dihydro-2H-spiro(cyclopentane-1,1'-naphthalen-4-yl]amino}-quinolin-2(1H)-one 3-{([3-Fluoro-2-methoxyphenyl)-cyclopentyl}-2-hydroxy-2-(trifluoromethyl)-pentanal Analogously to the synthesis of 4-(3-fluoro-2-methoxyphenyl)-2-hydroxy-4-methyl-2-(trifluoromethyl)-pentanal in Example 3, 3-{(3-fluoro-2-methoxyphenyl)-cyclopentyl}-2-hydroxy-2-trifluoromethyl-pentanal starting from 2,6-difluoroanisole and cyclopentanecarbonitrile is obtained.

$^1$H-NMR (CD$_3$OD): δ=1.15-2.26 (m, 8H), 2.33 (d, 1H), 3.11 (d, 1H), 3.57 (s, 1H), 3.98 (d, 3H), 6.82-6.93 (m, 2H), 6.94-7.05 (m, 1H), 8.98 (s, 1H).

5-{[7-Fluoro-3-hydroxy-8-methoxy-3-(trifluoromethyl)-3,4-dihydro-2H-spiro(cyclopentane-1,1'-naphthalen-4-yl]amino}-quinolin-2(1H)-one Analogously to Example 10, the corresponding imine is produced starting from 350 g of 3-{(3-fluoro-2-methoxyphenyl)cyclobutyl}-2-hydroxy-2-(trifluoromethyl)-pentanal and 190 mg of 5-amino-quinolin-2(1H)-one. Analogously to Example 3, the imine is reacted with 5.25 ml of titanium tetrachloride solution (1 M in dichloromethane), and 193 mg of the title compound is obtained.

$^1$H-NMR (CDCl$_3$): δ=1.53-1.67 (m, 1H), 1.73-2.15 (m, 6H), 2.28-2.48 (m, 3H), 3.95 (d, 3H), 4.81 (bs, 1H), 5.06 (d, 1H), 5.55 (d, 1H), 6.47-6.58 (m, 3H), 6.82 (dd, 1H), 6.93 (dd, 1H), 7.32 (t, 1H), 8.18 (d, 1H).

Example 257

5-{[3,8-Dihydroxy-7-fluoro-3-(trifluoromethyl)-3,4-dihydro-2H-spiro(cyclopentane-1,1'-naphthalen-4-yl]amino}-quinolin-2(1H)-one Analogously to Example 3, 17 mg of the title compound is obtained starting from 60 mg of 5-{[7-fluoro-3-hydroxy-8-methoxy-3-(trifluoromethyl)-3,4-dihydro-2H-spiro(cyclopentane-1,1'-naphthalen-4-yl]amino}-quinolin-2(1H)-one with 0.25 ml of BBr$_3$ solution (1 M in dichloromethane) at room temperature.

$^1$H-NMR (CD$_3$OD): δ=1.45-1.57 (m, 1H), 1.72-1.88 (m, 2H), 1.90-2.12 (m, 3H), 2.18-2.43 (m, 3H), 2.70-2.85 (m, 1H), 5.18 (s, 1H), 6.51 (d, 1H), 6.63 (d, 1H), 6.70 (d, 1H), 6.78 (dd, 1H), 6.87 (dd, 1H), 7.38 (t, 1H), 8.22 (d, 1H).

Example 258

5-{[2,5-Dihydroxy-4,4-dimethyl-7-fluoro-2-(trifluoromethyl)-1,2,3,4-tetrahydronaphthalen-1-yl]amino}-2-methylphthalazin-1-one Analogously to Example 10, the corresponding imine is produced starting from 1.0 g of 4-(4-fluoro-2-methoxyphenyl)-2-hydroxy-4-methyl-2-(trifluoromethyl)pentanal and 560 mg of 5-amino-2-methylphthalazin-1-one. As in Example 3, the imine that is formed is reacted by reaction with 10 ml of boron tribromide solution (1 M in dichloromethane), and 45 mg of the title compound is obtained.

$^1$H-NMR (DMSO): δ=1.47 (s, 3H), 1.59 (s, 3H), 1.97 (d, 1H), 2.07 (d, 1H), 3.70 (s, 3H), 5.41 (s, 1H), 6.11 (s, 1H), 6.41 (dd, 1H), 6.56 (dd, 1H), 7.27 (d, 1H), 7.48 (d, 1H), 7.59 (t, 1H), 8.63 (s, 1H), 10.00 (s, 1H).

Examples 259 and 260

(−)-5-{[2,5-Dihydroxy-4,4-dimethyl-7-fluoro-2-(trifluoromethyl)-1,2,3,4-tetrahydronaphthalen-1-yl]amino}-2-methylphthalazin-1-one and (+)-5-{[2,5-Dihydroxy-4,4-dimethyl-7-fluoro-2-(trifluoromethyl)-1,2,3,4-tetrahydronaphthalen-1-yl]amino}-2-methylphthalazin-1-one Separation of (+/−)-5-{[2,5-dihydroxy-4,4-dimethyl-7-fluoro-2-(trifluoromethyl)-1,2,3,4-tetrahydronaphthalen-1-yl]amino}-2-methylphthalazin-1-one The enantiomer mixture is separated by chromatography on chiral carrier material (CHIRALPAK AD®, DAICEL Company) with hexane/ethanol (90:10, vvv). The
(−)-enantiomer: MS (EI): M$^+$=451, [α]$_D$−34.6° °(c=1.3, CHCl$_3$) and the
(+)-enantiomer: MS (EI): M$^+$=451, [α]$_D$+35.4° °(c=1.3, CHCl$_3$) are thus obtained.

Examples 261 and 262

5-{(7-Bromo-2,5-dihydroxy-4,4-dimethyl-2-(trifluoromethyl)-1,2,3,4-tetrahydronaphthalen-1-yl]amino}-2-methylphthalazin-1-one, Diastereomer B and 5-{(7-Bromo-2,5-dihydroxy-4,4-dimethyl-2-(trifluoromethyl)-1,2,3,4-tetrahydronaphthalen-1-yl]amino}-2-methylphthalazin-1-one, Diastereomer A Analogously to Example 10, the corresponding imine is produced starting from 800 mg of 4-(4-bromo-2-methoxyphenyl)-2-hydroxy-4-methyl-2-(trifluoromethyl)pentanal and 380 mg of 5-amino-2-methylphthalazin-1-one. As in Example 3, the imine that is formed is reacted by reaction with 9.4 ml of boron tribromide solution (1 M in dichloromethane), and 37 mg of diastereomer B of 5-{[7-bromo-2,5-dihydroxy-4,4-dimethyl-2-(trifluoromethyl)-1,2,3,4-tetrahydronaphthalen-1-yl]amino}-2-methylphthalazin-1-one is obtained as fraction A and 11 mg of diastereomer A of 5-{[7-bromo-2,5-dihydroxy-4,4-dimethyl-2-(trifluoromethyl)-1,2,3,4-tetrahydronaphthalen-1-yl]amino}-2-methylphthalazin-1-one is obtained as fraction B.

Fraction A: $^1$H-NMR (CD$_3$OD): δ=1.40 (s, 3H), 1.55 (s, 3H), 1.92 (d, 1H), 2.25 (d, 1H), 3.84 (s, 3H), 5.27 (s, 1H), 6.70 (d, 1H), 7.19-7.29 (m, 2H), 7.51 (t, 1H), 7.60 (d, 1H), 8.52 (s, 1H).

Fraction B: $^1$H-NMR (CD$_3$OD): δ=1.55 (s, 3H), 1.66 (s, 3H), 2.07 (d, 1H), 2.15 (d, 1H), 3.83 (s, 3H), 5.24 (s, 1H), 6.88 (d, 1H), 6.94 (d, 1H), 7.18-7.28 (m, 1H), 7.62-7.70 (m, 2H), 8.56 (s, 1H).

Example 263

5-{[7-Chloro-3,8-dihydroxy-3-(trifluoromethyl)-3,4-dihydro-2H-spiro(cyclohexane-1,1'-naphthalen-4-yl)]amino}-quinolin-2(1H)-one 3-[1-(3-Chloro-2-methoxyphenyl)-cyclohexyl]-2-hydroxy-2-(trifluoromethyl)propanal 9.57 g (30.79 mmol) of 3-[1-(3-chloro-2-methoxyphenyl)-cyclohexyl]-2-oxopropionic acid (this compound was produced starting from the corresponding starting materials, analogously to the instructions described in WO 98/54159) is mixed with 191 ml of ethanol and 3.4 ml of concentrated sulfuric acid. After five hours of refluxing, the batch is spun in until a dry state is reached, and the residue is mixed with 500 ml of saturated sodium bicarbonate solution. The aqueous phase is extracted three times with ethyl acetate, and the combined organic extracts are washed with brine. After the solvent is dried and spun off, the residue is chromatographed on silica gel (mobile solvent ethyl acetate/hexane). 7.07 g (67.8%) of the desired ester is obtained.

7.07 g (20.87 mmol) of ethyl-3-[1-(3-chloro-2-methoxyphenyl)-cyclohexyl]-2-oxopropionate is dissolved in 33 ml of tetrahydrofuran and mixed with 3.56 g (25.04 mmol) of (trifluoromethyl)-trimethylsilane. After 51.1 mg of tetrabutylammonium fluoride is added, the batch is stirred overnight. The reaction mixture is diluted with methyl tert-butyl ether, washed once with water and then with brine. After conventional working-up, the residue is chromatographed on silica gel (mobile solvent ethyl acetate/hexane). The isolated 5.71 g (60.4%) of the product is mixed in 70 ml of tetrahydrofuran with 3.98 g (12.61 mmol) of tetrabutylammonium fluoride and stirred for one hour at room temperature. After the reaction mixture is mixed with water, it is extracted with methyl tert-butyl ether. After conventional working-up, the residue is chromatographed on a Flashmaster. 2.63 g (51.1%) of the desired compound: ethyl-2-[1-(3-chloro-2-methoxyphenyl)-cyclohexylmethyl]-3,3,3-trifluoro-2-hydroxypropionate is isolated.

1.59 g (3.89 mmol) of the above-described ester is dissolved in 14 ml of diethyl ether and mixed at 0° C. in portions with 110.7 mg (2.92 mmol) of lithium aluminum hydride. After two hours of stirring between 0 and 5° C., 3.4 ml of saturated sodium bicarbonate solution is carefully added in drops. It is stirred vigorously for ten minutes at room temperature. After repeated extraction of the aqueous phase with methyl tert-butyl ether, the combined organic extracts are treated as usual. After chromatography on a Flashmaster, 750 mg (52.8%) of a mixture is obtained, which consists of the desired aldehyde in two thirds and consists of the ester in one third. In addition, 201.4 mg of the corresponding alcohol (COntaminated) is obtained.

5-{2-[1-(3-Chloro-2-methoxyphenyl)-cyclohexylmethyl]-3,3,3-trifluoro-2-hydroxypropylidenamino}-1H-quinolin-2-one 375 mg (0.683 mmol) of the aldehyde that is described in the paragraph above (together with the ester) is refluxed in 3.6 ml of xylene with 109.4 mg (0.683 mmol) of 5-amino-1H-quinolin-2-one and 388.3 mg (1.366 mmol) of titanium(IV)

isopropylate for three hours. After cooling, the reaction mixture is mixed with saturated sodium chloride solution and ethyl acetate. After ten minutes of vigorous stirring, the mixture is added to Extrelut and eluted with 100 ml of dichloromethane. After the solvent is spun off, the remaining residue is chromatographed on a Flashmaster. In addition to 145 mg of ester, 231.6 mg (66.9%, relative to the content of aldehyde) of the desired imine is isolated.

$^1$H-NMR (300 MHz, CDCl$_3$): δ=1.15-2.18 (9H), 2.38-2.65 (2H), 2.96 (1H), 3.93 (3H), 4.61 (1H), 6.40-6.60 (2H), 6.62-6.81 (2H), 7.08 (1H), 7.29-7.59 (3H), 8.07 (1H), 12.28 (1H).

5-{[7-Chloro-3-hydroxy-8-methoxy-3-(trifluoromethyl)-3,4-dihydro-2H-spiro(cyclohexane-1,1'-naphthalen-4-yl)]amino}-quinolin-2(1H)-one 151.6 mg (0.299 mmol) of the above-described imine is dissolved in 2.8 ml of dichloromethane. After the dropwise addition of 1.96 ml (1.796 mmol) of titanium tetrachloride at −15° C., it is stirred for four hours at this temperature. At 0° C., saturated sodium bicarbonate solution is carefully added, and the reaction mixture is extracted three times with ethyl acetate. The combined organic extracts are washed with brine, dried, and the solvent is spun off. After chromatography on a Flashmaster, 67.9 mg (44.8%) of the desired compound is obtained.

$^1$H-NMR (300 MHz, CD$_3$OD): δ=1.30-1.90 (8H), 2.18 (1H), 2.30-2.50 (1H), 2.53-2.70 (1H), 2.90 (1H), 4.00 (3H), 5.19 (1H), 6.52 (1H), 6.62 (1H), 6.70 (1H), 7.09 (1H), 7.23 (1H), 7.38 (1H), 8.23 (1H).

5-{[7-Chloro-3,8-dihydroxy-3-(trifluoromethyl)-3,4-dihydro-2H-spiro(cyclohexane-1,1'-naphthalen-4-yl)]amino}-quinolin-2(1H)-one 65.9 mg (0.13 mmol) of the cyclic ether that is described in the section above is mixed with 2.6 m of boron tribromide (1 M in dichloromethane) and stirred for three hours at room temperature. At −5° C., saturated sodium bicarbonate solution is carefully added in drops, and the reaction mixture is then extracted three times with ethyl acetate. The combined organic extracts are dried on sodium sulfate, and the residue that remains after the solvent is spun off is chromatographed on a Flashmaster. 51.3 mg (80.1%) of the desired phenol is isolated.

$^1$H-NMR (300 MHz, DMSO-d$_6$): δ=1.15-1.87 (8H), 2.01 (1H), 2.40-2.90 (3H, the DMSO signal is in this range), 5.29 (1H), 6.02 (1H), 6.20 (1H), 6.43 (1H), 6.48-6.65 (2H), 6.75 (1H), 7.15-7.30 (2H), 8.20 (1H), 9.10 (1H), 11.58 (1H).

Example 264

5-{[7-Chloro-3,8-dihydroxy-3-(trifluoromethyl)-3,4-dihydro-2H-spiro(cyclohexane-1,1'-naphthalen-4-yl)]amino}-2H-isoquinolin-1-one 5-{[7-Chloro-3-hydroxy-8-methoxy-3-(trifluoromethyl)-3,4-dihydro-2H-spiro(cyclohexane-1,1'-naphthalen-4-yl)]amino}-2H-isoquinolin-1-one 149.7 mg (0.295 mmol) of the imine (produced according to the instructions described in Example 263 with use of the corresponding starting materials) is cyclized with 1.93 ml (1.772 mmol) of titanium tetrachloride. After conventional working-up and chromatography, 34.9 m (23.3%) of the desired compound is obtained.

$^1$H-NMR (300 MHz, DMSO-d$_6$): δ=1.20-1.85 (8H), 2.05-2.50 (3H), 2.69 (1H), 3.93 (3H), 5.34 (1H), 5.98 (1H), 6.13 (1H), 6.80 (1H), 6.97 (1H), 7.05 (1H), 7.18 (1H), 7.20-7.38 (2H), 7.50 (1H), 11.25 (1H).

5-{[7-Chloro-3,8-dihydroxy-3-(trifluoromethyl)-3,4-dihydro-2H-spiro(cyclohexane-1,1'-naphthalen-4-yl)]amino}-2H-isoquinolin-1-one 26.8 mg (0.053 mmol) of the above-described ether is subjected to ether cleavage as described in Example 263. After carrying out the reaction in the usual way and after chromatography, 13.5 mg (51.8%) of the desired phenol is obtained.

$^1$H-NMR (300 MHz, DMSO-d$_6$): δ=1.15-1.85 (8H), 2.00 (1H), 2.40-2.90 (3H), 5.30 (1H), 5.95 (1H), 6.09 (1H), 6.73 (1H), 6.81 (1H), 7.04 (1H), 7.10-7.30 (3H), 7.50 (1H), 9.12 (1H), 11.23 (1H).

Example 265

7'-Chloro-4'-[(8-fluoro-2-methylquinazolin-5-yl)amino]-3',4'-dihydro-8'-methoxy-3'-(trifluoromethyl)-spiro[cyclohexane-1,1'(2'H)-naphthalen]-3'-ol 1.61 ml (1.488 mmol) of titanium(IV) chloride is added in drops at −20° C. to 129.8 mg (0.248 mmol) of the corresponding imine, dissolved in 2.4 ml of dichloromethane. After 1½ hours of stirring in a temperature range of between −20° C. and +5° C., the batch is worked up as usual. After chromatography on a Flashmaster, 11.4 mg (8.8%) of the desired compound is isolated.
MS (CI): 524 (100%)

Example 266

5-{[7-Chloro-3-hydroxy-8-methoxy-3-(trifluoromethyl)-3,4-dihydro-2H-spiro(cyclopropyl-1,1'-naphthalen-4-yl)]amino}-quinolin-2(1H)-one 3-[1-(3-Chloro-2-methoxyphenyl)-cyclopropyl]-2-hydroxy-2-(trifluoromethyl)propanal 15.12 g (56.27 mmol) of 3-[1-(3-chloro-2-methoxyphenyl)-cyclopropyl]-2-oxopropionic acid (this compound was produced starting from the corresponding starting materials, analogously to the instructions described in WO 98/54159) is mixed with 350 ml of ethanol and 6.3 ml of concentrated sulfuric acid. After five hours of refluxing, the batch is spun in until a dry state is reached, and the residue is mixed with 700 ml of saturated sodium bicarbonate solution. The aqueous phase is extracted three times with ethyl acetate, and the combined organic extracts are washed with sodium bicarbonate solution and brine. After the solvent is dried and spun off, the residue is chromatographed on silica gel (mobile solvent ethyl acetate/hexane). 12.36 g (74%) of the desired ester is obtained.

6.18 g (20.83 mmol) of ethyl-3-[1-(3-chloro-2-methoxyphenyl)-cyclopropyl]-2-oxopropionate is dissolved in 33 ml of tetrahydrofuran and mixed with 3.55 g (24.99 mmol) of (trifluoromethyl)-trimethylsilane. After 51 mg of tetrabutylammonium fluoride is added, the batch is stirred overnight. The reaction mixture is diluted with methyl tert-butyl ether, washed once with water and then with brine. After conventional working-up, the residue is chromatographed on silica gel (mobile solvent ethyl acetate/hexane). The isolated 5.65 g (66.4%) of product is mixed in 76 ml of tetrahydrofuran with 4.34 g (13.75 mmol) of tetrabutylammonium fluoride, and it is stirred for one hour at room temperature. After the reaction mixture is mixed with water, it is extracted with methyl tert-butyl ether. After conventional working-up, the residue is chromatographed on a Flashmaster. 2.39 g (47.4%) of the desired compound: ethyl-2-[1-(3-chloro-2-methoxyphenyl)-cyclopropylmethyl]-3,3,3-trifluoro-2-hydroxypropionate is isolated.

0.850 mg (2.32 mmol) of the above-described ester is dissolved in 8 ml of diethyl ether and mixed at 0° C. in portions with 66 mg (1.74 mmol) of lithium aluminum hydride. After two hours of stirring between 0 and 5° C., 2.7 ml of saturated sodium bicarbonate solution is carefully added in drops. It is stirred vigorously at room temperature for 10 minutes. After repeated extraction of the aqueous phase with methyl tert-butyl ether, the combined organic extracts are treated as usual. After chromatography on a Flashmaster, 490 mg (65.5%) of a mixture is obtained, which consists of just under two thirds of the desired aldehyde and one third of the ester.

5-{2-[1-(3-Chloro-2-methoxyphenyl)-cyclopropylm-ethyl]-3,3,3-trifluoro-2-hydroxy-propylidenamino}-1H-quinolin-2-one 490 mg (0.972 mmol) of the aldehyde that is described in the section above (as a mixture with the ester) is refluxed in 5.1 ml of xylene with 155.7 mg (0.972 mmol) of 5-amino-1H-quinolin-2-one and 552.6 mg (1.944 mmol) of titanium (IV) isopropylate for three hours. After cooling, the reaction mixture is mixed with saturated sodium chloride solution and ethyl acetate. After ten minutes of vigorous stirring, the mixture is added to Extrelut and eluted with 200 ml of dichloromethane. After the solvent is spun off, the remaining residue is chromatographed on a Flashmaster. In addition to 93.9 mg of ester, 312.8 mg (69.2%, relative to the aldehyde content), of the desired imine is isolated.

$^1$H-NMR (300 MHz, CDCl$_3$): δ=0.63-0.75 (1H), 0.79-0.90 (1H), 1.04-1.19 (2H), 2.10 (1H), 3.10 (1H), 4.00 (3H), 4.73 (1H), 6.74 (1H), 6.64 (1H), 6.75 (1H), 6.88-7.02 (2H), 7.29-7.43 (2H), 7.70 (1H), 8.10 (1H), 12.32 (1H).

5-{[7-Chloro-3-hydroxy-8-methoxy-3-(trifluorom-ethyl)-3,4-dihydro-2H-spiro(cyclopropane-1,1'-naph-thalen-4-yl)]amino}-quinolin-2(1H)-one 232.8 mg (0.501 mmol) of the above-described imine is dissolved in 4.7 ml of dichloromethane. After dropwise addition of 3.3 ml (3.009 mmol) of titanium tetrachloride at −20° C., it is stirred for four hours at this temperature. At 0° C., saturated sodium bicarbonate solution is carefully added, and the reaction mixture is extracted three times with ethyl acetate. The combined organic extracts are washed with brine, dried, and the solvent is spun off. After chromatography on a Flashmaster, 111.8 mg (48%) of the desired compound is obtained.

$^1$H-NMR (300 MHz, DMSO-d$_6$): δ=0.78-1.15 (3H), 1.78-2.09 (3H), 3.75 (3H), 5.06 (1H), 6.10-6.30 (3H), 6.45 (1H), 6.60 (1H), 6.98 (1H), 7.20 (1H), 7.30 (1H), 8.23 (1H), 11.60 (1H).

Example 267

5-{[7-Chloro-3,8-dihydroxy-3-(trifluoromethyl)-3,4-dihydro-2H-spiro(cyclopropane-1,1'-naphthalen-4-yl)]amino}-2H-isoquinolin-1-one 5-{[7-Chloro-3-hydroxy-8-methoxy-3-(trifluorom-ethyl)-3,4-dihydro-2H-spiro(cyclopropane-1,1'-naph-thalen-4-yl)]amino}-2H-isoquinolin-1-one 113.8 mg (0.245 mmol) of the imine (produced according to the instructions, described in Example 263, with use of the corresponding starting materials), dissolved in 2.3 ml of dichloromethane, is cyclized with 1.6 ml (1.472 mmol) of titanium tetrachloride. After conventional working-up and chromatography, 36.8 m (32.3%) of the desired compound is obtained.

$^1$H-NMR (400 MHz, DMSO-d$_6$): δ=0.80-1.12 (3H), 1.82-2.09 (3H), 3.76 (3H), 5.09 (1H), 5.95 (1H), 6.37 (1H), 6.68 (1H), 6.81 (1H), 6.96 (1H), 7.16-7.28 (2H), 7.30 (1H), 7.52 (1H), 11.30 (1H).

5-{[7-Chloro-3,8-dihydroxy-3-(trifluoromethyl)-3,4-dihydro-2H-spiro(cycloptopan-1,1'-naphthalen-4-yl)]amino}-2H-isoquinolin-1-one 22.7 mg (0.049 mmol) of the above-described ether is subject to ether cleavage as described in Example 263. After carrying out the reaction in the usual way and after chromatography, 10.9 mg (45.5%) of the desired phenol is obtained.

$^1$H-NMR (400 MHz, CD$_3$OD): δ=0.55-0.63 (1H), 0.73-0.84 (1H), 1.40-1.51 (1H), 1.80 (1H), 1.95-2.10 (2H), 5.02 (1H), 6.69 (1H), 6.75 (1H), 6.80 (1H), 6.98 (1H), 7.08 (1H), 7.25 (1H), 7.59 (1H).

Example 268

7'-Chloro-4'-[(8-fluoro-2-methylquinazolin-5-yl) amino]-3',4'-dihydro-3'-(trifluoromethyl)spiro[cyclo-propane-1,1° (2'H)-naphthalene]-3',8'-diol 7'-Chloro-4'-[(8-fluoro-2-methylquinazolin-5-yl) amino]-3',4'-dihydro-8'-methoxy-3'-(trifluorom-ethyl)-spiro[cyclopropane-1,1'(2'H)-naphthalen]-3'-ol 1.64 ml (1.512 mmol) of titanium(IV) chloride is added in drops at −20° C. to 121.3 mg (0.252 mmol) of the corresponding imine, dissolved in 2.4 ml of dichloromethane. After 1½ hours of stirring in a temperature range of between −20° C. and +5° C., the batch is worked up as usual. After chromatography on a Flashmaster, 7.4 mg (6.1%) of the desired compound (slightly contaminated) is isolated.

$^1$H-NMR (400 MHz, CDCl$_3$): δ=0.84-1.10 (3H), 1.92-2.13 (3H), 2.82 (3H), 3.79 (3H), 4.90 (1H), 5.65 (1H), 6.34 (1H), 7.00 (1H), 7.16 (1H), 7.37 (1H), 9.35 (1H).

7'-Chloro-4'-[(8-fluoro-2-methylquinazolin-5-yl) amino]-3',4'-dihydro-3'-(trifluoromethyl)spiro[cyclo-propane-1,1'(2'H)-naphthalene]-3',8'-diol 40 mg (0.083 mmol) of the corresponding imine is mixed at 0° C. with 1.1 ml of a 1 M solution of boron tribromide in dichloromethane. After ¾ hour of stirring at this temperature, saturated sodium bicarbonate solution is carefully added in drops, and the reaction mixture is then extracted three times with ethyl acetate. The combined organic extracts are washed with brine, dried, and the solvent is spun off. After chromatography on a Flashmaster, 15 mg (38.6%) of the desired phenol is obtained.

MS (CI): 468 (100%)

Example 269

[6-Hydroxy-1-methoxy-8,8-dimethyl-5-(2-oxo-1,2-dihydroquinolin-5-ylamino)-6-(trifluoromethyl)-5,6,7,8-tetrahydronaphthalen-2-yl]-acetonitrile Methyl-2-methoxy-3-methylbenzoate (RS 2690 F2)

199.9 g (1.45 mol) of potassium carbonate is introduced into 1.5 l of dimethylformamide. At room temperature, 100 g (657.29 mol) of 2-hydroxy-3-methylbenzoic acid, dissolved in 250 ml of dimethylformamide, is added in drops. After 30 minutes of stirring, 90 ml of methyl iodide is added in drops, and the batch is stirred overnight. The reaction mixture is added to ice water and extracted three times with methyl tert-butyl ether. The organic phases are washed with water and brine. After drying, the solvent is spun off, and the residue is chromatographed on silica gel (mobile solvent ethyl acetate/hexane). 70.21 g (59.3%) of the desired compound is isolated.

$^1$H-NMR (300 MHz, CDCl$_3$): δ=2.32 (3H), 3.85 (3H), 3.93 (3H), 7.07 (1H), 7.35 (1H), 7.65 (1H).

2-(2-Methoxy-3-methylphenyl)-propan-2-ol 70.21 g (389.64 mmol) of methyl-2-methoxy-3-methylbenzoate, dissolved in 640 ml of tetrahydrofuran, is added in drops to 311.7 ml of methylmagnesium bromide in diethyl ether (3M). In this case, the reaction mixture is heated to about 48° C. The batch is stirred for three hours at room temperature. About 1.5 l of saturated ammonium chloride solution is now added in drops while being cooled in an ice bath, and it is stirred vigorously for one hour. After 3× extraction with methyl tert-butyl ether, the combined organic extracts are washed with brine, dried, and the solvent is spun off. 71.37 g (>100%) of the desired compound, which is further incorporated in crude form, is isolated.

$^1$H-NMR (300 MHz, CDCl$_3$): δ=1.65 (6H), 2.33 (3H), 3.89 (3H), 4.55 (1H), 6.99 (1H), 7.10 (1H), 7.18 (1H).

Ethyl-4-(2-methoxy-3-methylphenyl)-4-methyl-2-oxopentanoate 71.37 g (395.96 mmol) of 2-(2-methoxy-3-methylphenyl)-propan-2-ol and 149 g (791.92 mmol) of 2-trimethylsilanyloxyacrylic acid ethyl ester are introduced into 1.1 l of dichloromethane. At −78° C., 44.8 ml (379.91 mmol) of tin tetrachloride is added in drops, and the batch is then stirred for three hours at this low temperature. 1.4 l of semiconcentrated potassium carbonate solution is carefully added in drops, and the reaction mixture is thus brought to room temperature. The batch is filtered, and the filtrate is extracted three times with ethyl acetate. The combined organic extracts are washed with brine, dried on sodium sulfate, and the solvent is spun off. The residue is chromatographed several times on silica gel (mobile solvent ethyl acetate/hexane). 45.81 g (41.6%) of the desired compound is isolated.

$^1$H-NMR (300 MHz, CDCl$_3$): δ=1.30 (3H), 1.50 (6H), 2.30 (3H), 3.39 (2H), 3.78 (3H), 4.17 (2H), 6.97 (1H), 7.07 (1H), 7.15 (1H).

Ethyl-2-hydroxy-4-(2-methoxy-3-methylphenyl)-4-methyl-2-(trifluoromethyl)pentanoate 20 g (71.90) of ethyl-4-(2-methoxy-3-methylphenyl)-4-methyl-2-oxopentanoate and 12.3 g (86.28 mmol) of trifluoromethyl)trimethylsilane are introduced into 117 ml of tetrahydrofuran. At room temperature, 180 mg of tetrabutylammonium fluoride is added (heating to about 35° C.). After stirring overnight, 22.7 g (71.90 mmol) of tetrabutylammonium fluoride is added, and the batch is stirred for three hours at room temperature. After dilution with methyl tert-butyl ether, the organic phase is washed three times with water and once with brine. After the solvent is dried and spun off, the residue is chromatographed on silica gel (mobile solvent ethyl acetate/hexane). 16.33 g (65.2%) of the desired compound is isolated.

$^1$H-NMR (300 MHz, CDCl$_3$): δ=1.19 (3H), 1.43 (3H), 1.49 (3H), 2.30-2.44 (4H), 2.82 (1H), 3.50-3.68 (2H), 3.84 (3H), 4.00-4.13 (2H), 6.92 (1H), 7.00-7.10 (2H).

4-(2-Methoxy-3-methylphenyl)-4-methyl-(trifluoromethyl)-pentane-1,2-diol 16.33 g (46.88 mmol) of the above-described ester is dissolved in 160 ml of diethyl ether and mixed at 0° C. in portions with 3.56 g (93.76 mmol) of lithium aluminum hydride. After stirring over a weekend at room temperature, saturated sodium bicarbonate solution is carefully added in drops and then stirred vigorously for one hour. After 3× extraction with methyl tert-butyl ether, the combined organic extracts are washed with brine, dried, and the residue is chromatographed on silica gel after the solvent is spun off (mobile solvent ethyl acetate/hexane). 10.76 g (74.9%) of the desired diol is isolated.

$^1$H-NMR (300 MHz, CDCl$_3$): δ=1.49 (3H), 1.58 (3H), 1.84 (1H), 2.24 (1H), 2.36 (3H), 2.59 (1H), 2.88 (1H), 3.28-3.40 (2H), 3.88 (3H), 6.99 (1H), 7.10 (1H), 7.20 (2H).

4-(3-Bromomethyl-2-methoxyphenyl)-4-methyl-2-(trifluoromethyl)pentane-1,2-diol 3 g (9.79 mmol) of 4-(2-methoxy-3-methylphenyl)-4-methyl-(trifluoromethyl)-pentane-1,2-diol is dissolved in 22 ml of carbon tetrachloride, mixed with 1.91 g (10.60 mmol) of NBS and 5 mg of benzoyl peroxide and refluxed for 24 hours. After the succinimide is filtered off through a glass-fiber filter, it is rewashed with dichloromethane, and the solvent is spun off. The residue (5.42 g>100%) is incorporated in crude form into the next stage.

[2-Methoxy-3-(4,4,4-trifluoro-3-hydroxy-3-hydroxymethyl-1,1-dimethylbutyl)phenyl]acetonitrile 5.42 g (14.07 mmol) of the above-described bromine compound is mixed in a mixture that consists of dimethylformamide and water (14 and 10.5 ml) with 1.37 g (14.07 mmol) of potassium cyanide and stirred overnight at room temperature. The reaction mixture is mixed with water and extracted three times with methyl tert-butyl ether. The combined organic phases are washed with brine, and the solvent is spun off after drying. 2.6 g (55.8%) of the desired compound is obtained after chromatography on a Flashmaster.

$^1$H-NMR (300 MHz, CDCl$_3$): δ=1.49 (3H), 1.60 (3H), 1.72 (1H), 2.22 (1H), 2.50 (1H), 2.92 (1H), 3.20-3.45 (2H), 3.80 (2H), 3.88 (3H), 7.13 (1H), 7.30-7.42 (2H).

[2-Methoxy-3-(4,4,4-trifluoro-3-hydroxy-3-formyl-1,1-dimethylbutyl)phenyl]acetonitrile 0.26 ml (2.99 mmol) of oxalyl chloride is cooled in 6.6 ml of dichloromethane to −78° C. After dropwise addition of 0.42 ml (5.98 mmol) of dimethyl sulfoxide, dissolved in 1.2 ml of dichloromethane, it is stirred for 10 more minutes and then 900 mg (2.72 mmol) of [2-methoxy-3-(4,4,4-trifluoro-3-hydroxy-3-hydroxymethyl-1,1-dimethylbutyl)phenyl]acetonitrile in 2.6 ml of dichloromethane is added in drops. After two hours of stirring at −78° C., 1.88 ml (13.58 mmol) of triethylamine is added in drops, the batch is allowed to come to room temperature, and then it is stirred for 1½ hours at room temperature. After mixing with water, it is extracted three times with dichloromethane. The combined organic extracts are washed with 1% sulfuric acid, with saturated sodium bicarbonate solution and with brine. After the solvent is dried and spun off, the residue is chromatographed on a Flashmaster. 599.4 mg (67.1%) of the desired aldehyde remains.

$^1$H-NMR (300 MHz, CDCl$_3$): δ=1.45 (3H), 1.51 (3H), 2.32 (1H), 3.20 (1H), 3.51 (1H), 3.78 (2H), 3.89 (3H), 7.09 (1H), 7.19 (1H), 7.35 (1H), 9.06 (1H).

{2-Methoxy-3-(4,4,4-trifluoro-3-hydroxy-1,1-dimethyl-3-[(2-oxo-1,2-dihydroquinolin-5-ylimino)-methyl]-butyl)-phenyl}acetonitrile 200 mg (0.607 mmol) of the above-described aldehyde in 3.4 ml of xylene is refluxed for three hours with 97.3 mg (0.607 mmol) of 5-amino-1H-quinolin-2-one and 345.1 mg (1.214 mmol) of titanium(IV) isopropylate for three hours. After the reaction is completed, brine solution and ethyl acetate are added. After 30 minutes of vigorous stirring at room temperature, the batch is added to Extrelut and eluted with 200 ml of dichloromethane. After the solvent is spun off, the residue is chromatographed on a Flashmaster. 228.7 mg (79.8%) of the desired imine is isolated.

$^1$H-NMR (300 MHz, CDCl$_3$): δ=1.45 (3H), 1.59 (3H), 2.38 (1H), 3.26 (1H), 3.34-3.55 (2H), 3.85 (3H), 4.66 (1H), 6.29 (1H), 6.69-6.80 (2H), 6.90 (1H), 7.16 (1H), 7.30-7.47 (2H), 7.51 (1H), 7.97 (1H), 12.18 (1H).

6-Hydroxy-1-methoxy-8,8-dimethyl-5-(2-oxo-1,2-dihydroquinolin-5-ylamino)-6-(trifluoromethyl)-5,6,7,8-tetrahydronaphthalen-2-yl]-acetonitrile 141.2 mg (0.299 mmol) of imine is mixed at 0° C. with 4.5 ml of a 1 M solution of boron tribromide in dichloromethane, and it is stirred for four hours. After the dropwise addition of saturated sodium bicarbonate solution, it is extracted three times with ethyl acetate. The combined organic extracts are washed with brine. After the solvent is dried and spun off, the residue is chromatographed on a Flashmaster. 8 mg (5.8%) of the desired compound is isolated.

$^1$H-NMR (300 MHz, CDCl$_3$): δ=1.52 (3H), 1.70 (3H), 2.05 (1H), 2.19 (1H), 3.69 (2H), 3.79 (3H), 5.00-5.16 (2H), 5.64 (1H), 6.38 (1H), 6.50 (1H), 6.62 (1H), 7.05-7.19 (2H), 7.30 (1H), 8.15 (1H), 10.76 (1H).

Example 270

[5-(8-Fluoro-2-methylquinazolin-5-ylamino)-6-hydroxy-1-methoxy-8,8-dimethyl-6-(trifluoromethyl)-5,6,7,8-tetrahydronaphthalen-2-yl]-acetonitrile {2-Methoxy-3-[4,4,4-trifluoro-3-(8-fluoro-2-methylquinazolin-5yl-iminomethyl)-3-hydroxy-1,1-dimethylbutyl]phenyl}acetonitrile 200 mg (0.61 mmol) of the aldehyde that is described in Example 269 is refluxed with 107.5 mg (0.61 mmol) of 5-amino-8-fluoro-2-methylquinazoline and 345.1 mg (1.214 mmol) of titanium tetrachloride in 3.4 ml of xylene for 3 hours. After conventional working-up and chromatography, 129.5 mg (43.7%) of the desired imine is isolated.

$^1$H-NMR (300 MHz, CDCl$_3$): δ=1.41 (3H), 1.67 (3H), 2.35 (1H), 2.99 (3H), 3.35 (1H), 3.38-3.56 (2H), 3.85 (3H), 4.16 (1H), 6.50-6.60 (2H), 6.75 (1H), 7.17 (1H), 7.45 (1H), 7.55 (1H), 9.47 (1H).

[5-(8-Fluoro-2-methylquinazolin-5-ylamino)-6-hydroxy-1-methoxy-8,8-dimethyl-6-(trifluoromethyl)-5,6,7,8-tetrahydronaphthalen-2-yl]-acetonitrile 100.9 mg (0.21 mmol) of the above-described imine is cyclized and worked up as usual with 3.1 ml of a 1 M solution of boron tribromide in dichloromethane at 0° C. After chromatography on a Flashmaster and subsequent plate separation, 7.5 mg (7.7%) of the desired compound is isolated.

$^1$H-NMR (300 MHz, CDCl$_3$): δ=1.58 (3H), 1.74 (3H), 2.09-2.28 (2H), 2.95 (3H), 3.78 (2H), 3.83 (3H), 5.02 (1H), 5.30 (1H), 5.61 (1H), 6.69 (1H), 7.18-7.32 (2H), 7.50 (1H), 9.38 (1H).

Example 271

1-(7-Fluoro-2-methylquinazolin-5-ylamino)-5-methoxy-4,4,6-trimethyl-2-(trifluoromethyl)-1,2,3,4-tetrahydronaphthalen-2-ol 2-Hydroxy-4-(2-methoxy-3-methylphenyl)-4-methyl-2-(trifluoromethyl)pentanal 2 g (6.53 mmol) of the 4-(2-methoxy-3-methylphenyl)-4-methyl-(trifluoromethyl)-pentane-1,2-diol that is described in Example 269 is oxidized to aldehyde according to Swern analogously to the description in this example. After conventional working-up and purification on a Flashmaster, 1.20 g (60.3%) of the desired aldehyde is isolated.

$^1$H-NMR (300 MHz, CDCl$_3$): δ=1.46 (3H), 1.50 (3H), 2.23 (1H), 2.32 (3H), 3.38 (1H), 3.60 (1H), 3.85 (3H), 6.93 (1H), 7.00 (1H), 7.10 (1H), 8.95 (1H).

1,1,1-Trifluoro-2-[(7-fluoro-2-methylquinazolin-5-ylimino)-methyl]-4-(2-methoxy-3-methylphenyl)-4-methylpentan-2-ol 150 mg (0.493 mmol) of the described aldehyde is reacted as usual and as already described several times with 87.3 mg (0.498 mmol) of 5-amino-7-fluoro-2-methylquinazoline and 280.3 mg (0.986 mmol) of titanium tetraisopropylate in 2.5 ml of xylene to form imine. After chromatography, 174.9 mg (76.6%) of the desired compound is isolated.

$^1$H-NMR (300 MHz, CDCl$_3$): δ=1.41 (3H), 1.65 (3H), 2.01 (3H), 2.29 (1H), 2.90 (3H), 3.49 (1H), 3.80 (3H), 4.55 (1H), 6.19 (1H), 6.50-6.60 (2H), 7.03 (1H), 7.40 (1H), 7.62 (1H), 9.30 (1H).

1-(7-Fluoro-2-methylquinazolin-5-ylamino)-5-methoxy-4,4,6-trimethyl-2-(trifluoromethyl)-1,2,3,4-tetrahydronaphthalen-2-ol 174.9 mg (0.377 mmol) of the above-described imine is cyclized at 0° C. with titanium tetrachloride in dichloromethane. The execution, working-up and chromatography are carried out as already described several times. 159.7 mg (91.3%) of the desired compound is isolated as a diastereomer mixture at a 9:1 ratio (the NMR data relative to the main diastereomer).

$^1$H-NMR (300 MHz, CDCl$_3$): δ=1.59 (3H), 1.73 (3H), 2.10-2.28 (2H), 2.32 (3H), 2.86 (3H), 3.81 (3H), 4.99 (1H), 6.05 (1H), 6.10 (broad, 1H), 6.52 (1H), 6.89 (1H), 6.95-7.16 (2H), 9.20 (1H).

Example 272

1-(7,8-Difluoro-2-methylquinazolin-5-ylamino)-5-methoxy-4,4,6-trimethyl-2-(trifluoromethyl)-1,2,3,4-tetrahydronaphthalen-2-ol 1,1,1-Trifluoro-2-[(7,8-difluoro-2-methylquinazolin-5-ylimino)-methyl]-4-(2-methoxy-3-methylphenyl)-4-methylpentan-2-ol 150 mg (0.493 mmol) of the described aldehyde is reacted as usual and as already described several times with 96.2 mg (0.493 mmol) of 5-amino-7,8-difluoro-2-methylquinazoline and 280.3 mg (0.986 mmol) of titanium tetraisopropylate in 2.5 ml of xylene to form imine. After chromatography, 155.5 mg (65.5%) of the desired compound is isolated.
$^1$H-NMR (300 MHz, CDCl$_3$): δ=1.40 (3H), 1.63 (3H), 2.07 (3H), 2.28 (1H), 2.98 (3H), 3.50 (1H), 3.83 (3H), 4.49 (1H), 6.28 (1H), 6.52-6.62 (2H), 7.03 (1H), 7.62 (1H), 9.36 (1H).

1-(7,8-Difluoro-2-methylquinazolin-5-ylamino)-5-methoxy-4,4,6-trimethyl-2-(trifluoromethyl)-1,2,3,4-tetrahydronaphthalen-2-ol 155.5 mg (0.323 mmol) of the above-described imine is cyclized with titanium tetrachloride in dichloromethane at 0° C. The execution, working-up and chromatography are carried out as already described several times. 101.6 mg (65.3%) of the desired compound is isolated.
$^1$H-NMR (300 MHz, CDCl$_3$): δ=1.60 (3H), 1.73 (3H), 2.08-2.28 (2H), 2.32 (3H), 2.93 (3H), 3.81 (3H), 4.93 (1H), 5.42 (1H), 5.81 (1H), 6.58 (1H), 6.95-7.09 (2H), 9.24 (1H).

Example 273

5-[2,6-Dihydroxy-4,4-dimethyl-2-(trifluoromethyl)-1,2,3,4-tetrahydronaphthalen-1-ylamino]-2-methyl-2H-phthalazin-1-one 2-(3-Methoxyphenyl)-2-methylpropanenitrile 50 g (339.72 mmol) of 3-methoxybenzylcyanide is dissolved in 530 ml of DMF and mixed with 96.4 g (6792.4 mmol) of methyl iodide. After cooling to 0° C., 21.5 g (492.2 mmol) of NaH (55% suspension) is added in portions to the reaction mixture within four hours. After 18 hours at room temperature, the batch is poured into 700 ml of ice water and extracted three times with 500 ml each of diethyl ether. The combined organic phases are washed with water and brine. After drying on sodium sulfate, the desiccant is filtered off, and the solvent is spun off in a rotary evaporator. After chromatography on silica gel (mobile solvent ethyl acetate/hexane), 48.9 g (82.2%) of the desired compound is obtained.
$^1$H-NMR (300 MHz, CDCl$_3$): δ=1.73 (6H), 3.85 (3H), 6.85 (1H), 7.02 (1H), 7.07 (1H), 7.31 (1H).

2-(3-Methoxyphenyl)-2-methylpropanal 25 g (142.67 mmol) of the above-described nitrile is dissolved in 570 ml of toluene. At −65 to −60° C., 178 ml of a 1.2 molar solution of DIBAH in toluene is added in drops within 75 minutes. After two hours of stirring at this temperature, 815 ml of a 20% L-(+)-tartaric acid solution is begun to be added in drops. After 150 milliliters, the temperature is increased to −10° C. The remainder of the tartaric acid solution is quickly added, and the batch is stirred vigorously for 16 hours at room temperature. The reaction mixture is shaken twice with 600 ml each of diethyl ether. The combined organic extracts are shaken with water and brine, dried, and the solvent is spun off. The residue that is obtained (25.1 g=98.8%) is incorporated in crude form into the next stage.
$^1$H-NMR (300 MHz, CDCl$_3$): δ=1.47 (6H), 3.83 (3H), 6.78-6.90 (3H), 7.30 (1H), 9.50 (1H).

Ethyl-E-4-(3-methoxyphenyl)-4-methylpent-2-enoate 33.6 g (114.3 mmol) of phosphonoacetic acid triethyl ester is introduced into 148 ml of tetrahydrofuran. At 0° C., 79.7 ml of a 2 M solution of LDA in THF/heptane/ethylbenzene is added in drops (1½ hours). After one hour of stirring, 24.3 g (136.34 mmol) of 2-(3-methoxyphenyl)-2-methylpropanal, dissolved in 130 ml of tetrahydrofuran, is added in drops at 0° C. After five days of stirring at room temperature, the reaction mixture is poured into 250 ml of dilute ammonium chloride solution and extracted twice with 400 ml each of diethyl ether. The combined organic extracts are treated as usual, and the residue that is obtained is chromatographed on silica gel (mobile solvent ethyl acetate/hexane). 27.2 g (80.4%) of the desired compound is isolated.
$^1$H-NMR (300 MHz, CDCl$_3$): δ=1.30 (3H), 1.49 (6H), 3.81 (3H), 4.20 (2H), 5.80 (1H), 6.78 (1H), 6.85 (1H), 6.90 (1H), 7.12 (1H), 7.25 (1H).

Ethyl-4-(3-methoxyphenyl)-4-methylpentanoate 27.2 g (109.5 mmol) of ethyl-E-4-(3-methoxyphenyl)-4-methylpent-2-enoate is mixed in 293 ml of ethyl acetate with 2.72 g of palladium on carbon (10%) and stirred under hydrogen atmosphere for 18 hours at room temperature. The catalyst is removed by filtration through a glass-fiber filter, and the residue that remains after the concentration by evaporation (27.2 g=99.2%) is incorporated in crude form into the next stage.
$^1$H-NMR (300 MHz, CDCl$_3$): δ=1.21 (3H), 1.32 (6H), 1.90-2.10 (4H), 3.82 (3H), 4.05 (2H), 6.74 (1H), 6.89 (1H), 6.93 (1H), 7.25 (1H).

Ethyl-4-(3-methoxyphenyl)-2-hydroxy-4-methylpentanoate 27.2 g (108.65 mmol) of ethyl-4-(3-methoxyphenyl)-4-methylpentanoate is dissolved in 380 ml of tetrahydrofuran, and the reaction mixture is cooled to −70° C. to −65° C. Within two hours, 304 ml of a 0.5 molar solution of potassium-bis-(trimethylsilylamide) in toluene is added in drops, and the reaction mixture is then stirred for 75 more minutes at −70° C. 39.7 g (152.11 mmol) of Davis reagent, dissolved in 380 ml of tetrahydrofuran, is now added in drops within 90 minutes. After two hours of stirring at −70° C., 195 ml of saturated ammonium chloride solution is slowly added in drops, the cold bath is removed and it is stirred vigorously for thirty minutes. After extraction with diethyl ether (twice with 800 ml each), the combined organic extracts are treated as usual with water and brine. After the solvent is spun off, the residue is chromatographed on silica gel (mobile solvent ethyl acetate/hexane). 20.9 g (72.4%) of the desired compound is isolated.
$^1$H-NMR (300 MHz, CDCl$_3$): δ=1.29 (3H), 1.40 (3H), 1.48 (3H), 1.85 (1H), 2.20 (1H), 2.50 (1H), 3.81 (3H), 3.99 (1H), 4.18 (2H), 6.76 (1H), 6.95 (1H), 7.00 (1H), 7.28 (1H).

Ethyl-4-(3-methoxyphenyl)-4-methyl-2-oxopentanoate 2019 g (78.47 mmol) of ethyl 4-(3-methoxyphenyl)-2-hydroxy-4-methyl-pentanoate is dissolved in 820 ml of dichloromethane and mixed with 273 ml of dimethyl sulfoxide. After 39.7 g (392.36 mmol) of triethylamine is added, the batch is mixed in portions with 31.2 g (196.18 mmol) of $SO_3$/pyridine complex and then stirred for 16 hours at room temperature. About 400 ml of dichloromethane is drawn off in a rotary evaporator. Then, the reaction mixture is mixed with 312 ml of saturated ammonium chloride solution while being cooled slightly, and it is stirred vigorously for 20 minutes. After 2× extraction with diethyl ether (800 ml each), the combined organic phases are washed with water and brine. The residue that remains after the solvent is spun off is chromatographed on silica gel (mobile solvent ethyl acetate/hexane). 15.59 g (75.3%) of the desired compound is isolated.

$^1$H-NMR (300 MHz, CDCl$_3$): δ=1.28 (3H), 1.48 (6H), 3.18 (2H), 3.80 (3H), 4.12 (2H), 6.74 (1H), 6.90 (1H), 6.95 (1H), 7.25 (1H).

Ethyl-4-(3-methoxyphenyl)-4-methyl-2-(trifluoromethyl)-2-(trimethylsilyloxy)-pentanoate 15.59 g (58.98 mmol) of ethyl-4-(3-methoxyphenyl)-4-methyl-2-oxopentanoate is dissolved in 96 ml of tetrahydrofuran and mixed at 0° C. with 10.1 g (70.78 mmol) of (trifluoromethyl)-trimethylsilane. After 144.5 mg of tetrabutylammonium fluoride is added, it is stirred for 2¾ hours at 0 to 5° C. The batch is added to 150 ml of ice water, extracted twice with diethyl ether (300 ml each), and the combined organic extracts are treated as usual. After the solvent is spun off, the residue is chromatographed on silica gel (mobile solvent ethyl acetate/hexane). 17.10 g (71.3%) of the desired product (COntaminated) is isolated, which is incorporated in crude form into the next stage.

4-(3-Methoxyphenyl)-2-(trifluoromethyl)-pentane-1,2-diol 6.77 g (16.65 mmol) of (rac.) ethyl-4-(3-methoxyphenyl)-4-methyl-2-(trifluoromethyl)-2-(trimethylsilyloxy)-pentanoate is dissolved in 61 ml of diethyl ether and mixed at 0° C. in portions with 1.26 g (33.31 mmol) of lithium aluminum hydride. The reaction mixture is stirred for one hour at 5° C. and for 1½ hours at room temperature. For hydrolysis, the mixture is mixed drop by drop with 30 ml of saturated NaHCO$_3$ solution while being cooled in an ice bath. It is vigorously stirred for one hour while being cooled in an ice bath and overnight at room temperature. The precipitate is suctioned off and washed with diethyl ether. The filtrate is concentrated by evaporation in a rotary evaporator, and the residue is chromatographed on silica gel (mobile solvent ethyl acetate/hexane). 5.64 g (71.2%) of a mixture in which the trimethylsilyl group sits in part on the primary hydroxyl group and in part on the secondary hydroxyl group is isolated. The mixture (5.64 g) is therefore dissolved in 72 ml of tetrahydrofuran without further purification and mixed with 4 g (12.79 mmol) of tetrabutylammonium fluoride trihydrate, and it is stirred for 90 minutes at room temperature. The reaction mixture is diluted with water and extracted twice with 150 ml each of diethyl ether. After the combined organic phases are washed with water and brine, the solvent is dried and spun off. The crude product (5.8 g) is chromatographed together with another produced batch (7.97 g of feedstock; 10.4 g of yield of crude product) on silica gel (mobile solvent ethyl acetate/hexane). 10.07 g of the desired diol is isolated from the two batches.

$^1$H-NMR (300 MHz, CDCl$_3$): δ=1.40 (3H), 1.53 (3H), 2.10-2.25 (1H), 2.80 (1H), 3.29-3.48 (2H), 3.83 (3H), 6.78 (1H), 6.97 (1H), 7.00 (1H), 7.28 (1H).

4-(3-Methoxyphenyl)-2-hydroxy-2-(trifluoromethyl)-pentanal 10.07 g (34.45 mmol) of the above-described diol is oxidized to the corresponding aldehyde as already described several times according to Swern. After chromatography on silica gel (mobile solvent ethyl acetate/hexane), 7.16 g (71.6%) of the desired compound is obtained.

$^1$H-NMR (300 MHz, CDCl$_3$): δ=1.38 (3H), 1.48 (3H), 2.32 (1H), 2.69 (1H), 3.69 (1H), 3.82 (3H), 6.78 (1H), 6.88 (1H), 6.93 (1H), 7.25 (1H), 8.88 (1H).

5-[4-(3-Methoxyphenyl)-2-hydroxy-4-methyl-2-(trifluoromethyl)-pentylidenamino]-2-methyl-2H-phthalazin-1-one 300 mg (1.033 mmol) of the above-described 4-(3-methoxyphenyl)-2-hydroxy-2-(trifluoromethyl)-pentanal is reacted with 180.9 mg (1.033 mmol) of 5-amino-2-methyl-2H-phthalazin-1-one to form imine. After reaction, conventional working-up and chromatography, 318.2 mg (68.8%) of the desired imine is obtained.

$^1$H-NMR (300 MHz, CDCl$_3$): δ=1.36 (3H), 1.55 (3H), 2.49 (1H), 2.78 (1H), 3.50 (3H), 3.90 (3H), 4.72 (1H), 6.40 (1H), 6.59 (1H), 6.78 (1H), 6.90 (1H), 7.05 (1H), 7.28 (1H), virtually under the chloroform), 7.53 (1H), 8.30 (1H), 8.43 (1H).

5-(2-Hydroxy-6-methyl-4,4-dimethyl-2-(trifluoromethyl)-1,2,3,4-tetrahydronaphthalen-1-ylamino)-2-methyl-2H-phthalazin-1-one 100 mg (0.223 mmol) of imine is cyclized with titanium tetrachloride in dichloromethane as described in Example 146. 43.4 mg (43.4%) of the desired compound, specifically as a diastereomer mixture, is isolated.

MS (ES+): 448 (100%)

5-[2,6-Dihydroxy-4,4-dimethyl-2-(trifluoromethyl)-1,2,3,4-tetrahydronaphthalen-1-ylamino]-2-methyl-2H-phthalazin-1-one 37 mg (0.082 mmol) of the ether that is described in the section above is reacted with boron tribromide as described in Example 146. After the reaction is carried out and after conventional working-up, 20.9 mg (58.4%) of the desired compound is obtained, specifically as a diastereomer mixture.

MS (ES+): 434 (100%)

Example 274

1-(8-Fluoro-2-methylquinazolin-5-ylamino)-4,4-dimethyl-2-(trifluoromethyl)-1,2,3,4-tetrahydronaphthalene-2,6-diol

4-(3-Methoxyphenyl)-1,1,1-trifluoro-2-[([8-fluoro-2-methylquinazolin-5-ylimino]-methyl]-4-methyl-pentan-2-ol 400 mg (1.722 mmol) of 4-(3-methoxyphenyl)-2-hydroxy-2-(trifluoromethyl)-pentanal is reacted as described in Example 146 with 305.1 mg (1.722 mmol) of 5-amino-8-fluoro-2-methylquinazoline to form imine. After chromatography, 494.4 mg (79.8%) of the desired imine is isolated.

¹H-NMR (CDCl₃): δ=1.34 (3H), 1.58 (3H), 2.40 (1H), 2.79 (1H), 3.00 (3H), 3.48 (3H), 4.78 (1H), 6.29-6.42 (2H), 6.74 (1H), 6.90 (1H), 7.00 (1H), 7.28-7.40 (2H), 9.64 (1H).

1-(8-Fluoro-2-methylquinazolin-5-ylamino)-6-methoxy-4,4-dimethyl-2-(trifluoromethyl)-1,2,3,4-tetrahydronaphthalen-2-ol (AM 2016)

150 mg (0.347 mmol) of imine is cyclized in 2.5 ml of dichloromethane at 0° C. with 1 ml of titanium tetrachloride as described in Example 146. After chromatography on silica gel (mobile solvent methanol/dichloromethane), 87.1 mg (58.1%) of the desired compound is obtained.
¹H-NMR (300 MHz, CD₃OD): δ=1.42 (3H), 1.58 (3H), 2.08-2.23 (2H), 2.87 (3H), 3.79 (3H), 5.28 (1H), 6.73 (1H), 6.82 (1H), 6.99 (1H), 7.23 (1H), 7.68 (1H), 9.68 (1H).

1-(8-Fluoro-2-methylquinazolin-5-ylamino)-4,4-dimethyl-2-(trifluoromethyl)-1,2,3,4-tetrahydronaphthalene-2,6-diol 60 mg (0.133 mmol) of 4-(3-methoxyphenyl)-1,1,1-trifluoro-2-{[8-fluoro-2-methylquinazolin-5-ylimino]-methyl}-4-methylpentan-2-ol is mixed with 1.3 ml of a 1 M solution of boron tribromide in dichloromethane while being cooled in an ice bath. After 45 minutes of stirring at room temperature, the reaction mixture is mixed with ice, and saturated sodium bicarbonate solution is added drop by drop until a pH of 8 is reached. The cold bath is removed, and the mixture is stirred vigorously for 15 minutes. After extraction with ethyl acetate, the combined organic extracts are washed with water and then with brine. After drying, the solvent is spun off, and the residue is chromatographed on silica gel (mobile solvent ethyl acetate/hexane). Finally, 19.5 mg (33.5%) of the desired compound is obtained.
¹H-NMR (300 MHz, CD₃OD): δ=1.41 (3H), 1.56 (3H), 2.07-2.21 (2H), 2.89 (3H), 5.24 (1H), 6.60 (1H), 6.78-6.91 (2H), 7.13 (1H), 7.59 (1H), 9.68 (1H).

Example 275

5-(2,6-Dihydroxy-4,4-dimethyl-2-(trifluoromethyl)-1,2,3,4-tetrahydronaphthalen-1-ylamino)-2H-isoquinolin-1-one 5-[2-Hydroxy-4-(3-methoxyphenyl)-4-methyl-2-(trifluoromethyl)pentylidenamino]-2H-isoquinolin-1-one 271 mg (0.936 mmol) of 4-(3-methoxyphenyl)-2-hydroxy-2-(trifluoromethyl)-pentanal is reacted, as already described several times, with 150 mg (0.936 mmol) of 5-amino-2H-isoquinolin-1-one to form imine. After chromatography, 341.1 mg (84.5%) of the desired compound is isolated.
¹H-NMR (300 MHz, CDCl₃): δ=1.33 (3H), 1.55 (3H), 2.39 (1H), 2.79 (1H), 3.56 (3H), 4.95 (1H), 6.38-6.55 (2H), 6.78 (1H), 6.79-6.95 (2H), 7.09 (1H), 7.12-7.35 (3H), 8.31 (1H), 11.09 (1H).

5-(2-Hydroxy-6-methoxy-4,4-dimethyl-2-(trifluoromethyl)-1,2,3,4-tetrahydronaphthalen-1-ylamino)-2H-isoquinolin-1-one 150 mg (0.347 mmol) of the above-described imine is cyclized to the desired compound as described in Example 274 with titanium tetrachloride in dichloromethane. After chromatography, 18.8 mg (12.5%) is isolated.

¹H-NMR (300 MHz, CD₃OD): δ=1.42 (3H), 1.58 (3H), 2.05-2.24 (2H), 3.79 (3H), 5.15 (1H), 6.73 (1H), 6.89 (1H), 6.96 (1H), 7.05 (1H), 7.10-7.25 (2H), 7.49 (1H), 7.70 (1H).

5-(2,6-Dihydroxy-4,4-dimethyl-2-(trifluoromethyl)-1,2,3,4-tetrahydronaphthalen-1-ylamino)-2H-isoquinolin-1-one 90 mg (0.208 mmol) of the above-described imine is cyclized directly with boron tribromide to the free phenol as described in Example 274. After conventional working-up and chromatography, 53.8 mg (61.7%) of the desired compound is obtained as a diastereomer mixture at a 3:2 ratio.
MS (ES+): 419 (100%)

Example 276

5-(2,6-Dihydroxy-4,4-dimethyl-2-(trifluoromethyl)-1,2,3,4-tetrahydronaphthalen-1-ylamino)-1H-quinolin-2-one 5-[2-Hydroxy-4-(3-methoxyphenyl)-4-methyl-2-(trifluoromethyl)pentylidenamino]-1H-quinolin-2-one 300 mg (1.033 mmol) of 4-(3-methoxyphenyl)-2-hydroxy-2-(trifluoromethyl)-pentanal is reacted, as already described several times, with 165.4 mg (1.033 mmol) of 5-amino-1H-quinolin-2-one to form imine. After chromatography, 414.3 mg (92.7%) of the desired compound is isolated.
¹H-NMR (300 MHz, CDCl₃): δ=1.33 (3H), 1.53 (3H), 2.40 (1H), 2.78 (1H), 3.58 (3H), 4.85 (1H), 6.08 (1H), 6.49 (1H), 6.72-6.83 (2H), 6.90 (1H), 7.08 (1H), 7.28-7.38 (3H), 8.18 (1H), 12.53 (1H).

5-(2-Hydroxy-6-methoxy-4,4-dimethyl-2-(trifluoromethyl)-1,2,3,4-tetrahydronaphthalen-1-ylamino)-1H-quinolin-2-one 150 mg (0.347 mmol) of the above-described imine is cyclized to the desired compound as described in Example 274 with titanium tetrachloride in dichloromethane. After chromatography, 35.8 mg (23.8%) of diastereomer A is isolated, and another 14.3 mg (9.5%) as a diastereomer mixture. The spectroscopic data refer to the pure diastereomer.
¹H-NMR (300 MHz, CD₃OD): δ=1.42 (3H), 1.59 (3H), 2.05-2.24 (2H), 3.80 (3H), 5.18 (1H), 6.52 (1H), 6.61 (1H), 6.65-6.79 (2H), 6.95 (1H), 7.20 (1H), 7.39 (1H), 8.23 (1H).

5-(2,6-Dihydroxy-4,4-dimethyl-2-(trifluoromethyl)-1,2,3,4-tetrahydronaphthalen-1-ylamino)-1H-quinolin-2-one 90 mg (0.208 mmol) of the above-described imine is cyclized directly with boron tribromide to free phenol as described in Example 274. After conventional working-up and chromatography, 37.6 mg (43.1%) of the desired compound is obtained as a diastereomer mixture in a 4:1 ratio.
MS (ES+): 419 (100%)

Example 277

7-Fluoro-1-(8-fluoro-2-methylquinazolin-5-ylamino)-4,4-dimethyl-2-(trifluoromethyl)-1,2,3,4-tetrahydronaphthalene-2,6-diol

4-Bromomethyl-1-fluoro-2-methoxybenzene 41.7 g (297.54 mmol) of 2-fluoro-5-methylanisole is refluxed overnight with 59.9 g (327.48 mmol) of N-bromosuccinimide and 145 mg of benzoyl peroxide in 945 ml of carbon tetrachloride. The reaction mixture is filtered [through] a glass-fiber filter, and after the solvent is spun off, the residue (72.85 g>100%) is incorporated in crude form into the next stage.

(4-Fluoro-3-methoxy-phenyl)-acetonitrile 72.85 g of the above-described bromine compound is added in a mixture that consists of 330 ml of dimethylformamide and 209 ml of water. After 32.5 g (498.86 mmol) of potassium cyanide is added at room temperature (slight heating), the batch is stirred overnight at room temperature. The reaction mixture is poured into ice water and extracted three times with methyl tert-butyl ether. The combined organic extracts are washed with brine, and the solvent is spun off after drying. The residue is chromatographed on silica gel (mobile solvent ethyl acetate/hexane). 33.34 g (61.4%) of the desired nitrile is isolated.

$^1$H-NMR (CDCl$_3$): 3.72 (2H), 3.93 (3H), 6.83 (1H), 6.93 (1H), 7.09 (1H).

2-(4-Fluoro-3-methoxyphenyl)-2-methylpropionitrile 16.67 g (100.93 mmol) of (4-fluoro-3-methoxyphenyl)-acetonitrile is introduced with 30.1 g (211.96 mmol) of methyliodide into 158 ml of dimethylformamide. At 0° C., 8.50 g (211.96 mmol) of a 55-60% sodium hydride suspension is added in portions. After stirring overnight at room temperature, the reaction mixture is poured into ice water and then extracted three times with methyl tert-butyl ether. The combined organic extracts are washed with water and with brine. After the solvent is dried and spun off, the residue is chromatographed on silica gel (mobile solvent ethyl acetate/hexane). 5.11 g (26.2%) of the desired compound and 6.18 g of the monomethyl compound, which is realkylated, are isolated.

$^1$H-NMR (CDCl$_3$): 1.72 (6H), 3.92 (3H), 6.95 (1H), 7.00-7.12 (2H).

2-(4-Fluoro-3-methoxyphenyl)-2-methylpropionaldehyde 9.37 g (48.50 mmol) of 2-(4-fluoro-3-methoxyphenyl)-2-methylpropionitrile is reduced with 39.98 ml (72.48 mmol) of a 1.2 M solution of DIBAL in toluene at −78° C., specifically as described in some preceding examples. For hydrolysis, isopropanal and tartaric acid are used. 9.31 g of a mixture that is produced from up to a third of the starting material and two thirds of the desired aldehyde is isolated. This mixture is subjected again to a DIBAL reaction at −78° C. and after working-up, a mixture (9.18 g) that consists of nitrile, aldehyde and the corresponding alcohol exists. This mixture is reduced another time with DIBAL, but this time at a temperature of −10 to 0° C. After undergoing hydrolysis with isopropanol, 1.45 g of the desired aldehyde and 5.68 g of the corresponding alcohol are isolated. This alcohol is oxidized to aldehyde as already described several times under Swern conditions. After conventional working-up and purification, 5.09 g of the desired aldehyde is isolated.

$^1$H-NMR (CDCl$_3$): 1.48 (6H), 3.90 (3H), 6.75-6.87 (2H), 7.09 (1H), 9.49 (1H).

Ethyl-(E)-(4-fluoro-3-methoxyphenyl)-4-methyl-pent-2-enoate 6.10 g (27.23 mmol) of triethylphosphonoacetate is dissolved in 16.5 ml of tetrahydrofuran. At 0° C., 1.49 ml (29.12 mmol) of LDA is added in drops, and the batch is stirred for 30 minutes at 0° C. After dropwise addition of 5.34 g (27.22 mmol) of the above-described aldehyde, dissolved in 16.5 ml of tetrahydrofuran, the reaction mixture is stirred overnight at room temperature. At 0° C., water is carefully added in drops, stirred vigorously for ten minutes and then shaken three times with methyl tert-butyl ether. The combined organic extracts are washed with brine and dried. After the solvent is spun off, the residue is chromatographed on silica gel (mobile solvent ethyl acetate/hexane). 5.75 g (79.3%) of the desired compound is isolated.

$^1$H-NMR (CDCl$_3$): 1.29 (3H), 1.48 (6H), 3.90 (3H), 4.20 (2H), 5.80 (1H), 6.79-6.90 (2H), 7.02 (1H), 7.10 (1H).

Ethyl-(4-fluoro-3-methoxyphenyl)-4-methylpentanoate 5.75 g (21.59 mmol) of ethyl-(E)-(4-fluoro-3-methoxyphenyl)-4-methylpent-2-enaote is hydrogenated in 80 ml of ethanol with the aid of 307.3 mg of PdC (10%) overnight in hydrogen atmosphere. The reaction mixture is suctioned off through a glass-pleated filter, and the solvent is spun off. 5.69 g (98.3%) of the desired compound, which is further incorporated in crude form, is isolated.

$^1$H-NMR (CDCl$_3$): 1.22 (3H), 1.31 (6H), 1.90-2.10 (4H), 3.90 (3H), 4.08 (2H), 6.83 (1H), 6.91 (1H), 7.00 (1H).

Ethyl-4-(4-fluoro-3-methoxyphenyl)-2-hydroxy-4-methylpentanoate 5.69 g (21.21 mmol) of ethyl-(4-fluoro-3-methoxyphenyl)-4-methylpentanoate is reacted with 7.76 g (26.70 mmol) of Davis reagent as described in Example 273. According to the working-up and chromatography on silica gel (mobile solvent ethyl acetate/hexane) that are described there, 2.98 g (49.5%) of the desired compound is obtained.

$^1$H-NMR (300 MHz, CDCl$_3$): δ=1.29 (3H), 1.40 (3H), 1.48 (3H), 1.83 (1H), 2.20 (1H), 2.56 (1H), 3.85-3.99 (4H), 4.13 (2H), 6.90 (1H), 6.95-7.08 (2H).

Ethyl-4-(4-fluoro-3-methoxyphenyl)-4-methyl-2-oxopentanoate 2.78 g (9.78 mmol) of ethyl-4-(4-fluoro-3-methoxyphenyl)-2-hydroxy-4-methylpentanoate is oxidized in Example 273 with SO$_3$/Py in dichloromethane to the corresponding a ketoester. After chromatography on a Flashmaster, 2.48 g (89.9%) of the desired compound is obtained.

$^1$H-NMR (300 MHz, CDCl$_3$): δ=1.28 (3H), 1.48 (6H), 3.15 (2H), 3.90 (3H), 4.12 (2H), 6.88 (1H), 6.90-7.03 (2H).

4-(4-Fluoro-3-methoxyphenyl)-2-hydroxy-4-methylphenyl)-2-(trifluoromethyl)-pentanal 2.48 g (8.79 mmol) of ethyl-4-(4-fluoro-3-methoxyphenyl)-4-methyl-2-oxopentanoate is converted into aldehyde via the sequence described in Example 273 of trifluoromethylation with Rupperts reagent, reduction of ester with lithium aluminum hydride to alcohol and subsequent oxidation of alcohol according to Swern. 382.3 mg of the desired aldehyde is ultimately isolated over the three stages.

$^1$H-NMR (300 MHz, CDCl$_3$): δ=1.38 (3H), 1.48 (3H), 2.32 (1H), 2.66 (1H), 3.68 (1H), 3.90 (3H), 6.80-6.92 (2H), 7.02 (1H), 8.88 (1H).

1,1,1-Trifluoro-4-(4-fluoro-3-methoxyphenyl)-2-[(8-fluoro-2-methylquinazolin-5-ylimino)-methyl]-4-methylpentan-2-ol 127.4 mg (0.413 mmol) of 4-(4-fluoro-3-methoxyphenyl)-2-hydroxy-4-methylphenyl)-2-(trifluoromethyl)-pentanal is reacted with 73.2 mg (0.413 mmol) of 8-fluoro-2-methylquinazoline and 235.1 mg (0.827 mmol) of titanium(IV) isopropylate in 2.2 ml of xylene as already described several times to form the corresponding imine. After chromatography on a Flashmaster, 138.5 mg (71.7%) of the desired compound is isolated.

$^1$H-NMR (CDCl$_3$): δ=1.35 (3H), 1.56 (3H), 2.44 (1H), 2.72 (1H), 2.99 (3H), 3.68 (3H), 4.77 (1H), 6.38 (1H), 6.70-6.90 (3H), 7.38-7.48 (2H), 9.65 (1H).

7-Fluoro-1-(8-fluoro-2-methylquinazolin-5-ylamino)-4,4-dimethyl-2-(trifluoromethyl)-1,2,3,4-tetrahydronaphthalene-2,6-diol 20 mg (0.043 mmol) of the above-described imine is reacted with 0.6 ml of boron tribromide (1 M solution in dichloromethane) at 0° C. and thus converted into the cyclized phenol. After chromatography on a Flashmaster, 7.1 mg (36.6%) is isolated.

$^1$H-NMR (CD$_3$OD)=1.41 (3H), 1.56 (3H), 2.06-2.22 (2H), 2.89 (3H), 5.24 (1H), 6.84 (1H), 6.89-7.04 (2H), 7.59 (1H), 9.69 (1H).

Example 278

5-[7-Fluoro-2-hydroxy-6-methoxy-4,4-dimethyl-2-(trifluoromethyl)-1,2,3,4-tetrahydronaphthalen-1-ylamino]-1H-quinolin-2-one

5-[4-(4-Fluoro-3-methoxyphenyl)-2-hydroxy-4-methyl-2-(trifluoromethyl)-pentylidenamino]-1H-quinolin-2-one 127 mg (0.413 mmol) of the aldehyde that is described in Example 277 is reacted as described there with 66.32 mg (0.413 mmol) of 5-amino-1H-quinolin-2-one to form imine.

After chromatography on a Flashmaster, 89.2 mg (47.9%) of the desired compound is isolated.

$^1$H-NMR (CDCl$_3$): δ=1.37 (3H), 1.53 (3H), 2.43 (1H), 2.71 (1H), 3.71 (3H), 4.85 (1H), 6.10 (1H), 6.70-6.92 (4H), 7.30-7.42 (3H), 8.15 (1H), 12.42 (1H).

5-[7-Fluoro-2-hydroxy-6-methoxy-4,4-dimethyl-2-(trifluoromethyl)-1,2,3,4-tetrahydronaphthalen-1-ylamino]-1H-quinolin-2-one 89.2 mg (0.198 mmol) of the above-described imine is reacted in 1.9 ml of dichloromethane with 1.3 ml (1.188 mmol) of titanium tetrachloride to form cyclic ether. After chromatography on a Flashmaster, 5.7 mg of the desired compound is obtained.

$^1$H-NMR (CDCl$_3$): δ=1.40 (3H), 1.60 (3H), 2.00-2.29 (2H), 3.88 (3H), 5.00 (1H), 5.07 (1H), 5.68 (1H), 6.45-6.60 (3H), 6.85-7.02 (2H), 7.32 (1H), 8.20 (1H), 10.05 (1H).

Example 279

6-Fluoro-1-[(2-methylquinolin-5-yl)amino]-4-ethyl-2-(trifluoromethyl)-1,2,3,4-tetrahydronaphthalene-2,5-diol $^1$H-NMR (300 MHz, CD$_3$OD): δ=0.97 (s, 3H), 1.79 (qdd, 1H), 1.96 (qdd, 1H), 2.19 (dd, 1H), 2.36 (dd, 1H), 2.73 (s, 3H), 3.40 (m, 1H), 4.98 (d, 1H), 5.12 (d, 1H), 6.60 (d, 1H), 6.89 (d, 2H), 7.23 (d, 1H), 7.43 (d, 1H), 7.51 (t, 1H), 8.11 (d, 1H).

Examples 280 and 281

5-{[7-Bromo-2,5-dihydroxy-4,4-dimethyl-2-(trifluoromethyl)-1,2,3,4-tetrahydronaphthalen-1-yl]amino}-quinolin-2(1H)-one Diastereomer A and

5-{[7-Bromo-2,5-dihydroxy-4,4-dimethyl-2-(trifluoromethyl)-1,2,3,4-tetrahydronaphthalen-1-yl]amino}-quinolin-2(1H)-one, Diastereomer B Analogously to Example 10, the corresponding imine is produced starting from 800 mg of 4-(4-bromo-2-methoxyphenyl)-2-hydroxy-4-methyl-2-(trifluoromethyl)pentanal and 348 mg of 5-amino-quinolin-2(1H)-one. 16 mg of diastereomer A of 5-{[7-bromo-2-,5-dihydroxy-4,4-dimethyl-2-(trifluoromethyl)-1,2,3,4-tetrahydronaphthalen-1-yl]amino}-quinolin-2(1H)-one (fraction A) and 79 mg of diastereomer B of 5-{[7-bromo-2,5-dihydroxy-4,4-dimethyl-2-(trifluoromethyl)-1,2,3,4-tetrahydronaphthalen-1-yl]amino}-quinolin-2(1H)-one are obtained by reaction of 800 mg of imine with 7.9 ml of boron tribromide solution (1H in dichloromethane).

Fraction A: $^1$H-NMR (CD$_3$OD): δ=1.40 (s, 3H), 1.55 (s, 3H), 1.90 (d, 1H), 2.25 (d, 1H), 5.22 (s, 1H), 6.11 (d, 1H), 6.58 (d, 1H), 6.67 (d, 1H), 7.12-7.30 (m, 3H), 8.20 (d, 1H).

Fraction B: $^1$H-NMR (CD$_3$OD): δ=1.54 (s, 3H), 1.65 (s, 3H), 2.05 (d, 1H), 2.14 (d, 1H), 5.13 (s, 1H), 6.53 (d, 1H), 6.62 (d, 1H), 6.72 (d, 1H), 6.87 (s, 1H), 6.94 (s, 1H), 7.40 (t, 1H), 8.22 (d, 1H).

Example 282

1,6-Dihydroxy-8,8-dimethyl-5-(1-oxo-1,2-dihydroisoquinolin-5-ylamino)-6-(trifluoromethyl)-5,6,7,8-tetrahydronaphthalene-2-carbonitrile 75 mg (0.166 mmol) of 5-(6-chloro-2,5-dihydroxy-4,4-dimethyl-2-(trifluoromethyl)-1,2,3,4-tetrahydronaphthalin-1-ylamino)-2H-isoquinolin-1-one is dissolved in 1.3 ml of 1-methyl-2-pyrrolidinone and reacted in the microwave with 16.27 mg (0.332 mmol) of sodium cyanide and 36.27 mg (0.166 mmol) of nickel(II) bromide as described in Example 160. The black reaction mixture is added through a glass-fiber filter. After washing with ethyl acetate, the filtrate is mixed with an additional 60 ml of ethyl acetate. It is shaken with water and with brine. After drying, the solvent is spun off, and the residue is chromatographed on silica gel (amine plate: mobile solvent methanol/dichloromethane). 16.2 mg (22.1%) of the desired nitrile is isolated.

MS (ES+): 444 (100%); IR (microscope, matrix: diamond): 2230.

The entire disclosures of all applications, patents and publications, cited herein and of corresponding German Application No. 103 47 383.1, filed Oct. 8, 2003, are incorporated by reference herein.

The invention claimed is:

1. A compound of formula (I),

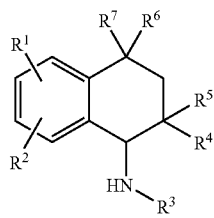

(I)

in which
R$^1$ and R$^2$, independently of one another, mean a hydrogen atom, a hydroxy group, a halogen atom, an optionally substituted (C$_1$-C$_{10}$)-alkyl group, an optionally substituted (C$_1$-C$_{10}$)-alkoxy group, a (C$_1$-C$_{10}$)-alkylthio group, a (C$_1$-C$_5$)-perfluoroalkyl group, a cyano group, or a nitro group,
or R$^1$ and R$^2$ together mean a group that is —O—(CH$_2$)$_n$—O—, —O—(CH$_2$)$_n$—CH$_2$—, —O—CH=CH—, —(CH$_2$)$_{n+2}$—, —NH—(CH$_2$)$_{n+1}$, N(C$_1$-C$_3$-alkyl)-(CH$_2$)$_{n+1}$, or —NH—N=CH—,
wherein n=1 or 2, and the terminal oxygen atoms and/or carbon atoms and/or nitrogen atoms are linked to directly adjacent ring-carbon atoms,
or NR$^8$R$^9$, wherein R$^8$ and R$^9$, independently of one another, mean hydrogen, C$_1$-C$_5$-alkyl or (CO)—C$_1$-C$_5$-alkyl,
R$^3$ means a C$_1$-C$_{10}$-alkyl group that optionally is substituted by 1-3 hydroxy groups, halogen atoms, 1-3 (C$_1$-C$_5$)-alkoxy groups, an optionally substituted (C$_3$-C$_7$)-cycloalkyl group, an optionally substituted heterocyclyl group, an optionally substituted aryl group, a monocyclic or bicyclic heteroaryl group that optionally contains 1-4 nitrogen atoms and/or 1-2 oxygen atoms and/or 1-2 sulfur atoms and/or 1-2 keto groups and that optionally is substituted by one or more (C$_1$-C$_5$)-alkyl groups,
which optionally substituted by 1-3 hydroxy groups or 1-3 COOR$^{13}$ groups, wherein R$^{13}$ means hydrogen or a C$_1$-C$_5$-alkyl group,
(C$_1$-C$_5$)-alkoxy groups, halogen atoms, hydroxy groups, NR$^8$R$^9$ groups, exomethylene groups, or oxygen, which is linked via any position to the amine of the tetrahydronaphthalene system and is optionally hydrogenated at one or more locations,
R$^4$ means a hydroxy group, a group OR$^{10}$, or an O(CO)R$^{10}$ group, wherein R$^{10}$ means a hydroxy protective group or a C$_1$-C$_{10}$-alkyl group,
R$^5$ means a (C$_1$-C$_{10}$)-alkyl group or an optionally partially or completely fluorinated (C$_1$-C$_{10}$)-alkyl group,
R$^6$ and R$^7$, independently of one another, mean a hydrogen atom, a methyl or ethyl group or together with the carbon atom of the tetrahydronaphthalene system mean a (C$_3$-C$_6$)-cycloalkyl ring, or a pharmaceutically acceptable salt thereof.

2. A stereoisomer of formula (I),

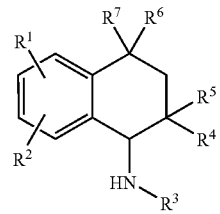

(I)

in which
R$^1$ and R$^2$, independently of one another, mean a hydrogen atom, a hydroxy group, a halogen atom, a (C$_1$-C$_{10}$)-alkyl group, a (C$_1$-C$_{10}$)-alkoxy group, a (C$_1$-C$_{10}$)-alkylthio group, a (C$_1$-C$_5$)-perfluoroalkyl group, a cyano group, or a nitro group, or R$^1$ and R$^2$ together mean —O—(CH$_2$)$_n$—O—, —O—(CH$_2$)$_n$—CH$_2$—, —O—CH=CH—, —(CH$_2$)$_{n+2}$—, —NH—(CH$_2$)$_{n+1}$, —N(C$_1$-C$_3$-alkyl)-(CH$_2$)$_{n+1}$, or —NH—N=CH—, wherein n=1 or 2, and the terminal oxygen atoms and/or carbon atoms and/or nitrogen atoms are linked to directly adjacent ring-carbon atoms,
or NR$^8$R$^9$, wherein R$^8$ and R$^9$, independently of one another, are hydrogen, C$_1$-C$_5$-alkyl or (CO)—C$_1$-C$_5$-alkyl,
R$^3$ means a C$_1$-C$_{10}$ alkyl group that is optionally substituted by 1-3 hydroxy groups, halogen atoms, or 1-3 (C$_1$-C$_5$)-alkoxy groups, an optionally substituted (C$_3$-C$_7$)-cycloalkyl group, an optionally substituted heterocyclyl group, an optionally substituted aryl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted by one or more (C$_1$-C$_5$)-alkyl groups
which is optionally substituted by 1-3 hydroxy groups or 1-3 COOR$^6$ groups,
(C$_1$-C$_5$)-alkoxy groups, halogen atoms, or exomethylene groups, which is linked via any position to the amine of the tetrahydronaphthalene system and is optionally hydrogenated at one or more locations,
R$^4$ means a hydroxy group, or a group OR$^{10}$, wherein R$^{10}$ means a C$_1$-C$_{10}$-alkyl group,
R$^5$ means a (C$_1$-C$_5$)-alkyl group or an optionally partially or completely fluorinated (C$_1$-C$_5$)-alkyl group,
R$^6$ and R$^7$, independently of one another, mean a hydrogen atom, a methyl or ethyl group or together with the carbon atom of the tetrahydronaphthalene system mean a (C3-C6)-cycloalkyl ring, or a pharmaceutically acceptable salt thereof.

3. A stereoisomer of formula (I),

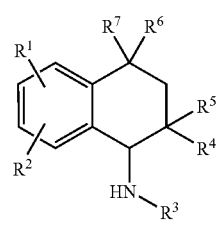

(I)

in which
- $R^1$ and $R^2$, independently of one another, mean a hydrogen atom, a hydroxy group, a halogen atom, a $(C_1-C_{10})$-alkyl group, a $(C_1-C_{10})$-alkoxy group, a $(C_1-C_{10})$-alkylthio group, a $(C_1-C_5)$-perfluoroalkyl group, a cyano group, or a nitro group, or $R^1$ and $R^2$ together mean —O—$(CH_2)$—O—, —O—$(CH_2)_n$—$CH_2$-, —O—CHCH—, or —$(CH_2)_{n+2}$-, wherein n =1 or 2, and the terminal oxygen atoms and/or carbon atoms are linked to directly adjacent ring-carbon atoms, or $NR^8 R^9$, wherein $R^8$ and $R^9$, independently of one another, mean hydrogen, $C_1-C_5$-alkyl or (CO)—$C_1-C_5$-alkyl,
- $R^3$ means a $C_1-C_{10}$-alkyl group that is optionally substituted by 1-3 hydroxy groups, halogen atoms, an optionally substituted phenyl group, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1-C_5$)-alkyl groups, 1-2 ($C_1-C_5$)-alkoxy groups, 1-3 halogen atoms, or 1-2 exomethylene groups, which is linked via any position to the amine of the tetrahydronaphthalene system and is optionally hydrogenated at one or more locations,
- $R^4$ means a hydroxy group,
- $R^5$ means a $(C_1-C_5)$-alkyl group or an optionally partially or completely fluorinated $(C_1-C_5)$-alkyl group,
- $R^6$ and $R^7$, independently of one another, mean a hydrogen atom, a methyl or ethyl group, or together with the carbon atom of the chain mean a $(C_3-C_6)$-cycloalkyl ring, or a pharmaceutically acceptable salt thereof.

4. A stereoisomer of formula (I),

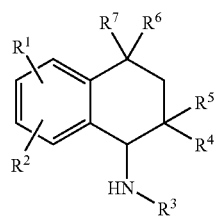

in which
- $R^1$ and $R^2$, independently of one another, mean a hydrogen atom, a hydroxy group, a halogen atom, a $(C_1-C_5)$-alkyl group, a $(C_1-C_5)$-alkoxy group, or $R^1$ and $R^2$ together mean —O—$(CH_2)$—O—, —O—$(CH_2)_n$—$CH_2$-, —O—CH=CH—, or —$(CH_2)_{n+2}^-$, wherein n =1 or 2, and the terminal oxygen atoms and/or carbon atoms are linked to directly adjacent ring-carbon atoms,
- $R^3$ means a $C_1$—$C_{10}$—alkyl group that is optionally substituted by 1-3 hydroxy groups, halogen atoms, a phenyl, phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazole or indolyl group that optionally is substituted with $C_1-C_5$-alkyl, halogen, hydroxy, or $C_1-C_5$-alkoxy, which is linked via any position to the amine of the tetrahydronaphthalene system and is optionally substituted in one or more places with 1-2 keto groups, 1-2 ($C_1-C_3$)-alkyl groups, 1-2 ($C_1-C_3$)- alkoxy groups, 1-3 halogen atoms, or 1-2 exomethylene groups, and is optionally hydrogenated at one or more locations,
- $R^4$ means a hydroxy group,
- $R^5$ means a $(C_1-C_5)$-alkyl group, or an optionally partially or completely fluorinated $(C_1-C_5)$-alkyl group,
- $R^6$ and $R^7$, independently of one another, mean a hydrogen atom, a methyl or ethyl group or together with the carbon atom of the tetrahydronaphthalene system mean a $(C_3-C_6)$-cycloalkyl ring, or a pharmaceutically acceptable salt thereof.

5. A stereoisomer of formula (I),

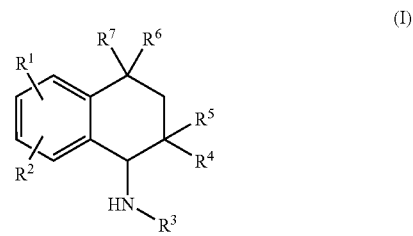

in which
- $R^1$ and $R^2$, independently of one another, mean a hydrogen atom, a hydroxy group, a halogen atom, a $(C_1-C_5)$-alkyl group, a $(C_1-C_5)$-alkoxy group, or together a $(C_1-C_2)$-alkylenedioxy group, wherein $R^1$ $R^2$ are directly adjacent,
- $R^3$ means a phenyl, phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazole or indolyl group that optionally is substituted with $C_1-C_5$-alkyl, halogen, hydroxy, or $C_1-C_5$-alkoxy, which is linked via any position to the amine of the tetrahydronaphthalene system, and is optionally substituted in one or more places with 1-2 keto groups, 1-2 ($C_1-C_3$)-alkyl groups, or 1-2 exomethylene groups, and is optionally hydrogenated at one or more locations,
- $R^4$ means a hydroxy group,
- $R^5$ means a $(C_1-C_5)$-alkyl group or an optionally partially or completely fluorinated $(C_1-C_5)$-alkyl group,
- $R^6$ and $R^7$, independently of one another, mean a hydrogen atom, a methyl or ethyl group, or together with the carbon atom of the tetrahydronaphthalene system mean a $(C_3-C_3)$-cycloalkyl ring, or a pharmaceutically acceptable salt thereof.

6. A method for treating an inflammatory disease, comprising administering to a subject in need thereof an effective amount of a compound of claim 1, wherein the inflammatory disease is a lung disease, a rheumatic disease, an allergic disease, a dermatologic disease, an eye disease, a chronic, obstructive lung disease, primary bronchial asthma, bronchitis, rheumatoid arthritis, contact dermatitis, atopic dermatitis, psoriasis, rosacea, or conjunctivitis.

7. A pharmaceutical composition, comprising a compound of claim 1 and a pharmaceutically acceptable carrier.

8. A process for preparing a compound of formula I according to claim 1, comprising cyclizing a compound of formula II

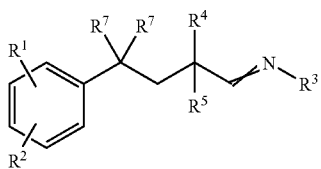

(II)

in which $R^1$, $R^2$, $R^3$, $R^4$, $R^5$, $R^6$, and $R^7$ are defined as for the compound of formula I, optionally either without additional reagent, in a solvent or concentrated organic acid, or with the addition of an inorganic or organic acid or Lewis acid.

9. A pharmaceutically acceptable salt of a compound according to claim 1.

10. A compound according to claim 1, wherein $R^5$ stands for a completely fluorinated $(C_1-C_5)$-alkyl group.

11. A compound according to claim 1, wherein $R^5$ stands for trifluoromethyl or pentafluoroethyl.

12. A compound, which is
4-{[8-Fluoro-2,5-dihydroxy-4,4-dimethyl-2-(trifluoromethyl)-1,2,3,4-tetrahydronaphthalen-1-yl]amino}-2,3-dihydroisoindol-1-one
5-{[7-Chloro-2,5-dihydroxy-4,4-dimethyl-2-(trifluoromethyl)-1,2,3,4-tetrahydronaphthalen-1-yl]amino}-isoquinolin-1 (2H)-one
(+)-6-Fluoro-1-[(1H-indazol-4-yl)amino]-4,4-dimethyl-2-(trifluoromethyl)-1,2,3,4-tetrahydronaphthalene-2,5-diol
(−)-6-Fluoro-1-[(1H-indazol-4-yl)amino]-4,4-dimethyl-2-(trifluoromethyl)-1,2,3,4-tetrahydronaphthalene-2,5-diol
4-{[8-Fluoro-2,5-dihydroxy-4,4-dimethyl-2-(trifluoromethyl)-1,2,3,4-tetrahydronaphthalen-1-yl]amino}-6-fluoro-2,3-dihydroisoindol-1-one
4-{[5-Fluoro-2,6-dihydroxy-4,4-dimethyl-2-(trifluoromethyl)-1,2,3,4-tetrahydronaphthalen-1-yl]amino}-2,3-dihydroisoindol-1-one
4-{[7-Bromo-2,5-dihydroxy-4,4-dimethyl-2-(trifluoromethyl)-1,2,3,4-tetrahydronaphthalen-1-yl]amino}-1,3-dihydroindol-2-one
(+)-4-({7-Hydroxy-9,9-dimethyl-7-(trifluoromethyl)-6,7,8,9-tetrahydronaphtho[1,2-d]-1,3-dioxol-6-yl}amino)-2,3-dihydroisoindol-1-one
(−)-4-({7-Hydroxy-9,9-dimethyl-7-(trifluoromethyl)-6,7,8,9-tetrahydronaphtho[1,2-d]-1,3-dioxol-6-yl}amino)-2,3-dihydroisoindol-1-one
5-{[8-Chloro-2,5-dihydroxy-4,4-dimethyl-2-(trifluoromethyl)-1,2,3,4-tetrahydronaphthalen-1-yl]amino}-isoquinolin-1(2H)-one
8-Bromo-1-[(1H-indazol-4-yl)amino]-4,4-dimethyl-2-(trifluoromethyl)-1,2,3,4-tetrahydronaphthalene-2,5-diol)
1-[(1H-Indazol-4-yl)amino]-4,4-dimethyl-2-(trifluoromethyl)-1,2,3,4-tetrahydronaphthalen-2-ol
1-[(2-Methylbenzothiazol-7-yl)amino]-4,4-dimethyl-2-(trifluoromethyl)-1,2,3,4-tetrahydronaphthalen-2-ol
6-[(1H-Indazol-4-yl)amino]-9,9-dimethyl-7-(trifluoromethyl)-6,7,8,9-tetrahydro-naphtho[1,2-d]-1,3-dioxol-7-ol
1-[(2-Methylquinolin-5-yl)amino]-4,4-dimethyl-2-(trifluoromethyl)-1,2,3,4-tetrahydronaphthalen-2-ol
1-[(Quinolin-5-yl)amino]-4,4-dimethyl-2-(trifluoromethyl)-1,2,3,4-tetrahydronaphthalen-2-ol
5-{[2-Hydroxy-4,4-dimethyl-2-(trifluoromethyl)-1,2,3,4-tetrahydronaphthalen-1-yl]amino}-quinolin-2(1H)-one
1-[(2-Methoxyquinolin-5-yl)amino]-4,4-dimethyl-2-(trifluoromethyl)-1,2,3,4-tetrahydronaphthalen-2-ol
1-[(Phenylamino)-4,4-dimethyl-2-(trifluoromethyl)-1,2,3,4-tetrahydronaphthalen-2-ol
4-{[2-Hydroxy-4,4-dimethyl-2-(trifluoromethyl)-1,2,3,4-tetrahydronaphthalen-1-yl]amino 1-2-(trifluoromethyl)benzonitrile
5-{[5-Bromo-2-hydroxy-4,4-dimethyl-2-(trifluoromethyl)-1,2,3,4-tetrahydronaphthalen-1-yl]amino}-isoquinolin-1(2H)-one
5-Bromo-1-[(1H-indazol-4-yl)amino]-4,4-dimethyl-2-(trifluoromethyl)-1,2,3,4-tetrahydronaphthalen-2-ol
5-Bromo-4,4-dimethyl-1-propylamino-2-(trifluoromethyl)-1,2,3,4-tetrahydronaphthalen-2-ol
5-Bromo-1-[(3-hydroxypropyl)amino]-4,4-dimethyl-2-(trifluoromethyl)-1,2,3,4-tetrahydronaphthalen-2-ol
5-{[8-Fluoro-2,5-dihydroxy-4,4-dimethyl-2-(trifluoromethyl)-1,2,3,4-tetrahydronaphthalen-1-yl]amino}-isoquinolin-1(2H)-one
4-{[7-Chloro-2,5-dihydroxy-4,4-dimethyl-2-(trifluoromethyl)-1,2,3,4-tetrahydronaphthalen-1-yl]amino}-6-fluoro-2,3-dihydroisoindol-1-one
5-{[6-Fluoro-2-hydroxy-5-methoxy-4,4-dimethyl-2-(trifluoromethyl)-1,2,3,4-tetrahydronaphthalen-1-yl]amino}-isoquinolin-1(2H)-one
5-{[6-Fluoro-2,5-dihydroxy-4,4-dimethyl-2-(trifluoromethyl)-1,2,3,4-tetrahydronaphthalen-1-yl]amino}-isoquinolin-1(2H)-one
5-{[6-Fluoro-2,5-dihydroxy-4,4-dimethyl-2-(trifluoromethyl)-1,2,3,4-tetrahydronaphthalen-1-yl]amino}-isoquinolin-1(2H)-one
4-{[6-Fluoro-2,5-dihydroxy-4,4-dimethyl-2-(trifluoromethyl)-1,2,3,4-tetrahydronaphthalen-1-yl]amino}-2,3-dihydroisoindol-1-one
6-Chloro-1-[(1H-indazol-4-yl)amino]-4,4-dimethyl-2-(trifluoromethyl)-1,2,3,4-tetrahydronaphthalene-2,5-diol
cis-7-Chloro-1-[(2-methylquinazolin-5-yl)amino]-4,4-dimethyl-2-(trifluoromethyl)-1,2,3,4-tetrahydronaphthalen-2-ol
5,8-Difluoro-1-[(2-methylquinazolin-5-yl)amino]-4,4-dimethyl-2-(trifluoromethyl)-1,2,3,4-tetrahydronaphthalen-2-ol
5-{[4,4-Dimethyl-6-fluoro-2-hydroxy-5-methoxy-2-trifluoromethyl-1,2,3,4-tetrahydronaphthalen-1-yl]amino}-quinolin-2(1H)-one
5-{[4,4-Dimethyl-2-hydroxy-5-methoxy-2-trifluoromethyl-1,2,3,4-tetrahydronaphthalen-1-yl]amino}-quinolin-2(1H)-one
5-{[2,5-Dihydroxy-4,4-dimethyl-2-trifluoromethyl-1,2,3,4-tetrahydronaphthalen-1-yl]amino}-quinolin-2(1H)-one
(−)-{[4,4-Dimethyl-2-hydroxy-5-methoxy-2-trifluoromethyl-1,2,3,4-tetrahydronaphthalen-1-yl]amino}-quinolin-2(1H)-one
(+){[4,4-Dimethyl-2-hydroxy-5-methoxy-2-trifluoromethyl-1,2,3,4-tetrahydronaphthalen-1-yl]amino}-quinolin-2(1H)-one
(+)-{[2,5-Dihydroxy-4,4-dimethyl-2-trifluoromethyl-1,2,3,4-tetrahydronaphthalen-1-yl]amino}-quinolin-2(1H)-one
(−)-{[2,5-Dihydroxy-4,4-dimethyl-2-trifluoromethyl-1,2,3,4-tetrahydronaphthalen-1-yl]amino}-quinolin-2(1H)-one 5-{[7-Chloro-2,5-dihydroxy-4,4-dimethyl-2-trifluoromethyl-1,2,3,4-tetrahydronaphthalen-1-yl]amino}-quinolin-2(1H)-one 5-{[2,5-Dihydroxy-4,4-dimethyl-6-fluoro-2-trifluoromethyl-1,2,3,4-tetrahydronaphthalen-1yl]amino}quinolin-2(1H)-one (−)-5-{[2,5-Dihydroxy-4,4-dimethyl-6-fluoro-2-trifluoromethyl-1,2,3,4-tetrahydronaphthalen-1-yl]amino}-quinolin-2(1H)-one (+)-5-{[2,5-Dihydroxy-4,4-dimethyl-6-fluoro-2-trifluoromethyl-1,2,3,4-tetrahydronaphthalen-1-yl]amino}-quinolin-2(1H)-one 5-{[4,4-Dimethyl-5-methoxy-7-methyl-2-trifluoromethyl-1,2,3,4-tetrahydronaphthalen-1-yl]amino}-quinolin-2(1H)-one 5-{[4,4-Dimethyl-7-fluoro-2-hydroxy-5-methoxy-2-trifluoromethyl-1,2,3,4-tetrahydronaphthalen-1-yl]amino}-quinolin-2(1H)-one (+)-5-{[2,5-Dihydroxy-4,4-dimethyl-2-trifluoromethyl-1,2,3,4-tetrahydronaphthalen-1-yl]amino}-quinolin-2(1H)-one 4-{[2-Hydroxy-4,4-dimethyl-5-methoxy-2-trifluoromethyl-1,2,3,4-tetrahydronaphthalen-1-yl]amino}-phthalide 7-Chloro-1-[(1H-indazol-4-yl)amino]-4,4-dimethyl-2-(trifluoromethyl)-1,2,3,4-tetrahydronaphthalene-2,5-diol (−)-7-Chloro-1-[(1H-indazol-4-yl)amino]-4,4-dimethyl-2-(trifluoromethyl)-1,2,3,4-tetrahydronaphthalene-2,5-diol (+)-7-Chloro-1-[(1H-indazol-4-yl)amino]-4,4-dimethyl-2-(trifluoromethyl)-1,2,3,4-tetrahydronaphthalene-2,5-diol 7-Fluoro-1-[(1H-indazol-4-yl)amino]-4,4-dimethyl-5-methoxy-2-(trifluoromethyl)-1,2,3,4-tetrahydronaphthalen-2-ol 7-Fluoro-1-[(1H-indazol-4-yl)amino]-4,4-dimethyl-2-(trifluoromethyl)-1,2,3,4-tetrahydronaphthalene-2,5-diol (−)-7-Fluoro-1-[(1H-indazol-4-yl)amino]-4,4-dimethyl-2-(trifluoromethyl)-1,2,3,4-tetrahydronaphthalene-2,5-diol (+)-7-Fluoro-1-[(1H-indazol-4-yl)amino]-4,4-dimethyl-2-(trifluoromethyl)-1,2,3,4-tetrahydronaphthalene-2,5-diol 5-Fluoro-1-[(1H-indazol-4-yl)amino]-4,4-dimethyl-2-(trifluoromethyl)-1,2,3,4-tetrahydronaphthalene-2,5-diol 5-Fluoro-1-[(1H-indazol-4-yl)amino]-4,4-dimethyl-2-(trifluoromethyl)-1,2,3,4-tetrahydronaphthalene-2,5-diol 1-[(1H-indazol-4-yl)amino]-4,4-dimethyl-5-methoxy-2-(trifluoromethyl)-1,2,3,4-tetrahydronaphthalen-2-ol 1-[(1H-Indazol-4-yl)amino]-4,4-dimethyl-5-methoxy-2-(trifluoromethyl)-1,2,3,4-tetrahydronaphthalen-2-ol 1-[(1H-Indazol-4-yl)amino]-4,4-dimethyl-2-(trifluoromethyl)-1,2,3,4-tetrahydronaphthalene-2,5-diol 7-Chloro-1-[(1H-indazol-4-yl)amino]-4,4-dimethyl-2-(trifluoromethyl)-1,2,3,4-tetrahydronaphthalen-2-ol 1-[(1-Methyl-indazol-4-yl)amino]-4,4-dimethyl-5-methoxy-2-(trifluoromethyl)-1,2,3,4-tetrahydronaphthalen-2-ol 7-Ethyl-1-[(1H-indazol-4-yl)amino]-4,4-dimethyl-5-methoxy-2-(trifluoromethyl)-1,2,3,4-tetrahydronaphthalen-2-ol 7-Ethyl-1-[(1H-indazol-4-yl)amino]-4,4-dimethyl-2-(trifluoromethyl)-1,2,3,4-tetrahydronaphthalen-2-ol 1-[(1-Methyl-indazol-4-yl)amino]-4,4-dimethyl-2-(trifluoromethyl)-1,2,3,4-tetrahydronaphthalene-2,5-diol 5-{[7-Fluoro-2-hydroxy-4,4-dimethyl-5-methoxy-2-(trifluoromethyl)-1,2,3,4-tetrahydronaphthalen-1-yl]amino}-isoquinolin-1(2H)-one 5-{[7-Fluoro-2,5-dihydroxy-4,4-dimethyl-2-(trifluoromethyl)-1,2,3,4-tetrahydronaphthalen-1-yl]amino}-isoquinolin-1(2H)-one (−)-5-{[7-Fluoro-2,5-dihydroxy-4,4-dimethyl-2-(trifluoromethyl)-1,2,3,4-tetrahydronaphthalen-1-yl]amino}-isoquinolin-1(2H)-one (+)-5-{[7-Fluoro-2,5-dihydroxy-4,4-dimethyl-2-(trifluoromethyl)-1,2,3,4-tetrahydronaphthalen-1-yl]amino}-isoquinolin-1(2H)-one 5-{[6-Fluoro-2-hydroxy-4,4-dimethyl-5-methoxy-2-(trifluoromethyl)-1,2,3,4-tetrahydronaphthalen-1-yl]amino}-2-methylphthalazin-1-one 5-{[6-Fluoro-2-hydroxy-4,4-dimethyl-5-methoxy-2-(trifluoromethyl)-1,2,3,4-tetrahydronaphthalen-1-yl]amino}-phthalazin-1(2H)-one 5-{[7-Chloro-2,5-dihydroxy-4,4-dimethyl-2-(trifluoromethyl)-1,2,3,4-tetrahydronaphthalen-1-yl]amino}-2-methylphthalazin-1-one 5-{[6-Fluoro-2-hydroxy-4,4-dimethyl-5-methoxy-2-(trifluoromethyl)-1,2,3,4-tetrahydronaphthalen-1-yl]amino}-2-methylphthalazin-1-one 5-{[6-Fluoro-2,5-dihydroxy-4,4-dimethyl-2-(trifluoromethyl)-1,2,3,4-tetrahydronaphthalen-1-yl]amino}-2-methylphthalazin-1-one 5-{[6-Fluoro-2,5-dihydroxy-4,4-dimethyl-2-(trifluoromethyl)-1,2,3,4-tetrahydronaphthalen-1-yl]amino}-phthalazin-1(2H)-one 5-{[2-Hydroxy-4,4-dimethyl-5-methoxy-2-(trifluoromethyl)-1,2,3,4-tetrahydronaphthalen-1-yl]amino}-phthalazin-1(2H)-one 5-{[2,5-Dihydroxy-4,4-dimethyl-2-(trifluoromethyl)-1,2,3,4-tetrahydronaphthalen-1-yl]amino}-phthalazin-1(2H)-one 5-{[2-Hydroxy-4,4-dimethyl-5-methoxy-2-(trifluoromethyl)-1,2,3,4-tetrahydronaphthalen-1-yl]amino}-2-methylphthalazin-1-one 5-{[2,5-Dihydroxy-4,4-dimethyl-2-(trifluoromethyl)-1,2,3,4-tetrahydronaphthalen-1-yl]amino}-2-methylphthalazin-1-one 5-{[2,5-Dihydroxy-4,4-dimethyl-2-(trifluoromethyl)-1,2,3,4-tetrahydronaphthalen-1-yl]amino}-2-methylphthalazin-1-one (−)-5-{[2-Hydroxy-4,4-dimethyl-5-methoxy-2-(trifluoromethyl)-1,2,3,4-tetrahydronaphthalen-1-yl]amino}-2-methylphthalazin-1-one (+)-5-{[2-Hydroxy-4,4-dimethyl-5-methoxy-2-(trifluoromethyl)-1,2,3,4-tetrahydronaphthalen-1-yl]amino}-2-methylphthalazin-1-one (−)-5-{[2,5-Dihydroxy-4,4-dimethyl-2-(trifluoromethyl)-1,2,3,4-tetrahydronaphthalen-1-yl]amino}-2-methylphthalazin-1-one (+)-5-{[2,5-Dihydroxy-4,4-dimethyl-2-(trifluoromethyl)-1,2,3,4-tetrahydronaphthalen-1-yl]amino}-2-methylphthalazin-1-one (−)-5-{[2,5-Dihydroxy-4,4-dimethyl-2-(trifluoromethyl)-1,2,3,4-tetrahydronaphthalen-1-yl]amino}-2-methylphthalazin-1-one (+)-5-{[2,5-Dihydroxy-4,4-dimethyl-2-(trifluoromethyl)-1,2,3,4-tetrahydronaphthalen-1-yl]amino}-2-methylphthalazin-1-one cis-1-[(2-Methylquinazolin-5-yl)amino]-4,4-dimethyl-2-(trifluoromethyl)-1,2,3,4-tetrahydronaphthalen-2-ol trans-5-Methoxy-1-[(2-methylquinazolin-5-yl)amino]-4,4-dimethyl-2-(trifluoromethyl)-1,2,3,4-tetrahydronaphthalen-2-ol cis-6-Chloro-5-methoxy-1-[(2-methylquinazolin-5-yl)amino]-4,4-dimethyl-2-(trifluoromethyl)-1,2,3,4-tetrahydronaphthalen-2-ol cis-6-Fluoro-5-methoxy-1-[(2-methylquinazolin-5-yl)amino]-4,4-dimethyl-2-(trifluoromethyl)-1,2,3,4-tetrahydronaphthalen-2-ol cis-6-[(2-Methylquinazolin-5-yl)amino]-9,9-dimethyl-7-(trifluoromethyl)-6,7,8,9-tetrahydronaphtho[1,2-d]-1,3-dioxol-7-ol cis-6-Chloro-1-[(2-methylquinazolin-5-yl)amino]-4,4-dimethyl-2-(trifluoromethyl)-1,2,3,4-tetrahydronaphthalene-2,5-diol cis-6-Fluoro-1-[(2-methylquinazolin-5-yl)amino]-4,4-dimethyl-2-(trifluoromethyl)-1,2,3,4-tetrahydronaphthalene-2,5-diol cis-6-[(7-Fluoro-2-methylquinazolin-5-yl)amino]-9,9-dimethyl-7-(trifluoromethyl)-6,7,8,9-tetrahydro-naphtho[1,2-d]-1,3-dioxol-7-ol trans-5-Methoxy-1-[(7-fluoro-2-methylquinazolin-5-yl)amino]-4,4-dimethyl-2-(trifluoromethyl)-1,2,3,4-tetrahydronaphthalen-2-ol cis-6-Chloro-1-[(7-fluoro-2-methylquinazolin-5-yl)amino]-4,4-dimethyl-2-(trifluoromethyl)-1,2,3,4-tetrahydronaphthalene-2,5-diol cis-6-Fluoro-1-[(7-fluoro-2-methylquinazolin-5-yl)amino]-4,4-dimethyl-2-(trifluoromethyl)-1,2,3,4-tetrahydronaphthalene-2,5-diol trans-7-Fluoro-1-[(7-fluoro-2-methylquinazolin-5-yl)amino]-5-methoxy-4,4-dimethyl-2-(trifluoromethyl)-1,2,3,4-tetrahydronaphthalen-2-ol cis-6-Chloro-1-[(8-fluoro-2-methylquinazolin-5-yl)amino]-4,4-dimethyl-2-(trifluoromethyl)-1,2,3,4-tetrahydronaphthalene-2,5-diol cis-1-[(8-Fluoro-2-methylquinazolin-5-yl)amino]-4,4-dimethyl-2-(trifluoromethyl)-1,2,3,4-tetrahydronaphthalen-2-ol trans-8-Fluoro-1-[(8-fluoro-2-methylquinazolin-5-yl)amino]-5-methoxy-4,4-dimethyl-2-(trifluoromethyl)-1,2,3,4-tetrahydronaphthalen-2-ol cis-7-Chloro-1-[(-8-fluoro-2-methylquinazolin-5-yl)amino]-4,4-dimethyl-2-(trifluoromethyl)-1,2,3,4-tetrahydronaphthalen-2-ol cis-6-Chloro-1-[(8-fluoro-2-methylquinazolin-5-yl)amino]-5-methoxy-4,4-dimethyl-2-(trifluoromethyl-1,2,3,4-tetrahydronaphthalen-2-ol cis-6-Fluoro-1-[(8-fluoro-2-methylquinazolin-5-yl)amino]-5-methoxy-4,4-dimethyl-2-(trifluoromethyl)-1,2,3,4-tetrahydronaphthalen-2-ol cis-6-[(8-Fluoro-2-methylquinazolin-5-yl)amino]-9,9-dimethyl-7-(trifluoromethyl)-6,7,8,9-tetrahydro-naphtho [1,2-d]-1,3-dioxol-7-ol cis-6-Fluoro-1-[(8-fluoro-2-methylquinazolin-5-yl)amino]-4,4-dimethyl-2-(trifluoromethyl)-1,2,3,4-tetrahydronaphthalene-2,5-diol cis-6-[(2-Methylquinolin-5-yl)amino]-9,9-dimethyl-7-(trifluoromethyl)-6,7,8,9-tetrahydronaphtho[1,2-d]-1,3-dioxol-7-ol cis-6-[(2-Methyl-1,7-naphthyridin-5-yl)amino]-9,9-dimethyl-7-(trifluoromethyl)-6,7,8,9-tetrahydro-naphtho[1,2-d]-1,3-dioxol-7-ol Rac.-5,8-Difluoro-1-[(1H-indazol-4-yl)amino]-4,4-dimethyl-2-(trifluoromethyl)-1,2,3,4-tetrahydronaphthalen-2-ol Rac.-5-Fluoro-1-[(2-methylquinazolin-5-yl)amino]-6-methoxy-4,4-dimethyl-2-(trifluoromethyl)-1,2,3,4-tetrahydronaphthalene-2-diol Rac.-5-Fluoro-1-[(2-methylquinazolin-5-yl)amino]-4,4-dimethyl-2-(trifluoromethyl)-1,2,3,4-tetrahydronaphthalene-2,5-diol Rac.-5-Fluoro-1-[(2-methylquinazolin-5-yl)amino]-6-methoxy-4,4-dimethyl-2-(trifluoromethyl)-1,2,3,4-tetrahydronaphthalene-2-diol 6-Fluoro-1-{[(2-hydroxymethyl)-quinolin-5-yl)amino]1-5-methoxy-4,4-dimethyl-2-(trifluoromethyl)-1,2,3,4-tetrahydronaphthalen-2-ol 1-[(5-Chloro-1H-indazol-4-yl)amino]-6-fluoro-5-methoxy-4,4-dimethyl-2-(trifluoromethyl)-1,2,3,4-tetrahydronaphthalen-2-ol 1-(5-Methyl-1H-indazol-4-ylamino)-6-fluoro-4,4-dimethyl-2-trifluoromethyl-1,2,3,4-tetrahydronaphthalene-2,5-diol 7-Bromo-1-[(1H-indazol-4-yl)amino]-5-methoxy-4,4-dimethyl-2-(trifluoromethyl)-1,2,3,4-tetrahydronaphthalen-2-ol 5-[(2-Hydroxy-4,4-pentamethylene-2-(trifluoromethyl)-1,2,3,4-tetrahydro-1-naphthyl)amino]-2-quinolone cis-1-[(8-Fluoro-2-methylquinazolin-5-yl)amino]-2-(trifluoromethyl)-1,2,3,4-tetrahydronaphthalene-2-diol cis-1-[(8-Fluoro-2-methylquinazolin-5-yl)amino]-4,4-dimethyl-2-(trifluoromethyl)-1,2,3,4-tetrahydronaphthalene-2,5-diol cis-1-[(7,8-Difluoro-2-methylquinazolin-5-yl)amino]-4,4-dimethyl-2-(trifluoromethyl)-1,2,3,4-tetrahydronaphthalen-2-ol cis-1-[(7,8-Difluoro-2-methylquinazolin-5-yl)amino]-4,4-dimethyl-6-fluoro-5-methoxy-2-(trifluoromethyl)-1,2,3,4-tetrahydronaphthalen-2-ol 5-{[2-Hydroxy-4,4-dimethyl-2,5-bis(trifluoromethyl)-1,2,3,4-tetrahydronaphthalen-1-ylamino}1-quinolin-2(1H)-one 5-{[6-Chloro-2-hydroxy-4,4-dimethyl-2-(trifluoromethyl)-1,2,3,4-tetrahydronaphthalen-1-yl]amino-quinolin-2(1H)-one 5-{[2-Hydroxy-4,4-dimethyl-2-(trifluoromethyl)-1,2,3,4-tetrahydronaphthalen-1-yl]amino}-1-methylquinolin-2(1H)-one 5-{[2-Hydroxy-4,4-dimethyl-2-(trifluoromethyl)-5,6-trimethylene-1,2,3,4-tetrahydronaphthalen-1-yl]amino}-quinolin-2(1H)-one 5-{[6-Chloro-2-hydroxy-4,4-dimethyl-5-methoxy-2-(trifluoromethyl)-1,2,3,4-tetrahydronaphthalen-1-yl]amino}-quinolin-2(1H)-one 5-{[6-Chloro-2,5-dihydroxy-4,4-dimethyl-2-(trifluoromethyl)-1,2,3,4-tetrahydronaphthalen-1-yl]amino}-quinolin-2(1H)-one 5-{[5-Bromo-2-hydroxy-4,4-dimethyl-2-(trifluoromethyl)-1,2,3,4-tetrahydronaphthalen-1-yl]amino}-quinolin-2(1H)-one 5-{[6-Chloro-2-hydroxy-5-methoxy-2-(trifluoromethyl)-4,4-trimethylene-1,2,3,4-tetrahydronaphthalen-1-yl]amino}-quinolin-2(1H)-one  5-{[6-Chloro-2,5-dihydroxy-2-(trifluoromethyl)-4,4-trimethylene-1,2,3,4-tetrahydronaphthalen-1-yl]amino}-quinolin-2(1H)-one 5-{[5-Difluoromethoxy-2-hydroxy-4,4-dimethyl-2-(trifluoromethyl)-1,2,3,4-tetrahydronaphthalen-1-yl]amino}-quinolin-2(1H)-one 4-{[6-Chloro-2-hydroxy-4,4-dimethyl-5-methoxy-2-(trifluoromethyl)-1,2,3,4-tetrahydronaphthalen-1-yl]amino}-indazole 5-(6-Chloro-2-hydroxy-7-methoxy-4,4dimethyl-2-(trifluoromethyl)-1,2,3,4-tetrahydronaphthalen-1-ylamino)-1H-quinolin-2-one 5-(6-Chloro-2-hydroxy-7-methoxy-4,4-dimethyl-2-(trifluoromethyl)-1,2,3,4-tetrahydronaphthalen-1-ylamino)-2H-isoquinolin-1-one 5-(6-Chloro-2-hydroxy-7-methoxy-4,4-dimethyl-2-(trifluoromethyl)-1,2,3,4-tetrahydronaphthalen-1-ylamino)-2H-phthalazin-1-one 6-Chloro-7-methoxy-4,4-dimethyl-1-(2-methylquinolin-5-ylamino)-2-(trifluoromethyl)-1,2,3,4-tetrahydronaphthalen-2-ol 6-Chloro-1-(8-fluoro-2-methylquinazolin-5-ylamino)-7-methoxy-4,4-dimethyl-2-(trifluoromethyl-1,2,3,4-tetrahydronaphthalen-2-ol 5-(6-Chloro-2,7-dihydroxy-4,4-dimethyl-2-(trifluoromethyl)-1,2,3,4-tetrahydronaphthalen-1-ylamino)-1H-quinolin-2-one:

1-(8-Fluoro-2-methylquinazolin-5-ylamino)-7-methoxy-4,4-dimethyl-2-(trifluoromethyl)-1,2,3,4-tetrahydronaphthalen-2-ol 5-(2-Hydroxy-7-methoxy-4,4-dimethyl-2-(trifluoromethyl)-1,2,3,4-tetrahydronaphthalen-1-ylamino)-1H-quinolin-2-one 5-(2-Hydroxy-7-methoxy-4,4-dimethyl-2-(trifluoromethyl)-1,2,3,4-tetrahydronaphthalen-1-ylamino)-2H-isoquinolin-1-one 5-(2-Hydroxy-7-methoxy-4,4-dimethyl-2-(trifluoromethyl)-1,2,3,4-tetrahydronaphthalen-1-ylamino)-2H-phthalazin-1-one 7-Methoxy-4,4-dimethyl-1-(2-methylquinolin-5-ylamino)-2-(trifluoromethyl)-1,2,3,4-tetrahydronaphthalen-2-ol 4,4-Dimethyl-1-(2-methylquinolin-5-ylamino)-2-(trifluoromethyl)-1,2,3,4-tetrahydronaphthalene-2,7-diol 5-(2,7-Dihydroxy-4,4-dimethyl-2-(trifluoromethyl)-1,2,3,4-tetrahydronaphthalen-1-ylamino)-2H-phthalazin-1-one 1-(8-Fluoro-2-methylquinazolin-5-ylamino)-4,4-dimethyl-2-(trifluoromethyl)-1,2,3,4-tetrahydronaphthalene-2,7-diol 5-(2,7-Dihydroxy-4,4-dimethyl-2-(trifluoromethyl)-1,2,3,4-tetrahydronaphthalen-1-ylamino)-1H-quinolin-2-one 5-(2-Hydroxy-5-methoxy-2-(trifluoromethyl)-1,2,3,4-tetrahydronaphthalen-1-ylamino)-1H-quinolin-2-one 1-(8-Fluoro-2-methylquinazolin-5-ylamino)-5-methoxy-2-(trifluoromethyl)-1,2,3,4-tetrahydronaphthalen-2-ol 7-Chloro-1-(8-fluoro-2-methylquinazolin-5-ylamino)-4,4-dimethyl-2-(trifluoromethyl)-1,2,3,4-tetrahydronaphthalene-2,6-diol 5-(7-Chloro-2,6-dihydroxy-4,4-dimethyl-2-(trifluoromethyl)-1,2,3,4-tetrahydronaphthalen-1-ylamino-2H-isoquinolin-1-one 5-(7-Chloro-2,6-dihydroxy-4,4-dimethyl-2-(trifluoromethyl)-1,2,3,4-tetrahydronaphthalen-1-ylamino-2-methyl-2H-phthalazin-1-one 5-(7-Chloro-2,6-dihydroxy-4,4-dimethyl-2-(trifluoromethyl)-1,2,3,4-tetrahydronaphthalen-1-ylamino-1H-quinolin-2-one 7-Chloro-1-(2-methylquinazolin-5-ylamino)-4,4-dimethyl-2-(trifluoromethyl)-1,2,3,4-tetrahydronaphthalene-2,6-diol 7-Chloro-1-(7-fluoro-2-methylquinazolin-5-ylamino)-4,4-dimethyl-2-(trifluoromethyl)-1,2,3,4-tetrahydronaphthalene-2,6-diol 7-Chloro-1-(7,8-difluoro-2-methylquinazolin-5-ylamino)-4,4-dimethyl-2-(trifluoromethyl)-1,2,3,4-tetrahydronaphthalene-2,6-diol 4-(7-Chloro-2,6-dihydroxy-4,4-dimethyl-2-(trifluoromethyl)-1,2,3,4-tetrahydronaphthalen-1-ylamino)-1,3-dihydroindol-2-one 8,8-Dimethyl-5-(naphthalen-1-ylamino)-6-(trifluoromethyl)-5,6,7,8-tetrahydronaphthalene-1,6-diol 8,8-Dimethyl-5-(naphthalen-2-ylamino)-6-(trifluoromethyl)-5,6,7,8-tetrahydronaphthalene-1,6-diol 2-Chloro-5-(6-hydroxynaphthalen-1-ylamino)-8,8-dimethyl-6-(trifluoromethyl)-5,6,7,8-tetrahydronaphthalene-1,6-diol 2-Chloro-5-(5-hydroxynaphthalen-1-ylamino)-8,8-dimethyl-6-(trifluoromethyl)-5,6,7,8-tetrahydronaphthalene-1,6-diol 3-Chloro-5-(6-hydroxynaphthalen-1-ylamino)-8,8-dimethyl-6-(trifluoromethyl)-5,6,7,8-tetrahydronaphthalene-1,6-diol 2-Chloro-8,8-dimethyl-5-(pyridin-3-ylamino)-6-(trifluoromethyl)-5,6,7,8-tetrahydronaphthalene-1,6-diol 1,6-Dihydroxy-8,8-dimethyl-5-(pyridin-3-ylamino)-6-(trifluoromethyl)-5,6,7,8-tetrahydronaphthalene-2-carbonitrile 2-Chloro-8,8-dimethyl-5-(pyridin-4-ylamino)-6-(trifluoromethyl)-5,6,7,8-tetrahydronaphthalene-1,6-diol 5-(2,5-Dihydroxy-6-isopropyl-4,4-dimethyl-2-(trifluoromethyl)-1,2,3,4-tetrahydronaphthalen-1-ylamino)-2H-isoquinolin-1-one 5-(2,5-Dihydroxy-6-isopropyl-4,4-dimethyl-2-(trifluoromethyl)-1,2,3,4-tetrahydronaphthalen-1-ylamino)-1H-quinolin-2-one 5-(7-Fluoro-2-methylquinazolin-5-ylamino)-2-isopropyl-8,8-dimethyl-6-(trifluoromethyl)-5,6,7,8-tetrahydronaphthalene-1,6-diol 5-(7,8-Difluoro-2-methylquinazolin-5-ylamino)-2-isopropyl-8,8-dimethyl-6-(trifluoromethyl)-5,6,7,8-tetrahydronaphthalene-1,6-diol 5-(8-Fluoro-2-methylquinazolin-5-ylamino)-2-isopropyl-8,8-dimethyl-6-(trifluoromethyl)-5,6,7,8-tetrahydronaphthalene-1,6-diol 4-(2,5-Dihydroxy-6-isopropyl-,4-dimethyl-2-(trifluoromethyl)-1,2,3,4-tetrahydronaphthalen-1-ylamino-1,3-dihydro-indol-2-one cis-6-Chloro-1-[(7,8-difluoro-2-methylquinazolin-5-yl)amino]-4,4-dimethyl-5-methoxy-2-(trifluoromethyl)-1,2,3,4-tetrahydronaphthalen-2-ol cis-1-[(8-Fluoro-2-methylquinazolin-5-yl)amino]-7-methoxy-2-(trifluoromethyl)-1,2,3,4-tetrahydronaphthalen-2-ol cis-6-Chloro-1-[(7,8-difluoro-2-methylquinazolin-5-yl)amino]-4,4-dimethyl-2-(trifluoromethyl)-1,2,3,4-tetrahydronaphthalene-2,5-diol cis-1-[(7,8-Difluoro-2-methylquinazolin-5-yl)amino]-6-fluoro-4,4-dimethyl-2-(trifluoromethyl)-1,2,3,4-tetrahydronaphthalene-2,5-diol cis-1-[(8-Fluoro-2-methylquinazolin-5-yl)amino]-2-(trifluoromethyl)-1,2,3,4-tetrahydronaphthalene-2,7-diol 2-Hydroxy-3-(1-phenylcyclohexyl)-2-(trifluoromethyl) propanal dis-4'-[(7,8-Difluoro-2-methylquinazolin-5-yl)amino]-3,4'-dihydro-3'-(trifluoromethyl)-spiro[cyclohexane-[1,1'(2'H)-naphthalen]-3'-ol cis-1-[(7,8-Difluoro-2-methylquinazolin-5-yl)amino]-4,4-dimethyl-2-(trifluoromethyl)-1,2,3,4-tetrahydronaphthalene-2,5-diol Trans-1-[(7,8-Difluoro-2-methylquinazolin-5y1)amino]-6-fluoro-4,4-dimethyl-2-(trifluoromethyl)-1,2,3,4-tetrahydronaphthalene-2,5-diol cis-5-{3',4'-Dihydro-3'-hydroxy-3'-(trifluoromethyl)-spiro]cyclohexane-1,1'(2'H)-naphthalen-4'-yl]amino}-quinolin-2(1H)-one cis-4'-[(8-Fluoro-2-methylquinazolin-5-yl)amino]-3',4'-dihydro-3'-(trifluoromethyl)-spiro[cyclopropane-1,1'(2'H)-naphthalen]-3'-ol cis-6-Chloro-1-[(8-fluoro-2-methyloquinazolin-5-yl)amino]-4,4-dimethyl-2-(pentafluoroethyl)-1,2,3,4-tetrahydronaphthalene-2,5-diol Cis-6-Chloro-1-[(7-fluoro-2-methylquinazolin-5-yl)amino]-4,4-dimethyl-2-(pentafluoroethyl)-1,2,3,4-tetrahydronaphthalene-2,5-diol Trans-6-Chloro-1-[(7-fluoro-2-methylquinazolin-5-yl)amino]-4,4-dimethyl-2-(pentafluoroethyl)-1,2,3,4-tetrahydronaphthalene-2,5-diol cis-5-{[6-Chloro-2-hydroxy-5-methoxy-4,4-dimethyl-2-(pentafluoroethyl)-1,2,3,4-tetrahydronaphthalen-1-yl]amino}-quinolin-2(1H)-one cis-5-{[2,5-Dihydroxy-4,4-dimethyl-2-(pentafluoroethyl)-1,2,3,4-tetrahydronaphthalen-1-yl]amino}-quinolin-2(1H)-one cis-7'-Fluoro-4'-[(8-fluoro-2-methylquinazolin-5-yl)-amino]-3',4'-dihydro-8'-methoxy-3'-(trifluoromethyl)-spiro[cyclohexane-1,1'(2'H)-naphthalen]-3'-ol Cis-7'-Fluoro-4'-[(8-fluoro-2-methylquinazolin-5-yl)amino]-3',4'-dihydro-3'-(trifluoromethyl)-spiro[cyclohexane-1,1'(2'H)-naphthalene]-3',8'-diol cis-7'-Fluoro-4'-[(7-fluoro-2-methylquinazolin-5-yl)amino]-3',4'-dihydro-8'-methoxy-3'-(trifluoromethyl)-spiro[cyclohexane-1,1'(2'H)-naphthalen]-3'-ol cis-5-(7'-Fluoro-3',4'-dihydro-3-hydroxy-8'-methoxy-3-(trifluoromethyl)-spiro[cyclohexane-1,1'(2H)-naphthalen-4'-yl]amino}-quinolin-2(1H)-one cis-6-Chloro-1-[(7-fluoro-2-methylquinazolin-5-yl)amino]-4,4,-dimethyl-2-(pentafluoroethyl)-1,2,3,4-tetrahydronaphthalene-2,5-diol cis-6-Chloro-1-[(2-methylquinazolin-5y1)amino]-4,4-dimethyl-2-(pentafluoroethyl)-1,2,3,4-tetrahydronaphthalene-2,5-diol cis-5-{7'-Chloro-3',4'-dihydro-3',8'-dihydroxy-3'-(trifluoromethyl)-spiro[cyclohexane-1,1'(2'H) -naphthalen-4'-yl]-amino}-quinolin-2(1H)-one cis-6-Fluoro-1-[(8-fluoro-2-methylquinazolin-5-yl)amino]-5-methoxy-4,4-dimethyl-2-(pentafluoroethyl)-1,2,3,4-tetrahydronaphthalen-2-ol cis-1-[(7,8-Difluoro-2-methylquinazolin-5-yl)amino]-6-fluoro-5-methoxy-4,4-dimethyl-2-(pentafluoroethyl)-1,2,3,4-tetrahydronaphthalen-2-ol cis-1-[(7,8-Difluoro-2-methylquinazolin-5-yl)amino]-4,4-dimethyl-6-fluoro-2-(pentafluoroethyl)-1,2,3,4-tetrahydronaphthalene-2,5-diol cis-5-{[6-Fluoro-2-hydroxy-5-methoxy-4,4-dimethyl-2-(pentafluoroethyl)-1,2,3,4-tetrahydronaphthalen-1-yl]amino}-quinolin-2(1H)-one cis-6-Fluoro-1-[(8-fluoro-2-methylquinazolin-5-yl)amino]-4,4-dimethyl-2-(pentafluoroethyl)-1,2,3,4-tetrahydronaphthalene-2,5-diol cis-4'-[(7,8-Difluoro-2-methylquinazolin-5-yl)amino]-7'-fluoro-3',4'-dihydro-8'-methoxy-3'-(trifluoromethyl)-spiro[cyclopropane-1,1'(2'H)-naphthalen]-3'-ol cis-7'-Fluoro-3',4'-dihydro-8'-methoxy-4'-[(2-methylquinazolin-5-yl)amino]-3'-(trifluoromethyl)-spiro[cyclopropane-1,1'(2'H)-naphthalen]-3'-ol cis-7'-Fluoro-3',4'-dihydro-4'-[(2-methylquinazolin-5-yl)amino]-3'-(trifluoromethyl)-spiro[cyclopropane-1,1'(2'H)-naphthalene-3',8'-diol cis-4'-[(7,8-Difluoro-2-methylquinazolin-5-yl)amino]-7-fluoro-3',4'-dihydro-3'-(trifluoromethyl)-spiro[cyclopropane-1,1'(2'H)-naphthalene]-3',8'-diol cis-1-[(7,8-Difluoro-2-methylquinazolin-5-yl)amino]-5-fluoro-6-methoxy-4,4-dimethyl-2-(trifluoromethyl)-1,2,3,4-tetrahydronaphthalen-2-ol cis-1-[(7,8-Difluoro-2-methylquinazolin-5-yl)amino]-5-fluoro4,4-dimethyl-2-(trifluoromethyl)-1,2,3,4-tetrahydronaphthalene-2,6-diol cis-7'-Fluoro-4'-[(8-fluoro-2-methylquinazolin-5-yl)amino]-3',4'-dihydro-3'-(trifluoromethyl)-spiro[cyclopropane-1,1'(2'H)-naphthalene]-3',8'-diol cis-7'-Fluoro-4'-[(7-fluoro-2-methylquinazolin-5-yl)amino]-3',4'-dihydro-3'-(trifluoromethyl)-spiro[cyclohexane-1,1'(2'H)-naphthalene]-3',8'-diol cis-6-Chloro-5-methoxy-1-[(2-methylquinolin-5-yl)amino]-4,4-dimethyl-2-(trifluoromethyl)-1,2,3,4-tetrahydronaphthalen-2-ol cis-6-Chloro-1-[(2-methylquinolin-5-yl)amino]-4,4-dimethyl-2-(trifluoromethyl)-1,2,3,4-tetrahydronaphthalene-2,5-diol cis-1-[(2-Methyl-1-quinolin-5-yl)amino]-4,4-dimethyl-2-(trifluoromethyl)-1,2,3,4-tetrahydronaphthalen-2-ol-N-oxide cis-6-Chloro-1-[(2-methylquinolin-5-yl)amino]-4,4-dimethyl-2-(trifluoromethyl)-1,2,3,4-tetrahydronaphthalene-2,5-diol N-oxide cis-6-[(2-Methyl-quinolin-5-yl)amino]-9,9-dimethyl-7-(trifluoromethyl)-6,7,8,9-tetrahydro-naphthol[1,2-d]-1,3-dioxol-7-ol N-oxide cis-7'-Fluoro-4'-[(7-fluoro-2-methylquinazolin-5-yl)amino]-3',4'-dihydro-3'-(trifluoromethyl)-spiro[cyclopropane-1,1'(2'H)-aphthalene]-3',8'-diol cis-5-(7'-Fluoro-3',4'-dihydro-3',8'-dihydroxy-3'-(trifluoromethyl)-spiro[cyclopropane-1,1'(2'H)-naphthalen-4'-yl]-amino}-inolin-2(1H)-one Cis-7'-Chloro-4'-[(7-fluoro-2-methylquinazolin-5-yl)amino]-3',4'-dihydro-3'-(trifluoromethyl)-spiro[cyclopropane-1,1'(2'H)-naphthalene]-3',8'-diol Cis-7'-Chloro-3',4'-dihydro-4'-[(2-methylquinolin-5-yl)amino]-3'-(trifluoromethyl)-spiro[cyclopropane-1,1'(2'H)-naphthalene]-3',8'-diol cis-7'-Chloro-3',4'-dihydro-4'-[(2-methyl-quinolin-5-yl)amino]-3'-(trifluoromethyl)-spiro[cyclopropane-1,1'(2'H)-naphthalene]-3',8'-diol N-oxide cis-7'-Chloro-4'-[(7-fluoro-2-methylquinazolin-5-yl)amino]-3,4'-dihydro-8'-methoxy-3'-(trifluoromethyl)-spiro[cyclohexane-1,1'(2H)-naphthalen]-3'-ol cis-7'-Chloro-4'-[(7-fluoro-2-methylquinazolin-5-yl)amino]-3,4'-dihydro-3'-(trifluoromethyl)-spiro[cyclohexane-1,1'(2'H)-naphthalene]-3',8'-diol cis-7'-Chloro-3',4'-dihydro-4'-[(2-methylquinazolin-5-yl)amino]-3'-(trifluoromethyl)-spiro[cyclopropane-1,1'(2'H)-naphthalene-3',8'-diol (−)-2-Chloro-5-(1H-indazol-4-ylamino)-8,8-dimethyl-6-(trifluoromethyl)-5,6,7,8-tetrahydronaphthalene-1,6-diol (+)-2-Chloro-5-(1H-indazol-4-ylamino)-8,8-dimethyl-6-(trifluoromethyl)-5,6,7,8-tetrahydronaphthalene-1,6-diol 5-{[4,4-Dimethyl-2-hydroxy-5-methoxy-2-(pentafluoroethyl)-1,2,3,4-tetrahydronaphthalen-1-yl]amino}-quinolin-2(1H)-one 5-{[6-Chloro-4,4-dimethyl-2-hydroxy-5-methoxy-2-(trifluoromethyl)-1,2,3,4-tetrahydronaphthalen-1-yl]amino}-6-methylquinolin-2(1H)-one 5-{[2,5-Dihydroxy-2-(trifluoromethyl)-4,4,7-trimethyl-1,2,3,4-tetrahydronaphthalen-1-yl]amino{-quinolin-2(1)-one 5-{[2-Hydroxy-5-methoxy-2-(pentafluoroethyl)-4,4,7-trimethyl-1,2,3,4-tetrahydronaphthalen-1-yl]amino}-quinolin-2(1H)-one 5-{[2-Hydroxy-5-methoxy-2-(trifluoromethyl)-4,4,6-trimethyl-1,2,3,4-tetrahydronaphthalen-1-yl]amino}-quinolin-2(1H)-one 4-}[4,4-Dimethyl-2-hydroxy-5-methoxy-2-(trifluoromethyl)-1,2,3,4-tetrahydronaphthalen-1-yl]amino}-phthalide 4-{[2,5-dihydroxy-4,4-dimethyl-2-(trifluoromethyl)-1,2,3,4-tetrahydronaphthalen-1-yl]amino}-phthalide (−)-4-{[4,4-Dimethyl-2-hydroxy-5-methoxy-2-(trifluoromethyl)-1,2,3,4-tetrahydronaphthalen-1-yl]amino}-phthalide (+)-4-{[4,4-dimethyl-2-hydroxy-5-methoxy-2-(trifluoromethyl)-1,2,3,4-tetrahydronaphthalen-1-yl]amino}-phthalide (−)-4-{[2,5-Dihydroxy-4-4-dimethyl-2-(trifluoromethyl)-1,2,3,4-tetrahydronaphthalen-1-yl]amino}-phthalide (+)-4-{[2,5-Dihydroxy-4-4-dimethyl-2-(trifluoromethyl)-1,2,3,4-tetrahydronaphthalen-1-yl]amino}-phthalide 5-{[5-Methoxy-2-hydroxy-2-(trifluoromethyl)-4,4,7-trimethyl-1,2,3,4-tetrahydronaphthalen-1-yl]amino}-2-methylphthalazin-1-one (+)-{[5-Methoxy-2-hydroxy-2-(trifluoromethyl)-4,4,7-trimethyl-1,2,3,4-tetrahydronaphthalen-1yl]amino}-2-methylphthalazin-1-one (+){[5-Methoxy-2-hydroxy-2-(trifluoromethyl)-4,4,7-trimethyl-1,2,3,4-tetrahydronaphthalen-1-yl]amino}-2-methylphthalazin-1-one 5-{[6-Chloro-4,4-dimethyl-5-methoxy-2-hydroxy-2-(trifluoromethyl)-1,2,3,4-tetrahydronaphthalin-1-yl]amino}-2-methylphthalazin-1-one (−)-{[6-Chloro-4,4-dimethyl-5-methoxy-2-hydroxy-2-(trifluoromethyl)-1,2,3,4-tetrahydronaphthalen-1-yl]amino}-2-methylphthalazin-1-one (+)-{[6-Chloro-4,4-dimethyl-5-methoxy-2-hydroxy-2-(trifluoromethyl)-1,2,3,4-tetrahydronaphthalen-1-yl]amino}-2-methylphthalazin-1-one 5-{[6-Chloro-2,5-dihydroxy-4,4-dimethyl-2-(trifluoromethyl)-1,2,3,4-tetrahydronaphthalen-1-yl]amino}-amino}-2-methylphthalazin-1-one (−)-5-{[6-Chloro-2,5-dihydroxy-4,4-dimethyl-2-(trifluoromethyl)-1,2,3,4-tetrahydronaphthalen-1-yl]amino}-amino}-2-methylphthalazin-1-one (+)-5{[6-Chloro-2,5-dihydroxy-4,4-dimethyl-2-(trifluoromethyl)-1,2,3,4-tetrahydronaphthalen-1-yl]amino}-amino}-2-methylphthalazin-1-one (+){[2,5-Dihydroxy-2-(trifluoromethyl)-4,4,7-trimethyl-1,2,3,4-tetrahydronaphthalen-1-yl]amino}-amino}-2-methylphthalazin-1-one 5-{[-Methoxy-2-hydroxy-2-(trifluoromethyl)-4,4,6-trimethyl-1,2,3,4-tetrahydronaphthalen-1-yl]amino}-2-methylphthalazin-1-one 5-{[6-Chloro-4,4-dimethyl-5-methoxy-2-hydroxy-2-(trifluoromethyl)-1,2,3,4-tetrahydronaphthalen-1-yl]amino}-phthalazin-1-one tetrahydronaphthalen-1-yl]amino}-8-fluoro-quinolin-2(1H)-one 2-Amino-5-{[4,4-dimethyl-6-fluoro-2-hydroxy-5-methoxy-2-(trifluoromethyl)-1,2,3,4-tetrahydronaphthalen-1-yl]amino}-8-fluoro-quinoline 5-{[7-Fluoro-3-hydroxy-8-methoxy-3-(trifluoromethyl)-3,4-dihydro-2H-spiro(cyclobutane-1,1'-naphthalen-4-yl]amino}-quinolin-2(1H)-one 5-{[3,8-Dihydroxy-7-fluoro-3-(trifluoromethyl)-3,4-dihydro-2H-spiro(cyclobutane-1,1'-naphthalen-4-yl]amino}-quinolin-2(1H)-one 5-{[7-Fluoro-3-hydroxy-8-methoxy-3-(trifluoromethyl)-3,4-dihydro-2H-spiro(cyclopentane-1,1'-naphthalen-4-yl]amino}-quinolin-2(1H)-one 5-{[3,8-Dihydroxy-7-fluoro-3-(trifluoromethyl)-3,4-dihydro-2H-spiro(cyclopentane-1,1'-naphthalen-4-yl]amino}-quinolin-2(1H)-one 5-{[2,5-Dihydroxy-4,4-dimethyl-7-fluoro-2-(trifluoromethyl)-1,2,3,4-tetrahydronaphthalen-1-yl]amino}-2-methylphthalazin-1-one (−)-{[2,5-Dihydroxy-4,4-dimethyl-7-fluoro-2-(trifluoromethyl)-1,2,3,4-tetrahydronaphthalen-1-yl]amino}-2-methylphthalazin-1-one (+)-5-{[2,5-Dihydroxy-4,4-dimethyl-7-fluoro-2-(trifluoromethyl)-1,2,3,4-tetrahydronaphthalen-1-yl]amino}-2-methylphthalazin-1-one 5-{(7-Bromo-2,5-dihydroxy-4,4-dimethyl-2-(trifluoromethyl)-1,2,3,4-tetrahydronaphthalen-1-yl]amino}-2-methylphthalazin-1-one 5-{(7-Bromo-2,5-dihydroxy-4,4-dimethyl-2-(trifluoromethyl)-1,2,3,4-tetrahydronaphthalen-1-yl]amino}-2-methylphthalazin-1-one 5-{[7-Chloro-3,8-dihydroxy-3-(trifluoromethyl)-3,4-dihydro-2H-spiro(cyclohexane-1,1'-naphthalen-4-yl)]amino}-quinolin-2(1H)-one (−)-{[6-Chloro-4,4-dimethyl-5-methoxy-2-hydroxy-2-(trifluoromethyl)-1,2,3,4-tetrahydronaphthalin-1-yl]amino}-phthalazin-1-one (+)-5{[6-Chloro-4,4-dimethyl-5-methoxy-2-hydroxy-2-(trifluoromethyl)-1,2,3,4-tetrahydronaphthalin-1-yl]amino}-phthalazin-1-one 5-{[6-Chloro-2,5-dihydroxy-4,4-dimethyl-2-(trifluoromethyl)-1,2,3,4-tetrahydronaphthalen-1-yl]amino}-amino}-phthalazin-1-one (−)-5{[6-Chloro-2,5-dihydroxy-4,4-dimethyl-2-(trifluoromethyl)-1,2,3,4-tetrahydronaphthalen-1-yl]amino}-amino}-phthalazin-1-one (+)-5{[6-Chloro-2,5-dihydroxy-4,4-dimethyl-2-(trifluoromethyl)-1,2,3,4-tetrahydronaphthalen-1-yl]amino}-amino}-phthalazin-1-one 5-{[2-Hydroxy-5-methoxy-2-(trifluoromethyl)-4,4,7-trimethyl-1,2,3,4-tetrahydronaphthalen-1-yl]amino}-phthalazin-1-one (−)-5{[2-Hydroxy-5-methoxy-2-(trifluoromethyl)-4,4,7-trimethyl-1,2,3,4-tetrahydronaphthalen-1-yl]amino}-phthalazin-1-one (+)-5{[2-Hydroxy-5-methoxy-2-(trifluoromethyl)-4,4,7-trimethyl-1,2,3,4-tetrahydronaphthalen-1-yl]amino}-2-methylphthalazin-1-one 5-{[2-Hydroxy-5-methoxy-2-(pentafluoroethyl)-4,4,7-trimethyl-1,2,3,4-tetrahydronaphthalen-1-yl]amino}-phthalazin-1-one 5-{[6-Chloro-4,4-dimethyl-2-hydroxy-5-methoxy-2-(trifluoromethyl)-1,2,3,4-tetrahydronaphthalen-1-yl]amino}-8-fluoro-quinolin-2(1H)-one 2-Amino-5-{[6-chloro-4,4-dimethyl-2-hydroxy-5-methoxy-2-(trifluoromethyl)-1,2,3,4-tetrahydronaphthlen-1-yl]amino}-8-fluoro-quinoline 5-{[4,4-Dimethyl-6-fluoro-2-hydroxy-5-methoxy-2-(trifluoromethyl)-1,2,3,4

5-{[7-Chloro-3,8-dihydroxy-3-(trifluoromethyl)-3,4-di-hydro-2H-spiro(cyclohexane-1,1'-naphthalen-4-yl)]amino}-2H-isoquinolin-1-one 7'-Chloro-4'-[(8-fluoro-2-methylquinazolin-5-yl)amino]-3',4'-dihydro-8'-methoxy-3'-(trifluoromethyl)-spiro[cyclohexane-1,1'(2'H)-naphthalen]-3'-ol 5-{[7-Chloro-3-hydroxy-8-methoxy-3-(trifluoromethyl)-3,4-dihydro-2H-spiro(cyclopropyl-1,1,'-naphthalen-4-yl)]amino}-quinolin-2(1H)-one 5-{[7-Chloro-3,8-dihydroxy-3-(trifluoromethyl)-3,4-di-hydro-2H-spiro(cyclopropane-1,1,'-naphthalen-4-yl)]amino}-2H-isoquinolin-1-one 7'-Chloro-4'-[(8-fluoro-2-methylquinazolin-5-yl)amino]-3',4'-dihydro-3'-(trifluoromethyl) spiro[cyclopropane-1,1'(2'H)-naphthalene]-3',8'-diol

[6-Hydroxy-1-methoxy-8,8-dimethyl-5-(2-oxo-1,2-dihydroquinolin-5-ylamino)-6-(trifluoromethyl)-5,6,7,8-tetrahydronaphthalen-2-yl]-acetonitrile

[5-(8-Fluoro-2-methylquinazolin-5-ylamino)-6-hydroxy-1-methoxy-8,8-dimethyl-6-(trifluoromethyl)-5,6,7,8-tetrahydronaphthalen-2-yl]-acetonitrile 1-(7-Fluoro-2-methylquinazolin-5-ylamino)-5-methoxy-4,4,6-trimethyl-2-(trifluoromethyl)-1,2,3,4-tetrahydronaphthalen-2-ol 1-(7,8-Difluoro-2-methylquinazolin-5-ylamino)-5-methoxy-4,4,6-trimethyl-2-(trifluoromethyl)-1,2,3,4-tetrahydronaphthalen-2-ol 5-[2,6-Dihydroxy-4,4-dimethyl-2-(trifluoromethyl)-1,2,3,4-tetrahydronaphthalen-1-ylamino]-2-methyl-2H-phthalazin-1-one 1-(8-Fluoro-2-methylquinazolin-5-ylamino)-4,4-dimethyl-2-(trifluoromethyl)-1,2,3,4-tetrahydronaphthalene-2,6-diol 5-(2,6-Dihydroxy-4,4-dimethyl-2-(trifluoromethyl)-1,2,3,4-tetrahydronaphthalen-1-ylamino)-2H-isoquinolin-1-one 5-(2,6-Dihydroxy-4,4-dimethyl-2-(trifluoromethyl)-1,2,3,4-tetrahydronaphthalen-1-ylamino)-1H-quinolin-2-one 7-Fluoro-1-(8-fluoro-2-methylquinazolin-5-ylamino)-4,4-dimethyl-2-(trifluoromethyl)-1,2,3,4-tetrahydronaphthalene-2,6-diol 5-[7-Fluoro-2-hydroxy-6-methoxy-4,4-dimethyl-2-(trifluoromethyl)-1,2,3,4-tetrahydronaphthalen-1-ylamino]-1H-quinolin-2-one 6-Fluoro-1-[(2-methylquinolin-5-yl)amino]-4-ethyl-2-(trifluoromethyl)-1,2,3,4-tetrahydronaphthalene-2,5-diol 5-{[7-Bromo-2,5-dihydroxy-4,4-dimethyl-2-(trifluoromethyl)-1,2,3,4-tetrahydronaphthalen-1-yl]amino}-quinolin-2(1H)-one or 5-{[7-Bromo-2,5-dihydroxy-4,4-dimethyl-2-(trifluoromethyl)-1,2,3,4-tetrahydronaphthalen-1-yl]amino}-quinolin-2(1H)-one, or a pharmaceutically acceptable salt thereof.

13. A method for treating an inflammatory disease, comprising administering to a subject in need thereof an effective amount of a compound of claim 12, wherein the inflammatory disease is a lung disease, a rheumatic disease, an allergic disease, a dermatologic disease, an eye disease, a chronic, obstructive lung disease, primary bronchial asthma, bronchitis, rheumatoid arthritis, contact dermatitis, atopic dermatitis, psoriasis, rosacea, or conjunctivitis.

14. A pharmaceutical composition, comprising a compound of claim 12 and a pharmaceutically acceptable carrier.

15. A pharmaceutically acceptable salt of a compound according to claim 12.

16. A method for treating an inflammatory disease, comprising administering to a subject in need thereof an effective amount of a stereoisomer of claim 2, wherein the inflammatory disease is a lung disease, a rheumatic disease, an allergic disease, a dermatologic disease, an eye disease, a chronic, obstructive lung disease, primary bronchial asthma, bronchitis, rheumatoid arthritis, contact dermatitis, atopic dermatitis, psoriasis, rosacea, or conjunctivitis.

17. A method for treating an inflammatory disease, comprising administering to a subject in need thereof an effective amount of a stereoisomer of claim 3, wherein the inflammatory disease is a lung disease, a rheumatic disease, an allergic disease, a dermatologic disease, an eye disease, a chronic, obstructive lung disease, primary bronchial asthma, bronchitis, rheumatoid arthritis, contact dermatitis, atopic dermatitis, psoriasis, rosacea, or conjunctivitis.

18. A method for treating an inflammatory disease, comprising administering to a subject in need thereof an effective amount of a stereoisomer of claim 4, wherein the inflammatory disease is a lung disease, a rheumatic disease, an allergic disease, a dermatologic disease, an eye disease, a chronic, obstructive lung disease, primary bronchial asthma, bronchitis, rheumatoid arthritis, contact dermatitis, atopic dermatitis, psoriasis, rosacea, or conjunctivitis.

19. A method for treating an inflammatory disease, comprising administering to a subject in need thereof an effective amount of a stereoisomer of claim 5, wherein the inflammatory disease is a lung disease, a rheumatic disease, an allergic disease, a dermatologic disease, an eye disease, a chronic, obstructive lung disease, primary bronchial asthma, bronchitis, rheumatoid arthritis, contact dermatitis, atopic dermatitis, psoriasis, rosacea, or conjunctivitis.

20. A stereoisomer according to claim 2, wherein $R^5$ stands for trifluoromethyl or pentafluoroethyl.

21. A method according to claim 6, wherein the inflammatory disease is a lung disease, a rheumatic disease, an allergic disease, a dermatologic disease or an eye disease.

22. A method according to claim 6, wherein the inflammatory disease is a chronic, obstructive lung disease, primary bronchial asthma, bronchitis, rheumatoid arthritis, contact dermatitis, atopic dermatitis, psoriasis, rosacea or conjunctivitis.

23. A method according to claim 6, wherein the inflammatory disease is primary bronchial asthma, bronchitis, rheumatoid arthritis, contact dermatitis, atopic dermatitis, psoriasis, rosacea or conjunctivitis.

24. A method according to claim 13, wherein the inflammatory disease is a lung disease, a rheumatic disease, an allergic disease, a dermatologic disease or an eye disease.

25. A method according to claim 13, wherein the inflammatory disease is a chronic, obstructive lung disease, primary bronchial asthma, bronchitis, rheumatoid arthritis, contact dermatitis, atopic dermatitis, psoriasis, rosacea or conjunctivitis.

26. A method according to claim 13, wherein the inflammatory disease is primary bronchial asthma, bronchitis, rheumatoid arthritis, contact dermatitis, atopic dermatitis, psoriasis, rosacea or conjunctivitis.

* * * * *

UNITED STATES PATENT AND TRADEMARK OFFICE
CERTIFICATE OF CORRECTION

PATENT NO. : 7,638,515 B2  
APPLICATION NO. : 10/961406  
DATED : December 29, 2009  
INVENTOR(S) : Rehwinkel et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 844 days.

Signed and Sealed this

Ninth Day of November, 2010

David J. Kappos  
*Director of the United States Patent and Trademark Office*